(12) United States Patent
Larsen et al.

(10) Patent No.: US 6,353,023 B1
(45) Date of Patent: Mar. 5, 2002

(54) INHIBITORS OF PROTEIN TYROSINE PHOSPHATASE

(75) Inventors: Scott D. Larsen, Kalamazoo; Paul D. May, Richland; John E. Bleasdale, Portage, all of MI (US); Charlotta Liljebris, Uppsala (SE); Heinrich Josef Schostarez, Portage, MI (US); Tjeerd Barf, Uppsala (SE)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/138,642

(22) Filed: Aug. 24, 1998

Related U.S. Application Data

(60) Provisional application No. 60/057,730, filed on Aug. 28, 1997.

(51) Int. Cl.[7] ............... C07C 237/22; A61K 31/216
(52) U.S. Cl. ............... 514/533; 514/563; 560/41; 562/450
(58) Field of Search ............... 560/41; 502/450; 514/533, 563

(56) References Cited

U.S. PATENT DOCUMENTS 3,912,756 A 10/1975 Wolff et al.

FOREIGN PATENT DOCUMENTS

| DE | 2320387   |   | 10/1974 |       |
|----|-----------|---|---------|-------|
| DE | 151304    | A | 10/1981 |       |
| EP | 0832875   | A1| 4/1998  |       |
| WO | 9 623813  |   | 8/1996  |       |
| WO | 96/23813  | * | 8/1996  | 560/1 |
| WO | 9630332   |   | 10/1996 |       |
| WO | 9 630332  |   | 10/1996 |       |
| WO | 9633968   |   | 10/1996 |       |
| WO | 9638415   |   | 12/1996 |       |
| WO | 9 640109  |   | 12/1996 |       |
| WO | 9 640113  |   | 12/1996 |       |
| WO | 9807699   |   | 2/1998  |       |

OTHER PUBLICATIONS

Desmarais, Arch. Biochem. Biophys. 354 (2) 225–231, 1998.*
Desmarais, Arch. Biochem. Biophys. 354 (2) 225–231, 1998.*
F.D. King, Medicinal Chemistry: Principles And Practice, pp. 206–209 (1994), XP002033086.
Paul S. Charifson et al., Biochemistry, 36, pp. 6283–6293 (1997), XP002087254.

* cited by examiner

*Primary Examiner*—Robert Gerstl
(74) *Attorney, Agent, or Firm*—Fish & Richardson P.C.

(57) ABSTRACT

The present invention comprises small molecular weight, non-peptidic inhibitors of formula I and II of Protein Tyrosine Phosphatase 1 (PTP1) which are useful for the treatment and/or prevention of Non-Insulin Dependent Diabetes Mellitus (NIDDM).

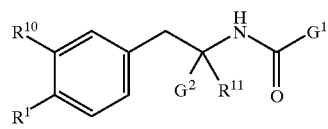

I

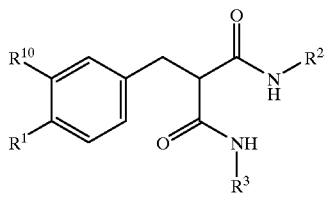

II

26 Claims, No Drawings

INHIBITORS OF PROTEIN TYROSINE PHOSPHATASE

CROSS-REFERENCE TO RELATED APPLICATIONS

This application claims the benefit of provisional application U.S. Ser. No. 60/057,730, filed 28 Aug. 1997, under 35 USC 119(e)(i).

The present invention comprises small molecular weight, non-peptidic inhibitors of Protein Tyrosine Phosphatase 1 (PTP1) which are useful for the treatment and/or prevention of Non-Insulin Dependent Diabetes Mellitus (NIDDM).

BACKGROUND OF THE INVENTION

The mechanism of insulin action depends critically upon the phosphorylation of tyrosine residues in several proteins in the insulin signalling cascade. Enzymes that dephosphorylate these proteins, protein tyrosine phosphatases (PTPs), are important negative regulators of insulin action. Therefore, the use of specific PTP inhibitors may therapeutically enhance insulin action.

The insulin resistance that is central to noninsulin-dependent diabetes mellitus (NIDDM) appears to involve a defect in an early process in insulin signal transduction rather than a structural defect in the insulin receptor itself. (J. M. Olefsky, W. T. Garvey, R. R. Henry, D. Brillon, S. Matthai and G. R. Freidenberg, G. R. (1988).) Cellular mechanisms of insulin resistance in non-insulin-dependent (Type II) diabetes. (Am. J. Med. 85: Suppl. 5A, 86–105.) A drug that improved insulin sensitivity would have several advantages over traditional therapy of NIDDM using sulfonylureas, which do not alleviate insulin resistance but instead compensate by increasing insulin secretion.

The binding of insulin to the α-subunits of the insulin receptor permits the β-subunits to catalyze phosphorylation of target proteins on tyrosine residues. There are 22 tyrosine residues in each insulin receptor β-subunit itself and autophosphorylation of at least 6 of these tyrosines, in 3 distinct domains, is known to be involved in insulin action. (C. R. Kahn (1994) Insulin action, diabetogenes, and the cause of type II diabetes. Diabetes 43: 1066–1084.) Autophosphorylation of $Tyr^{960}$ in the juxtamembrane domain is important for receptor internalization and for the interaction of the receptor with downstream signalling molecules such as insulin receptor substrate 1 (IRS-1).) (T. J. O'Neill, A. Craparo and T. A. Gustafson (1994) Characterization of an interaction between insulin receptor substrate 1 and the insulin receptor by using the two-hybrid system. Mol. Cell Biol. 14: 6433–6442.) Autophosphorylation of tyrosine residues 1146, 1150 and 1151 in the regulatory domain permits continued tyrosine kinase activity of β-subunits, even after insulin has dissociated from the α-subunits, and activates the kinase toward other protein substrates. (R. Herrera and O. M. Rosen (1986) Autophosphorylation of the insulin receptor in vitro: designation of phosphorylation sites and correlation with receptor kinase activation. J. Biol. Chem. 261: 11980–11985.) Deletion of autophosphorylation sites at $Tyr^{1316}$ and $Tyr^{1322}$ in the C-terminal domain attenuates the metabolic actions of insulin, but augments its mitogenic actions. (H. Maegawa, D. McClain, G. Freidenberg, J. Olefsky, M. Napier, T. Lipari, T. Dull, J. Lee, and A. Ullrich (1988) Properties of a human insulin receptor with a COOH-terminal truncation. II. Truncated receptors have normal kinase activity but are defective in signalling metabolic effects. J. Biol. Chem. 263: 8912–8917.) (Y. Takata, N. J. G. Webster, and J. M. Olefsky (1991) Mutation of the two carboxyl-terminal tyrosines results in an insulin receptor with normal metabolic signalling but enhanced mitogenic signalling properties. J. Biol. Chem. 266: 9135–9139.) Dephosphorylation of these autophosphorylated sites occurs rapidly in vivo, suggesting that a protein tyrosine phosphatase (PTPase) is involved in terminating insulin action. A compound that inhibited this PTPase, therefore, should potentiate insulin action. Indeed, vanadate potentiates insulin action, at least in part, by such a mechanism (Y. Schechter (1990). Insulin-mimetic effects of vanadate. Possible implications for future treatment of diabetes. Diabetes 39: 1–5.) The PTPase(s) that act on the insulin receptor, however, has not been identified definitively.

It has been estimated that the human genome encodes as many as 500 PTP enzymes (T. Hunter (1995) Protein kinases and phosphatases: The Yin and Yang of protein phosphorylation and signalling. Cell 80:225–236), but less than 100 have been identified and have been grouped into 4 subfamilies (E. A. Fauman and M. A. Saper (1996) Structure and function of the protein tyrosine phosphatases. Trends Biochem. Sci. 21:413–417.) Members of the tyrosine-specific PTP sub-family are further divided into the receptor PTPases (such as CD45 and LAR) which typically have a large variable extracellular domain, a single transmembrane spanning region, and two intracellular phosphatase catalytic domains and the non-receptor PTPases. This latter group includes PTP that resemble PTP1. (D. A. Pot and J. E. Dixon (1992) A thousand and two protein tyrosine phosphatases. Biochim. Biophys. Acta 1136: 35–43.) There is data to support the proposition that the insulin receptor PTPase may be PTP1-like. For instance, an insulin-dependent association of PTP1 with insulin receptors has been described. (D. Bandyopadhyay, A. Kursari, K. A. Kenner, F. Liu, J.Chernoff, T. A. Gustafson, J. Kusari (1997) Protein-tyrosine phosphatase 1B complexes with the insulin receptor in vivo and is tyrosine-phosphorylated in the presence of insulin. J. Biol. Chem. 272: 1639–1645; and L. Seely, et al. (1996) Protein tyrosine phosphatase 1B interacts with the activated insulin receptor. Diabetes 45:1379.) Furthermore, PTP1 dephosphorylates purified insulin receptors sequentially in the order observed in vivo (i.e., $Tyr^{1150}$=$Tyr^{1151}$>$Tyr^{1146}$), (C. Ramachandran, R. Aebersold, N. Tonks and D. A. Pot (1992) Sequential dephosphorylation of a multiply phosphorylated insulin receptor peptide by protein tyrosine phosphtases. Biochemistry 31: 4232–4238) and insulin acutely increases PTP1 mRNA in hepatoma cells. (N. Hashimoto and B. J. Goldstein (1992) Differential regulation of mRNAs encoding three protein-tyrosine phosphatases by insulin and activation of protein kinase C. Biochem. Biophys. Res. Commun. 188: 1305–1311.) Insulin resistance induced in Rat 1 fibroblasts by high glucose (27 mM) is preceded by an approximate doubling of cytosolic PTP1 activity that is blocked by the insulin-sensitizer, pioglitazone. (H. Maegawa, R. Ide, M. Hasegawa, S. Ugi, K. Egawa, M. Iwanishi, R. Kikkawa, Y. Shigeta, and A. Kashiwagi (1995) Thiazolidinedione derivatives ameliorate high glucose-induced insulin resistance via the normalization of protein tyrosine phosphatase activities. J. Biol. Chem. 270: 7724–7730.) Thus, a specific inhibitor of PTP1 could be used to potentiate insulin action. While there are no known small molecules that specifically inhibit PTP1, it was found that osmotic loading of hepatoma cells with neutralizing antibodies against PTP1b (the human homologue of rat PTP1) resulted in increased autophosphorylation of insulin receptors and phosphorylation of IRS-1 in response to insulin. (F. Ahmad, P.-M. Li, J. Meyerovitch, and B. J. Goldstein (1995) Osmotic loading of neutralizing antibodies demonstrates a role for PTPase 1B in negative regulation of the insulin signalling pathway. Diabetes 44: Suppl. 1 104A.) See also B. J. Goldstein (1993) Regulation of insulin receptor signaling by protein-tyrosine dephosphorylation. Receptor 3: 1–15.)

INFORMATION DISCLOSURE

International Publication No. WO 96/30332, "O-Malonyltyrosyl Compounds, O-Malonyltyrosyl Compound-Containing Peptides, and Uses thereof," published Oct. 3, 1996, disclose non-phosphorus containing O-malonyltyrosyl compounds, derivatives thereof, uses of the O-malonyltyrosyl compounds in the synthesis of peptides, and O-malonyltyrosyl compound-containing peptides. The O-malonyltyrosyl compounds and O-malonyltyrosyl compound-containing peptides are disclosed as being useful as inhibitors of protein-tyrosine phosphatase; however, no specific non-peptidic compounds or data is disclosed.

International Publication No. WO 96/23813, "Peptides and Compounds that Bind to SH2 Domains," published Aug. 8, 1996, discloses tyrosine-containing peptides and compounds which bind to the SH2 domain or domains of various proteins, as well as methods for identifying such peptides and compounds. These peptides and compounds have application as agonists and antagonists of SH2 domain containing proteins, and as diagnostic or therapeutic agents for the diagnosis or treatment of disease conditions.

International Publication No. WO 96/40113, "Phosphatase Inhibitors," published Dec. 19, 1996, discloses heterocyclic nitrogen containing compounds, such as nitropyridine or nitrothiazole, capable of inhibiting protein tyrosine phosphatase activity. Such molecules are disclosed as being useful to modulate or regulate signal transduction by inhibiting protein tyrosine phosphatase activity and to treat various disease states including diabetes mellitus.

International Publication No. WO 96/40109, "Methods of Inhibiting Phosphatase Activity and Treatment of Disorders Associated Therewith Using Napthopyrones and Derivatives Thereof," published Dec. 19, 1996, discloses the use of naphthopyrone compounds to inhibit protein tyrosine phosphatase activity. Such compounds are disclosed as being useful to modulate or regulate signal transduction by inhibiting protein tyrosine phosphatase activity and to treat various disease states including diabetes mellitus.

The compounds of the present invention have surprising activity in that they are small molecular weight and non-peptidic compounds.

SUMMARY OF THE INVENTION

A compound of formula I or II

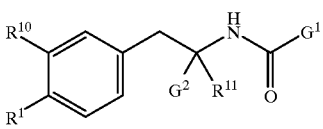

I

-continued

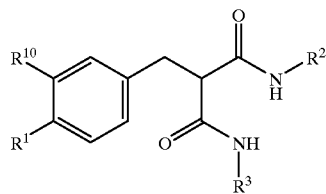

II wherein $G^1$ is
 a) —$R^2$, or
 b) —$NR^8R^4$;
wherein $G^2$ is
 a) $CONHR^3$,
 b) H,
 c) $CH_2OH$, or
 d) $CH{=}CHR^3$;
wherein $R^1$ is
 a) —$OSO_3H$,
 b) —$OCH(CO_2R^5)_2$,
 c) —$OCH_2(CO_2R^5)$,
 d) —$OCH(CO_2R^5)CH_2CO_2R^5$,
 e) —$OC(CO_2R^5){=}CHCO_2R^5$,
 f) —$CH_2CH(CO_2R^5)_2$,
 g) —$CH{=}C(CO_2R^5)_2$,
 h) —$OCH_2CONHOH$,
 i) —$N(CH_2CO_2R^5)_2$, or
 j) —$OCHF(CO_2R^5)$;
wherein $R^2$ is
 a) —$C_1$–$C_{10}$ alkyl optionally substituted with one or two —$CO_2R^5$ bonded to the same or different carbon atoms or with one —CO—$NH_2$,
 b) —$C_3$–$C_8$ cycloalkyl optionally substituted with one —$CO_2R^5$,
 c) —$C_0$–$C_6$ alkyl-phenyl optionally substituted with one or two —$CO_2R^5$ bonded to the same or different carbon atoms or with —$CH_2CH(CO_2R^5)_2$,
 d) —$CH(R^7)NHXR^6$, or
 e)

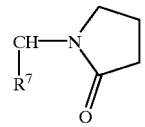

wherein $R^3$ is
 a) —$C_1$–$C_{12}$ alkyl, optionally substituted with one to three —O—, —S—, —N—, —O—$C_1$–$C_4$ alkyl, —S—$C_1$–$C_4$ alkyl, —O—$G^3$, —S—$G^3$, or —OH,
 b) —$C_1$–$C_4$ alkyl-$C_3$–$C_6$ cycloalkyl,
 c) —$C_2$–$C_{12}$ alkenyl,
 d) —$C_3$–$C_{12}$ alkynyl,
 e) —$C_0$–$C_{10}$ alkyl($G^3$)$_n$ wherein alkyl is optionally substituted with one to three —O—, —S—or —N—, or
 f) —$CH(CONH_2)C_1$–$C_{12}$ alkyl;
wherein $R^4$ is
 a) —H,
 b) —$C_1$–$C_{18}$ alkyl or alkenyl, or c) —$C_0$–$C_6$-alkyl-$G^3$;
wherein $R^5$ is
  a) —H,
  b) —$C_1$–$C_{10}$ alkyl, or
  c) —$C_1$–$C_5$ alkyl-phenyl;
wherein $R^6$ is
  a) $C_1$–$C_{10}$ alkyl,
  b) $C_0$–$C_6$ alkyl-$G^3$,
  c) $C_1$–$C_6$ alkyl CONH$_2$,
  d) $C_1$–$C_6$ alkyl NHCO$_2$R$^5$,
  e) $C_1$–$C_6$ alkyl-OR$^5$,
  f) $C_1$–$C_6$ alkyl-NHSO$_2$Me,
  g) $C_1$–$C_6$ alkyl-O—$G^3$,
  h) $C_1$–$C_6$ alkyl-S—$G^3$, or
  i) —$C_1$–$C_6$ alkyl-CO$_2$R$^5$;
wherein $R^7$ is
  a) —H,
  b) —$C_1$–$C_6$ alkyl-$G^3$
  c) —$C_1$–$C_6$ alkyl-CO$_2$R$^5$
  d) $C_1$–$C_6$ alkyl CONH$_2$,
  e) $C_1$–$C_6$ alkyl NHCO$_2$R$^5$,
  f) $C_1$–$C_{10}$ alkyl,
  g) $C_1$–$C_{10}$ cycloalkyl,
  h) —$C_1$–$C_6$ alkyl-SR$^5$, or
  i) —$C_1$–$C_6$ alkyl-S(=O)R$^5$;
wherein $R^8$ is
  a) $C_0$–$C_6$ alkyl-$G^3$,
  b) CH(R$^7$)CO$_2$R$^5$,
  c) CH(R$^7$)CH$_2$CO$_2$R$^5$, or
  d) CH(R$^7$)CONHCH$_2$CO$_2$R$^5$;
wherein $G^3$ is
  a) phenyl substitued by zero (0) to three (3) $R^9$,
  b) naphthyl substitued by zero (0) to three (3) $R^9$, or
  c) het substituted by zero (0) to three (3) $R^9$;
wherein het is a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and if chemically feasible, the nitrogen and sulfur atoms may be in the oxidized forms;
wherein $R^9$ may be any of the following:
  a) $C_1$–$C_8$ alkyl substituted by zero (0) to three (3) halo,
  b) $C_2$–$C_8$ alkenyl,
  c) OH,
  d) O—$C_1$–$C_5$ alkyl,
  e) O—$C_0$–$C_5$ alkyl-phenyl
  e) —(CH$_2$)$_n$—O—$C_1$–$C_5$ alkyl substituted by zero (0) to three (3) hydroxy,
  f) —(CH$_2$)$_n$—O—$C_2$–$C_7$ alkenyl substituted by zero (0) to three (3) hydroxy,
  g) halo,
  h) NH$_2$,
  i) amino-$C_1$–$C_5$ alkyl,
  j) mono-or di-$C_1$–$C_5$ alkylamino,
  k) —C(O)—$C_1$–$C_5$ alkyl,
  l) —CHO,
  m) —C(O)—$C_0$–$C_5$ alkyl-phenyl
  n) —COOR$^5$
  o) —CON(R$^5$)$_2$,
  p) —$C_3$–$C_7$ cycloalkyl,
  q) —NO$_2$,
  r) —CN,
  s) —SO$_3$H,
  t) —SO$_2$N(R$_5$)$_2$,
  u) —O[(CH$_2$)$_2$—O]$_n$—CH$_3$,
  v) —[CH$_2$—O]$_n$—$C_1$–$C_3$ alkyl,
  w) —NR$^5$(CO)—NR$^5$,
  x) —CF$_3$,
  y) —NR$^5$(CO)$C_1$–$C_5$ alkyl,
  z) —N(R$^5$)—SO$_2$—R$^5$,
  a1) —O—C(O)—R$^5$,
  b1) —S(O)—R$^5$,
  c1) —SR$^5$, or
  d1) —SO$_2$—R$^5$;
wherein $R^{10}$ is
  a) —H,
  b) CO$_2$R$^5$,
  c) CONHOH,
  d) 5-tetrazolyl,
  e) F, or
  f) OCH$_2$CO$_2$R$^5$;
wherein $R^{11}$ is
  a) H, or
  b) methyl;
wherein X is —CO— or —SO$_2$— or —CO$_2$—;
wherein n is zero, one, two or three;
or a pharmaceutically acceptable salt thereof;
provided that when $R^{10}$ is H, $R^1$ is other than —OCH$_2$(CO$_2$R$^5$).

The present invention particularly provides the compounds of formula III or IV

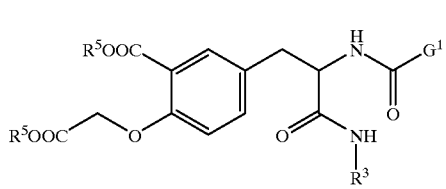

III

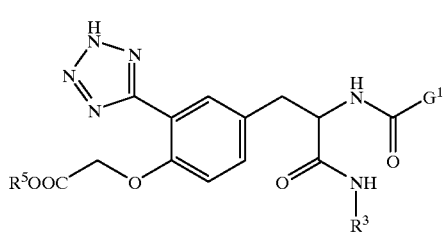

IV wherein $G^1$ is
  a) —CH(CH$_2$phenyl)NHCO$_2$t-Bu,
  b) —CH(CH$_2$phenyl)NHCOC$_1$–$C_3$ alkyl-$G^3$,
  c) —CH(CH$_2$phenyl)NHCOC$_1$–$C_3$ alkyl-CO$_2$R$^5$, d)

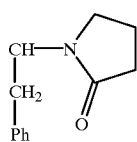

wherein R³ is
  a) —C₅–C₆ alkyl, or
  b) —C₃–C₆ alkyl-phenyl;
wherein R⁵ is —H;
wherein the configuration of the chiral center(s) is (S).

The compounds of the present invention are named according to the IUPAC or CAS nomenclature system.

The carbon atoms content of various hydrocarbon-containing moieties is indicated by a prefix designating the minimum and maximum number of carbon atoms in the moiety, i.e., the prefix $C_i$–$C_j$ indicates a moiety of the integer "i" to the integer "j" carbon atoms, inclusive. Thus, for example, $C_1$–$C_3$ alkyl refers to alkyl of one to three carbon atoms, inclusive, or methyl, ethyl, propyl, and isopropyl, straight and branched forms thereof.

Also, the carbon atom content of various hydrocarbon-containing moieties of the present invention may be indicated by a subscripted integer representing the number of carbon and hydrogen atoms in the moiety, e.g., "$C_nH_{2n}$" indicates a moiety of the integer "n" carbon atoms, inclusive, and the integer "2n" hydrogen atoms, inclusive. Thus, for example, "$C_nH_{2n}$" wherein n is one to three carbon atoms, inclusive, and two to six hydrogen atoms, inclusive, or methyl, ethyl, propyl and isopropyl, and all isomeric, straight and branched forms thereof.

Examples of alkyl of one to nine carbon atoms, inclusive, are methyl, ethyl, propyl, butyl, pentyl, hexyl, heptyl, octyl, and nonyl, and all isomeric forms thereof and straight and branched forms thereof.

Examples of alkenyl of one to five carbon atoms, inclusive, are ethenyl, propenyl, butenyl, pentenyl, all isomeric forms thereof, and straight and branched forms thereof.

By "halo" is meant the typical halogen atoms, such as fluorine, chlorine, bromine, and iodine.

The present invention encompasses all possible combinations of configurations at each of the possible chiral centers. The preferred configuration for the chiral center depicted in formula I is (S), and the preferred configuration for the chiral center present in R² (d and e) is (S).

The compounds of formulae I and II of the present invention are prepared as described in the Charts, Preparations and Examples below, or are prepared by methods analogous thereto, which are readily known and available to one of ordinary skill in the art of organic synthesis.

CHART A

Commercially available tyrosine benzyl ester A-1 is acylated with monomethyl succinate under standard amide coupling conditions employing 1-(3-dimethylaminopropyl)-3-ethylcarbodiimide hydrochloride (EDC) as the coupling reagent (Tet. Lett. 1993, 34:7685) to afford A-2. Alkylation of the phenol is effected with diethylchloromalonate in acetone with potassium carbonate as catalyst, conditions analogous to those previously described for alkylation of phenols (J. Am. Chem. Soc. 1951, 73:872). Standard hydrogenolysis of the benzyl ester A-3 affords A-4, which is then acylated with various amines (R³NH₂) under the influence of EDC. The target acids A-5 are obtained by saponification.

CHART B

Commercially available Cbz-tyrosine (B-1) is coupled with n-pentylamine under standard EDC conditions, affording amide B-2. Alkylation of the phenol as described in Chart A gives ether B-3, which is then hydrogenolytically deprotected to obtain amine B-4, isolated as the corresponding HCl salt. Acylation of the free amine with various carboxylic acids R²COOH is accomplished with EDC. Final saponification with dilute lithium hydroxide followed by acidification gives the sparingly soluble malonic acids B-5.

CHART C

Amine hydrochloride B-4 (from Chart B) is acylated with various isocyanates in the presence of triethylamine in methylene chloride to afford the corresponding urethanes. Saponification of the esters then provides the acids C-1.

CHART D

Amine B-4 (from Chart B) is converted to the corresponding isocyanate D-1 by reaction with diphosgene and Proton Sponge at 0 C. (J. Org. Chem. 1996, 61:3883). Addition of N-benzylglycine ethyl ester followed by saponification then affords the desired urethane triacid D-2.

CHART E

Commercially available Boc-(L)-tyrosine E-1 is coupled with n-pentylamine, as described for Chart B, to give E-2. The Boc group is removed with HCl in acetic acid, and the resulting amine E-3 is coupled with a mono succinate ester as described for Chart A. The resulting phenol amides E-4 and E-5 are added directly to a dialkyl acetylenedicarboxylate in the presence of triethylamine (Aust. J. Chem. 1995, 48:677). Fumarate ester E-6 is hydrogenated with 10% palladium on carbon to give the saturated triacid E-8. Alternatively, fumarate ester E-7 is saponified to give the unsaturated triacid E-9.

CHART F

Amine hydrochloride E-3 (from Chart E) is reacted with succinic anhydride in the presence of triethylamine to afford the acid F-1. Sulfation of the phenol is effected with sulfur trioxide/pyridine complex in DMF (Int. J. Pep. Prot. Res. 1990, 35:566) and purification is accomplished with reverse phase HPLC to give F-2.

CHART G

Previously described E-2 (from Chart E) is treated with trifluoromethanesulfonic anhydride in the presence of pyridine to afford triflate G-1. Palladium-catalyzed cross-coupling of G-1 with tributyl(vinyl)tin affords G-2. G-2 is then ozonized followed by reduction with dimethyl sulfide to give G-3. This aldehyde is then condensed with dibenzylmalonate in the presence of piperidine acetate to afford G-4. Deprotection of the Boc group with saturated HCl/HOAc affords G-5 which is subsequently reacted with succinic anhydride to afford G-6. Hydrogenation of G-6 with H₂ and 10% Pd/C gives final triacid G-7.

CHART H

Direct saponfication of dibenzylester G-6 (from Chart G) affords the unsaturated triacid H-1.

CHART I

Alkylation of phenol E-4 (from Chart E) is accomplished by a carbenoid insertion reaction with di-t-butyl diazomalonate (Synthesis 1974, 347) catalyzed by rhodium acetate (J. Med. Chem. 1995, 38:4270), affording malonate ether I-1. Removal of the t-butyl esters is accomplished with trifluroacetic acid in methylene chloride, and the benzyl ester is removed by hydrogenolysis, affording the desired triacid I-3.

CHART J

Amide E-2 (from Chart E) is alkylated on the phenolic hydroxyl with dibenzyl bromomalonate as described for Chart A (potassium carbonate/acetone) to give J-3. The Boc group is removed with HCl in acetic acid, affording the amine hydrochloride J-4. The free amine is added to various cyclic anhydrides in the presence of triethylamine, giving acids J-5. Hydrogenolysis of the benzyl esters then affords the desired triacids J-6.

CHART K

Chart K describes an alternative synthesis of A-5 (from Chart A) (now K-6 in Chart K) wherein benzyl esters are used as the protecting group for the malonate carboxyls instead of ethyl esters. Tyrosine t-butyl ester K-1 is acylated with monobenzyl succinate under the influence of EDC to afford amide K-2. Alkylation with dibenzyl bromomalonate under the conditions described in Chart A affords ether K-3. The t-butyl ester is removed with TFA in methylene chloride, giving carboxylic acid K-4, which is coupled with various amines using EDC as the coupling reagent. Final deprotection of K-5 is accomplished by hydrogenolysis to give K-6.

CHART L

Chart L describes an extension of Chart J wherein amine J-4 (from chart J) is coupled (EDC) with a protected amino acid to afford L-2. The Boc group is removed with HCl in acetic acid to give amine L-3. Addition to succinic anhydride followed by hydrogenolysis of the benzyl esters L-4 then provides the desired tetracids L-5.

CHART M

Cbz-tyrosine M-1 is coupled (EDC) with norleucine amide to provide M-2. Alkylation of the phenol with diethyl chloromalonate as described for Chart A gives ether M-3. The Cbz group is removed by hydrogenation, and the resulting free amine M-4 is acylated with succinic anhydride. Carboxylic acid M-5 is then saponified to give the target triacid M-6.

CHART N

Commercially available N-1 is condensed with dibenzylmalonate in the presence of piperidine acetate to afford N-2. N-2 is coupled to previously described J-4 (from Chart J) to afford N-3. Hydrogenation of N-3 leads to final tetraacid N-4.

CHART O

Direct hydrogenation of benzyl ester L-2 (from Chart L) gives the Boc-protected triacid O-1.

CHART P

Acylation of amine L-3 (from Chart L) with hexanoyl chloride gives amide P-1. Hydrogenation then removes the benzyl esters, providing triacid P-2.

CHART Q

Commercially available Q-1 is N-protected as the Boc derivative by reaction with $Boc_2O$, and the resulting compound is converted to amylamide Q-2 by coupling (EDC) with amylamine. Palladium catalyzed carbonylation with carbon monoxide and methanol affords methyl ester Q-3. Alkylation of the phenolic oxygen with methylbromoacetate yields ether Q-4, which is N-deblocked with trifluoroacetic acid in methylene chloride and then acylated with succinic anhydride, leading to amide Q-5. Saponification under standard conditions then produced the desired triacid Q-6.

CHART R

Q-4 is deblocked with HCl/dioxane before coupling with 3-phenylpropanoic acid in the presence of EDC and saponified to afford R-4. Alternatively, Q-4 may be deblocked as before, followed by coupling with Boc-L-Phe to afford R-1. R-1 may be saponified directly to R-2, or the Boc group can be removed with HCl/dioxane, and the resulting amine can be coupled with an acid chloride or carboxylic acid to afford R-3 after saponification.

CHART S

S-1 is alkylated with diethylchloromalonate to afford S-2. Removal of the Boc group with HCl/dioxane followed by coupling with Boc-L-p-benzoyl-Phe gives S-3. Removal of the Boc group again followed by addition of succinic anhydride and saponification provides triacid S-4.

CHART T

Iodotyrosine Q-2 is converted to nitrile T-1 by the action of zinc cyanide and Pd catalyst. Alkylation with methyl bromoacetate affords ether T-2, which is coupled with Boc-L-Phe after deblocking of the amine group with HCl. The nitrile is converted to the corresponding tetrazole T-4 with TMS-azide and catalytic dibutyltin oxide. Final saponification affords the acid T-5.

CHART U

Q-2 is carbonylated with carbon monoxide and palladium catalyst to afford esters U-1 and Q-3. The phenols are alkylated with methyl or benzyl bromoacetate to afford U-2 and U-3. The Boc group is removed with TFA, followed by coupling with Boc-L-Phe, affording amides U-4 and U-5. Catalytic hydrogenation removes the benzyl esters, providing U-6 and U-7. Coupling of the free carboxylic acids with hydroxylamine generates the hydroxamic acids U-8 and U-9, and the methyl esters are saponified with lithium hydroxide to provide acids U-10 and U-1.

CHART V

Ester V-1 is reduced with DIBAL to afford aldehyde V-2, which is subsequently converted by a Wittig reaction to olefin V-3. The phenol is alkylated with dibenzyl bromomalonate to afford ether V-4. Deprotection of the amine with TFA, followed by acylation of the free amine with monobenzylsuccinate affords amide V-5. Saponification of the esters (LiOH) then provides the triacid V-6.

CHART W

Commercially available acid W-1 is amidated with n-pentylamine (EDC), and the resulting amide W-2 is catalytically hydrogenated to aniline W-3. The aniline is bis (alkylated) with methyl bromoacetate to afford W-4. Removal of the Boc group (TFA) followed by acylation of the amine with Boc-L-Phe affords W-5. Final saponification (LiOH) then provides the diacid W-6.

CHART X

Commercially available meta-iodotyrosine is esterified with benzyl alcohol before coupling with Boc-L-Phe, affording X-2. The iodine is carboxylated with CO under palladium catalysis, providing ester X-3, which is alkylated with methyl bromoacetate. The resulting ether X-4 is hydrogenated to remove the benzyl ester protecting group, and the resulting acid X-5 is reduced with sodium borohydride via the corresponding acyl imidazole to alcohol X-6. Final saponification of the esters affords the diacid X-7.

CHART Y

Commercially available methyl tyrosine Y-1 is protected as the N-Boc derivative under standard conditions before conversion of the carboxylic acid to amide Y-3. This amide is alkylated with dibenzyl bromomalonate to afford ether Y-4. Boc cleavage with HCl is followed by acylation of the free amine with succinic anhydride, providing acid Y-5. Final saponification with LiOH affords triacid Y-6.

CHART Z

Meta fluorotyrosine Z-1 is converted to triacid Z-6 exactly as described in Chart Y.

CHART AA

4-Hydroxybenzaldehyde AA-1 is alkylated with diethyl chloromalonate to afford ether AA-2. Mono ethyl malonate AA-3 is coupled with amylamine under standard conditions (DEPC) to afford amide AA-4. Hydrolysis of the ester with aq NaOH provides acid AA-5. Coupling of AA-5 with beta-alanine ethyl ester provides malondiamide AA-6, which is condensed with aldehyde AA-2 under Knoevenagel conditions. The resulting methylidene malondiamide AA-7 (a mixture of olefin isomers) is saturated by catalytic hydrogenation, and the ester AA-8 is saponified to triacid AA-9 with aq NaOH.

CHART BB

Amine B-4 (from Chart B) is acylated with the appropriate protected amino acid under the influence of EDC and triethylamine. The resulting amides BB-1 is directly saponified to give BB-3. Alternatively, where $R^6$ is t-butylcarboxy (Boc), the Boc group is removed with HCl/acetic acid, and the resulting free amine acylated with succinic anhydride. Final saponification then affords the triacids BB-2.

CHART CC

Diol CC-1 (reference given in Example 142) is bis (alkylated) with ethyl bromoacetate, and the resulting bis (ether) CC-2 is hydrogenated to remove the benzyl ester. The carboxylic acid CC-3 is coupled with amylamine under standard conditions (DEPC) before cleavage of the Boc group with TFA. Free amine CC-5 is then coupled with Boc-L-Phe (DEPC), and the resulting amide CC-6 is saponified to the diacid CC-7.

CHART DD

Diester Q-4 (Chart Q) is reacted with TFA to cleave the Boc group, and the free amine DD-1 is coupled (DEPC) with the appropriate amino acid (see Example 143) to afford amide DD-2. Saponification provides diacid DD-3.

CHART EE

Q-2 (Chart Q) is carbonylated with CO under palladium catalysis to afford ester EE-1. The phenol is alkylated with ethyl bromofluoroacetate/potassium carbonate to afford ether EE-2. Boc deprotection and amide coupling of the free amine with Boc-L-Phe under standard conditions affords diester EE-3, which is saponified to provide the diacid EE-4.

CHART FF

Acid X-5 (Chart X) is coupled with 4-phenylbutylamine under standard amide coupling conditions to provide FF-1. Saponification of the esters affords diacid FF-2.

Preferred methods of preparation are depicted in Charts A, B, BB, Q and R.

The present invention provides for compounds of formulae I and II or pharmacologically acceptable salts and/or hydrates thereof. Pharmacologically acceptable salts refers to those salts which would be readily apparent to a manufacturing pharmaceutical chemist to be equivalent to the parent compound in properties such as formulation, stability, patient acceptance and bioavailability. Examples of salts of the compounds of formula I include lithium, sodium and potassium.

Where $R^5$ is other than H, the compounds would not be expected to have intrinsic activity, but would be expected to possess activity in vivo following hydrolysis by non-specific esterases to the corresponding carboxylic acids.

The compounds of the present invention are useful for treating patients with noninsulin-dependent diabetes mellitus (NIDDM) and related diseases. For this indication, these compounds may be administered by oral, intranasal, transdermal, subcutaneous and parenteral (including intramuscular and intravenous) routes in doses of 0.1 mg to 1000 mg/kg of body weight per day.

Those skilled in the art would know how to formulate the compounds of this invention into appropriate pharmaceutical dosage forms. Examples of the dosage forms include oral formulations, such as tablets or capsules, or parenteral formulations, such as sterile solutions.

When the compounds in this invention are administered orally, an effective amount is from about 0.1 mg to 100 mg per kg of body weight per day. Either solid or fluid dosage forms can be prepared for oral administration. Solid compositions, such as compressed tablets, are prepared by mixing the compounds of this invention with conventional ingredients such as talc, magnesium stearate, dicalcium phosphate, magnesium aluminum silicate, calcium sulfate, starch, lactose, acacia, methyl cellulose, or functionally similar pharmaceutical diluents and carriers. Capsules are prepared by mixing the compounds of this invention with an inert pharmaceutical diluent and placing the mixture into an appropriately sized hard gelatin capsule. Soft gelatin capsules are prepared by machine encapsulation of a slurry of the compounds of this invention with an acceptable inert oil such as vegetable oil or light liquid petrolatum.

Syrups are prepared by dissolving the compounds of this invention in an aqueous vehicle and adding sugar, aromatic flavoring agents and preservatives. Elixirs are prepared using a hydroalcoholic vehicle such as ethanol, suitable sweeteners such as sugar or saccharin and an aromatic flavoring agent. Suspensions are prepared with an aqueous vehicle and a suspending agent such as acacia, tragacanth, or methyl cellulose.

When the compounds of this invention are administered parenterally, they can be given by injection or by intravenous infusion. An effective amount is from about 0.1 mg to 100 mg per kg of body weight per day. Parenteral solutions are prepared by dissolving the compounds of this invention in aqueous vehicle and filter sterilizing the solution before placing in a suitable sealable vial or ampule. Parenteral suspensions are prepared in substantially the same way except a sterile suspension vehicle is used and the compounds of this invention are sterilized with ethylene oxide or suitable gas before it is suspended in the vehicle.

The exact route of administration, dose, or frequency of administration would be readily determined by those skilled in the art and is dependant on the age, weight, general physical condition, or other clinical symptoms specific to the patient to be treated.

The utility of representative compounds of the present invention has been demonstrated in the biological assays described below:

PTP1 Assays: A construct, which consisted of a C-terminal truncation of rat PTP1 (amino acid residues 1–322) (cloned from a rat brain library) with an N-terminal glutathione S-transferase (GST) tag and an adjacent thrombin cleavage site, was inserted into vector plasmid pGEX-2T and transformed into E.coli strain TG-1 under the control of a lac promoter (K. L. Guan and J. E. Dixon (1991) Eukaryotic proteins expressed in Escherichia coli: an improved thrombin cleavage and purification procedure of fusion proteins with glutathione S-transferase. Analyt. Biochem. 192: 262–267). The GST-fusion protein was purified on a glutathione agarose affinity column, the GST tag was cleaved with thrombin, and the active enzyme was recovered for use in an assay to identify PTP inhibitors.

The equivalent construct of human PTP1B (amino acid residues 1–321) (cloned from a human placental library), without the GST tag and thrombin cleavage site, was inserted into a pMB replicon and transformed into E. coli BL21(DE3), a strain containing a chromosomal copy of the gene for T7 RNA polymerase under control of a lacUV5 promoter. Expression of PTP1B was induced with isopropyl thiogalactose and the soluble protein was purified by ion exchange, hydrophobic interaction and gel exclusion chromatography for use in the assay to identify PTP inhibitors.

PTP1 activity is measured using either p-nitrophenol phosphate (pNPP) or a triphosphopeptide (that matches residues 1142 through 1153 of the β-subunit and the insulin receptor) as substrate in a 96-well microtiter plate format. An assay pH of 7.2 is used for standard assays (measured $_{405}$=9800 at pH 7.2).

Human PTP1B, which is highly homologous to rat PTP1, was assayed exactly as described above for PTP1. The PTP1 inhibitors described here also inhibit PTP1B with similar or identical potencies.

Standard assays are conducted at room temperature in a total volume of 0.2 ml that contains Hepes buffer (50 mM, pH 7.2), NaCl (50 mM), EDTA (1 mM), DTT (1 mM), bovine serum albumin (1 mg/ml), pNPP (1 mM) and PTP1 (35 ng/ml). Compounds (2 $\mu$l of 10 mM solutions) are pipetted into wells of microtiter plates followed by 198 $\mu$l of premixed reaction mix (with PTP1 and pNPP added immediately before use). The rate of change in $A_{405}$ is recorded for 60 min. Two wells on each plate contain DMSO controls and two wells contain sodium orthovanadate (1 mM) which inhibits PTP1-catalyzed hydrolysis of pNPP completely. Data are expressed as percent inhibition relative to the average of the DMSO controls measured on the same microtiter plate.

When triphosphopeptide[1142–1153] is used as substrate, the rate of release of inorganic phosphate is measured using a Malachite Green/phosphomolybdate reaction (A. A. Baykov, O. A. Evtushenko, and S. M. Avaeva (1988) A Malachite Green procedure for orthophosphate determination and its use in alkaline phosphatase-based enzyme immunoassay. Anal. Biochem. 171: 266–270.) in a microtiter plate format. Standard assays are conducted at room temperature in a total volume of 50 $\mu$l that contains Hepes buffer (50 mM, pH 7.2), NaCl (50 mM), EDTA (1 mM), DTT (1 mM), bovine serum albumin (1 mg/ml), triphosphopeptide[1142–1153] (200 $\mu$M) and PTP1 (87 ng/ml). Reactions are terminated with the addition of 0.15 ml of Malachite Green/ammonium molybdate reagent [10 ml Malachite Green (0.44 g in 6N $H_2SO_4$), 2.5 ml ammonium molybdate (7.5% w/v), 0.2 ml Tween 20 (11% w/v)] that is diluted with 8 parts of water immediately before use, and after 1 h absorbance at 650 nm is measured. The phosphate assay is calibrated using either $KH_2PO_4$ or pNPP (after ashing with $Mg(NO_3)_2$) which gives essentially identical standard curves. The phosphate assay is useful in the range of 1 to 10 nmol $P_i$.

The % inhibition of pNPP-hydrolysis by compounds of the present invention are listed in Table 1 and 2 below.

The following compounds of the present invention are preferred:
(S)-5-[[[[1-[[4-(Dicarboxymethoxy)phenyl]methyl]-2-oxo-2-(pentylamino)ethyl]amino]carbonyl]amino]-1,3-benzenedicarboxylic acid;

(S)—N-[[[1-[[4-(Dicarboxymethoxy)phenyl]methyl]-2-oxo-2-(pentylamino)ethyl]amino]carbonyl]-L-glutamic acid;

N-[(1,1-Dimethylethoxy)carbonyl]-L-α-aspartyl-O-(dicarboxymethyl)-N-pentyl-L-tyrosinamide;

N-(3-Carboxy-1-oxopropyl)-L-α-aspartyl-O-(dicarboxymethyl)-N-pentyl-L-tyrosinamide;

N-(3-Carboxy-1-oxopropyl)-L-α-glutamyl-O-(dicarboxymethyl)-N-pentyl-L-tyrosinamide;

N-(3-Carboxy-1-oxopropyl)-O-(dicarboxymethyl)-L-tyrosyl-L-norleuciramide;

N-(1-Oxohexyl)-L-α-aspartyl-O-(dicarboxymethyl)-N-pentyl-L-tyrosinamide;

N-[(Phenylmethoxy)carbonyl]-L-α-aspartyl-O-(dicarboxymethyl)-N-pentyl-L-tyrosinamide;

N-[(1,1-Dimethylethoxy)carbonyl]-D-α-aspartyl-O-(dicarboxymethyl)-N-pentyl-L-tyrosinamide;

4-Benzoyl-N-(3-carboxy-1-oxopropy)-L-phenylalanyl-O-(dicarboxymethyl)-N-pentyl-L-tyrosinamide; and (S)-2-(Carboxymethoxy)-5-[2-[(3-carboxy-1-oxopropyl) amino]-3-oxo-3-(pentylamino)propyl]benzoic acid.

The following compounds of the present invention are more preferred:
2-{4-[(2S)-2-({(2S)-2-[(3-carboxypropanoyl)amino]-3-phenylpropanoyl}amino)-3-oxo-3-(pentylamino)propyl]phenoxy}malonic acid;

5-[(2S)-2-({(2S)-2-[(tert-butoxycarbonyl)amino]-3-phenylpropanoyl}amino)-3-oxo-3-(pentylamino)propyl]-2-(carboxymethoxy)benzoic acid;

2-{4-[(2S)-2-{[(dibenzylamino)carbonyl]amino}-3-oxo-3-(pentylamino)propyl]phenoxy}malonic acid;

2-(carboxymethoxy)-5-[(2S)-2-{[(dibenzylamino)carbonyl]amino}-3-oxo-3-(pentylamino)propyl]benzoic acid;

2-(carboxymethoxy)-5-[(2S)-2-({(2S)-2-[(3-carboxypropanoyl)amino]-3-phenylpropanoyl}amino)-3-oxo-3-(pentylamino)propyl]benzoic acid;

2-(carboxymethoxy)-5-{(2S)-3-oxo-3-(pentylamino)-2-[((2S)-3-phenyl-2-{[2-(5-sulfanyl-1H-1,2,3,4-tetraazol-1-yl)acetyl]amino}propanoyl)amino]propyl }benzoic acid;

2-(carboxymethoxy)-5-{(2S)-3-oxo-3-(pentylamino)-2-[((2S)-3-phenyl-2-{[2-(1H-1,2,3-triazol-5-ylsulfanyl) acetyl]amino}propanoyl)amino]propyl }benzoic acid;

2-[4-[(2S)-2-({(2S)-2-[(tert-butoxycarbonyl)amino]-3-phenylpropanoyl}amino)-3-oxo-3-(pentylamino)propyl]-2-(2H-1,2,3,4-tetraazol-5-yl)phenoxy]acetic acid;

2-(carboxymethoxy)-5-[(2S)-3-oxo-3-(pentylamino)-2-({(2S)-3-phenyl-2-[(2-phenylacetyl)amino]propanoyl}amino)propyl]benzoic acid;

2-(carboxymethoxy)-5-[(2S)-3-oxo-3-(pentylamino)-2-({(2S)-3-phenyl-2-[(4-phenylbutanoyl)amino]propanoyl}amino)propyl]benzoic acid;

2-(carboxymethoxy)-5-[(2S)-2-({(2S)-2-[(3-methoxypropanoyl)amino]-3-phenylpropanoyl}amino)-3-oxo-3-(pentylamino)propyl]benzoic acid;

2-(carboxymethoxy)-5-((2S)-3-oxo-3-(pentylamino)-2-{[(2S)-3-phenyl-2-({2-[4-(trifluoromethyl)phenyl]acetyl}amino)propanoyl]amino}propyl)benzoic acid;

2-(carboxymethoxy)-5-[(2S)-2-[((2S)-2-{[2-(4-methoxyphenyl)acetyl]amino}-3-phenylpropanoyl)amino]-3-oxo-3-(pentylamino)propyl]benzoic acid;

2-(carboxymethoxy)-5-[(2S)-3-oxo-3-(pentylamino)-2-({(2S)-3-phenyl-2-[(3-phenylpropanoyl)amino]propanoyl}amino)propyl]benzoic acid;

2-(carboxymethoxy)-5-[(2S)-3-oxo-2-{[(2R)-2-(2-oxo-1-pyrrolidinyl)-3-phenylpropanoyl]amino}-3-(pentylamino)propyl]benzoic acid; and 5-{(2S)-2-({(2S)-2-[(tert-butoxycarbonyl)amino]-3-phenylpropanoyl}amino)-3-[(4-phenylbutyl)amino]propyl}-2-(carboxymethoxy)benzoic acid.

DESCRIPTION OF PREFERRED EMBODIMENTS

EXAMPLE 1

(S)-4-Oxo-4-[[2-oxo-2-(pentylamino)-1-[[4-(sulfooxy)phenyl]-methyl]ethyl]amino]butanoic acid (Formula F-2, Chart F)

PREPARATION OF E-2 (Chart E): To a 0° C. mixture of Boc-L-tyrosine (2.04 g) and amylamine (0.93 mL) in methylene chloride (30 mL) is added 1-(3-dimethylaminopropyl)-3-ethylcarbodiimide (EDC) (1.53 g). The white mixture is stirred at 0 C for 5 min and at room temp for 23 hrs. The resulting solution is diluted with methylene chloride (30 mL) and washed successively with 0.5 M HCl (40 mL), water (20 mL) and sat aq sodium bicarbonate (25 mL). The organic phase is dried over magnesium sulfate and concentrated to a foam (1.84 g), sufficiently pure to carry into the next step. An analytical sample is obtained by flash chromatography (1/1 ethyl acetate/hexane) as a glass.

Physical characteristics are as follows: $^1$H NMR (CDCl$_3$) δ7.01, 6.74, 5.90, 5.17, 4.21, 3.13, 2.93, 1.41, 1.1–1.4, 0.85; IR (mull) 3341, 3318, 3004, 1684, 1651, 1615, 1595, 1517, 1393, 1293, 1267, 1248, 1170, 1048, 828; MS (EI) m/z 350 (M+), 234, 233, 188, 180, 177, 147, 143, 136, 107, 57 cm$^{-1}$; HRMS (EI) found 350.2209. Anal. Found: C, 64.27; H, 8.54; N, 7.82.

PREPARATION OF E-3 (Chart E): To a solution of E-2 (5.28 g) in dioxane (40 mL) chilled in an ice bath is added a freshly prepared solution of HCl in dioxane (about 3 M, 25 mL). The solution is then stirred at room temp for 1.5 hrs when a TLC indicates the reaction is done. The solution is diluted rapidly with ether (350 mL) until no further precipitation is evident. The mixture is stirred vigorously until all insoluble material is adhering to the sides of the flask. After decanting the supernatant, the crude material is taken up in more ether (200 mL) and sonicated until a fine solid (required about 1 hr). Filtration gives a hygroscopic white powder (4.32 g).

Physical characteristics are as follows: $^1$H NMR (DMSO) δ9.3, 8.40, 8.25, 6.98, 6.68, 3.08, 2.9, 1.0–1.35, and 0.83.

PREPARATION OF F-1 (Chart F): Triethylamine (307 uL) is added to a 0 C. mixture of E-3 (287 mg) in methylene chloride (4 mL), causing rapid dissolution. To this solution is added succinic anhydride (100 mg), and the reaction is stirred at room temp for 25 h. The reaction is then diluted with ethyl acetate (20 mL) and washed successively with 0.5 M HCl (10 mL) and brine (10 mL). The organic phase is dried over magnesium sulfate and concentrated to a viscous oil (350 mg) that solidified on standing and is analytically pure.

Physical characteristics are as follows: $^1$H NMR (DMSO) δ9.1, 7.98, 7.74, 6.96, 6.60, 4.30, 2.9–3.1, 2.8, 2.60, 2.3, 1.1–1.4, 0.83; $^{13}$C NMR (CDCl$_3$) 175.1, 173.1, 172.2, 155.9, 129.8, 127.8, 114.8, 55.3, 39.2, 39.0, 36.7, 30.0, 28.8, 28.7, 28.5, 22.0, 13.0; IR (mull) 3296, 3102, 2728, 1715, 1642, 1615, 1596, 1548, 1516, 1401, 1239, 1173, 1117, 832, 722; MS (EI) m/z 350 (M+), 233, 177, 162, 147, 144, 143, 136, 107, 91, 55 cm$^{-1}$; MS (FAB) m/z 351 (M+H), 352, 351, 350, 236, 233, 136, 121, 107, 88, 43. HRMS (FAB) found 351.1928. Anal. Found: C, 60.34; H, 7.48; N, 7.72.

PREPARATION OF F-2 (Chart F): A solution of F-1 (100 mg) and pyridine sulfur trioxide complex (500 mg) in DMF:pyridine (1:1, 10 mL) is stirred under nitrogen at room temp for 20 hrs. NMR analysis of an aliquot indicates complete conversion to product. Solvent is removed under vacuum, leaving a solid that is purified by reverse phase HPLC.

Physical characteristics are as follows: $^1$H NMR (DMSO) δ8.03, 7.79, 7.06, 7.01, 4.33, 2.99, 2.87, 2.68, 2.3, 1.1–1.3, 0.83; ES MS m/z (negative ion) 429, 214.

EXAMPLE 2

(S)-[4-[2-[[1,4-Dioxo-4-(phenylmethoxy)butyl]amino]-3-oxo-3-(pentylamino)propyl]phenoxy]propanedioic acid (Formula I-2, Chart I)

PREPARATION OF E-4 (Chart E): EDC (368 mg) is added to a 0 C. solution of E-3 (500 mg), (mono)benzyl succinate (368 mg) and triethylamine (270 uL) in methylene chloride (7 mL). The reaction is stirred at room temp for 24 h. After dilution with ethyl acetate (40 mL), the mixture is washed successively with 0.5 M HCl, water and sat aq sodium bicarbonate (20 mL each). The organic phase is dried over magnesium sulfate and concentrated to a white amorphous solid (694 mg) that is analytically pure.

Physical characteristics are as follows: $[\alpha]^{25}_D$ –5.4° (c 0.017, methanol); $^1$H NMR (CDCl$_3$) δ7.33, 7.05, 6.74, 6.21, 5.90, 5.68, 5.13, 5.09, 4.54, 3.12, 3.06, 2.90, 2.4–2.85, 1.1–1.4, 0.86; IR (mull) 3379, 3285, 1706, 1640, 1617, 1552, 1517, 1339, 1271, 1218, 1196, 1181, 1174, 749, 694; MS (EI) m/z 440 (M+), 233, 226, 208, 147, 136, 108, 107, 91, 79, 77. Anal. Found: C, 67.89; H, 7.23; N, 6.38.

PREPARATION OF I-1 (Chart I): A solution of di-tert-butyl diazomalonate (396 mg) in benzene (2 mL) is added over 6 h to an 80 C. mixture of E-4 (342 mg) and rhodium (II) acetate (7 mg) in benzene (33 mL) via syringe pump, during which time most of the starting material goes into solution. The blue-green solution is stirred at that temp for an additional hour and then overnight at room temp. The reaction is filtered through a medium frit and then concentrated in vacuo. Flash chromatography (80 g silica, 70% ethyl acetate/hexane) provides the title material (232 mg) as a foam (Rf=0.45).

Physical characteristics are as follows: $^1$H NMR (CDCl$_3$) δ7.33, 7.12, 6.89, 6.10, 5.81, 5.12, 5.08, 4.94, 4.52, 3.1, 2.6–2.95, 2.45, 1.49, 1.1–1.4, 0.86; MS (FAB) m/z 655 (M+H), 655, 599, 447, 92, 91, 88, 86, 57, 41, 29. HRMS (FAB) found 655.3588.

PREPARATION OF I-2 (Chart I): Trifluoroacetic acid (5 mL) is added to a solution of I-1 (225 mg) in methylene chloride (5 mL) with ice bath chilling. The solution is stirred at room temp for 2 h. Concentration in vacuo affords the title compound as a light amber foam, sufficiently pure to carry into the next step.

Physical characteristics are as follows: $^1$H NMR (CD$_3$OD) $\delta$7.33, 7.15, 6.89, 5.23, 5.10, 4.48, 3.05, 2.80, 2.35–2.7, 1.1–1.5, 0.88; MS (FAB) m/z 543 (M+H), 544, 543, 542, 441, 92, 91, 88, 86, 43. HRMS (FAB) found 543.2332.

EXAMPLE 3

(S)-[4-[2-[(3-Carboxy-1-oxopropyl)amino]-3-oxo-3-(pentylamino)-propyl]phenoxy]propanedioic acid (Formula I-3, Chart I)

Crude I-2 (approx. 0.29 mmol) is dissolved in ethyl acetate and concentrated in vacuo three times to get rid of traces of trifluoroacetic acid. The residue is then dissolved in methanol (10 mL) and subjected to three cycles of evacuation and nitrogen purge at 0 C. before the introduction of 10% Pd/C (20 mg). The mixture is then hydrogenated at 1 atm for 1.5 h. The mixture is filtered through Celite and concentrated in vacuo. The crude glass is taken up in methylene chloride (40 mL) and sonicated until it is all suspended. Filtration gives a brittle white amorphous solid (116 mg) that is analytically pure (m.p. 117–120 C., dec).

Physical characteristics are as follows: $[\alpha]^{25}_D$=–0.7° (c 0.0058, methanol); $^1$H NMR (CD$_3$OD) $\delta$8.13, 7.81, 7.17, 6.90, 5.23, 4.48, 3.1, 2.81, 2.3–2.6, 1.2–1.5, 0.89; MS (FAB) m/z 453 (M+H), 453, 238, 194, 136, 133, 101, 88, 86, 55, 43. HRMS (FAB) found 453.1859. Anal. Found: C, 54.25; H, 6.31; N, 5.97.

EXAMPLE 4

(S)-[4-[2-[[[(Carboxymethyl)amino]carbonyl]amino]-3-oxo-3-(pentylamino)propyl]phenoxy]propanedioic acid (Formula C-1 (R$^2$=CH$_2$CO$_2$H), Chart C)

To a solution of amine hydrochloride B-4 (50 mg) and triethylamine (16 uL) in methylene chloride (1 mL) is added ethyl isocyanatoacetate (13 uL) neat. TLC analysis shows reaction is nearly done after 5 min. After stirring for a total of 1 hr at room temp., the reaction is diluted with ethyl acetate (5 mL) and washed successively with 1 M HCl, water, and brine (2 mL each). The organic layer is dried over magnesium sulfate and concentrated in vacuo to a colorless oil (58 mg).

Physical characteristics are as follows: $^1$H NMR (CDCl$_3$) $\delta$7.11, 6.82, 6.57, 6.48, 6.11, 5.10, 4.49, 4.28, 4.15, 3.94, 3.82, 2.8–3.2, 1.1–1.4, 0.83; MS (ES+): 537.9 (M+H), 559.8 (M+Na).

To a solution of the crude triester from above in 3:1:1 THF:MeOH:water (1 mL) at room temp is added lithium hydroxide monohydrate (21 mg). The solution is stirred for 3 hrs. The solvent is evaporated in vacuo, and the residue is acidified with 1M HCl (1 mL). To the slightly cloudy mixture is added brine (2 mL), resulting in a copious ppt. The mixture is extracted with ethyl acetate, and the extracts are dried over magnesium sulfate. Concentration gives a glass (50 mg). This material is sonicated with methylene chloride (20 mL) for 30 min, and the resulting fine white solid is collected by filtration, giving the title product as an amorphous powder (32 mg).

Physical characteristics are as follows: $^1$H NMR (DMSO) $\delta$7.84, 7.06, 6.79, 6.33, 6.29, 5.25, 4.25, 3.65, 2.85–3.05, 2.78, 2.63, 1.1–1.4, 0.82; MS (ES–): 451.7; HRMS (FAB) found 454.1820. Anal. Found: C, 51.50; H, 5.94; N, 8.89.

EXAMPLE 5

(S)-[4-[2-[[[(5-Carboxypentyl)amino]carbonyl]amino]-3-oxo-3-(pentylamino)propyl]phenoxy]propanedioic acid (Formula C-1, Chart C)

By the two-step procedure described for Example 4, the title product is obtained as a foam (44 mg). Saponification is effected in 3:1 THF:MeOH (2 mL) with added 2.5 M aq LiOH (0.3 mL). Sonication does not produce a filtratable solid, so the methylene chloride is decanted, and the residue is dried under vacuum.

Physical characteristics are as follows: $^1$H NMR (DMSO) $\delta$7.82, 7.04, 6.79, 6.00, 5.90, 5.25, 4.25, 2.8–3.0, 2.76, 2.65, 2.16, 1.45, 1.1–1.35, 0.82; MS (ES–): 508.1; HRMS (FAB) found 510.2446. Anal. Found: C, 54.63; H, 6.93; N, 8.02.

EXAMPLE 6

(S)-[4-[2-[[[(4-Carboxyphenyl)amino]carbonyl]amino]-3-oxo-3-(pentylamino)propyl]phenoxy]propanedioic acid (Formula C-1, Chart C)

By the procedure described for Example 5 is obtained the title product as a glass that slowly solidifies (57 mg).

Physical characteristics are as follows: $^1$H NMR (DMSO) $\delta$9.06, 8.05, 7.77, 7.42, 7.07, 6.81, 6.42, 5.26, 4.38, 3.01, 2.7–2.9, 1.1–1.4, 0.82; MS (ES–): 514.0; HRMS (FAB): Found=516.1979.

EXAMPLE 7

(S)-[4-[2-[[[(2-Carboxyethyl)amino]carbonyl]amino]-3-oxo-3-(pentylamino)propyl]phenoxy]propanedioic acid (Formula C-1, Chart C)

By the procedure described for Example 5 is obtained the title compound (43 mg) as a glass. Sonication in methylene chloride was not performed.

Physical characteristics are as follows: $^1$H NMR (DMSO) $\delta$7.83, 7.04, 6.79, 6.11, 5.25, 4.22, 3.13, 2.96, 2.76, 2.61, 2.27, 1.1–1.4, 0.82; MS (ES–): 465.8; HRMS (FAB) found 468.1982.

EXAMPLE 8

(S)-5-[[[[1-[[4-(Dicarboxymethoxy)phenyl]methyl]-2-oxo-2-(pentylamino)ethyl]amino]carbonyl]amino]-1,3-benzene-dicarboxylic acid (Formula C-1, Chart C)

By the procedure described for Example 5 is obtained the title compound as a glass (61 mg).

Physical characteristics are as follows: $^1$H NMR (DMSO) $\delta$8.15, 8.04, 7.99, 7.08, 6.82, 6.32, 5.26, 4.37, 2.7–3.1, 1.1–1.4, 0.82; MS (ES–): 557.8; HRMS (FAB) 560.1880. Anal. Found: C, 54.21; H, 5.28; N, 6.89.

EXAMPLE 9

(S)-N-[[[1-[[4-(Dicarboxymethoxy)phenyl]methyl]-2-oxo-2-(pentylamino)ethyl]amino]carbonyl]-L-glutamic acid (Formula C-1, Chart C)

(S)-(–)-2-isocyanatoglutaric acid, diethyl ester (24 uL) is added to a 0 C. mixture of B-4 (50 mg) and triethylamine (16 uL) in THF (1 mL). After 1 hr, 2.5 M aq LiOH (0.4 mL) is added directly to the reaction mixture, and the two-phase mixture is stirred vigorously for 1.5 hrs. The mixture is diluted with 1 M HCl (2 mL), saturated with solid NaCl, and extracted with ethyl acetate (3×2 mL). Drying of the extracts over magnesium sulfate and concentration leaves a glass (68 mg), which is sonicated with methylene chloride (20 mL) for 1 h. Filtration and drying in vacuo leaves the title compound as a white powder (52 mg).

Physical characteristics are as follows: $^1$H NMR (DMSO) δ7.84, 7.05, 6.79, 6.44, 6.14, 5.25, 4.22, 4.05, 2.95, 2.80, 2.68, 2.21, 1.85, 1.65, 1.1–1.4, 0.82; MS (ES–): 523.9. IR (mull) 3358, 2670, 2605, 1727, 1625, 1564, 1512, 1416, 1341, 1230, 1185, 1114, 855, 833, 805, cm$^{-1}$. HRMS (FAB) found 526.2051. Anal. Found: C, 51.54; H, 6.06; N, 7.85.

EXAMPLE 10

(S)-[4-[2-[[[(Carboxymethyl)(phenylmethyl)amino] carbonyl]-amino]-3-oxo-3-(pentylamino)propyl] phenoxy]propanedioic acid (Formula D-2, Chart D)

To a 0 C. solution of B-4 (50 mg), and Proton Sponge (71 mg) in methylene chloride (1 mL) is added diphosgene (8 uL). The solution is stirred at 0 C. for 45 min before dilution with more methylene chloride (2 mL) and washing successively with 1 M HCl, water, and sat aq sodium bicarbonate (2 mL each). The extracts are dried over magnesium sulfate and concentrated in vacuo, leaving D-1 as an oil.

Physical characteristics are as follows: $^1$H NMR (CDCl$_3$) δ7.17, 6.94, 6.15, 5.18, 4.30, 3.2–3.32, 2.92, 1.5, 1.3, 0.90.

To a solution of D-1 in THF (1 mL) is added N-benzylglycine ethyl ester (21 uL). The solution is stirred at room temp for 1.5 h before the addition of 2.5 M aq LiOH (0.3 mL). The resulting mixture is stirred vigorously at room temp for 1.5 h. The mixture is diluted with 1M HCl (2 mL), saturated with brine, and extracted with ethyl acetate. The extracts are dried over magnesium sulfate and concentrated in vacuo, leaving a glass (65 mg). Sonication with methylene chloride (20 mL) for 30 min followed by filtration afforded the title compound as a white solid (41 mg).

Physical characteristics are as follows: $^1$H NMR (DMSO) δ7.69, 7.25, 7.10, 6.77, 6.48, 5.25, 4.40, 4.27, 3.81, 2.7–3.1, 1.1–1.4, 0.84; MS (ES–): 541.9. HRMS (FAB) found 544.2293. Anal. Found: C, 58.10; H, 6.08; N, 7.56.

EXAMPLE 11

(S)-[4-[2-[[[(Carboxymethyl)[[4-(phenylmethoxy) phenyl]methyl]-amino]carbonyl]amino]-3-oxo-3- (pentylamino)propyl]phenoxy]-propanedioic acid (Refer to Chart D)

4-(4-benzyloxy)benzylglycine methyl ester is prepared from 4-(benzybxy)-benzaldehyde and glycine methyl ester by the method of Zydowsky et al (J. Org. Chem. 1988, 53:5607). Using the method described for Example 10, this material affords the title compound as a white powder (54 mg). Sonication with methylene chloride does not provide the product as a filterable solid; it is isolated by decantation and drying of the insoluble residue.

Physical characteristics are as follows: $^1$H NMR (DMSO) δ7.69, 7.25–7.5, 7.10, 7.04, 6.91, 6.79, 6.45, 5.27, 5.06, 4.32, 4.25, 3.77, 3.0, 2.85, 2.75, 1.1–1.4, 0.84; MS (ES–): 647.9. IR (mull) 3346, 3063, 3032, 1732, 1612, 1587, 1538, 1511, 1422, 1341, 1297, 1230, 1177, 1113, 697, cm$^{-1}$. Anal. Found: C, 61.89; H, 6.05; N, 6.30.

EXAMPLES 12–24

(General Synthesis of Formula J-6, Chart J)

PREPARATION OF J-3: To a stirring solution of E-2 (2.0 g) in acetone (50 ml) is added K$_2$CO$_3$ (1.57 g) at ambient temperature. To the resulting heterogeneous mixture is added dibenzyl bromomalonate (2.89 g) and the mixture stirred at ambient temperature overnight. The resulting amber suspension is diluted with H$_2$O (100 ml) and extracted with EtOAc (2×100 ml). The combined organic layers are dried over MgSO$_4$ and solvent removed in vacuo. The residue is purfied via SiO$_2$ flash chromatography (eluant 2: 1 EtOAc/hexane) to afford 1.26 g title compound as a white solid.

Physical characteristics are as follows: $^1$H NMR (CDCl$_3$) δ0.84, 1.16–1.38, 1.39, 2.96, 3.13, 4.21, 5.20, 5.08, 5.23, 5.85, 6.83, 7.07, 7.25; IR (mull) 3346, 3326, 1748, 1683, 1657, 1540, 1522, 1510, 1313, 1297, 1238, 1221, 1188, 1173, 698,cm$^{-1}$. MS(FAB) m/z 633 (MH$^+$), 633, 578, 577, 533, 515, 92, 91, 88, 86, 57. Anal. Found: C, 68.06; H, 6.91; N, 4.33.

PREPARATION OF J-4: To a stirring solution of J-3 (2.85 g) in HOAc (25 ml) at ambient temperature, is added 1.5N HCl/ HOAc (20 ml) and the resulting solution is stirred at ambient temperature for 2 h). The solvent is evaporated to 30 ml and triturated with Et$_2$O (400 ml). The resulting turbid suspension is stirred at ambient temperature for 30 min, sonicated and filtered to afford 2.50 g title compound as a white solid.

Physical characteristics are as follows: $^1$H NMR (DMSO) δ0.80, 1.18, 2.93, 3.04, 3.87, 5.20, 5.83, 6.91, 7.13, 7.32, 8.39; IR (liq.) 3035, 2957, 2932, 2872, 2861, 1763, 1748, 1661, 1511, 1500, 1456, 1224, 1185, 1167, 697, cm$^{-1}$. MS (FAB) m/z 533 (MH$^+$), 1067, 1066, 535, 534, 533, 418, 143, 92, 91, 88. Anal. Found: C, 64.74; H, 6.54; N, 4.88.

GENERAL PREPARATION OF J-5: To a stirring solution of J-4 (0.20 g) in CH$_2$Cl$_2$ (10 ml) is added triethylamine (0.078 g) at 0 C. The requisite cyclic anhydride (0.35 mmol) is added in one portion and the resulting solution allowed to stir for 16 h while warming to ambient temperature. The solution is diluted with CH$_2$Cl$_2$ (50 ml) and washed with 10% HCl/ H$_2$O (2×50 ml). The combined organic phases are dried over MgSO$_4$ and solvent removed in vacuo to afford material suitable for subsequent transformations.

GENERAL PREPARATION OF J-6: To a solution of the requisite dibenzylester J-5 in MeOH (~0.02 M) at ambient temperature is added 10% Pd/C (10 weight %) and the resulting mixture hydrogenated at atmospheric pressure for 3 h. The mixture is filtered through Celite and solvent removed to afford analytically pure material.

The following examples (12–24) are prepared by the general synthesis of J-6 outlined above, using the appropriate commercially available anhydrides (Chart J).

EXAMPLE 12

(S)-[4-[2-[(4-Carboxy-1-oxobutyl)amino]-3-oxo-3- (pentylamino)-propyl]phenoxy]propanedioic acid 0.115 g as an amorphous white solid. $^1$H NMR (DMSO) δ0.84, 1.15–1.36, 1.61, 2.06, 2.68, 2.84, 3.00, 4.38, 5.25, 6.80, 7.13, 7.86, 8.00; IR (mull) 3305, 3070, 2729, 2669, 2599, 1730, 1626, 1551, 1512, 1341, 1231, 1185, 1112, 855, 831, cm$^{-1}$. MS (FAB) m/z 467 (MH$^+$), 481, 468, 467, 423, 238, 194, 91, 88, 59, 43. Anal. Found: C, 54.90; H, 6.52; N, 5.47.

EXAMPLE 13

[1R-[1 (S*),2]]-[4-[2-[[(2-Carboxycyclohexyl) carbonyl]amino]-3-oxo-3-(pentylamino)propyl] phenoxy]propanedioic acid 0.068 g as an amorphos white solid. $^1$H NMR (DMSO) δ0.84, 1.12–1.50, 1.80, 2.4–3.15, 3.35, 5.22, 6.65, 6.78, 7.0, 7.08, 7.22, 7.62, 7.75; IR (mull) 3336, 2731, 2674, 2595, 1727, 1630, 1537, 1512, 1338, 1296, 1229, 1184, 1130, 1103, 854,cm$^{-1}$. MS(FAB) m/z 507 (MH$^+$), 508, 507, 238, 194, 136, 102, 91, 88, 81, 43. Anal. Found: C, 57.50; H, 6.67; N, 5.33.

EXAMPLE 14

(S)-[4-[2-[[(Carboxymethoxy)acetyl]amino]-3-oxo-3-(pentyl-amino)propyl]phenoxy]propanedioic acid 0.096 g as an amorphous solid. $^1$H NMR (DMSO) δ0.83, 1.20–1.32, 2.76–3.01, 3.89, 4.03, 4.45, 5.23, 6.78, 7.08, 7.77, 7.95; IR (mull) 3340, 2730, 2670, 2596, 1745, 1632, 1543, 1512, 1346, 1230, 1184, 1144, 833, 721, 668, cm$^{-1}$. MS (FAB) m/z 469 (MH$^+$), 497, 483, 469, 107, 88, 86, 75, 43, 39, 23. Anal. Found: C, 52.07; H, 5.98; N, 5.67.

EXAMPLE 15

(S)-[4-[2-[[[1-(Carboxymethyl)cyclopentyl]acetyl]amino]-3-oxo-3-(pentylamino)propyl]phenoxy]propanedioic acid 0.108 g as an amorphous solid. $^1$H NMR (DMSO) δ0.82, 1.20–1.47, 2.18–2.35, 2.60–2.92, 2.99, 4.40, 5.22, 7.79, 7.11, 7.83, 8.00; IR (mull) 3294, 3069, 2728, 2668, 2604, 1732, 1629, 1613, 1554, 1512, 1331, 1280, 1229, 1182, 1110 cm$^{-1}$. MS (FAB) m/z 462 (MH$^+$), 535, 521, 143, 136, 109, 88, 81, 67, 43, 39. Anal. Found: C, 58.00; H, 6.87; N, 5.06.

EXAMPLE 16

(S)-[4-[2-[(Carboxyacetyl)amino]-3-oxo-3-(pentylamino)propyl]-phenoxy]propanedioic acid 0.101 g as an amorphous solid. $^1$H NMR (DMSO) δ0.82, 1.19–1.31, 2.69, 2.85–3.21, 4.37, 5.23, 6.78, 7.09, 7.86, 8.27; IR (mull) 3326, 3079, 3041, 2591, 1740, 1634, 1557, 1513, 1441, 1424, 1231, 1185, 1115, 855, 833, cm$^{-1}$. MS (FAB) m/z 439 (MH$^+$, 99), 453, 440, 439, 395, 331, 177, 133, 118, 88, 23. Anal. Found 53.18; H, 5.86; N, 5.91.

EXAMPLE 17

(S)-[4-[2-[(4-Carboxy-3,3-dimethyl-1-oxobutyl)amino]-3-oxo-3-(pentylamino)propyl]phenoxy]propanedioic acid 0.96 g as an amorphous solid. $^1$H NMR (DMSO) δ0.85, 1.11–1.40, 2.12, 2.67, 2.85, 2.98, 5.22, 5.73, 6.78, 7.11, 7.84, 7.97. IR (mull) 3296, 3069, 2729, 2670, 2606, 1727, 1612, 1557, 1512, 1329, 1231, 1184, 1115, 830, 720, cm$^{-1}$. Anal. Found: C, 55.71; H, 6.90; N, 5.32.

EXAMPLE 18

(S)-[4-[2-[(2-Carboxybenzoyl)amino]-3-oxo-3-(pentylamino)-propyl]phenoxy]propanedioic acid 0.070 g as an amorphous solid. $^1$H NMR (DMSO) δ0.83, 1.22, 1.40, 2.73, 3.08, 4.50, 5.27, 6.83, 6.97, 7.15, 7.50, 7.70, 7.89, 8.52; IR (mull) 3341, 3065, 3033, 1720, 1627, 1599, 1580, 1538, 1512, 1488, 1271, 1232, 1185, 1147, 1103, cm$^{-1}$. MS (FAB) m/z 501 (MH$^+$), 501, 154, 149, 137, 117, 109, 92, 59, 45, 41. MS (FAB) m/z 501 (MH$^+$), 501, 154, 149, 137, 117, 109, 59, 57, 43, 41. Anal. Found: C, 57.36; H, 5.74; N, 5.30.

EXAMPLE 19

[2(S)]-[4-[2-[[(3-Carboxybicyclo[2.2.2]oct-2-yl)carbonyl]amino]-3-oxo-3-(pentylamino)propyl]phenoxy]propanedioic acid 0.072 g as a white amorphous solid. $^1$H NMR (DMSO) δ0.83, 0.98–1.60, 1.76, 2.00, 2.47–3.11, 4.35, 5.20, 6.75, 7.06, 7.5–7.9; IR (mull) 3326, 1772, 1732, 1704, 1639, 1547, 1512, 1355, 1340, 1292, 1228, 1183, 1106, 1085, 907, cm$^{-1}$. MS (FAB) m/z 533 (MH$^+$), 353, 309, 194, 136, 107, 88, 43, 41, 39, 23. Anal. Found: C, 59.26; H, 6.77; N, 4.84.

EXAMPLE 20

(S)-[4-[2-[[(1,1-Dimethylethoxy)carbonyl]amino]-3-oxo-3-(pentyl-amino)propyl]phenoxy]propanedioic acid 0.203 g as a low melting white solid. $^1$H NMR (MeOH) δ0.88, 1.16–1.58, 2.80, 2.97, 3.10, 4.19, 5.23, 6.89, 7.16, 7.80; IR (mull) 3326, 1738, 1693, 1639, 1614, 1588, 1512, 1393, 1297,1233, 1169, 1114, 1085, 1051, 1022,cm$^{-1}$. MS(FAB) m/z 453(MH$^+$), 453, 409, 397, 370, 353, 194, 88, 57, 41, 29. Anal. Found: C, 59.08; H, 7.15; N, 6.23.

EXAMPLE 21

(S)-3-[[[1-[[4-(Dicarboxymethoxy)phenyl]methyl]-2-oxo-2-(pentylamino)ethyl]amino]carbonyl]pentanedioic acid 0.037 g as an amorphous solid. $^1$H NMR (DMSO) δ0.83, 1.22, 2.24, 2.69, 2.98, 4.30, 5.21, 6.77, 7.08, 7.60, 8.10; HRMS (FAB) found 511.1933. Anal. Found: C, 51.39; H, 6.18; N, 5.42.

EXAMPLE 22

[1(S)]-[4-[2-[[(2-Carboxycyclopropyl)carbonyl]amino]-3-oxo-3-(pentylamino)-propyl]-phenoxy]propanedioic acid 0.068 g as an amorphous solid. $^1$H NMR (DMSO) δ0.82, 1.22, 1.92, 2.72, 2.98, 4.32, 5.24, 6.78, 7.09, 7.82, 8.40; IR (mull) 3330, 2730, 2598, 1729, 1612, 1554, 1512, 1229, 1184, 1114, 979, 855, 834, 808, 623, cm$^{-1}$. MS (FAB) m/z 465 (MH$^+$), 466, 465, 421, 238, 194, 113, 107, 102, 88, 63. Anal. Found: C, 55.01; H, 6.18; N, 5.74.

EXAMPLE 23

[2(S)]-[4-[2-[[(3-Carboxybicyclo[2.2.1]hept-2-yl)carbonyl]amino]-3-oxo-3-(pentylamino)propyl]phenoxy]propanedioic acid 0.049 g. (quant). $^1$H NMR (DMSO) δ0.80, 1.21, 1.43–2.10, 2.12–2.42, 2.60–3.10, 4.34, 5.15, 6.75, 7.05, 7.60, 7.80; IR (mull) 3311, 2727, 2670, 1722, 1632, 1543, 1511, 1295, 1228, 1184, 1113, 1083, 846, 831, 721, cm$^{-1}$. MS (FAB) m/z 519 (MH$^+$), 519, 353, 238, 194, 177, 167, 88, 67, 43, 23. Anal. Found: C, 58.39; H, 6.52; N, 4.81.

EXAMPLE 24

[1R-[1 (S*),2 ]]-[4-[2-[[(2-Carboxycyclohexyl)carbonyl]amino]-3-oxo-3-(pentylamino)propyl]phenoxy]propanedioic acid 0.109 g as a waxy white solid. $^1$H NMR (DMSO) δ0.82, 1.20, 1.53–1.96, 2.40, 2.54–2.89, 3.00, 4.29, 5.23, 6.76, 7.08, 7.52, 7.90; IR (mull) 3307, 2729, 2671, 1727, 1631, 1543, 1511, 1299, 1226, 1184, 1113, 910, 855, 832, 721, cm$^1$. MS (FAB) m/z 507 (MH$^+$), 508, 507, 353, 238, 194, 143, 109, 88, 81, 43. Anal. Found: C, 56.11; H, 6.65; N, 5.31.

EXAMPLE 25

N-[(1,1-Dimethylethoxy)carbonyl]-L-α-aspartyl-O-(dicarboxy-methyl)-N-pentyl-L-tyrosinamide
(Formula O-1 (n=1), Chart O)

PREPARATION OF L-2 (n=1, Chart L): To a stirring solution of J-4 (0.25 g) and triethylamine (0.044 g) is added Boc-Asp(OBn)OSu (0.185 g) at 0 C. The resulting solution is stirred for 16 h allowing the mixture to warm to ambient temperature. The resulting solution is diluted with $CH_2Cl_2$ (50 ml) and washed with 10% aqueous HCl (3× 50 ml). the organic layer is dried over $MgSO_4$ and solvent removed to afford 0.33 g title compound as a white solid. $^1H$ NMR ($CDCl_3$) δ0.84, 1.15–1.43, 2.76, 2.93, 3.09, 4.41, 4.48, 5.10, 5.23, 5.29, 5.44, 5.91, 6.89, 6.85, 7.10, 7.30; IR (mull) 3308, 1744, 1694, 1646, 1527, 1511, 1500, 1355, 1280, 1223, 1169, 1115, 749, 738, 697, $cm^{-1}$. MS (FAB) m/z 838 ($MH^+$), 783, 739, 515, 178, 92, 91, 88, 86, 57, 41. Anal. Found: C, 66.86; H, 6.59; N, 5.00.

PREPARATION OF O-1 (n=1): To a solution of L-2 (0.317 g) in MeOH (15 ml) at ambient temperature is added 10% Pd-C (50 mg) and the resulting mixture hydrogenated at atmospheric pressure for 2 h. The mixture is filtered through Celite and solvent removed to afford 0.208 g title compound as a white solid. $^1H$ NMR (DMSO) δ0.82, 1.12–1.40, 2.30–2.52, 2.70–3.06, 4.16, 4.32, 5.20, 6.76, 7.60, 7.12, 7.69, 7.78. IR (mull) 3334, 2729, 1726, 1668, 1637, 1512, 1395, 1341, 1280, 1233, 1180, 1165, 1114, 1053, 855, $cm^{-1}$.MS (FAB) m/z 568 ($MH^+$), 512, 468, 88, 88, 86, 57, 43, 41, 29, 23. Anal. Found: C, 52.55; H, 6.53; N, 7.08.

EXAMPLE 26

N-(3-Carboxy-1-oxopropyl)-L-α-aspartyl-O-(dicarboxymethyl)-N-pentyl-L-tyrosinamide
(Formula L-5, n=1, Chart L)

PREPARATION OF L-3: To a solution of L-2 (0.263 g) in HOAc (5 ml) is added 1.5 M HCl/ HOAc (5 ml) and the resulting solution allowed to stand for 2 h. The solvent is removed in vacuo to afford 0.24 g (quant) title compound as a white solid. $^1H$ NMR (DMSO) δ0.79, 1.17, 2.94, 4.05, 4.40, 5.12, 5.19, 5.81, 6.86, 7.14, 7.34, 8.02, 8.70; IR (mull) 3300, 3034, 1744, 1671, 1649, 1554, 1510, 1500, 1305, 1285, 1221, 1188, 1099, 746, 697, $cm^{-1}$. MS (FAB) m/z 738 ($MH^+$), 741, 740, 739, 178, 92, 91, 88, 88, 86, 43.

PREPARATION OF L-4: To a stirring solution of L-3 (0.10 g) and triethylamine (0.028 g) in $CH_2Cl_2$ (8 ml) at 0 C. is added succinic anhydride (0.015 g, 0.13 mmol). The resulting solution is stirred for 16 h allowing the solution to warm to ambient temperature. The mixture is diluted with $CH_2Cl_2$ (50 ml) and washed with 10% aqueous HCl (2×50 ml). The organic layer is dried over $MgSO_4$ and solvent removed to afford 0.076 g title compound as a white solid. $^1H$ NMR ($CDCl_3$) δ0.85, 1.23, 1.40, 2.37, 2.68, 3.14, 4.57, 4.72, 5.01, 5.16, 5.21, 6.36, 6.80, 7.05, 7.25; MS (FAB) m/z 838 ($MH^+$), 839, 838, 533, 516, 515, 418, 178, 92, 91, 88. Anal. Found: C, 65.53; H, 6.01; N, 4.98.

PREPARATION OF L-5 (n=1): To a stirring solution of L-4 (0.07 g) in MeOH (5 ml) is added 10% Pd-C (10 mg). The resulting mixture is hydrogenated at atmospheric pressure for 2 h and filtered through celite. The solvent is removed to afford 0.044 g title compound as a white amorphous solid. $^1H$ NMR (DMSO) δ0.82, 1.20, 2.33, 2.43, 2.72, 2.96, 4.27, 4.42, 5.2, 6.74, 7.06, 7.60, 7.70, 8.30; IR (mull) 3326, 3069, 3036, 2601, 1726, 1638, 1544, 1512, 1407, 1342, 1231, 1183, 1115, 832, 637, $cm^{-1}$. MS(FAB) m/z 568 ($MH^+$), 582, 569, 568, 238, 177, 102, 88, 88, 39, 23. Anal. Found: C, 51.15; H, 5.79; N, 6.64.

EXAMPLE 27

N-[(1,1-Dimethylethoxy)carbonyl]-L-α-glutamyl-O-(dicarboxy-methyl)-N-pentyl-L-tyrosinamide
(Formula O-1 (n=2), Chart O)

By an analogous procedure as described for Example 25 is obtained 0.21 g title compound as a white amorphous solid. $^1H$ NMR (DMSO) δ0.81, 1.18, 1.71, 2.12, 2.96–3.10, 3.82, 4.38, 5.19, 6.76, 6.96, 7.08, 7.77, 7.84; IR (mull) 3316, 3067, 2730, 2604, 1720, 1639, 1512, 1395, 1341, 1232, 1168, 1106, 1056, 855, 832, $cm^{-1}$. MS(FAB) m/z 582 ($MH^+$), 133, 102, 88, 84, 57, 43, 41, 39, 29, 23. Anal. Found: C, 53.72; H, 6.75; N, 6.96.

EXAMPLE 28

N-(3-Carboxy-1-oxopropyl)-L-α-glutamyl-O-(dicarboxymethyl)-N-pentyl-L-tyrosinamide
(Formula L-5 (n=2), Chart L)

By a procedure analogous to that described for Example 26 is obtained 0.082 g title compound as a white solid. $^1H$ NMR (DMSO) δ0.82, 1.20, 1.32, 1.55–1.90, 2.14, 2.38, 2.72, 2.92, 4.11, 4.30, 5.21, 6.77, 7.67, 7.77, 8.08; IR (mull) 3316, 3069, 2730, 2605, 1722, 1634, 1546, 1512, 1414, 1341, 1231, 1183, 1116, 834, 721, $cm^{-1}$. MS (FAB) m/z 582 ($MH^+$), 582, 238, 133, 102, 102, 88, 84, 43, 39, 23. Anal. Found: C, 51.51; H, 6.00; N, 6.89.

EXAMPLES 29–35

(General Synthesis of Formula K-6, Chart K)

PREPARATION OF K-2: To a stirring solution of H-Tyr-OBu$^t$ (3.0 g) in $CH_2Cl_2$ (150 ml) at 0 C. is added EDC (2.42 g) and mono-benzyl succinate (2.62 g). The mixture is stirred for 16 h allowing the solution to warm to ambient temperature. The resulting solution is washed with 10% $HCl/H_2O$ (150 ml), the solvent dried over $Na_2SO_4$ and evaporated in vacuo. The residue is purified via flash column chromatography (eluant 2:1 hexane/EtOAc) to afford 5.06 g. $^1H$ NMR ($CDCl_3$) δ1.41, 2.50, 2.67, 2.99, 4.68, 5.11, 5.54, 6.12, 6.71, 6.98, 7.33; IR (liq.) 3351, 2979, 1734, 1654, 1615, 1595, 1516, 1455, 1393, 1369, 1356, 1232, 1155, 752, 698, $cm^{-1}$. MS (EI) m/z 427 ($M^+$), 226, 209, 208, 164, 136, 108, 107, 92, 91, 57.). Anal. Found: C, 67.17; H, 6.80; N, 3.27.

PREPARATION OF K-3: To a stirring solution of K-2 (3.55 g) in acetone (175 ml) at ambient temperature is added $K_2CO_3$ (2.29 g). Dibenzylbromomalonate (3.31g) is added and the mixture stirred at ambient temperature overnight. The solvent is removed in vacuo and the residue suspended between $EtOAc/H_2O$ (100 ml each). The layers are shaken, the organic layer separated, dried over $Na_2SO_4$, and the solvent removed. The residue is purified vie flash column chromatography to afford 1.72 g title compound as a yellow oil. $^1H$ NMR ($CDCl_3$) δ1.39, 2.49, 2.68, 3.00, 4.66, 5.11, 5.23, 5.24, 6.05, 6.82, 7.03, 7.33; MS (EI) m/z 709 ($M^+$), 368, 312, 108, 107, 91, 79, 77, 57, 56, 55. Anal. Found: C, 69.21; H, 6.15; N, 2.03.

PREPARATION OF K-4: To a stirring solution of K-3 (1.56 g) in $CH_2Cl_2$ (40 ml) is added trifluoroacetic acid (100 ml). The resulting solution is stirred for 2 h and solvent removed in vacuo to afford 1.42 g (quant) title compound as a slightly pink oil. $^1H$ NMR ($CDCl_3$) δ2.52, 2.67, 3.07, 4.81, 5.10, 5.20, 5.25, 6.43, 6.83, 7.40, 7.31, 7.80; IR (liq.) 3035, 1741, 1641, 1612, 1535, 1511, 1500, 1456, 1388, 1351, 1219, 1180, 1118, 751, 698, $cm^{-1}$. MS (FAB) m/z 654 ($MH^+$), 656, 655, 654, 564, 447, 446, 181, 107, 92, 91.

GENERAL PREPARATION OF K-5: To a stirring solution of K-4 in $CH_2Cl_2$ (0.035 M) at 0 C. is added EDC (1 eq) followed by the requisite amine. The mixture is stirred for 16 h, allowing the solution to warm to ambient temperature. The mixture is diluted with $CH_2Cl_2$ (50 ml), washed with 10% $HCl/H_2O$ (2×50 ml) and saturated $NaHCO_3$. The solvent is dried over Na$_2$SO$_4$ and removed in vacuo. Purification from SiO$_2$ flash column chromatography (eluant 1:1 EtOAc/ hexane) is done to afford title compound.

GENERAL PREPARATION OF K-6: To a stirring solution of requisite ester K-5 in MeOH (0.03M) is added 10% Pd-C (10% w/w). The resulting mixture is hydrogenated at atmospheric pressure for 3 h and filtered through celite. The solvent is removed in vacuo to afford desired material.

The following examples (29–35) are prepared by the general synthesis of K-6 outlined above, using the appropriate commercially available amines (Chart K).

EXAMPLE 29

(S)-[4-[2-[(3-Carboxy-1-oxopropyl)amino]-3-(hexylamino)-3-oxopropyl]phenoxy]propanedioic acid 0.052 g as a waxy solid. $^1$H NMR (DMSO) δ0.82, 1.19, 2.32, 2.66, 2.90, 4.32, 5.22, 6.76, 7.09, 7.77, 8.03; IR (mull) 3308, 3069, 3034, 2730, 2597, 1728, 1630, 1550, 1511, 1402, 1341, 1229, 1183, 1111, 833, cm$^{-1}$. HRMS (FAB) found 467.2040. Anal. Found: C, 55.39; H, 6.56; N, 5.62.

EXAMPLE 30

(S)-[4-[2-[(3-Carboxy-1-oxopropyl)amino]-3-[(cyclohexylmethyl)-amino]-3-oxopropyl]phenoxy]propanedioic acid 0.048 g as a waxy solid. $^1$H NMR (DMSO) δ0.78, 1.12, 1.32, 1.62, 2.30, 2.62–2.92, 4.32, 5.22, 6.78, 7.09, 7.76, 8.02; IR (mull) 3318, 3068, 3034, 2730, 2665, 2599, 1728, 1629, 1550, 1512, 1402, 1350, 1228, 1184, 1108, cm$^{-1}$. MS (FAB) m/z 479 (MH$^+$), 480, 479, 435, 331, 177, 127, 114, 71, 57, 55. HRMS (FAB) found 479.2029. Anal. Found: C, 56.68; H, 6.46; N, 5.59.

EXAMPLE 31

(S)-[4-[2-[(3-Carboxy-1-oxopropyl)amino]-3-[(2,2-diethoxyethyl)-amino]-3-oxopropyl]phenoxy]propanedioic acid 0.062 g as a waxy solid. $^1$H NMR (DMSO) δ1.07, 2.30, 2.66, 2.85, 3.15, 3.42, 3.55, 4.38, 5.25, 5.73, 6.78, 7.12, 7.92, 8.06; IR (mull) 3327, 2728, 2669, 2606, 1732, 1638, 1546, 1512, 1351, 1230, 1183, 1116, 1053, 833, 721, cm$^{-1}$. MS(FAB) m/z 499 (MH$^+$), 453, 251, 194, 177, 136, 107, 101, 88, 57, 23. Anal. Found: C, 50.80; H, 6.05; N, 5.57.

EXAMPLE 32

(S)-[4-[2-[(3-Carboxy-1-oxopropyl)amino]-3-[(3-methylbutyl)-amino]-3-oxopropyl]phenoxy]propanedioic acid 0.061 g as an amorphous solid. $^1$H NMR (DMSO) δ0.83, 1.22, 1.48, 2.32, 2.75, 2.82, 3.00, 4.35, 5.22, 6.78, 7.09, 7.74, 8.04; IR (mull) 3315, 3065, 2728, 2669, 2603, 1729, 1630, 1549, 1512, 1341, 1229, 1182, 1111, 833, 721, cm$^{-1}$. MS (FAB) m/z 453 (MH$^+$), 475, 453, 431, 194, 136, 88, 86, 55, 43, 23. Anal. Found: C, 54.45; H, 6.36; N, 5.85.

EXAMPLE 33

(S)-[4-[2-[(3-Carboxy-1-oxopropyl)amino]-3-oxo-3-[[2-(1-piperidinyl)ethyl]amino]propyl]phenoxy]propanedioic acid 0.047 g as a white solid. $^1$H NMR (DMSO) δ1.47, 1.66, 2.33, 2.76, 3.05, 4.30, 5.04, 6.64, 7.01, 8.02, 8.16; IR (mull) 3300, 3032, 2729, 2687, 2587, 1722, 1649, 1541, 1512, 1299, 1234, 1182, 1096, 833, 638, cm$^{-1}$. MS (FAB) m/z 494 (MH$^+$), 495, 494, 450, 392, 133, 98, 71, 57, 45, 43. Anal. Found: C, 53.22; H, 6.63; N, 7.88.

EXAMPLE 34

(S)-[4-[2-[(3-Carboxy-1-oxopropyl)amino]-3-[[3-(4-morpholinyl)-propyl]amino]-3-oxopropyl]phenoxy]propanedioic acid 0.059 g as a waxy solid. $^1$H NMR (DMSO) δ2.32, 2.50–2.80, 2.97, 3.76, 4.31, 5.10, 6.68, 7.00, 7.79, 8.05; IR (mull) 3303, 2728, 2620, 1725, 1646, 1545, 1512, 1298, 1234, 1183, 1140, 1107, 1049, 834, 638, cm$^{-1}$. MS (FAB) m/z 510 (MH$^+$), 511, 510, 466, 463, 308, 241, 177, 100, 57, 39. Anal. Found: C, 50.54; H, 6.12; N, 7.35.

EXAMPLE 35

(S)-[4-[2-[(3-Carboxy-1-oxopropyl)amino]-3-[[3-(1H-imidazol-1-yl)-propyl]amino]-3-oxopropyl]phenoxy]propanedioic acid 0.049 g as an amorphous solid. $^1$H NMR (DMSO/DCl) δ0.93, 1.80–1.93, 2.28, 3.03, 4.02, 5.00, 6.78, 7.12, 7.30, 7.63, 7.71; IR (mull) 3283, 3132, 3032, 1717, 1644, 1565, 1511, 1406, 1332, 1300, 1235, 1181, 1089, 834, 633, cm$^{-1}$. MS(FAB) m/z 491 (MH$^+$), 505, 383, 357, 236, 222, 174, 127, 124, 118, 107.

EXAMPLE 36

N-(3-Carboxy-1-oxopropyl)-O-(dicarboxymethyl)-L-tyrosyl-L-norleucinamide (Formula M-6, Chart M)

PREPARATION OF M-2: To a stirring solution of CBZ-L-Tyr-OH (0.50 g) in CH$_2$Cl$_2$ (25 ml) at 0 C. is added H-L-Nle-NH$_2$ HCl (0.264 g), N-methyl morpholine (0.16 g) and EDC (0.303 g). The resulting turbid mixture is stirred for 16 h and allowed to warm to ambient temperature in which time a solid forms. The solid is collected, washed with CH$_2$Cl$_2$ and dried in vacuo to afford 0.374 g title compound as a white solid. $^1$H NMR (DMSO) δ0.82, 1.22, 1.40–1.80, 2.59, 2.87, 4.15, 4.92, 6.62, 7.02, 7.28, 7.41, 7.85.

PREPARATION OF M-3: To a stirring solution of M-2 (0.30 g) in acetone (30 ml) at ambient temperature is added diethyl chloromalonate (0.149 g) and K$_2$CO$_3$ (0.194 g). The resulting mixture is stirred for 16 h and solvent removed in vacuo. The residue is suspended between EtOAc/ H$_2$O (100 ml each), the layers shaken, the organic layer separated, dried over Na$_2$SO$_4$, and solvent removed in vacuo. The residue is suspended in hexane, sonicated and filtered, to afford 0.295 g title compound as a white solid. $^1$H NMR (DMSO) δ0.83, 1.15, 1.50, 2.68, 2.95, 4.21, 4.92, 5.61, 6.83, 7.26, 7.49, 7.91; IR (mull) 3286, 1747, 1696, 1674, 1643, 1538, 1510, 1334, 1296, 1290, 1260, 1225, 1186, 1028, 698, cm$^{-1}$. MS (FAB) m/z 586 (MH$^+$), 586, 569, 434, 384, 305, 265, 176, 92, 91, 86. Anal. Found: C, 61.09; H, 6.56; N, 7.03.

PREPARATION OF M-4: To a solution of M-3 (0.25 g) in MeOH is added 10% Pd-C (25 mg) and the mixture hydrogenated at atmospheric pressure for 3 h. The mixture is filtered through celite and solvent removed in vacuo to afford 0.168 g title compound as a clear yellow oil. $^1$H NMR (DMSO) δ0.89, 1.13, 1.62, 2.82, 2.75, 3.16, 3.60, 4.32, 5.16, 5.40, 6.11, 6.90, 7.13, 7.75; IR (liq.) 3327, 2959, 2935, 1767, 1746, 1666, 1612, 1511, 1445, 1371, 1298, 1226, 1183, 1097, 1027, cm$^{-1}$. MS (EI) m/z 451 (M$^+$), 434, 295, 294, 266, 265, 186, 169, 141, 107, 86.

PREPARATION OF M-5: To a stirring solution of M-4 (0.157 g) in CH$_2$Cl$_2$ (5 ml) at 0 C. is added triethyl amine (0.039 g) followed by succinic anhydride (0.035 g). The resulting solution is stirred overnight allowing the solution to warm to ambient temperature. CH$_2$Cl$_2$ (20 ml) is added and the organics washed with 10% HCl/ H$_2$O (2×50 ml). The organic layer is dried over Na$_2$SO$_4$ and solvent removed to afford 0.090 g title compound as a waxy solid. $^1$H NMR (DMSO) δ0.083, 1.17, 1.50, 1.65, 2.29, 2.65, 2.95, 4.20, 4.42, 5.60, 6.83, 6.97, 7.14, 7.82, 8.10; IR (mull) 3280, 3206, 1745, 1716, 1676, 1666, 1631, 1548, 1511, 1424, 1324, 1300, 1228, 1184, 1098, cm$^{-1}$. MS (FAB) m/z 552 (MH$^+$), 566, 553, 552, 434, 305, 294, 265, 131, 115, 86. Anal. Found: C, 55.96; H, 6.73; N, 7.41.

PREPARATION OF M-6: To a stirring solution of M-5 (0.050g) in THF/MeOH (1:3 v/v, 5 ml) is added LiOH/ H$_2$O (2.5 M, 0.18 ml). H$_2$O (3 ml) is added and the mixture is stirred for 3 h. The solution is diluted with H$_2$O (20 ml) and extracted with EtOAc (2×25 ml). The organic layers are combined, dried over Na$_2$SO$_4$ and the solvent removed to afford 0.036 g title compound as a waxy solid. $^1$H NMR (DMSO) δ0.83, 1.19, 1.53, 1.68, 2.30, 2.71, 2.95, 4.02, 4.40, 5.30, 6.79, 6.99, 7.09, 7.13, 7.80, 8.10; HRMS (FAB) found 496.1929.

EXAMPLE 37

N-(1-Oxohexyl)-L-α-aspartyl-O-(dicarboxymethyl)-N-pentyl-L-tyrosinamide (Formula P-2, Chart P)

PREPARATION OF P-1: To a stirring solution of L-3 (0.25 g) in CH$_2$Cl$_2$ (8 ml) at 0 C. is added hexanoyl chloride (0.043 g, 0.32). The resulting solution is stirred for 16 h, allowing the mixture to warm to ambient temperature. The solution is diluted with CH$_2$Cl$_2$ (20 ml) and washed with 10% HCl/ H$_2$O (3×50 ml). The organic layer is dried over Na$_2$SO$_4$ and sovent removed to afford 0.164 g title compound as a white solid. $^1$H NMR (DMSO) δ0.81, 1.20, 2.03, 2.54, 2.73, 2.79, 4.32, 4.60, 5.04, 5.19, 5.77, 6.82, 7.06, 7.31, 7.81, 8.11; IR (mull) 3286, 1765, 1739, 1663, 1639, 1543, 1511, 1499, 1299, 1276, 1223, 1170, 749, 733, 695, cm$^-$. MS (FAB) m/z 836 (MH$^+$), 837, 533, 515, 418, 178, 92, 91, 88, 88, 43. Anal. Found: C, 68.75; H, 6.95; N, 5.01.

PREPARATION OF P-2: To a stirring solution of P-1 (0.175 g) in MeOH (15 ml) is added 10% Pd-C (25 mg). The mixture is hydrogenated at atmospheric pressure for 3 h, and filtered through celite. The solvent is removed to afford 0.113 g title compound as a white solid. $^1$H NMR (DMSO) δ0.82, 1.22, 1.44, 2.04, 2.38, 2.62, 2.63–3.10, 4.32, 4.51, 5.19, 6.75, 7.04, 7.74, 8.10; IR (mull) 3308, 3069, 3035, 2731, 2597, 1729, 1636, 1541, 512, 1418, 1341, 1230, 1183, 1114, 637, cm$^{-1}$. MS (FAB) m/z 566 (MH$^+$), 588, 566, 177, 99, 88, 88, 71, 43, 39, 23. Anal. Found: C, 55.95; H, 7.05; N, 7.24.

EXAMPLE 38

(S)-[[4-[3-[[1-[[4-(Dicarboxymethoxy)phenyl]methyl]-2-oxo-2-(pentylamino)ethyl]amino]-3-oxopropyl]phenyl]methyl]-propanedioic acid (Formula N-4, Chart N)

PREPARATION OF N-2: To a stirring suspension of 4-formyl cinnamic acid (N-1, 0.50 g) and dibenzylmalonate (0.806 g) is added piperidine (0.290 g) and acetic acid (3 drops). The mixture is refluxed for 16 h, cooled to ambient temperature, and solvent diluted with EtOAc (50 ml). The organics are washed with 10% HCl/H$_2$O (2×50 ml), solvent dried over Na$_2$SO$_4$ and evaporated to afford 0.485 title compound as a white solid. $^1$H NMR (DMSO) δ5.25, 5.27, 6.54, 7.35, 7.50, 7.75; IR (mull) 1724, 1696, 1680, 1628, 1442, 1426, 1414, 1315, 1260, 1224, 1215, 1202, 1185, 699, 694, cm$^{-1}$. MS (EI) m/z 442 (M$^+$), 442, 246, 245, 227, 127, 114, 92, 91, 77, 65. Anal. Found: C, 70.77; H, 4.87.

PREPARATION OF N-3: To a stirring suspension of N-2 (0.194 g) and J-4 (0.25 g) at 0 C. is added triethyl amine (0.045 g) and EDC (0.085 g). The mixture is stirred for 16 h allowing the solution to warm to ambient temperature. The mixture is diluted with CH$_2$Cl$_2$ (50 ml) and washed with 10% HCl/ H$_2$O (2×50 ml). The organic layer is dried over Na$_2$SO$_4$ and evaporated to dryness. The residue is purified via flash column chromatography (eluant 1:1 EtOAc/hexane) to afford 0.038 g title compound as a white solid. $^1$H NMR (CDCl$_3$) δ0.84, 1.25, 3.00, 3.20, 4.62, 5.21, 5.25, 5.27, 5.28, 5.51, 6.38, 6.87, 7.13, 7.32, 7.54, 7.73; MS (ES+) 957.

PREPARATION OF N-4: To a stirring solution of N-3 (0.030 g) in MeOH/THF (5:3 v/v, 8 ml) is added 10% Pd-C (10 mg). The mixture is hydrogenated at atmospheric pressure for 16 h. The sovent is filtered and evaporated to afford 0.016 g title compound as a white solid. $^1$H NMR (DMSO) δ0.82, 1.33, 2.28, 2.63, 2.80–3.10, 3.2–4.0, 4.40, 5.12, 6.75, 7.06, 7.73, 8.03; MS (FAB) m/z 601 (MH$^+$), 601, 219, 193, 177, 107, 88, 57, 43, 39, 23.

EXAMPLE 39

(S)-[[4-[2-[(3-Carboxy-1-oxopropyl)amino]-3-oxo-3-(pentylamino)-propyl]phenyl]methyl]propanedioic acid (Formula G-7, Chart G)

PREPARATION OF G-1: To a stirring solution of E-2 (5.0 g) and pyridine (2.58 g) in CH$_2$Cl$_2$ (50 ml) at 0 C. is added trifluoromethane sulfonic anhydride (4.42 g) dropwise over 15 min. After addition, the mixture is stirred for 1 h at 0 C. and diluted with CH$_2$Cl$_2$ (50 ml). The organics are washed with 10% HCl/ H$_2$O (2×50 ml), separated and dried over Na$_2$SO$_4$. The solvent is filtered through a pad of SiO$_2$ (50 g) and washed with CH$_2$Cl$_2$ (75 ml). The solvent is removed to afford 2.54 g title compound as a yellow solid. $^1$H NMR (CDCl$_3$) δ0.86, 1.18–1.50, 1.40, 3.09, 4.27, 5.07, 5.90, 7.19, 7.28; IR (mull) 3346, 1683, 1651, 1540, 1523, 1504, 1429, 1271, 1252, 1211, 1169, 1144, 901, 638, 607, cm$^{-1}$. MS (EI) m/z 482 (M$^+$), 426, 409, 312, 268, 243, 232, 143, 135, 107, 57. Anal. Found: C, 50.10; H, 5.83; N, 5.88.

PREPARATION OF G-2: To stirring mixture of G-1 (0.60 g), LiCl (0.158 g) and tributylvinyl tin (0.591 g) in DMF (10 ml) at ambient temperature is added dichlorobis (triphenylphosphine)palladium(II) (0.087 g). The mixture is heated to 90 C. and stirred for 16 h. The resulting black mixture is cooled to ambient temperature, poured into ice/H$_2$O, and extracted with EtOAc (3×75 ml). The organic layers are combined, dried over Na$_2$SO$_4$, and solvent removed. The residue is purified via SiO$_2$ flash column chromatography (eluant 2:1 hexane/ EtOAc) to afford 0.365 g title compund as a white solid. $^1$H NMR (CDCl$_3$) δ0.84, 1.13–1.40, 1.36, 3.06, 4.23, 5.06, 5.22, 5.68, 5.70, 6.67, 7.15, 7.33; IR (mull) 3337, 1690, 1680, 1656, 1540, 1523, 1331, 1321, 1309, 1299, 1269, 1251, 1170, 906, 631, cm$^{-1}$. MS (EI) m/z 360 (M$^+$), 304, 244, 243, 190, 187, 146, 143, 118, 117, 57.

PREPARATION OF G-3: O$_3$ (g) is bubbled through a stirring solution of G-2 (0.30 g) in CH$_2$Cl$_2$ (50 ml) at −78 C.

until the blue endpoint is observed. The reaction mixture is capped with a septum and stirred an additional 1.5 h at −78 C. Dimethylsulfide (0.78 g) is added at −78 C and the mixture allowed to warm to ambient temperature (over 1 h). The solvent is removed, the residue taken up in $Et_2O$ (50 ml) and washed with $H_2O$ (2×50 ml). The organic layer is dried over $Na_2SO_4$, solvent removed in vacuo, and residue purified via 30 $SiO_2$ flash column chromatography (eluant 2:1 hexane/ EtOAc) to afford 0.172 g title compound as a white solid. $^1H$ NMR $CDCl_3$) δ0.85, 1.15–1.36, 1.39, 3.14, 4.30, 5.05, 5.08, 7.38, 7.81, 10.00; IR (mull) 3324, 1700, 1689, 1651, 1607, 1576, 1529, 1333, 1313, 1300, 1270, 1253, 1224, 1214, 1170, $cm^{-1}$. MS (EI) m/z 362 ($M^+$), 306, 289, 243, 193, 192, 149, 148, 143, 120, 57. Anal. Found: C, 65.39; H, 8.43; N, 7.47.

PREPARATION OF G-4: G-3 (0.50 g), dibenzyl malonate (0.47 g), piperidine 0.023 g), and HOAc (3 drops) in benzene (15 ml) are heated to reflux for 2 h. The mixture is cooled to ambient temperature, diluted with EtOAc (50 ml) and washed with 10% $HCl/H_2O$ (2×50 ml). The organic layer is dried over $Na_2SO_4$, the solvent removed, and the residue purified via $SiO_2$ flash column chromatography (eluant 2:1 hexane/ EtOAc)to afford 0.060 g title compound as a slightly yellow oil. $^1H$ NMR $CDCl_3$) δ0.84, 1.17–1.39, 1.40, 3.02, 3.13, 4.21, 5.00, 5.28, 5.67, 7.09, 7.32, 7.72; IR (mull) 3328, 1726, 1685, 1653, 1632, 1542, 1527, 1321, 1267, 1234, 1213, 1200, 1185, 749, 696, $cm^{-1}$. MS (EI) m/z 628 ($M^+$), 571, 511, 420, 414, 386, 278, 143, 92, 91, 57. Anal. Found: C, 70.21; H, 7.05; N, 4.48.

PREPARATION OF G-5: To a stirring solution of G-4 (0.65 g) in HOAc (10 ml) is added 1.5 M HCl/HOAc (10 ml). The mixture is allowed to stand at ambient temperature for 2 h and the solvent removed to afford 0.58 g (quant) title compound as a slightly yellow amorphous solid. $^1H$ NMR (DMSO) δ0.76, 1.03, 1.17, 2.89, 3.02, 3.94, 5.25, 5.29, 7.22, 7.36, 7.73, 8.34, 8.41; IR (liq.) 3065, 3034, 2957, 2933, 2872, 2861, 1730, 1669, 1629, 1499, 1456, 1260, 1204, 1185, 697, $cm^{-1}$. MS (FAB) m/z 529 ($MH^+$), 1058, 531, 530, 529, 414, 143, 92, 91, 88, 43. Anal. Found: C, 67.22; H, 6.81; N, 4.94.

PREPARATION OF G-6: To a stirring solution of G-5 (0.507 g) in $CH_2Cl_2$ (15 ml) at 0 C. is added triethylamine (0.20 g) followed by succinic anhydride (0.089 g). The mixture is stirred for 16 h allowing to warm to ambient temperature. The mixture is diluted with $CH_2Cl_2$ (50 ml) and washed with 10% $HCl/H_2O$ (2×50 ml). The organic layer is dried over $Na_2SO_4$ and solvent removed to afford 0.557 title compound as a yellow amorphous solid. $^1H$ NMR $CDCl_3$) δ0.83, 1.11–1.28, 2.47, 2.63, 3.03, 4.57, 5.25, 5.27, 5.93, 6.88, 7.09, 7.27, 7.70; IR (mull) 3287, 3089, 3064, 3032, 1726, 1640, 1610, 1543, 1356, 1260, 1213, 1198, 1181, 745, 695, $cm^{-1}$. MS (FAB) m/z 629 ($MH^+$), 631, 630, 629, 521, 414, 92, 91, 88, 86, 43. Anal. Found: C, 68.45; H, 6.50; N, 4.50.

PREPARATION OF G-7: To a stirring solution of G-6 (0.15 g) in MeOH (20 ml) is added 10% Pd-C (15 mg) and the mixture hydrogenated at atmospheric pressure for 3 h. The solvent is filtered through celite and removed in vacuo to afford 0.105 g title compound as an amorphous solid. $^1H$ NMR (DMSO) δ0.82, 1.15–1.30, 2.31, 2.71, 2.96, 3.09, 4.35, 7.07, 7.77, 8.06; IR (mull) 3300, 2730, 2618, 1716, 1632, 1551, 1517, 1422, 1404, 1244, 1212, 1171, 956, 853, 655, $cm^{-1}$. MS (FAB) m/z 451 ($MH^+$), 604, 452, 451, 407, 236, 192, 102, 88, 86, 43. Anal. Found: C, 57.00; H, 6.74; N, 6.06.

EXAMPLE 40

(S)-[[4-[2-[(3-Carboxy-1-oxopropyl)amino]-3-oxo-3-(pentylamino)-propyl]phenyl]methylene] propanedioic acid (Formula H-1, Chart H)

To a stirring solution of G-6 (0.15 g) in THF/MeOH (3:1 v/v, 5 ml) at ambient temperature is added $LiOH/H_2O$ (2.5 M, 0.52 ml). The mixture is stirred for 3 h and acidified to pH~4 with 10% $HCl/H_2O$. The aqueous layer is extracted with EtOAc (2×50 ml), the organic layers combined and dried over $Na_2SO_4$. The solvent is removed to afford 0.062 g title compound as a waxy solid. $^1H$ NMR (DMSO) δ0.82, 1.13–1.17, 2.30, 2.78, 2.96, 7.20, 7.29, 7.45, 7.81, 8.10; IR (mull) 3302, 3066, 3031, 2624, 1715, 1630, 1550, 1515, 1442, 1422, 1243, 1212, 1187, 699, 665, $cm^{-1}$. MS (FAB) m/z 449 ($MH^+$), 481, 450, 449, 363, 177, 133, 118, 88, 86, 43.

EXAMPLES 41–50

(General Synthesis of Formula A-5, Chart A)

PREPARATION OF A-2: To a mixture of L-tyrosine benzyl ester p-toluenesulfonate salt (5.0 g) and triethylamine in $CH_2Cl_2$ (25 mL) at 0 C. is added EDC (2.2 g) and monomethyl succinate (1.5 g). The mixture is warmed to room temperature and stirred overnight. The mixture is diluted with EtOAc (150 mL), and washed with 1 M HCl (50 mL), sat. $NaHCO_3$ (50 mL), and sat. NaCl (50 mL). The organic phase is dried ($MgSO_4$), and the solvent is removed under reduced pressure. The residue is purified by flash chromatography ($SiO_2$, 60% EtOAc/hexane) to provide 3.4 g of title compound as a colorless oil which slowly solidified to a white solid: $^1H$ NMR ($CDCl_3$) δ7.33, 6.84, 6.65, 6.15, 5.62, 5.14, 4.87, 3.67, 3.01, 2.64, 2.47; MS (EI) m/z 385 ($M^+$), 254, 209, 208, 147, 136, 132, 115, 107, 91, 55; Anal. Found: C, 65.41; H, 6.00; N, 3.61.

PREPARATION OF A-3: To a mixture of A-2 (2.64 g) and $K_2CO_3$ (1.9 g) in acetone (20 mL) is added diethyl chloromalonate (2.2 mL). The mixture is stirred vigorously for 18 h. The mixture is partitioned between EtOAc and $H_2O$. The organic phase is washed with sat. $NaHCO_3$ and sat. NaCl. After drying ($MgSO_4$), the solvent is removed under reduced pressure. The residue is purified by flash chromatography (150 g $SiO_2$, 50% EtOAc/hexane) to provide 2.9 g of A-3 as a colorless oil: $^1H$ NMR $CDCl_3$) δ7.37, 7.29, 6.90, 6.80, 6.06, 5.12, 4.86, 4.31, 3.67, 3.05, 2.62, 2.48, 1.30; MS (ES−) 542.

PREPARATION OF A-4: A Parr flask is charged with A-3 (150 mg), 10% Pd/C (25 mg) qnd abs. EtOH (25 mL), and the mixture is hydrogenated (35 psi) for 45 minutes. The mixture is filtered through Celite and concentrated to provide 110 mg (87%) of A-4 as a colorless oil: $^1H$ NMR $CDCl_3$) δ7.11, 6.88, 6.23, 5.17, 4.79, 4.30, 3.67, 3.15, 3.06, 2.63, 2.28, 1.30; MS (ES−) 452.

GENERAL PREPARATION OF A-5: To a mixture of A-4 (1 eq.) in $CH_2Cl_2$ (0.2 M) at 0 C. is added EDC (1 eq.) followed by the requisite amine. The reaction is warmed to room temperature and stirred for 18 h. The mixture is diluted with EtOAc and washed with 1 M HCl, sat $NaHCO_3$, and sat. NaCl. The organic phase is dried ($MgSO_4$) and concentrated under reduced pressure. The residue is dissolved in THF (3 mL), and a solution of LiOH $H_2O$ (6–8 eq.) in $H_2O$ (1 mL) is added. The mixture is stirred for 2–4 h. The mixture is acidified with 1M HCl, and extracted with EtOAc (3×). The combined organic phase is washed with sat. NaCl and dried ($MgSO_4$). The solvent is removed in vacuo to provide A-5 .

EXAMPLE 41

(S)-[4-[2-[(3-Carboxy-1-oxopropyl)amino]-3-[(3,3-diphenylpropyl)-amino]-3-oxopropyl]phenoxy] propanedioic acid (Chart A, A-5)

$^1H$ NMR (DMSO) δ8.04, 7.90, 7.25, 7.12, 6.77, 5.22, 4.34, 3.92, 2.89, 2.65, 2.31, 2.10; MS (ES+) 577; Anal. Found: C, 62.82; H, 5.77; N, 4.75.

EXAMPLE 42

(S)-[4-[3-[(1,3-Benzodioxol-5-ylmethyl)amino]-2-[(3-carboxy-1-oxopropyl)amino]-3-oxopropyl]phenoxy]propanedioic acid (Chart A, A-5)

$^1$H NMR (DMSO) δ8.32, 8.11, 7.10, 6.78, 5.59, 5.95, 5.23, 4.40, 4.14, 3.92, 2.70, 2.30; MS (ES−) 515.

EXAMPLE 43

(S)-[4-[2-[(3-Carboxy-1-oxopropyl)amino]-3-oxo-3-[(3-phenyl-propyl)amino]propyl]phenoxy]propanedioic acid (Chart A, A-5)

$^1$H NMR (DMSO) δ8.10, 7.89, 7.25, 7.15, 6.80, 5.23, 4.33, 3.01, 2.89, 2.70, 2.32, 1.61; MS (ES−) 499; Anal. Found: C, 58.46; H, 5.68; N, 5.47.

EXAMPLE 44

(S)-[4-[2-[(3-Carboxy-1-oxopropyl)amino]-3-[(1-naphthalenyl-methyl)amino]-3-oxopropyl]phenoxy]propanedioic acid (Chart A, A-5)

$^1$H NMR (DMSO) δ8.45, 8.17, 8.00, 7.92, 7.81, 7.41, 7.41, 7.25, 7.11, 6.77, 5.25, 4.70, 4.50, 3.94, 2.72, 2.32; MS (ES−) 521; HRMS (FAB) found 523.1722.

EXAMPLE 45

(S)-[4-[2-[(3-Carboxy-1-oxopropyl)amino]-3-(decylamino)-3-oxopropyl]phenoxy]propanedioic acid (Chart A, A-5)

$^1$H NMR (DMSO) δ8.06, 7.80, 7.10, 6.78, 5.24, 3.33, 2.98, 2.85, 2.65, 2.30, 1.21, 0.83; HRMS (FAB) found 523.2634; Anal. Found: C, 59.64; H, 7.88; N, 5.25.

EXAMPLE 46

(S)-[4-[3-[[2-[4-(Aminosulfonyl)phenyl]ethyl]amino]-2-[(3-carboxy-1-oxopropyl)amino]-3-oxopropyl]phenoxy]propanedioic acid (Chart A, A-5)

$^1$H NMR (DMSO) δ8.09, 8.00, 7.71, 7.35, 7.27, 5.27, 4.33, 2.84, 2.60–2.77, 2.31; MS (ES−) 564; Anal. Found: C, 48.88; H, 4.95; N, 7.04.

EXAMPLE 47

(S)-[4-[2-[(3-Carboxy-1-oxopropyl)amino]-3-oxo-3-[[[4-(trifluoromethyl)phenyl]methyl]amino]propyl]-phenoxy]-propanedioic acid (Chart A, A-5)

$^1$H NMR (DMSO) δ8.50, 8.18, 7.62, 7.31, 7.12, 6.80, 5.27, 4.43, 7.32, 3.91, 3.71, 2.33; MS (ES−) 539; Anal. Found: C, 52.27; H, 4.68; N, 5.12.

EXAMPLE 48

(S)-[4-[2-[(3-Carboxy-1-oxopropyl)amino]-3-oxo-3-[(2-phenoxy-ethyl)amino]propyl]phenoxy]propanedioic acid (Chart A, A-5)

$^1$H NMR (DMSO) δ8.15, 8.09, 7.27, 7.10, 6.92, 7.76, 5.23, 4.40, 3.90, 2.87, 2.65, 2.30; MS (FAB) m/z 503 (MH$^+$), 392, 391, 149, 113, 71, 69, 57, 55, 43, 41; HRMS (FAB) found 503.1656; Anal. Found: C, 57.51; H, 5.79; N, 4.96.

EXAMPLE 49

(S)-[4-[2-[(3-Carboxy-1-oxopropyl)amino]-3-[[2-(4-hydroxyphenyl)-ethyl]amino]-3-oxopropyl]phenoxy]propanedioic acid (Chart A, A-5)

$^1$H NMR (DMSO) δ8.06, 7.90, 7.09, 6.95, 6.79, 6.64, 5.27, 4.31, 3.15, 2.85, 2.63, 2.52, 2.33; MS (ES−) 501; HRMS (FAB) found 503.1656.

EXAMPLE 50

(S)-[4-[2-[(3-Carboxy-1-oxopropyl)amino]-3-[[(4-carboxyphenyl)-methyl]amino]-3-oxopropyl]phenoxy]propanedioic acid (Chart A, A-5)

$^1$H NMR (DMSO) δ8.49, 8.20, 7.85, 7.27, 7.13, 6.80, 5.28, 4.45, 4.31, 2.95, 2.71, 2.34; MS (FAB) m/z 517 (MH$^+$), 517, 391, 149, 113, 71, 69, 57, 55, 43, 41; HRMS (FAB) found 517.1451; Anal. Found: C, 54.60; H, 5.25; N, 4.82.

EXAMPLE 51

(S)-[4-[2-[(4-Amino-1,4-dioxobutyl)amino]-3-oxo-3-(pentylamino)-propyl]phenoxy]propanedioic acid (Chart B, B-5)

PREPARATION OF B-2: To a mixture of Cbz-Try-OH (2 g) in CH$_2$Cl$_2$ (75 mL) and DMF (5 mL) at 0 C. is added EDC (1.21 g). After a few minutes, amylamine (0.74 mL) is added, and the mixture is warmed to room temperature and stirred for 4.5 h. 10% HCl (50 mL) is added, and the phases are separated. The organic phase is washed with sat. NaCl (30 mL), dried (MgSO$_4$), and concentrated. The residue is purified by flash chromatography (75 g SiO$_2$, 50% EtOAc/hexane) to give 1.7 g of title compound as a white solid: $^1$H NMR CDCl$_3$) δ7.34, 7.06, 6.74, 5.53, 5.35, 5.09, 5.05, 4.25, 3.14, 3.15, 2.92, 1.14–1.35, 0.86; MS (EI) m/z 384 (M$^+$), 234, 233, 226, 177, 162, 147, 127, 107, 92, 91; Anal. Found: C, 68.53; H, 7.14; N, 7.25.

PREPARATION OF B-3: To a mixture of B-2 (200 mg) and K$_2$CO$_3$ (146 mg) in acetone (1.5 mL) is added diethyl chloromalonate (0.17 mL). The mixture is stirred vigorously for 18 h. The mixture is partitioned between EtOAc (10 mL) and H$_2$O (5 mL). The organic phase is washed with H$_2$O (1×5 mL) and sat. NaCl (1×5 mL). After drying (MgSO$_4$), the solvent is removed under reduced pressure. The residue is purified by flash chromatography (30 g SiO$_2$, 40% EtOAc/hexane) to provide 140 mg (49%) of title compound (B-3) as a white solid: $^1$H NMR (CDCl$_3$) δ7.33, 7.10, 6.88, 5.55, 5.31, 5.14, 5.08, 4.30, 3.12, 2.93, 1.30, 0.86; MS (ES−) 541.

PREPARATION OF B-4: To a solution of B-3 (2.9 g) in abs. EtOH (100 mL) and THF (10 mL) is added 10% Pd/C (0.29 g, moistened with abs. EtOH). The mixture is hydrogenated (40 psi) for 1 h. The mixture is filtered through Celite and concentrated under reduced pressure. The residue is dissolved in a 1 M solution of HCl in HOAc (10 mL). After stirring for several minutes, the mixture is concentrated to 2–3 mL. A large amount of Et$_2$O is added, and the mixture is cooled to 0 C. The Et$_2$O is decanted from the oil which had settled on the flask. The oil is washed with Et$_2$O, and the Et$_2$O is decanted again. To the oil is added Et$_2$O again, and the mixture is sonicated. The oil gradually crystallizes, and the solid is collected to provide 2.0 g of B-4 as an off-white solid: $^1$H NMR (DMSO) δ8.39, 8.23, 7.14, 6.90, 5.63, 4.20, 3.88, 3.05, 2.93, 1.19, 1.1–1.4, 0.82; MS (ES+) 409.1.

PREPARATION OF B-5: To a suspension of succinamic acid (40 mg) in CH$_2$Cl$_2$ (1 mL) at 0 C. is added EDC (65 mg) and HOBT (46 mg), and the mixture is stirred for a few minutes. B-4 (150 mg) and triethylamine (48 mL) are added, and the mixture is warmed to room temperature and stirred overnight. The mixture is partitioned between EtOAc and 1 M HCl. The organic phase is washed with sat. NaHCO$_3$, sat. NaCl, and dried (MgSO$_4$). After the solvent is removed under reduced pressure, the residue is purified by flash chromatography (11 g SiO$_2$, 6% MeOH/CH$_2$Cl$_2$) to yield 72 mg of a white solid. To a solution of the solid dissolved in THF (3 mL) and MeOH (1 mL) is added a solution of LiOH H$_2$O (30 mg) in H$_2$O (1 mL). The mixture is stirred at room temperature for 2.5 h. The mixture is neutralized with 1 M HCl and extracted with EtOAc (3×). The combined organic phase is washed with sat. NaCl and dried (MgSO$_4$). The solvent is removed in vacuo to give 27 mg of B-5 as a white solid: $^1$H NMR (DMSO) δ8.05, 7.85, 7.27, 1.12, 6.79, 6.75, 5.26, 4.30, 2.89–3.03, 2.89–3.03, 2.60–2.71, 2.12–2.32, 1.11–1.38, 0.83; MS (ES–) 450; HRMS (FAB) found 452.2051.

EXAMPLES 52–54

(General Synthesis of Formulae BB-2 and BB-3, Chart BB)

GENERAL PREPARATION OF BB-1: To a mixture of the N-protected amino acid (0.34 mmol) in CH$_2$Cl$_2$ (1 mL) at 0 C. is added EDC (0.34 mmol). After stirring for a few minutes, the compound (B-4) (150 mg) and triethylamine (48 mL) are added, and the mixture is warmed to room temperature and stirred overnight. The mixture is partitioned between EtOAc and 1 M HCl. The organic phase is washed with sat. NaHCO$_3$, sat. NaCl, and dried (MgSO$_4$). The solvent is removed under reduced pressure to provide BB-1 which used directly in the next step.

GENERAL PREPARATION OF BB-2: BB-1 (0.34 mmol) is dissolved in a 1 M solution of HCl in acetic acid (4 mL), and stirred at room temperature for 3 h. The solvent is removed under reduced pressure, and the residue is dissolved in a mixture of triethylamine (0.75 mmol) in CH$_2$Cl$_2$ (1.5 mL). The mixture is cooled to 0 C., and succinic anhydride (0.34 mmol) is added. The mixture is warmed to room temperature and stirred overnight. The mixture is partitioned between EtOAc and 1 M HCl, and the organic phase is washed with sat. NaCl and dried (MgSO$_4$). After the solvent is removed, the residue is dissolved in THF (3 mL), and a solution of LiOH H$_2$O (1–2 mmol) in H$_2$O (1 mL) is added. The mixture is stirred for 2–5 h. The mixture is neutralized with 1 M HCl and extracted with EtOAc (2×). The combined organic phase is washed with sat. NaCl and dried (MgSO$_4$). The solvent is removed in vacuo to provide BB-2.

GENERAL PREPARATION OF BB-3: Prepared by direct LiOH saponification of BB-1 with isolation as described in the general synthesis of BB-2.

EXAMPLE 52: N-[(Phenylmethoxy)carbonyl]-L-α-aspartyl-O-(dicarboxymethyl)-N-pentyl-L-tyrosinamide (Chart BB, BB-3)

Obtained 130 mg of title compound (BB-3) as a white solid. $^1$H NMR (DMSO) δ8.10, 7.80, 7.45, 7.31, 7.00, 6.78, 5.24, 5.00, 4.32, 2.80–3.00, 2.55–2.70, 1.10–1.35, 0.82; MS (FAB) m/z 602 (MH$^+$), 602, 392, 391, 149, 113, 91, 74, 71, 57, 43; HRMS (FAB) found 602.2363.

EXAMPLE 53

N-[(1,1-Dimethylethoxy)carbonyl]-D-α-aspartyl-O-(dicarboxy-methyl)-N-pentyl-L-tyrosinamide (Chart BB, BB-3)

Obtained 90 mg of title compound (BB-3) as a white solid. $^1$H NMR (DMSO) δ8.04, 7.80, 7.09, 6.85, 7.78, 5.24, 4.35, 4.19, 2.81–3.09, 2.70, 1.34, 110–1.40, 0.82; MS FAB) m/z 568 (MH$^+$), 468, 238, 194, 136, 133, 88, 57, 43, 41, 29; HRMS (FAB) found 568.2498; Anal. Found: C, 53.89; H, 6.58; N, 7.23.

EXAMPLE 54

4-Benzoyl-N-(3-carboxy-1-oxopropy)-L-phenylalanyl-O-(dicarboxy-methyl)-N-pentyl-L-tyrosinamide (Chart BB, BB-2)

Obtained 169 mg of title compound (BB-2) as an off-white solid. $^1$H NMR (DMSO) methyl)-N-pentyl-L-tyrosinamide8.12, 8.05, 7.75, 7.70–7.75, 7.35, 7.11, 6.81, 5.25, 4.51, 4.35, 2.70–3.05, 2.32, 1.10–1.35, 0.80; MS (FAB) m/z 704 (MH$^+$), 705, 704, 353, 238, 224, 194, 136, 107, 105, 88; HRMS (FAB) found 704.2804; Anal. Found: C, 62.15; H, 6.03; N, 5.87.

EXAMPLE 55

(S)-2-[4-[2-[(3-Carboxy-1-oxopropyl)amino]-3-oxo-3-(pentyl-amino)propyl]phenoxy]-2-butenedioic acid (Chart E, E-9)

To a mixture of E-5 (0.37 g) and triethylamine (0.17 ml) in THF (5 mL) is added dimethylacetylene dicarboxylate (0.25 mL), and the mixture is heated at 50 C. overnight. The mixture is diluted with Et$_2$O, and washed with 1 M HCl and sat. NaCl. The organic phase is dried (Na$_2$SO$_4$) and concentrated. The residue is purified by flash chromatography (SiO$_2$, 90% EtOAc/hexane) to yield 0.41 g of E-7 as a 1:1 mixture of isomers. To a mixture of (E-7, Chart E) (100 mg) in MeOH (5 mL) is added a solution of LiOH H$_2$O (50 mg) in H$_2$O (1.5 mL), and the mixture is stirred at room temperature overnight. The reaction mixture is concentrated in vacuo, and the residue is dissolved in H$_2$O. After cooling to 0 C., 1 M HCl is added until pH=1. The solid which slowly precipitates over several hours at 0 C. is collected and dried to provide 30 mg of E-9 (6:1 mixture of isomers) as a slight yellow solid: $^1$H NMR (MeOH) δ7.18, 6.86, 6.55, 5.10, 4.49, 3.10, 2.87, 2.39–2.54, 1.27–1.45, 0.90; HRMS (FAB) found 465.1856; Anal. Found: C, 54.20; H, 6.04; N, 5.77.

EXAMPLE 56

[2(S)]-[4-[2-[(3-Carboxy-1-oxopropyl)amino]-3-oxo-3-(pentylamino)propyl]phenoxy]butanedioic acid (Chart E, E-8)

To a suspension of E-4 (50 mg) and triethylamine (18 mL) in THF (0.3 mL) is added a solution of dibenzylacetylene dicarboxylate (35 mg) in THF (0.2 mL). The reaction mixture is heated at 50 C. for 20 h. The mixture is diluted with Et$_2$O, and washed with 1 M HCl and sat. NaCl. The organic phase is dried (Na$_2$SO$_4$), and the solvent is removed in vacuo. The residue is purified by flash chromatography (9 g SiO$_2$, 60% EtOAc/hexane) to provide 48 mg of E-6 as a 1:1 mixture of isomers. A mixture of E-6 (48 mg) and 10% Pd/C (5 mg) in MeOH (2 mL) is stirred under a hydrogen atmosphere (balloon) for 1 h. The mixture is filtered through Celite and concentrated to provide 27 mg of E-8 as a glass: $^1$H NMR (DMSO) δ8.02, 7.78, 7.08, 6.76, 4.92, 4.32, 2.6–3.0, 2.25–2.35, 1.1–1.4, 0.83; MS (FAB) m/z 467 (MH$^+$), 489, 468, 467, 349, 252, 136, 107, 88, 86, 43; HRMS (FAB) found 467.2040.

EXAMPLE 57

(R)-[4-[2-[(3-Carboxy-1-oxopropyl)amino]-3-oxo-3-(pentylamino)-propyl]phenoxy]propanedioic acid (Chart J, J-6)

Prepared by general method of Chart J from N-t-Boc-D-tyrosine. $^1$H NMR (MeOH) δ7.83, 7.16, 6.90, 5.21, 4.48; MS (ES–) 451; Anal. Found: C, 54.36; H, 6.41; N, 6.22.

EXAMPLE 58

(S)-2-(Carboxymethoxy)-5-[2-[(3-carboxy-1-oxopropyl)amino]-3-oxo-3-(pentylamino)propyl] benzoic acid (Chart Q, Q-6)

PREPARATION OF Q-2: To a stirring mixture of 3-iodo-L-tyrosine (10.0 g) in dioxane (100 mL), $H_2O$ (50 mL) and 1 M aqueous NaOH (50 mL) is added di-t-butyl dicarbonate (7.8 g) at 0° C. The mixture is stirred for 2 h allowing the solution to warm to ambient temperature, and is then washed with EtOAc (2×50 mL). The water layer is separated and carefully acidified with 4 M $NaHSO_4$ $H_2O$ in a beaker, and is then extracted with EtOAc (2×100 mL). The organic layer is dried ($NaSO_4$) and concentrated to afford 15.1 g of the crude acid as a yellow oil. The acid is suspended in $CH_2Cl_2$ (200 mL) and cooled with ice to 0° C. 1-(3-Dimethylaminopropyl)-3-ethylcarbodiimide hydrochloride (EDC, 6.2 g) is added and the mixture is stirred for 10 min at 0° C. 1-Pentylamine (3.8 mL) is added, and the mixture is stirred for 16 h allowing the solution to warm to ambient temperature. The mixture is washed with 10% aqueous HCl (2×100 mL), the organic layer dried ($MgSO_4$), and concentrated. The residue is purified by column chromatography ($SiO_2$, EtOAc), which furnishes 10.0 g of Q-2 as a white solid. $^1H$ NMR 400 MHz ($CDCl_3$) δ0.87, 1.21, 1.30, 1.41, 1.43, 2.93, 3.09–3.20, 4.17, 5.20, 6.00, 6.85, 7.05, 7.50; $^{13}C$ NMR ($CDCl_3$) δ13.95, 22.28, 28.26, 28.89, 29.04, 37.34, 39.54, 54.80, 80.37, 85.24, 115.04, 130.47, 130.86, 139.00, 154.27, 155.52, 171.01. Anal. Found: C, 47.5; H, 6.1.

PREPARATION OF Q-3: Triethylamine (0.61 mL) is added to a stirring suspension of Q-2 (1.05 g), palladium (II) acetate (14 mg) and 1,1'-bis(diphenylphosphino)-ferrocene (DPPF, 73 mg) in DMF/MeOH 4:1 (5 mL). The mixture is saturated with CO (1 atm) and stirred at 70° C. for 16 h. The mixture is extracted with EtOAc (5 mL), and the organic layer is washed with 10% aqueous HCl (2×2 mL), dried ($MgSO_4$) and concentrated. The residue is purified by column chromatography ($SiO_2$, EtOAc/n-hexane 1:2), which furnishes 0.54 g of Q-3 as a white solid. $^1H$ NMR 500 MHz ($CDCl_3$) δ0.86, 1.17, 1.25, 1.36, 1.41, 2.97, 3.12–3.21, 3.92, 4.21, 5.11, 5.81, 6.91, 7.30, 7.67; $^{13}C$ NMR ($CDCl_3$) δ13.86, 22.24, 28.26, 28.90, 29.05, 37.77, 39.47, 52.23, 54.69, 80.37, 112.25, 117.82, 127.54, 130.34, 136.76, 160.56, 170.32, 170.74. Anal. Found: C, 61.6; H, 7.7.

PREPARATION OF Q-4: A mixture of Q-3 (259 mg), methyl bromoacetate (66 mL) and freshly ground $K_2CO_3$ (96 mg) is suspended in acetone (5 mL). After being stirred for 24 h at ambient temperature, TLC (EtOAc/n-hexane 1:1) indicates that not all starting material has been consumed, and additional methyl bromoacetate (60 mL, 0.63 mmol) is added. After stirring for 24 h, $H_2O$ (2 mL) is added and the mixture is extracted with EtOAc (3 mL). The organic layer is dried ($MgSO_4$) and concentrated. The residue is purified by column chromatography ($SiO_2$, EtOAc/n-hexane 1:1), which furnishes 163 mg of Q-4 as a white solid. $^1H$ NMR 500 MHz ($CDCl_3$) δ0.87, 1.21, 1.28, 1.38, 1.41, 3.00, 3.16, 3.79, 3.88, 4.23, 4.70, 5.10, 6.81, 7.29, 7.66; $^{13}C$ NMR ($CDCl_3$) δ13.86, 22.21, 28.22, 28.88, 29.02, 37.51, 39.46, 52.04, 52.20, 55.87, 66.68, 80.19, 114.61, 121.21, 130.35, 132.59, 134.24, 154.25, 156.44, 165.97, 168.95, 170.69. Anal. Found: C, 60.6; H, 7.5.

PREPARATION OF Q-5: Trifluoroacetic acid (0.38 mL) is carefully added to a stirring solution of Q-4 (159 mg) in $CH_2Cl_2$ (3 mL) at 0° C. The mixture is stirred for 4 h allowing the solution to warm to ambient temperature. The volatiles are removed in vacuo and the residue is partitioned between EtOAc (3 mL) and saturated $NaHCO_3$ (3 mL). The organic layer is dried ($MgSO_4$), and concentrated to dryness to afford 130 mg of the crude amine as a colorless oil. The amine is dissolved in $CH_2Cl_2$ (3 mL) and cooled with ice to 0° C. Succinic anhydride (33 mg) and triethylamine (101 mL) is added and the mixture is stirred for 16 h allowing the solution to warm to ambient temperature. The mixture is diluted with $CH_2Cl_2$ (3 mL) and the organic phase is washed with 10% aqueous HCl (2×3 ml), dried ($MgSO_4$), and concentrated. The residue is purified by column chromatography ($SiO_2$, mobile impurities are eluted with 5% MeOH in $CH_2Cl_2$, and then 5% MeOH/1% HOAc in $CH_2Cl_2$ to bring of product). The collected fractions are concentrated, and the remaining HOAc is removed by azeotroping with toluene on a rotavapor and then drying over night under high vacuum, which furnishes 109 mg of Q-5 as a white solid. $^1H$ NMR 400 MHz (MeOH-$d_4$) δ0.95, 1.29, 1.38, 1.48, 2.43–2.64, 2.91, 3.13–3.22, 3.82, 3.92, 4.55, 4.83, 7.00, 7.43, 7.72, 7.97; $^{13}C$ NMR (MeOH-$d_4$) δ14.75, 23.78, 30.35, 30.52, 30.57, 31.81, 38.19, 40.99, 52.95, 53.00, 56.62, 67.31, 115.68, 122.18, 132.22, 133.74, 135.87, 158.12, 168.53, 171.27, 173.51, 174.98, 176.81. MS (ESI) 481 (M+H). Anal. Found: C, 57.3; H, 6.7.

PREPARATION OF Q-6: A solution of Q-5 (87 mg) and 2.5 M aqueous LiOH (435 mL) in THF/MeOH/$H_2O$ 3:1:1 (3 mL) is stirred at ambient temperature for 16 h. The reaction mixture is acidified with 10% aqueous HCl and extracted with EtOAc (4×2 mL). The organic layer is dried ($MgSO_4$) and concentrated to dryness which furnished 68 mg of Q-6 as a white solid. $^1H$ NMR 400 MHz (MeOH-$d_4$) δ0.66, 1.00, 1.08, 2.13–2.40, 2.65, 2.84–2.93, 4.28, 4.58, 6.79, 7.20, 7.56, 7.69; $^{13}C$ NMR (MeOH-$d_4$) δ14.75, 23.78, 30.34, 30.47, 30.52, 31.74, 38.22, 40.87, 56.58, 67.67, 115.90, 121.69, 132.74, 134.38, 136.40, 158.14, 169.50, 172.65, 173.41, 174.97, 176.76. MS (ESI) 453 (M+H). Anal. Found: C, 4.3; H, 6.3

Examples 59–64 were prepared according to the general procedure described for BB-2.

EXAMPLE 59

2-{4-[(2S)-2-({(2S)-3-[4-(benzyloxy)phenyl]-2-[(3-carboxypropanoyl)amino]propanoyl}amino)-3-oxo-3-(pentylamino)propyl]phenoxy}malonic acid (Chart BB, BB-2)

$^1H$ NMR (DMSO-$d_6$) δ8.05 (d, 1 H), 7.95 (d, 1 H), 7.66 (t, 1 H), 7.36 (m, 5 H), 7.09 (t, 4 H), 6.82 (dd, 4 H), 5.25 (s, 1 H), 5.02 (s, 2 H), 4.34 (m, 2 H), 2.97 (m, 2 H), 2.95–2.90 (m, 2 H), 2.90 (dd, 1 H), 2.61 (dd, 1 H), 2.30 (m, 4 H), 1.33–1.13 (m, 6 H), 0.82 (t, 3 H); MS (FAB) m/z (rel. intensity) 706 (MH$^+$, 36), 707 (15), 706 (36), 353 (15), 238 (13), 226 (28), 91 (99), 88 (16), 57 (20), 55 (15), 43 (20); HRMS (FAB) calcd for $C_{37}H_{43}N_3O_{11}$+$H_1$ 706.2975; found 706.2986.

EXAMPLE 60

2-{4-[(2S)-2-({(2R)-3-(4-benzoylphenyl)-2-[(3-carboxypropanoyl)amino]propanoyl}amino)-3-oxo-3-(pentylamino)propyl]phenoxy}malonic acid (Chart BB, BB-2)

$^1H$ NMR (DMSO-$d_6$) δ8.38 (d, 1 H), 8.10 (d, 1 H), 7.90 (t, 1 H), 7.67 (m, 3 H), 7.55 (m, 4 H), 7.25 (d, 2 H), 7.25 (d, 2 H), 7.79 (d, 2 H), 5.21 (s, 1 H), 4.52 (m, 1 H), 4.38 (m, 1 H), 3.00 (m, 2 H), 2.75–2.90 (m, 2 H), 2.60 (dd, 2 H), 2.27 (m, 4 H), 1.21 (m, 6 H), 0.83 (t, 3 H); MS (FAB) m/z (rel.

intensity) 704 (MH⁺, 99), 705 (42), 704 (99), 705 (42), 704 (99), 353 (20), 238 (35), 224 (70), 219 (27), 194 (19), 107 (28), 105 (34), 88 (49); HRMS (FAB) calcd for $C_{37}H_{41}N_3O_{11}+H_1$ 704.2819, found 704.2822.

EXAMPLE 61

(Chart BB, BB-2) 2-{4-[(2S)-2-[((2S)-2-[(3-carboxypropanoyl)amino]-3-{4-[(2,6-dichlorobenzyl)oxy]phenyl}propanoyl)amino]-3-oxo-3-(pentylamino)propyl]phenoxy}malonic acid ¹H NMR (DMSO-d₆) δ 8.10 (d, 1 H), 7.95 (d, 1 H), 7.67 (t, 1 H), 7.54 (m, 2 H), 7.45 (dd, 1 H), 7.11 (m, 4 H), 6.91 (d, 2 H), 6.81 (d, 2 H), 5.26 (s, 1 H), 5.15 (s, 2 H), 4.35 (m, 2 H), 2.98 (m, 2 H), 2.85 (m, 2 H), 2.73 (dd, 1 H), 2.62 (dd, 1 H), 2.33 (m, 4 H), 1.33–1.12 (m, 6 H), 0.81 (t, 3 H); MS (FAB) m/z (rel. intensity) 774 (MH⁺, 99), 776 (70), 775 (53), 774 (99), 391 (97), 294 (48), 161 (54), 159 (80), 149 (63), 136 (39), 88 (46); HRMS (FAB) calcd for $C_{37}H_{41}Cl_2N_3O_{11}+H_1$ 774.2196, found 774.2224.

EXAMPLE 62

(Chart BB, BB-2) 2-{4-[(2S)-2-({(2S)-3-[4-(tert-butoxy)phenyl]-2-[(3-carboxypropanoyl)amino]propanoyl}amino)-3-oxo-3-(pentylamino) propyl]phenoxy}malonic acid ¹H NMR (DMSO-d₆) δ 8.05 (d, 1 H), 7.90 (d, 1 H), 7.62 (t, 1 H), 7.10 (d, 2 H), 6.94 (d, 2 H), 6.80 (d, 2 H), 6.58 (d, 2 H), 5.26 (s, 1 H), 4.33 (m, 2 H), 2.95 (m, 2 H), 2.90–2.70 (m, 3 H), 2.51 (dd, 1 H), 2.40 (m, 9 H), 2.32 (m, 4 H), 1.35–1.10 (m, 6 H), 0.82 (t, 3 H); MS (FAB) m/z (rel. intensity) 672 (MH⁺, 2), 616 (56), 149 (99), 136 (55), 135 (67), 71 (48), 69 (48), 57 (83), 55 (60), 43 (66), 41 (48); HRMS (FAB) calcd for $C_{34}H_{45}N_3O_{11}+H_1$ 672.3132 found 672.3110.

EXAMPLE 63

(Chart BB, BB-2) 2-{4-[(2S)-2-({(2S)-2-[(3-carboxypropanoyl)amino]-3-phenylpropanoyl}amino)-3-oxo-3-(pentylamino)propyl]phenoxy}malonic acid ¹H NMR (DMSO-d₆) δ 8.10 (d, 1 H), 7.96 (d, 1 H), 7.69 (t, 1 H), 7.15 (m, 7 H), 6.80 (d, 2 H), 5.26 (s, 1 H), 4.35 (m, 2 H), 2.92 (m, 4 H), 2.71 (m, 2 H), 2.80 (m, 4 H), 1.25 (m, 6 H), 0.82 (t, 3 H); MS (FAB) m/z (rel. intensity) 600 (MH⁺, 35), 600 (35), 155 (22), 149 (50), 136 (20), 120 (99), 88 (27), 73 (32), 71 (23), 57 (34), 43 (26); HRMS (FAB) calcd for $C_{30}H_{37}N_3O_{10}+H_1$ 600.2557, found 600.2579.

EXAMPLE 64

(Chart BB, BB-2) 2-{4-[(2S)-2-{[(2S)-2-[(3-carboxypropanoyl)amino]-3-(4-methoxyphenyl)propanoyl]amino -3-oxo-3-(pentylamino)propyl]phenoxy}malonic acid ¹H NMR (DMSO-d₆) δ 8.02 (d, 1 H), 7.90 (d, 1 H), 7.64 (t, 1 H), 7.09 (m, 4 H), 6.78 (m, 4 H), 5.25 (s, 1 H), 4.35 (m, 2 H), 3.68 (s, 3 H), 2.98 (m, 2 H), 2.9–2.70 (m, 3 H), 2.60 (dd, 1 H), 2.30 (m, 4 H), 1.35–1.10 (m, 6 H), 0.82 (t, 3 H); MS (FAB) m/z (rel. intensity) 630 (MH⁺, 81), 631 (28), 630 (81), 353 (25), 250 (25), 238 (23), 177 (30), 161 (28), 150 (99), 121 (44), 88 (39); HRMS (FAB) calcd for $C_{31}H_{39}N_3O_{11}+H_1$ 630.2662 found 630.2661.

Examples 65–71 were prepared according to the general procedure described for BB-3.

EXAMPLE 65

(Chart BB, BB-3) 2-{4-[(2S)-2-({(2S)-3-(4-benzoylphenyl)-2-[(tert-butoxycarbonyl)amino]propanoyl}amino)-3-oxo-3-(pentylamino) propyl]phenoxy}malonic acid ¹H NMR (DMSO-d₆) δ 8.00 (d, 1 H), 7.88 (t, 1 H), 7.66 (m, 5 H), 7.53 (t, 2 H), 7.12 (d, 2 H), 7.00 (d, 1 H), 6.80 (d, 2 H), 5.23 (s, 1 H), 4.40 (m, 1 H), 4.30 (m, 1 H), 2.70–3.05 (m, 6 H), 1.10–1.30 (m, 15 H), 0.80 (t, 3 H); MS (FAB) m/z (rel. intensity) 704 (MH⁺, 6), 648 (30), 238 (23), 224 (49), 194 (30), 136 (20), 105 (33), 88 (99), 57 (88), 43 (24), 41 (22); HRMS (FAB) calcd for $C_{38}H_{45}N_3O_{10}+H_1$ 704.3183, found 704.3171.

EXAMPLE 66

(Chart BB, BB-3) 2-{4-[(2S)-2-[((2S)-2-[(tert-butoxycarbonyl)amino]-3-{4-[(2,6-dichlorobenzyl)oxy]phenyl}propanoyl)amino]-3-oxo-3-(pentylamino)propyl]phenoxy}malonic acid ¹H NMR (DMSO-d₆) δ 7.87 (m, 2 H), 7.53 (m, 2 H), 7.46 (m, 1 H), 7.11 (d, 2 H), 6.91 (d, 2 H), 6.89 (m, 1 H), 6.80 (d, 2 H), 5.23 (s, 1 H), 5.15 (s, 2 H), 4.40 (m, 1 H), 4.05 (m, 1 H), 2.97 (m, 2 H), 2.78 (m, 3 H), 2.60 (m, 1 H), 1.35–1.14 (m, 15 H), 0.81 (t, 3 H); MS (FAB) m/z (rel. intensity) 774 (MH⁺, 8), 296 (28), 294 (41), 238 (39), 194 (31), 161 (52), 159 (81), 136 (31), 88 (56), 57 (99), 41 (24); HRMS (FAB) calcd for $C_{38}H_{45}Cl_2N_3O_{10}+H_1$ 774.2560, found 774.2557.

EXAMPLE 67

(Chart BB, BB-3) 2-{4-[(2S)-2-({(2S)-2-[(tert-butoxycarbonyl)amino]-3-[4-(tert-butoxy)phenyl]propanoyl}amino)-3-oxo-3-(pentylamino)propyl]phenoxy}malonic acid ¹H NMR (DMSO-d₆) δ 7.90 (d, 2 H), 7.09 (t, 2 H), 6.85 (d, 1 H), 6.81 (t, 2 H), 5.23 (s, 1 H), 4.40 (m, 1 H), 4.08 (m, 1 H), 2.97 (m, 2 H), 2.77 (m, 3 H), 2.60 (m, 1 H), 1.27–1.14 (m, 24 H), 0.82 (t, J=7 Hz, 3 H); MS (FAB) m/z (rel. intensity) 672 (MH⁺, 2), 238 (25), 194 (22), 192 (19), 136 (79), 107 (39), 88 (48), 57 (99), 41 (26), 39 (23), 29 (25); HRMS (FAB) calcd for $C_{35}H_{49}N_3O_{10}+H_1$ 672.3496, found 672.3491.

EXAMPLE 68

(Chart BB, BB-3) 2-{4-[(2S)-2-{[(2S)-2-[(tert-butoxycarbonyl)amino]-3-(4-methoxyphenyl)propanoyl]amino}-3-oxo-3-(pentylamino)propyl]phenoxy}malonic acid ¹H NMR (DMSO-d₆) δ 7.85 (m, 2 H), 7.09 (m, 4 H), 6.78 (m, 5 H), 5.22 (s, 1 H), 4.40 (m, 1 H), 4.02 (m, 1 H), 3.68 (s, 3 H), 2.97 (m, 2 H), 3.90–3.70 (m, 3 H), 2.60 (m, 1 H), 1.34–1.12 (m, 15 H), 0.82 (t, 3 H); MS (FAB) m/z (rel. intensity) 630 (MH⁺, 11), 574 (24), 238 (29), 194 (31), 177 (34), 161 (29), 150 (99), 136 (24), 121 (65), 88 (64), 57 (87); HRMS (FAB) calcd for $C_{32}H_{43}N_3O_{10}+H_1$ 630.3026, found 630.3015.

EXAMPLE 69

(Chart BB, BB-3) 2-{4-[(2S)-2-({(2S)-2-[(tert-butoxycarbonyl)amino]-3-phenylpropanoyl}amino)-3-oxo-3-(pentylamino)propyl]phenoxy}malonic acid ¹H NMR (DMSO-d₆) δ 7.87 (m, 2 H), 7.17 (m, 5 H), 6.90 (d, 1 H), 6.80 (d, 2 H), 5.22 (s, 1 H), 4.41 (m, 1 H), 4.10 (m, 1 H), 2.97 (m, 2 H), 2.83 (m, 2 H), 2.70–250 (m, 2 H), 1.34–1.12 (m, 15 H), 0.82 (t, J=3 Hz, H); MS (FAB) m/z (rel. intensity) 600 (MH$^+$, 27), 600 (27), 544 (33), 238 (22), 136 (22), 133 (22), 120 (99), 88 (61), 57 (87), 43 (18), 41 (20); HRMS (FAB) calcd for $C_{31}H_{41}N_3O_9+H_1$ 600.2921, found 600.2923.

EXAMPLE 70

(Chart BB, BB-3) 2-{4-[(2S)-2-({(2S)-2-[(tert-butoxycarbonyl)amino]propanoyl}amino)-3-oxo-3-(pentylamino)propyl]phenoxy}malonic acid $^1$H NMR (DMSO-d$_6$) δ7.80 (m, 1 H), 7.69 (d, 1 H), 7.08 (d, 2 H), 6.95 (d, 1 H), 6.77 (d, 2 H), 5.22 (s, 1 H), 4.35 (m, 1 H), 3.80 (m, 1 H), 2.95 (m, 2 H), 2.95–2.85 (m, 1 H), 2.75 (m, 1 H), 1.35–1.15 (m, 15 H), 1.05 (d, 3 H), 0.82 (t, 3 H); MS (FAB) m/z (rel. intensity) 524 (MH$^+$, 13), 468 (39), 238 (25), 136 (21), 133 (20), 88 (99), 86 (19), 57 (71), 44 (58), 41 (19), 29 (18); HRMS (FAB) calcd for $C_{25}H_{37}N_3O_9+H_1$ 524.2607, found 524.2612.

EXAMPLE 71

(Chart BB, BB-3) 2-{4-[(2S)-2-({(2S)-3-[4-(benzyloxy)phenyl]-2-[tert-butoxycarbonyl)(methyl)amino]propanoyl}amino)-3-oxo-3-(pentylamino)propyl]phenoxy}malonic acid Prepared from B-4 and Boc-N-Me-Try(Bzl)-OH by general procedure for BB-3. $^1$H NMR (DMSO-d$_6$) δ7.85 (br m, 2 H), 7.35 (m, 5 H), 7.10 (m, 4 H), 7.88 (br m, 2 H), 6.78 (d, 2 H), 5.24 (s, 1 H), 5.02 (s, 2 H), 5.72 (br m, 1 H), 4.40 (br m, 1 H), 2.95 (m, 4 H), 2.80–7.70 (m, 2 H), 2.42 (br s, 3 H), 1.25 (m, 15 H), 0.83 (t, 3 H); MS (FAB) ml/z (rel. intensity) 720 (MH$^+$, 3), 620 (15), 253 (9), 241 (12), 240 (73), 238 (10), 237 (9), 91 (99), 57 (51), 41 (13), 29 (9); HRMS (FAB) calcd for $C_{39}H_{49}N_3O_{10}+H_1$ 720.3496, found 720.3511.

GENERAL PROCEDURE FOR THE PREPARATION OF BB-4 (Chart BB):

Where R6 is t-butyloxycarbonyl (Boc), the Boc group is removed with HCl/acetic acid or HCl/dioxane, and the resulting amine is acylated with the appropriate acid chloride, isocyanate, sulfonyl chloride, or carboxylic acid via standard procedures. Final saponification (as described for BB-2) affords the diacids BB-4.

EXAMPLE 72

(Chart BB, BB-4) 2-{4-[(2S)-2-[((2S)-3-(4-benzoylphenyl)-2-{[3-(4-hydroxyphenyl)propanoyl]amino}propanoyl)amino]-3-oxo-3-(pentylamino)propyl]phenoxy}malonic acid $^1$H NMR (DMSO-d$_6$) δ8.10 (d, 1 H), 8.05 (d, 1 H), 7.83 (t, 1 H), 7.65 (m, 3 H), 7.60 (m, 2 H), 7.51 (t, 2 H), 7.41 (d, 2 H), 7.11 (d, 2 H), 6.90 (d, 2 H), 6.80 (d, 2 H), 6.58 (d, 2 H), 5.24 (s, 1 H), 4.57 (m, 1 H), 4.48 (m, 1 H), 2.96 (m, 3 H), 2.80 (m, 3 H), 2.50 (m, 2 H), 2.25 (m, 2 H), 1.31–1.10 (m, 6 H), 0.79 (t, 3 H); MS (FAB) m/z (rel. intensity) 752 (MH$^+$, 45), 753 (21), 752 (45), 353 (41), 238 (25), 224 (99), 136 (23), 107 (74), 88 (39), 57 (20), 43 (19); HRMS (FAB) calcd for $C_{42}H_{45}N_3O_{10}+H_1$ 752.3183, found 752.3186.

EXAMPLE 73

(Chart BB, BB-4) 2-{4-[(2S)-2-{[(2S)-2-(acetylamino)-3-(4-benzoylphenyl)propanoyl]amino}-3-oxo-3-(pentylamino)propyl]phenoxy}malonic acid $^1$H NMR (DMSO-d$_6$) δ8.06 (d, 2 H), 7.79 (t, 1 H), 7.68 (dd, 2 H), 7.62 (m, 3 H), 7.55 (t, 2 H), 7.35 (d, 2 H), 7.10 (d, 2 H), 6.79 (d, 2 H), 5.24 (s, 1 H), 4.65 (m, 1 H), 4.38 (m, 1 H), 3.00 (m, 3 H), 2.88–3.70 (m, 3 H), 1.74 (s, 3 H), 1.33–1.10 (m, 6 H), 0.80 (t, 3 H); MS (FAB) m/z (rel. intensity) 646 (MH$^+$, 99), 647 (42), 646 (99), 353 (28), 238 (42), 224 (58), 194 (24), 136 (15), 105 (27), 88 (45), 43 (15); HRMS (FAB) calcd for $C_{35}H_{39}N_3O_9+H_1$ 646.2764, found 646.2770.

EXAMPLE 74

(Chart BB, BB-4) 2-{4-[(2S)-2-[((2S)-2-{[(tert-butylamino)carbonyl]amino}-3-phenylpropanoyl)amino]-3-oxo-3-(pentylamino)propyl]phenoxy}malonic acid $^1$H NMR (DMSO-d$_6$) 6 7.94 (d, 1 H), 7.80 (t, 1 H), 7.18 (m, 3 H), 7.08 (m, 4 H), 6.78 (d, 2 H), 5.73 (d, 1 H), 5.23 (s, 1 H), 4.35 (m, 1 H), 4.22 (m, 1 H), 2.97 (m, 2 H), 2.85 (m, 2 H), 2.65 (m, 2 H), 1.38–1.14 (m, 6 H), 1.13 (s, 9 H), 0.82 (t, 3 H); MS (FAB) m/z (rel. intensity) 599 (MH$^+$, 6), 500 (13), 247 (9), 121 (10), 120 (99), 102 (9), 88 (15), 58 (7), 57 (15), 43 (7), 41 (7); HRMS (FAB) calcd for $C_{31}H_{42}N_4O_8+H_1$ 599.3080, found 599.3088

EXAMPLE 75

(Chart BB, BB-4) 2-{4-[(2S)-2-({(2S)-2-[(methylsulfonyl)amino]-3-phenylpropanoyl}amino)-3-oxo-3-(pentylamino)propyl]phenoxy}malonic acid $^1$H NMR (DMSO-d$_6$) 6 8.33 (d, 1 H), 7.86 (t, 1 H), 7.41 (d, 1 H), 7.23 (m, 5 H), 7.14 (d, 2 H), 6.79 (d, 2 H), 5.24 (s, 1 H), 4.45 (m, 1 H), 4.01 (m, 1 H), 2.99 (m, 2 H), 2.85 (m, 2 H), 2.65 (m, 2 H), 2.20 (s, 3 H), 1.35–1.15 (m, 6 H), 0.83 (t, 3 H); MS (FAB) m/z (rel. intensity) 578 (MH+, 50), 578 (50), 238 (29), 198 (20), 136 (27), 120 (59), 119 (24), 118 (30), 91 (28), 88 (99), 43 (29); HRMS (FAB) calcd for $C_{27}H_{35}N_3O_9S+H_1$ 578.2172 found 578.2197.

EXAMPLE 76

(Chart BB, BB-4) 2-{4-[(2S)-2-[((2S)-2-{[3-(diethylamino)propanoyl]amino}-3-phenylpropanoyl)amino]-3-oxo-3-(pentylamino)propyl]phenoxy}malonic acid hydrochloride $^1$H NMR (DMSO-d6) δ8.39 (d, 1 H), 8.23 (d, 1 H), 7.86 (t, 1 H), 7.21 (m, 5 H), 7.11 (d, 2 H), 6.78 (d, 2 H), 5.25 (s, 1 H), 4.52 (m, 1 H), 4.39 (m, 1 H), 3.10 (t, 2 H), 2.95 (m, 10 H), 2.75–2.60 (m, 2 H), 1.33–1.15 (m, 6 H), 1.10 (t, 6 H), 0.82 (t, 3 H); MS (FAB) m/z (rel. intensity) 627 (MH+, 19), 627 (19), 583 (13), 123 (37), 120 (10), 105 (32), 103 (32), 91 (29), 86 (99), 58 (9), 57 (12); HRMS (FAB) calcd for $C_{33}H_{46}N_4O_8+H_1$ 627.3394, found 627.3402.

EXAMPLE 77

(Chart BB, BB-4) 2-(4-{(2S,5S)-5-benzyl-13,13-dimethyl-4,7,11-trioxo-2-[(pentylamino)carbonyl]-12-oxa-3,6,10-triazatetradec-1-yl}phenoxy)malonic acid $^1$H NMR (DMSO-d$_6$) δ8.03 (d, 1 H), 7.98 (d, 1 H), 7.76 (t, 1 H), 7.17 (m, 5 H), 7.10 (d, 2 H), 6.80 (d, 2 H), 7.60 (br s, 1 H), 5.24 (s, 1 H), 4.40 (m, 2 H), 2.98 (m, 4 H), 2.88 (m, 2 H), 3.75–3.62 (m, 2 H), 2.17 (m, 2 H), 1.34 (s, 9 H), 1.33–1.13 (M, 6 H), 0.82 (t, 3 H); MS (FAB) m/z (rel. intensity) 671 (MH+, 6), 572 (13), 571 (39), 219 (11), 191 (13 ), 136 (11), 121 (10), 120 (99), 88 (16), 57 (33), 41 (11); HRMS (FAB) calcd for $C_{34}H_{46}N_4O_{10}+H_1$ 671.3292, found 671.3300.

EXAMPLE 78

(Chart BB, BB-4) 2-{4-[(2S)-2-({(2S)-2-[(benzylsulfonyl)amino]-3-phenylpropanoyl}amino)-3-oxo-3-(pentylamino)propyl]phenoxy}malonic acid $^1$H NMR (DMSO-d$_6$) δ8.25 (d, 1 H), 7.82 (t, 1 H), 7.50 (d, 1 H), 7.23 (m, 9 H), 7.11 (m, 3 H), 6.76 (d, 2 H), 5.13 (s, 1 H), 4.45 (m, 1 H), 4.10 (m, 1 H), 3.80 (d, 1 H), 3.65 (d, 1 H), 3.90 (m, 4 H), 3.80–33.63 (m, 2 H), 1.33–1.10 (m, 6 H), 0.81 (t, 3 H); MS (FAB) m/z (rel. intensity) 654 (MH$^+$, 31), 654 (31), 210 (26), 120 (40), 91 (99), 88 (31), 69 (21), 57 (21), 55 (20), 43 (26), 41 (15); HRMS (FAB) calcd for C$_{33}$H$_{39}$N$_3$O$_9$S+H$_1$ 654.2485, found 654.2488.

EXAMPLE 79

(Chart BB, BB-4) 2-{4-[(2S)-2-({(2S)-2-[(3-methoxypropanoyl)amino]-3-phenylpropanoyl}amino)-3-oxo-3-(pentylamino)propyl]phenoxy}malonic acid $^1$H NMR (DMSO-d$_6$) δ7.98 (t, 2 H), 7.73 (br s, 1 H), 7.17 (m, 5 H), 7.08 (d, 2 H), 6.80 (d, 2 H), 5.23 (s, 1 H), 4.45 (m, 1 H), 4.35 (m, 1 H), 3.38 (m, 2 H), 3.11 (s, 3 H), 2.96 (m, 4 H), 2.72 (m, 2 H), 2.25 (m, 2 H), 1.22 (m, 6 H), 0.83 (t, 3 H); MS (FAB) m/z (rel. intensity) 586 (MH$^+$, 69), 587 (26), 586 (69), 542 (18), 353 (28), 251 (19), 234 (31), 206 (35), 121 (18), 120 (99), 88 (24); HRMS (FAB) calcd for C$_{30}$H$_{39}$N$_3$O$_9$+H$_1$ 586.2764, found 586.2757.

EXAMPLES 80##

General Synthesis of R-1, R-2, R-3 and R-4, Chart R)

GENERAL PREPARATION OF R-1: Q-4 (0.50 g, 1.0 mmol) was dissolved in a 4 M solution of HCl in dioxane (5 mL). Stirred at room temperature for 2 h. The solvent was removed under reduced pressure. The residue was dissolved in CH$_2$Cl$_2$ (5 mL) and triethylamine (0.43 mL, 3.1 mmol), and N-(tert-Butoxycarbonyl)-L-phenylalanine (0.28 g, 1.0 mmol) was added. After the mixture was cooled to 0° C., EDC (0.20 g, 1.0 mmol) and HOBT (0.14 g, 1.0 mmol) was added. The mixture was warmed to room temperature and stirred overnight. The mixture was partitioned between EtOAc and 1 M HCl. The organic phase was washed with sat. NaHCO$_3$, sat. NaCl and dried (MgSO$_4$) and concentrated to a glassy solid (0.54 g). The residue was purified by flash chromatography (40 g SiO$_2$, 60% EtOAc/heptane) to obtain 0.42 g (67%) of R-1 (R=PhCH$_2$) as a white powder. PNU-178773 $^1$H NMR (CDCl$_3$) δ7.48 (br s, 1 H), 7.30 (m, 3 H), 7.18 (m, 3 H), 6.76 (d, 1 H), 6.32 (br s, 1 H), 6.00 (br s, 1 H), 4.90 (br s, 1 H), 4.68 (s, 3 H), 4.55 (m, 1 H), 4.25 (m, 1 H), 3.88 (s, 3 H), 3.78 (s, 3 H), 3.07 (m, 4 H), 2.90 (m, 2 H), 1.40–1.20 (m, 15 H), 0.86 (t, 3 H); MS (ESI–) for C$_{33}$H$_{45}$N$_3$O$_9$ m/z 626 (M–H)$^-$; HRMS (FAB) calcd for C$_{33}$H$_{45}$N$_3$O$_9$+H$_1$ 628.3234, found 628.3233.

GENERAL PREPARATION OF R-2: R-2 was prepared by LiOH saponification of R-1 with isolation as described in the general synthesis of BB-2.

EXAMPLE 80

(Chart R, R-2) 5-[(2S)-2-({(2S)-2-[(tert-butoxycarbonyl)amino]propanoyl}amino)-3-oxo-3-(pentylamino)propyl]-2-(carboxymethoxy)benzoic acid $^1$H NMR (DMSO-d$_6$) δ7.87 (br s, 1 H), 7.54 (d, 1 H), 7.52 (br s, 1 H), 7.29 (dd, 1 H), 6.99 (d, 1 H), 6.89 (d, 1 H), 4.71 (s, 2 H), 4.39 (m, 1 H), 3.84 (m, 1 H), 2.97 (m, 3 H), 2.77 (m, 1 H), 1.40–1.15 (m, 15 H), 1.07 (d, 3 H), 0.84 (t, 3 H); MS (ESI–) for C$_{25}$H$_{37}$N$_3$O$_9$ m/z 522 (M–H)$^-$; MS (FAB) m/z (rel. intensity) 524 (MH$^+$, 1), 546 (45), 525 (22), 446 (16), 425 (23), 424 (99), 88 (60), 57 (56), 44 (46), 41 (18), 29 (17); HRMS (FAB) calcd for C$_{25}$H$_{37}$N$_3$O$_9$+NA$_1$ 546.2427, found 546.2438.

EXAMPLE 81

(Chart R, R-2) 5-[(2S)-2-({(2S)-2-[(tert-butoxycarbonyl)amino]-3-phenylpropanoyl}amino)-3-oxo-3-(pentylamino)propyl]-2-(carboxymethoxy)benzoic acid $^1$H NMR (DMSO-d$_6$) δ7.92 (br s, 1 H), 7.54 (br s, 1 H), 7.30 (d, 1 H), 7.18 (m, 6 H), 6.90 (d, 1 H), 4.68 (s, 2 H), 4.40 (m, 1 H), 4.05 (m, 1 H), 2.98 (m, 2 H), 2.83 (m, 2 H), 2.65 (m, 2 H), 1.33–1.10 (m, 15 H), 0.82 (t, 3 H); MS (FAB) m/z (rel. intensity) 600 (MH$^+$, 21), 622 (15), 600 (21), 501 (30), 500 (99), 238 (11), 120 (73), 88 (34), 57 (52), 43 (12), 41 (14); HRMS (FAB) calcd for C$_{31}$H$_{41}$N$_3$O$_9$+H$_1$ 600.2921, found 600.2923.

GENERAL PREPARATION OF R-3: R-3 was prepared by removal of the Boc group from R-1 with HCl/dioxane followed by coupling with the appropriate carboxylic acid with EDC and HOBT as described for R-1. Final saponification then affords R-3.

EXAMPLE 82

(Chart R, R-3) 2-(carboxymethoxy)-5-[(2S)-2-({(2S)-2-[(3-carboxypropanoyl)amino]-3-phenylpropanoyl}amino)-3-oxo-3-(pentylamino)propyl]benzoic acid $^1$H NMR (DMSO-d$_6$) δ8.10 (d, 1 H), 8.00 (d, 1 H), 7.78 (t, 1 H), 7.53 (d, 1 H), 7.29 (dd, 1 H), 7.16 (m, 5 H), 6.90 (d, 1 H), 4.71 (s, 2 H), 4.37 (m, 2 H), 2.95 (m, 4 H), 2.70 (m, 2 H), 2.29 (m, 4 H), 1.35–1.15 (m, 6 H), 0.82 (t, 3 H); MS (FAB) m/z (rel. intensity) 600 (MH$^+$, 20), 600 (20), 353 (12), 248 (11), 238 (12), 220 (15), 131 (9), 121 (10), 120 (99), 88 (32), 43 (11); HRMS (FAB) calcd for C$_{30}$H$_{37}$N$_3$O$_{10}$+H$_1$ 600.2557, found 600.2564.

EXAMPLE 83

(Chart R, R-3) 2-(carboxymethoxy)-5-[(2S)-2-[((2S)-2-{[2-(1H-indol-3-yl)acetyl]amino}-3-phenylpropanoyl)amino]-3-oxo-3-(pentylamino)propyl]benzoic acid $^1$H NMR (DMSO-d$_6$) δ8.09 (d, 1 H), 7.97 (d, 1 H), 7.88 (t, 1 H), 7.53 (br s, 1 H), 7.31 (m, 3 H), 7.14 (br s, 5 H), 7.01 (m, 2 H), 6.90 (t, 2 H), 4.71 (s, 2 H), 4.48 (m, 1 H), 4.39 (m, 1 H), 3.46 (d, 2 H), 2.97 (m, 4 H), 2.75 (m, 2 H), 1.35–1.15 (m, 6 H), 0.84 (t, 3 H); MS (ESI–) for C$_{36}$H$_{40}$N$_4$O$_8$MS m/z 655 (M–H)$^-$; MS (EI) m/z (rel. intensity) 304 (67), 157 (62), 131 (59), 130 (99), 128 (37), 117 (46), 103 (52), 91 (94), 77 (68), 55 (37); HRMS (FAB) calcd for C$_{36}$H$_{40}$N$_4$O$_8$+H$_1$ 657.2924, found 657.2894.

EXAMPLE 84

(Chart R, R-3) 2-(carboxymethoxy)-5-[(2S)-3-oxo-3-(pentylamino)-2-({(2S )-3-phenyl-2-[(2-phenylacetyl)amino]propanoyl}amino)propyl]benzoic acid $^1$H NMR (DMSO-d$_6$) δ8.20 (d, 1 H), 8.10 (d, 1 H), 7.90 (t, 1 H), 7.55 (d, 1 H), 7.29 (dd, 1 H), 7.18 (m, 8 H), 6.90

(d, 2 H), 6.90 (d, 1 H), 4.71 (s, 2 H), 4.45 (m, 2 H), 3.33 (m, 2 H), 2.97 (m, 4 H), 2.73 (m, 2 H), 1.35–1.15 (m, 6 H), 0.85 (t, 3 H); MS (ESI−) for $C_{34}H_{39}N_3O_8$ m/z 616 (M−H)$^−$; MS (EI) m/z (rel. intensity) 265 (40), 120 (56), 118 (26), 117 (29), 92 (50), 91 (99), 89 (30), 77 (28), 65 (54), 51 (25); HRMS (FAB) calcd for $C_{34}H_{39}N_3O_8+H_1$ 618.2815, found 618.2799.

EXAMPLE 85

(Chart R, R-3) 2-(carboxymethoxy)-5-[(2S)-3-oxo-3-(pentylamino)-2-({(2S)-3-phenyl-2-[(4-phenylbutanoyl)amino]propanoyl}amino) propyl]benzoic acid $^1$H NMR (DMSO-d$_6$) δ8.00 (br d, 2 H), 7.90 (br s, 1 H), 7.55 (br s, 1 H), 7.20 (m, 11 H), 6.90 (br d, 1 H), 4.70 (s, 2 H), 4.45 (m, 2 H), 2.97 (m, 4 H), 2.75 (m, 2 H), 2.36 (t, 2 H), 2.03 (t, 2 H), 1.62 (m, 2 H), 1.36–1.10 (m, 6 H), 0.83 (t, 3 H); MS (ESI−) for $C_{36}H_{43}N_3O_8$ m/z 644 (M−H)$^−$; MS (EI) m/z (rel. intensity) 189 (41), 120 (63), 119 (82), 104 (41), 91 (93), 73 (49), 65 (50), 64 (99), 63 (73), 59 (35); HRMS (FAB) calcd for $C_{36}H_{43}N_3O_8+H_1$ 646.3128, found 646.3113.

EXAMPLE 86

(Chart R, R-3) 5-[(2S)-2-{[(2S)-2-(acetylamino)-3-phenylpropanoyl]amino}-3-oxo-3-(pentylamino)propyl]-2-(carboxymethoxy)benzoic acid $^1$H NMR (DMSO-d$_6$) δ8.04 (m, 2 H), 7.84 (t, 1 H), 7.53 (d, 1 H), 7.30 (dd, 1 H), 7.19 (m, 5 H), 6.91 (d, 1 H), 4.71 (m, 2 H), 2.95 (m, 4 H), 2.70 (m, 2 H), 1.73 (s, 3 H), 1.35–1.15 (m, 6 H), 0.85 (t, 3 H); MS (ESI-) for $C_{28}H_{35}N_3O_8$ m/z 540 (M−H)$^−$; MS (EI) m/z (rel. intensity) 120 (22), 91 (99), 86 (14), 73 (82), 65 (18), 59 (17), 58 (18), 57 (15), 55 (17), 51 (19); HRMS (FAB) calcd for $C_{28}H_{35}N_3O_8+H_1$ 542.2502, found 542.2507.

EXAMPLE 87

(Chart R, R-3) 2-(carboxymethoxy)-5-[(2S)-2-({(2S)-2-[(3-methoxypropanoyl)amino]-3-phenylpropanoyl}amino)-3-oxo-3-(pentylamino)propyl]benzoic acid $^1$H NMR (DMSO-d$_6$) δ8.01 (d, 2 H), 7.85 (t, 1 H), 7.52 (d, 1 H), 7.30 (dd, 1 H), 7.22 (m, 5 H), 6.93 (d, 1 H), 4.69 (s, 2 H), 4.02 (m, 2 H), 3.39 (t, 2 H), 3.12 (s, 3 H), 2.96 (m, 4 H), 2.76 (m, 2 H), 2.27 (t, 2 H), 1.37–1.15 (m, 6 H), 0.85 (t, 3 H); MS (ESI−) for $C_{30}H_{39}N_3O_9$ m/z 584 (M−H)$^−$; MS (EI) m/z (rel. intensity) 120 (72), 119 (30), 91 (95), 86 (54), 84 (78), 73 (33), 57 (34), 55 (51), 51 (99), 50 (34); HRMS (FAB) calcd for $C_{30}H_{39}N_3O_9+H_1$ 586.2764, found 586.2757.

EXAMPLE 88

(Chart R, R-3) 2-(carboxymethoxy)-5-[(2S)-2-({(2S)-2-[(4-hydroxybutanoyl)amino]-3-phenylpropanoyl}amino)-3-oxo-3-(pentylamino)propyl]benzoic acid $^1$H NMR (DMSO-d$_6$) δ7.99 (m, 2 H), 7.86 (br s, 1 H), 7.53 (d, 1 H), 7.31 (m, 1 H), 7.19 (m, 5 H), 6.90 (d, 1 H), 4.71 (s, 2 H), 4.40 (m, 2 H), 3.30 (m, 2 H), 2.95 (m, 4 H), 2.72 (m, 2 H), 2.05 (m, 2 H), 1.50 (m, 2 H), 1.38–1.15 (m, 6 H), 0.84 (t, 3 H); MS (ESI−) for $C_{30}H_{39}N_3O_9$ m/z 584 (M−H)$^−$; MS (FAB) m/z (rel. intensity) 586 (MH$^+$, 1), 587 (15), 188 (11), 131 (10), 120 (99), 118 (18), 88 (21), 79 (14), 77 (11), 59 (10), 43 (14); HRMS (FAB) calcd for $C_{30}H_{39}N_3O_9+H_1$ 586.2764, found 586.2791.

EXAMPLE 89

(Chart R, R-3) 5-{(2S,5S)-5-benzyl-13,13-dimethyl-4,7,11-trioxo-2-[(pentylamino)carbonyl]-12-oxa-3,6,10-triazatetradec-1-yl}-2-(carboxymethoxy)benzoic acid $^1$H NMR (DMSO-d$_6$) δ8.03 (t, 1 H), 7.86 (t, 1 H), 7.56 (d, 1 H), 7.30 (dd, 1 H), 7.21 (m, 5 H), 6.92 (d, 1 H), 6.58 (br s, 1 H), 4.72 (s, 2 H), 4.42 (m, 2 H), 2.95 (m, 6 H), 2.73 (m, 2 H), 2.17 (m, 2 H), 1.36 (s, 9 H), 1.35–1.15 (m, 6 H), 0.84 (t, 3 H); MS (ESI−) for $C_{34}H_{46}N_4O_{10}$ m/z 669 (M−H)$^−$; MS (FAB) m/z (rel. intensity) 671 (MH$^+$, 2), 673 (16), 672 (38), 573 (24), 572 (67), 133 (12), 121 (12), 120 (99), 89 (17), 88 (20), 57 (24); HRMS (FAB) calcd for $C_{34}H_{46}N_4O_{10}+H_1$ 671.3292, found 671.3324.

EXAMPLE 90

(Chart R, R-3) 5-{(2S,5S)-5-benzyl-4,7,11,11-tetraoxo-2-[(pentylamino)carbonyl]-11lambda~6~-thia-3,6,10-triazadodec-1-yl}-2-(carboxymethoxy)benzoic acid $^1$H NMR (DMSO-d$_6$) δ8.10 (m, 2 H), 7.85 (t, 1 H), 7.56 (d, 1 H), 7.32 (dd, 1 H), 7.20 (m, 5 H), 6.90 (m, 2 H), 4.72 (s, 2 H), 4.45 (m, 2 H), 2.98 (m, 6 H), 2.82 (s, 3 H), 2.71 (m, 2 H), 2.27 (m, 2 H), 1.35–1.15 (m, 6 H), 0.85 (t, 3 H); MS (ESI−) for $C_{30}H_{40}N_4)_{10}S$ m/z 647 (M−H)$^−$; MS (FAB) m/z (rel. intensity) 649 (MH$^+$, 41), 650 (15), 649 (41), 297 (14), 269 (25), 133 (15), 131 (12), 120 (99), 88 (30), 79 (40), 43 (18); HRMS (FAB) calcd for $C_{30}H_{40}N_4O_{10}S+H_1$ 649.2543, found 649.2544.

EXAMPLE 91

(Chart R, R-3) 2-(carboxymethoxy)-5-[(2S)-2-[((2S)-2-{[2-(3-hydroxyphenyl)acetyl]amino}-3-phenylpropanoyl)amino]-3-oxo-3-(pentylamino)propyl]benzoic acid $^1$H NMR (DMSO-d$_6$) δ8.10 (m, 2 H), 7.86 (t, 1 H), 7.55 (d, 1 H), 7.30 (d, 1 H), 7.16 (m, 5 H), 7.00 (t, 1 H), 6.90 (d, 1 H), 6.59 (m, 2 H), 6.49 (d, 1 H), 4.72 (s, 2 H), 7.42 (m, 2 H), 3.32 (m, 2 H), 2.95 (m, 4 H), 2.75 (m, 2 H), 1.35–1.15 (m, 6 H), 0.85 (t, 3 H); MS (ESI+) for $C_{34}H_{39}N_3O_9$ m/z 634 (M+H)$^+$; MS (FAB) m/z (rel. intensity) 634 (MH$^+$, 7), 120 (99), 107 (31), 91 (27), 74 (46), 69 (28), 57 (29), 55 (28); HRMS (FAB) calcd for $C_{34}H_{39}N_3O_9+H_1$ 634.2764, found 634.2787.

EXAMPLE 92

(Chart R, R-3) 2-(carboxymethoxy)-5-[(2S)-2-[((2S)-2-{[2-(4-hydroxyphenyl)acetyl]amino}-3-phenylpropanoyl)amino]-3-oxo-3-(pentylamino)propyl]benzoic acid $^1$H NMR (DMSO-d$_6$) δ8.05 (t, 2 H), 7.86 (t, 1 H), 7.55 (d, 1 H), 7.30 (dd, 1 H), 7.17 (m, 5 H), 6.91 (d, 1 H), 6.84 (d, 2 H), 6.58 (d, 2 H), 4.72 (s, 2 H), 4.45 (m, 2 H), 3.35 (m, 2 H), 2.98 (m, 4 H), 2.75 (m, 2 H), 1.35–1.15 (m, 6 H), 0.85 (t, 3 H); MS (ESI+) for $C_{34}H_{39}N_3O_9$ m/z 634 (M+H)$^+$; MS (FAB) m/z (rel. intensity) 634 (MH$^+$, 10), 219 (15), 120 (99), 107 (32), 91 (20), 88 (22), 57 (16), 55 (13), 43 (22), 41 (15), 23 (19); HRMS (FAB) calcd for $C_{34}H_{39}N_3O_9+H_1$ 634.2764, found 634.2769.

EXAMPLE 93

(Chart R, R-3) 2-(carboxymethoxy)-5-[(2S)-2-[((2S)-2-{[2-(4-methylphenyl)acetyl]amino}-3-phenylpropanoyl)amino]-3-oxo-3-(pentylamino) propyl]benzoic acid $^1$H NMR (DMSO-$d_6$) δ 8.11 (d, 1 H), 8.06 (d, 1 H), 7.86 (t, 1 H), 7.55 (d, 1 H), 7.28 (dd, 1 H), 7.18 (m, 5 H), 7.00 (d, 2 H), 6.92 (m, 3 H), 4.71 (s, 2 H), 4.42 (m, 2 H), 3.33 (m, 2 H), 2.98 (m, 4 H), 2.73 (m, 3 H), 2.24 (s, 3 H), 1.35–1.15 (m, 6 H), 0.85 (t, 3 H); MS (FAB) m/z (rel. intensity) 632 (MH$^+$, 25), 632 (25), 280 (13), 252 (13), 121 (12), 120 (99 ), 105 (57), 103 (12), 91 (15), 88 (15), 23 (14); HRMS (FAB) calcd for $C_{35}H_{41}N_3O_8+H_1$ 632.2972, found 632.2980.

EXAMPLE 94

(Chart R, R-3) 2-(carboxymethoxy)-5-((2S)-3-oxo-3-(pentylamino)-2-{[(2S)-3-phenyl-2-({2-[4-(trifluoromethyl)phenyl]acetyl amino) propanoyl] amino}propyl)benzoic acid $^1$H NMR (DMSO-$d_6$) δ 8.32 (d, 1 H), 8.13 (d, 1 H), 7.87 (t, 1 H), 7.57 (m, 3 H), 7.28 (m, 3 H), 7.16 (m, 5 H), 6.90 (d, 1 H), 4.72 (s, 2 H), 4.51 (m, 1 H), 4.41 (m, 1 H), 4.48 (m, 2 H), 2.98 (m, 4 H), 2.75 (m, 2 H), 1.35–1.15 (m, 6 H), 0.84 (t, 3 H); MS (FAB) m/z (rel. intensity) 686 (MH$^+$, 28), 686 (28), 159 (23), 139 (36), 121 (17), 120 (99), 105 (25), 103 (26), 91 (30), 88 (26), 23 (19); HRMS (FAB) calcd for $C_{35}H_{38}F_3N_3O_8+H_1$ 686.2689, found 686.2719.

EXAMPLE 95

(Chart R, R-3) 2-(carboxymethoxy)-5-[(2S)-2-[((2S)-2-{[2-(4-methoxyphenyl)acetyl]amino}-3-phenylpropanoyl)amino]-3-oxo-3-(pentylamino) propyl]benzoic acid $^1$H NMR (DMSO-$d_6$) δ 8.08 (t, 2 H), 7.86 (t, 1 H), 7.55 (d, 1 H), 7.29 (dd, 1 H), 7.17 (m, 5 H), 6.98 (d, 2 H), 6.89 (d, 1 H), 6.76 (d, 2 H), 4.71 (s, 2 H), 4.43 (m, 2 H), 3.70 (s, 3 H), 3.20 (m, 2 H), 2.98 (m, 4 H), 2.75 (m, 2 H), 1.35–1.15 (m, 6 H), 0.85 (t, 3 H); MS FAB) m/z (rel. intensity) 648 (MH$^+$, 28), 648 (28), 148 (16), 139 (29), 123 (18), 121 (83), 120 (99), 105 (21), 103 (21), 91 (25), 88 (16); HRMS (FAB) calcd for $C_{35}H_{41}N_3O_9+H_1$ 648.2921, found 648.2915.

EXAMPLE 96

(Chart R, R-3) 2-(carboxymethoxy)-5-[(2S)-3-oxo-3-(pentylamino)-2-({(2S)-3-phenyl-2-[(3-phenylpropanoyl)amino]propanoyl}amino)propyl] benzoic acid $^1$H NMR (DMSO-$d_6$) δ 8.03 (t, 2 H), 7.85 (t, 1 H), 7.56 (d, 1 H), 7.31 (dd, 1 H), 7.14 (m, 10 H), 6.91 (d, 1 H), 4.71 (s, 2 H), 4.45 (m, 2 H), 2.96 (m, 4 H), 2.72 (m, 4 H), 2.32 (t, 2 H), 1.35–1.15 (m, 6 H), 0.84 (t, 3 H); MS (ESI–) for $C_{35}H_{41}N_3O_8$ m/z 630 (M–H)$^-$; MS (FAB) m/z (rel. intensity) 632 (MH$^+$, 3), 634 (15), 633 (38), 353 (7), 335 (6), 280 (12), 252 (10), 131 (7), 120 (99), 88 (18), 79 (17); HRMS (FAB) calcd for $C_{35}H_{41}N_3O_8+H_1$ 632.2972, found 632.2986.

EXAMPLE 97

(Chart R, R-4) 2-(carboxymethoxy)-5-{(2S)-3-oxo-3-(pentylamino)-2-[(3-phenylpropanoyl)amino] propyl}benzoic acid Prepared from Q-4 and hydrocinnamic acid according to the general procedure for R-1.

$^1$H NMR (DMSO-$d_6$) δ 8.08 (d, 1 H), 7.91 (t, 1 H), 7.55 (d, 1 H), 7.19 (m, 3 H), 7.13 (t, 3 H), 6.87 (d, 1 H), 4.70 (s, 2 H), 4.40 (m, 1 H), 2.98 (m, 2 H), 2.85 (dd, 1 H), 2.68 (m, 3 H), 2.32 (t, 2 H), 1.35–1.15 (m, 6 H), 0.83 (t, 3 H); MS (FAB) m/z (rel. intensity) 485 (MH$^+$, 99), 971 (10), 970 (16), 638 (8), 486 (30), 485 (99), 398 (9), 238 (23), 105 (8), 91 (11), 88 (70); HRMS (FAB) calcd for $C_{26}H_{32}N_2O_7+H_1$ 485.2288, found 485.2303.

EXAMPLE 98

PNU-176703 (Chart S, S-4) 2-{4-[2-({(2S)-3-(4-benzoylphenyl)-2-[(3-carboxypropanoyl)amino] propanoyl}amino)ethyl]phenoxy}malonic acid PREPARATION OF S-2: To a suspension of N-(tert-Butoxycarbonyl)tyramine (S-1, 0.20 g, 0.84 mmol) and $K_2CO_3$ (0.23 g, 1.7 mmol) in acetone (3 mL) was added diethyl chloromalonate (0.27 mL, 1.7 mmol). The mixture was stirred vigorously at room temperature for 24 h. The mixture was partitioned between EtOAc and $H_2O$. The organic phase was washed with sat. NaCl and dried ($MgSO_4$). After the solvent was removed, the residue was purified by flash chromatography (45 g $SiO_2$, 3% EtOAc/$CH_2Cl_2$) to provide 0.24 g of S-2 as a colorless oil.

$^1$H NMR (CDCl$_3$) δ 7.11 (d, 2 H), 6.90 (d, 2 H), 5.16 (s, 1 H), 4.51 (br s, 1 H), 4.32 (m, 4 H), 3.33 (q, 2 H), 2.73 (t, 2 H), 1.42 (s, 9 H), 1.30 (t, 6 H); MS (ESI–) for $C_{20}H_{29}NO_7$ m/z 394 (M–H)$^-$.

PREPARATION OF S-3: S-2 (239 mg, 0.6 mmol) was dissolved in 1 M HCl/acetic acid (4 mL) and stirred at room temperature for 4 h. The solvent was removed under reduced pressure. The residue was dissolved in $CH_2Cl_2$ (2 mL), and triethylamine (0.25 mL, 1.8 mmol) and Boc-p-Bz-Phe-OH (222 mg, 0.60 mmol) was added. The mixture was cooled to 0° C., and EDC (115 mg, 0.6 mmol) and HOBT (81 mg, 0.6 mmol) was added. The mixture was warmed to room temperature and stirred overnight. The mixture was partitioned between EtOAc and 1 M HCl. The organic phase was washed with sat. $NaHCO_3$, sat. NaCl, and dried ($MgSO_4$). After the solvent was removed under reduced pressure, the residue was purified by flash chromatography (25 g $SiO_2$, 15% EtOAc/$CH_2Cl_2$) to provide 108 mg of S-3 as a colorless glass.

$^1$H NMR CDCl$_3$) δ 7.76 (t, 4 H), 7.59 (t, 1 H), 7.46 (t, 2 H), 7.31 (d, 2 H), 7.01 (d, 2 H), 6.87 (d, 2 H), 5.90 (br s, 1 H), 5.16 (s, 1 H), 4.95 (br s, 1 H), 4.30 (q, 4 H), 3.40 (m, 2 H), 3.12 (m, 2 H), 2.66 (m, 2 H), 1.40 (s, 9 H), 1.30 (t, 6 H); MS (ESI–) for $C_{36}H_{42}N_2O_9$ m/z 645 (M–H)$^-$.

PREPARATION OF S-4: S-3 (108 mg, 0.17 mmol) was dissolved in 1 M HCl/acetic acid (2 mL) and stirred at room temperature for 3 h. The solvent was removed under reduced pressure. The residue was dissolved in $CH_2Cl_2$ (2 mL) and triethylamine (70 μL, 0.51 mmol). The mixture was cooled to 0° C., and succinic anhydride (17 mg, 0.17 mmol) was added. The mixture was warmed to room temperature and stirred overnight. The mixture was partitioned between EtOAc and 1 M HCl. The organic phase was washed with sat. NaCl, dried ($MgSO_4$), and concentrated. The residue was dissolved in THF (3 mL), and a solution of LiOH.$H_2O$ (28 mg, 0.68 mmol) in $H_2O$ (1 mL) was added. The mixture was stirred at room temperature for 3 h. The mixture was acidified (1 M HCl) and extracted with EtOAc. The organic phase was washed sat. NaCl and dried ($MgSO_4$). The solvent was removed in vacuo to provide 89 mg of S-4 as an off-white solid.

$^1$H NMR (DMSO-$d_6$) δ 8.18 (d, 1 H), 8.04 (t, 1 H), 7.65 (m, 5 H), 7.55 (t, 2 H), 7.37 (d, 2 H), 7.10 (d, 2 H), 6.82 (d,

2 H), 5.28 (s, 1 H), 4.45 (m, 1 H), 3.22 (m, 2 H), 3.03 (dd, 1 H), 2.80 (dd, 1 H), 2.57 (t, 2 H), 2.31 (m, 4 H); MS (FAB) m/z (rel. intensity) 591 (MH$^+$, 27), 591 (27), 391 (83), 149 (99), 113 (29), 71 (48), 69 (37), 57 (74), 55 (39), 43 (52), 41 (35); HRMS (FAB) calcd for $C_{31}H_{30}N_2O_{10}$+$H_1$ 591.1978, found 591.1981.

EXAMPLE 99

(Chart A, A-5) 2-[4-((2S)-2-[(3-carboxypropanoyl) amino]-3-{[(1S)-1-(hydroxymethyl)-3-methylbutyl] amino}-3-oxopropyl)phenoxy]malonic acid Prepared by the general procedure described for A-5.

$^1$H NMR (DMSO-d$_6$) δ7.99 (d, 1 H), 7.43 (d, 1 H), 7.11 (d, 2 H), 6.78 (d, 2 H), 5.25 (s, 1 H), 4.35 (m, 1 H), 7.72 (m, 1 H), 3.25 (dd, 1 H), 3.12 (dd, 1 H), 2.87 (dd, 1 H), 2.65 (dd, 1 H), 2.31 (m, 4 H), 1.52 (m, 1 H), 1.26 (m, 2 H), 0.82 (q, 6 H); MS (FAB) m/z (rel. intensity) 483 (MH+, 91), 484 (22), 483 (91), 139 (25), 123 (18), 118 (99), 105 (17), 103 (15), 91 (18), 86 (16), 55 (15); HRMS (FAB) calcd for $C_{22}H_{30}N_2O_{10}$+$H_1$ 483.1978, found 483.1999.

Examples 100–113 were prepared according to the general procedure described for BB-3.

EXAMPLE 100

(Chart BB, BB-3) 2-{4-[(2S)-2-({(2S)-2-[(tert-butoxycarbonyl)amino]-3-phenylpropanoyl}amino)-3-oxo-3-(pentylamino)propyl]phenoxy}malonic acid $^1$H NMR (DMSO-d$_6$) δ8.22 (bd, J=8 Hz, 1 H), 7.8 (bt, 1 H), 7.0–7.3 (m, 7 H), 6.80 (d overlapping m, J=8 Hz, 3 H), 5.21 (s, 1 H); 4.39 (m, 1 H), 4.15 (m, 1 H), 2.6–3.1 (m, 6 H), 1.1–1.4 (m, 6 H), 1.31 (s, 9 H), 0.86 (t, J=7 Hz, 3 H).

EXAMPLE 101

(Chart BB, BB-3) 2-{4-[(2S)-2-({(2R)-3-(benzylsulfanyl)-2-[(tert-butoxycarbonyl)amino] propanoyl}amino)-3-oxo-3-(pentylamino)propyl] phenoxy}malonic acid $^1$H NMR (DMSO-d$_6$) δ7.98 (d, J=8 Hz, 1 H), 7.85 (bt, J=6 Hz, 1 H), 7.15–7.3 (m, 5 H), 7.07 (d, J=8Hz, 2 H), 6.76 (d, J=8Hz, 2 H), 5.22 (s, 1 H), 4.38 (m, 1 H), 4.12 (m, 1 H), 3.71 (bs, 2 H), 2.4–3.0 (m, 6 H), 1.1–1.4 (m, 6 H), 1.38 (s, 9 H), 0.81 (t, J=7 Hz, 3 H);

MS (FAB) m/z (rel. intensity) 646 (MH$^+$, 11), 590 (16), 546 (21), 238 (17), 194 (18), 166 (22), 136 (27), 91 (99), 88 (69), 57 (60), 43 (16).

HRMS (FAB) calcd for $C_{32}H_{43}N_3O_9S$ +$H_1$ 646.2798, found 646.2769.

EXAMPLE 102

(Chart BB, BB-3) 2-{4-[(2S)-2-{[(2S)-2-[(tert-butoxycarbonyl)amino]-3-(2-naphthyl)propanoyl] amino}-3-oxo-3-(pentylamino)propyl] phenoxy}malonic acid $^1$H NMR (DMSO-d$_6$) δ7.99 (bd, J=8 Hz, 1 H), 7.8 (m, 3 H), 7.66 (bs, 1 H), 7.3–7.5 (m, 3 H), 7.1 (d, J=8Hz, 2 H), 6.80 (d, J=8Hz, 2 H), 5.24 (s, 1 H), 4.17 (m, 1 H), 2.7–3.1 (m, 6 H), 1.1-1.4 (m, 6 H), 1.22 (s, 9 H), 0.82 (t, J=7 Hz, 3 H);

Anal. Calcd for $C_{35}H_{43}N_3O_9$: C, 64.70; H, 6.67; N, 6.47. Found: C, 64.76; H, 6.86; N, 6.14.

MS (ESI–) for $C_{35}H_{43}N_3O_9$ m/z 648 (M–H)$^-$.

EXAMPLE 103

(Chart BB, BB-3) 2-{4-[(2S)-2-{[(2S)-2-[(tert-butoxycarbonyl)amino]-3-(1-naphthyl)propanoyl] amino}-3-oxo-3-(pentylamino)propyl] phenoxy}malonic acid $^1$H NMR (DMSO-d$_6$) δ8.08 (bd, J=8 Hz, 1 H), 7.9 (m, 2 H), 7.75 (d, J=7 Hz, 1 H), 7.5 (m, 2 H), 7.35 (t, J=7 Hz, 1 H), 7.25 (m, 1 H), 7.15 (d, J=8 Hz, 2 H), 6.82 (d, J=8 Hz, 2 H), 5.24 (s, 1 H), 4.44 (m, 1 H), 4.2 (m, 1 H), 2.7–3.1 (m, 6 H), 1.1–1.4 (m, 6 H), 1.22 (s, 9 H), 0.82 (t, J=7Hz, 3 H);

MS (FAB) m/z (rel. intensity) 650 (MH+, 37), 606 (38), 391 (27), 294 (83), 170 (80), 153 (90), 141 (39), 136 (27), 88 (83), 57 (99).

Anal. Calcd for $C_{35}H_{43}N_3O_9$.0.6 $H_2O$ C, 63.64; H, 6.75; N, 6.36. Found: C, 63.94; H, 6.86; N, 5.97.

EXAMPLE 104

(Chart BB, BB-3) 2-{4-[(2S)-2-({(2S)-6-{[(benzyloxy)carbonyl]amino}-2-[(tert-butoxycarbonyl)amino]hexanoyl}amino)-3-oxo-3-(pentylamino)propyl]phenoxy}malonic acid $^1$H NMR (DMSO-d$_6$) δ7.82 (bt, J=7 Hz, 1 H), 7.72 (d, J=8 Hz, 1 H), 7.32 (m, 5 H), 7.17 (bt, J=6 Hz, 1 H), 7.08 (d, J=8 Hz, 2 H), 6.87 (d, J=7 Hz, 1 H), 6.78 (d, J=8 Hz, 2 H), 5.22 (s, 1 H), 4.98 (s, 2 H), 4.35 (m, 1 H), 3.77 (m, 1 H), 2.7–3.1 (m, 6 H), 1.1–1.5 (m, 12 H), 1.35 (s, 9 H), 0.82 (t, J=7Hz, 3 H);

MS (FAB) m/z (rel. intensity) 715 (MH$^+$, 5), 615 (10), 133 (8), 92 (9), 91 (99), 88 (16), 84 (24), 57 (31), 43 (6), 41 (8), 29 (7).

HRMS (FAB) calcd for $C_{36}H_{50}N_4O_{11}$+$H_1$ 715.3554, found 715.3562.

Anal. Calcd for $C_{36}H_{50}N_4O_{11}$.1.2 $H_2O$: C, 58.72; H, 7.17; N, 7.61. Found: C, 58.68; H, 7.05; N, 7.35.

EXAMPLE 105

(Chart BB, BB-3)2-{4-[(2S)-2–1[(2S)-2-[(tert-butoxycarbonyl)amino]-4-(methylsulfanyl)butanoyl] amino}-3-oxo-3-(pentylamino)propyl] phenoxy}malonic acid $^1$H NMR (DMSO-d$_6$) δ7.84 (bt, J=6 Hz, 1 H), 7.75 (d, J=8 Hz, 1 H), 7.09 (d, J=8 Hz, 2 H), 6.77 (d, J=8Hz, 2 H), 7.01 (d, J=7Hz, 1 H), 5.21 (s, 1 H), 4.38 (m, 1 H), 3.90 (m, 1 H), 2.7–3.1 (m, 4 H), 2.31 (bt, J=7 Hz, 2 H), 1.97 (s, 3 H), 1.66 (m, 2 H), 1.1–1.4 (m, 6 H), 1.35 (s, 9 H), 0.82 (t, J=7 Hz, 3 H);

MS (FAB) m/z (rel. intensity) 584 (MH$^+$, 12), 484 (33), 238 (29), 194 (30), 104 (68), 88 (99), 61 (43), 57 (99), 56 (33), 43 (26), 41 (31).

HRMS (FAB) calcd for $C_{27}H_{41}N_3O_9S$+$H_1$ 584.2642, found 584.2620.

EXAMPLE 106

(Chart BB, BB-3) 2-{4-[(2S)-2–1 [(2S)-2-[(tert-butoxycarbonyl)amino]-4-(methylsulfinyl)butanoyl] amino}-3-oxo-3-(pentylamino)propyl] phenoxy}malonic acid $^1$H NMR (DMSO-d$_6$) δ7.9 (bm, 2 H), 7.10 (d, J=8 Hz, 2 H), 7.05 (bm, 1 H), 6.78 (d, J=8 Hz, 2 H), 5.23 (s, 1 H), 4.4 (m, 1 H), 3.95 (m, 1 H), 2.5–3.1 (m, 6 H), 2.47 (s, 3 H), 1.8 (m, 2 H), 1.1–1.4 (m, 6 H), 1.36 (s, 9 H), 0.82 (t, J=7Hz, 3 H);

MS (FAB) m/z (rel. intensity) 600 (M⁺, 48), 556 (41), 500 (40), 100 (30), 88 (50), 59 (64), 57 (71), 56 (99), 41 (32).

Anal. Calcd for $C_{27}H_{41}N_3O_{10}S \cdot 0.6\ H_2O$: C, 53.12; H, 6.97; N, 6.88. Found: C, 53.13; H, 6.95; N, 6.72.

EXAMPLE 107

(Chart BB, BB-3) 2-{4-[(2S)-2-{[(2S)-2-[(tert-butoxycarbonyl)amino]-3-(2,3,4,5,6-pentafluorophenyl)propanoyl]amino}-3-oxo-3-(pentylamino)propyl]phenoxy}malonic acid $^1$H NMR (DMSO-d$_6$) δ7.98 (bm, 1 H), 7.91 (bt, J=6 Hz, 1 H), 7.10 (bd, J=8 Hz, 2 H), 6.78 (d, J=8Hz, 2 H), 5.21 (s, 1 H), 4.4 (m, 1 H), 4.15 (m, 1 H), 2.6–3.1 (m, 6 H), 1.28 (s, 9 H), 1.1–1.4 (m, 6 H), 0.82 (t, J=7Hz, 3 H);

MS (FAB) m/z (rel. intensity) 690 (MH⁺, 14), 294 (28), 210 (24), 136 (29), 133 (49), 88 (95), 86 (33), 57 (99), 43 (18), 41 (29), 29 (27).

HRMS (FAB) calcd for $C_{31}H_{36}F_5N_3O_9+H_1$ 690.2449, found 690.2457.

Anal. Calcd for $C_{31}H_{36}F_5N_3O_9 \cdot 0.48\ H_2O$: C, 53.32; H, 5.34; N, 6.02. Found: C, 53.33; H, 5.49; N, 5.70.

EXAMPLE 108

(Chart BB, BB-3) 2-{4-[(2S)-2-({(2S)-2-[(tert-butoxycarbonyl)amino]-4-methylpentanoyl}amino)-3-oxo-3-(pentylamino)propyl]phenoxy}malonic acid $^1$H NMR (DMSO-d$_6$) δ7.83 (bt, J=6 Hz, 1 H), 7.69 (bd, J=8 Hz, 1 H), 7.07 (d, J=8Hz, 2 H), 6.91 (m, 1 H), 6.77 (d, J=8Hz, 2 H), 5.19 (s, 1 H), 4.38 (m, 1 H), 3.82 (m, 1 H), 2.6–3.0 (m, 4 H), 1.35 (s, 9 H), 1.1–1.6 (m, 9 H), 0.8 (overlapping t and d, 9 H); MS (ESI–) for $C_{28}H_{43}N_3O_9$ m/z 564.1 (M–H)⁻.

Anal. Calcd for $C_{28}H_{43}N_3O_9$: C, 59.45; H, 7.66; N, 7.43. Found: C, 59.56; H, 7.71; N, 7.06.

EXAMPLE 109

(Chart BB, BB-3) 2-{4-[(2S)-2-({(2S)-3-(benzyloxy)-2-[(tert-butoxycarbonyl)amino]propanoyl}amino)-3-oxo-3-(pentylamino)propyl]phenoxy}malonic acid $^1$H NMR (DMSO-d$_6$) δ7.94 (bd, J=6 Hz, 1 H), 7.83 (bt, 1 H), 7.31 (bs, 5 H), 7.09 (d, J=8 Hz, 2 H), 6.95 (bd, J=8 Hz, 1 H), 6.78 (d, J=8 Hz, 2 H), 5.22 (s, 2 H), 4.4 (m, 1 H), 4.2 (m, 1 H), 3.51 (m, 2 H), 2.6–3.1 (m, 4 H), 1.1–1.4 (m, 15 H), 0.84 (t, J=7 Hz, 3 H);

MS (ESI–) for $C_{32}H_{43}N_3O_{10}$ m/z 628.1 (M$^{H})^-$.

Anal. Calcd for $C_{32}H_{43}N_3O_{10}$: C, 61.04; H, 6.88; N, 6.67. Found: C, 60.98; H, 7.14; N, 6.33.

EXAMPLE 110

(Chart BB, BB-3) 2-14-[(2S)-2-({(2S)-4-amino-2-[(tert-butoxycarbonyl)amino]-4-oxobutanoyl}amino)-3-oxo-3-(pentylamino)propyl]phenoxy}malonic acid $^1$H NMR (DMSO-d$_6$) δ7.85 (bt, J=6 Hz, 1 H), 7.80 (d, J=8 Hz, 1 H), 7.3 (bs, 1 H), 7.08 (d, J=8 Hz, 2 H), 6.9 (m, 2 H), 6.78 (d, J=8Hz, 2 H), 5.21 (s, 1 H), 4.3 (m, 1 H), 4.16 (m, 1 H), 2.65–3.1 (m, 4 H), 2.40 (dd, J=15, 7 Hz, 1 H), 2.28 (dd, J=15, 8 Hz, 1 H), 1.35 (s, 9 H), 1.1–1.4 (m, 6 H), 0.83 (t, J=7 Hz, 3 H);

MS (FAB) m/z (rel. intensity) 567 (MH⁺, 19), 467 (43), 238 (26), 194 (30), 88 (76), 87 (47), 73 (34), 57 (99), 43 (27), 41 (31), 29 (33).

EXAMPLE 111

(Chart BB, BB-3) 2-{4-[(2S)-2-[(2-{[(benzyloxy) carbonyl]amino}acetyl)amino]-3-oxo-3-(pentylamino)propyl]phenoxy}malonic acid $^1$H NMR (DMSO-d$_6$) δ8.00 (d, J=8 Hz, 1 H), 7.88 (bt, 1 H), 7.32 (m, 5 H), 7.10 (d, J=8 Hz, 2 H), 6.79 (d, J=8 Hz, 6 H), 5.23 (s, 1 H), 5.00 (s, 2 H), 4.38 (m, 1 H), 3.4–3.7 (m, 2 H), 2.6–3.1 (m, 4 H), 1.1–1.4 (m, 6 H), 0.82 (t, J=7Hz, 3 H); MS (ESI–) for $C_{27}H_{33}n_3O_9$ m/z 542.2 (M–H)⁻.

Anal. Calcd for $C_{27}H_{33}N_3O_9 \cdot 0.4\ H_2O$: C, 58.87; H, 6.19; N, 7.63. Found: C, 58.86; H, 6.33; N, 7.41.

EXAMPLE 112

(Chart BB, BB-3) 2-{4-[(2S)-2-1 [(2S)-2-[(tert-butoxycarbonyl)amino]-3-(4-hydroxyphenyl) propanoyl]amino}-3-oxo-3-(pentylamino)propyl] phenoxy}malonic acid $^1$H NMR (DMSO-d$_6$) δ7.8–8.0 (m, 2 H), 7.10 (d, J=8 Hz, 2 H), 6.94 (d, J=8Hz, 2 H), 6.79 (d, J=8 Hz, 2 H), 6.59 (d overalapping m, J=8 Hz, 3 H), 5.22 (s, 1 H), 4.38 (m, 1 H), 4.0 (m, 1 H), 2.5–3.1 (m, 6 H), 1.1–1.4 (m, 6 H), 0.82 (t, J=7 Hz, 3 H);

MS (FAB) m/z (rel. intensity) 616 (MH⁺, 77), 616 (77), 560 (66), 516 (25), 336 (32), 238 (37), 194 (25), 136 (98), 133 (25), 88 (92), 57 (99).

HRMS (FAB) calcd for $C_{31}H_{41}N_3O_{10}+H_1$ 616.2870, found 616.2860.

Anal. Calcd for $C_{31}H_{41}N_3O_{10} \cdot 1.1\ H_2O$: C, 58.52; H, 6.86; N, 6.61. Found: C, 58.52; H, 6.80; N, 6.52.

EXAMPLE 113

(Chart BB, BB-3) 2-{4-[(2S)-2-({(2S)-2-[(tert-butoxycarbonyl)amino]-4-phenylbutanoyl}amino)-3-oxo-3-(pentylamino)propyl]phenoxy}malonic acid $^1$H NMR (DMSO-d$_6$) δ7.84 (t, J=6Hz, 1 H), 7.77 (d, J=8Hz, 1 H), 7.21 (d, J=8 Hz, 2 H), 7.1 (m, 6 H), 6.79 (d, J=8Hz, 2 H), 5.17 (s, 1 H), 4.4 (m, 1 H), 3.8 (m, 1 H), 2.7–3.0 (m, 4 H), 2.45 (m, 2 H), 1.71 (m, 2 H), 1.37 (s, 9 H), 1.1–1.4 (m, 6 H), 0.79 (t, J=7 Hz, 3 H);

MS (FAB) m/z (rel. intensity) 614 (MH⁺, 27), 558 (53), 514 (37), 238 (52), 194 (41), 134 (85), 117 (38), 91 (78), 88 (90), 57 (99), 41 (31).

HRMS (FAB) calcd for $C_{32}H_{43}N_3O_9+H_1$ 614.3077, found 614.3073.

Examples 114–115 were prepared by the general procedure described for R-2 (Chart R).

EXAMPLE 114

(Chart R, R-2) 5-[(2S)-2-({(2S)-2-[(tert-butoxycarbonyl)amino]-3-phenylpropanoyl}amino)-3-oxo-3-(pentylamino)propyl]-2-(carboxymethoxy) benzoic acid $^1$H NMR (DMSO-d$_6$) δ8.30 (d, J=8 Hz, 1 H), 7.84 (bt, J=6 Hz, 1 H), 7.58 (bs, 1 H), 7.27 (bd, J=8Hz, 1 H), 7.15 (m, 5 H), 6.88 (d, J=9Hz, 1 H), 6.79 (d, J=8 Hz, 1 H), 4.66 (s, 2 H), 4.38 (m, 1 H), 4.11 (m, 1 H), 2.5–3.1 (m, 6 H), 1.1–1.4

(m, 6 H), 1.27 (s, 9 H), 0.83 (t, J=7 Hz, 3 H); MS (ESI−) for $C_{31}H_{41}N_3O_9$ m/z 598.4 (M−H)⁻.

HRMS (FAB) calcd for $C_{31}H_{41}N_3O_9+H_1$ 600.2921, found 600.2930.

EXAMPLE 115

(Chart R, R-2) 5-[(2S)-2-{[(2S)-2-[(tert-butoxycarbonyl)amino]-3-(4-hydroxyphenyl)propanoyl]amino}-3-oxo-3-(pentylamino)propyl]-2-(carboxymethoxy)benzoic acid ¹H NMR (DMSO-$d_6$) δ7.85 (m, 2 H), 7.52 (bs, 1 H), 7.28 (dm, J=8 Hz, 1 H), 6.9 (m, 3 H), 6.78 (d, J=8 Hz, 1 H), 6.59 (d, J=8 Hz, 2 H), 4.68 (s, 2 H), 4.39 (m, 1 H), 3.97 (m, 1 H), 2.5–3.1 (m, 6 H), 1.1–1.4 (m, 6 H), 1.28 (s, 9 H), 0.82 (t, J=7 Hz, 3 H); MS (ESI−) for $C_{31}H_{41}N_3O_{10}$ m/z 614.3 (M−H)⁻.

HRMS (FAB) calcd for $C_{31}H_{41}N_3O_{10}+H_1$ 616.2870, found 616.2866.

Examples 116–124 were prepared by procedures analogous to that described for Example 10 (Chart D).

EXAMPLE 116

2-{4-[(2S)-2-({[(1-carboxy-2-phenylethyl)amino]carbonyl}amino)-3-oxo-3-(pentylamino)propyl]phenoxy}malonic acid Major diastereomer. ¹H NMR (DMSO-$d_6$) δ7.79 (bt, J=7 Hz, 1 H), 7.1–7.3 (m, 5 H), 7.04 (d, J=8Hz, 2 H), 6.78 (d, J=8Hz, 2 H), 6.35 (d, J=7Hz, 1 H), 6.30(d, J=7 Hz, 1 H), 5.26 (s, 1 H), 4.23 (m, 2 H), 2.6–3.1 (m, 6 H), 1.1–1.4 (m, 6 H), 0.82 (t, J=7 Hz, 3 H); MS (FAB) m/z (rel. intensity) 544 (MH⁺, 99), 545 (31), 544 (99), 353 (24), 238 (21), 194 (18), 166 (23), 136 (16), 120 (42), 88 (20), 43 (17). Minor diastereomer (apparent peaks): ¹H NMR (DMSO-$d_6$) δ6.96 (d, J=8 Hz), 5.22 (s);

HRMS (FAB) calcd for $C_{27}H_{33}N_3O_9+H_1$ 544.2295, found 544.2310.

Anal. Calcd for $C_{27}H_{33}N_3O_9$.1.9 $H_2O$: C, 56.13; H, 6.42; N, 7.27. Found: C, 56.13; H, 6.06; N, 7.26.

EXAMPLE 117

2-{4-[(2S)-2-({[benzyl(4-carboxybenzyl)amino]carbonyl}amino)-3-oxo-3-(pentylamino)propyl]phenoxy}malonic acid ¹H NMR (DMSO-$d_6$) δ7.85 (d, J=8 Hz, 2 H), 7.24 (m, 5 H), 7.06 (m, 4 H), 6.77 (d, J=8 Hz, 2 H), 5.27 (s, 1 H), 4.4 (m, 5 H), 2.7–3.1 (m, 4 H), 1.1–1.4 (m, 6 H), 0.83 (t, J=7 Hz, 3 H); MS (FAB) m/z (rel. intensity) 620 (MH+, 25), 621 (9), 620 (25), 139 (10), 135 (13), 107 (7), 105 (8), 103 (8), 92 (8), 91 (99), 43 (7).

HRMS (FAB) calcd for $C_{33}H_{37}N_3O_9+H_1$ 620.2607, found 620.2621.

Anal. Calcd for $C_{33}H_{37}N_3O_9$.0.81 $H_2O$: C, 62.49; H, 6.14; N, 6.63. Found: C, 62.49; H, 6.10; N, 6.73.

EXAMPLE 118

2-{4-[(2S)-2-[({[4-(carboxymethyl)benzyl][3-(trifluoromethyl) benzyl]amino}carbonyl)amino]-3-oxo-3-(pentylamino) propyl]phenoxy}malonic acid ¹H NMR (DMSO-$d_6$) δ7.76 (bt, J=7 Hz, 1 H), 7.4–7.6 (m, 4 H), 7.3 (bd,=7 Hz, 1 H), 7.15 (d, J=8Hz, 2 H), 7.07 (d, J=9Hz, 2 H), 7.01 (d, J=8Hz, 2 H), 6.75 (d, J=9 Hz, 2 H), 5.24 (s, 1 H), 4.2–4.5 (m, 5 H), 3.52 (s, 2 H), 2.7–3.1 (m, 4 H), 1.1–1.4 (m, 6 H), 0.83 (t, J=7Hz, 3 H);

MS (FAB) m/z (rel. intensity) 702 (MH⁺, 21), 702 (21), 324 (14), 322 (8), 159 (27), 150 (10), 149 (99), 107 (11), 105 (19), 104 (18), 91 (10).

HRMS (FAB) calcd for $C_{35}H_{38}F_3N_3O_9+H_1$ 702.2638, found 702.2637.

Anal. Calcd for $C_{35}H_{38}F_3N_3O_9$.0.44 $H_2O$: C, 59.24; H, 5.52; N, 5.92. Found: C, 59.24; H, 5.56; N, 5.89.

EXAMPLE 119

2-{4-[(2S)-2-{[({1-[4-(benzyloxy)benzyl]-2-hydroxy-2-oxoethyl}amino)carbonyl]amino}-3-oxo-3-(pentylamino)propyl]phenoxy}malonic acid ¹H NMR (major isomer peaks)(DMSO-$d_6$) δ7.3–7.5 (m, 5 H), 7.0–7.1 (m, 4 H), 6.88 (d, J=8 Hz, 2 H), 6.78 (d, J=8 Hz, 2 H), 5.26 (s, 1 H), 5.04 (s, 2 H), 4.2 (m, 2 H), 2.6–3.0 (m, 6 H), 1.1–1.4 (m, 6 H), 0.81 (t, J=7Hz, 3 H);

MS (FAB) m/z (rel. intensity) 544 (MH⁺, 99), 545 (31), 544 (99), 353 (24), 238 (21), 194 (18), 166 (23), 136 (16), 120 (42), 88 (20), 43 (17).

HRMS (FAB) calcd for $C_{27}H_{33}N_3O_9+H_1$ 544.2295, found 544.2310.

EXAMPLE 120

2-{4-[(2S)-2-[({[4-(aminosulfonyl)benzyl][3-(trifluoromethyl) benzyl]amino}carbonyl)amino]-3-oxo-3-(pentylamino)propyl]phenoxy}malonic acid ¹H NMR (DMSO-$d_6$) δ7.83 (bt, J=6 Hz, 1 H), 7.72 (d, J=8 Hz, 2 H), 7.45–7.6 (m, 3 H), 7.3 (m, 4 H), 7.08 (d, J=8.5 Hz, 2 H), 6.76 (d, J=8.5 Hz, 2 H), 6.67 (bd, J=8 Hz, 1 H), 5.27 (s, 1 H), 4.3–4.55 (m, 5 H), 2.7–3.1 (m, 4 H), 1.1–1.4 (m, 6 H), 0.83 (t, J=7 Hz, 3 H);

MS (FAB) m/z (rel. intensity) 723 (MH⁺, 37), 724 (15), 723 (37), 345 (16), 170 (81), 159 (99), 107 (28), 106 (17), 91 (29), 88 (16), 43 (29).

HRMS (FAB) calcd for $C_{33}H_{37}F_3N_4O_9S+H_1$ 723.2311, found 723.2315.

Anal. Calcd for $C_{33}H_{37}F_3N_4O_9S$.2.2 $H_2O$: C, 51.99; H, 5.48; N, 7.48. Found: C, 51.99; H, 5.35; N, 7.34.

EXAMPLE 121

2-{4-[(2S)-2-[({(3-carboxybenzyl)[3-(trifluoromethyl)benzyl]amino}carbonyl)amino]-3-oxo-3-(pentylamino)propyl]phenoxy}malonic acid ¹H NMR (DMSO-$d_6$) δ7.75 (m, 3 H), 7.2–7.6 (m, 6 H), 7.05 (d, J=8 Hz, 2 H), 6.73 (d, J=8 Hz, 2 H), 6.6 (bd, J=8 Hz, 1 H), 5.23 (s, 1 H), 4.2–4.6 (m, 5 H), 3.0 (m, 2 H), 2.7–2.9 (m, 2 H), 1.1–1.4 (m, 6H), 0.82 (t, J=7 Hz, 3 H);

MS (FAB) m/z (rel. intensity) 688 (MH⁺, 19), 689 (8), 688 (19), 601 (7), 310 (15), 160 (6), 159 (38), 136 (11), 135 (99), 91 (11), 43 (8).

HRMS (FAB) calcd for $C_{34}H_{36}F_3N_3O_9+H_1$ 688.2482, found 688.2489.

Anal. Calcd for $C_{34}H_{36}F_3N_3O_9$.1.05 $H_2O$: C, 57.80; H, 5.44; N, 5.95. Found: C, 57.79; H, 5.21; N, 5.77.

EXAMPLE 122

2-{4-[(2S)-2-[({benzyl[1-(carboxymethyl)-3-phenylpropyl]amino}carbonyl)amino]-3-oxo-3-(pentylamino)propyl]phenoxy}malonic acid NMR analysis indicated a 1:1 mixture of diastereomers.
¹H NMR (DMSO-$d_6$) δ7.7 (m, 1 H), 7.0–7.3 (m, 10 H), 6.93

(t, J=8 Hz, 2 H), 6.7 (overlapping t, J=8 Hz, 2 H), 5.19, 5.14 (two s, 1 H), 4.2–4.5 (m, 3 H), 2.2–3.1 (m, 9 H), 1.6 (m, 2 H), 1.1–1.4 (m, 6 H), 0.81, 0.80 (two t, J=7Hz, 3 H);

MS (FAB) m/z (rel. intensity) 662 (MH+, 27), 663 (11), 662 (27), 575 (9), 327 (6), 285 (8), 284 (34), 282 (6), 238 (8), 92 (9), 91 (99).

HRMS (FAB) calcd for $C_{36}H_{43}N_3O_9+H_1$ 662.3077, found 662.3080.

Anal. Calcd for $C_{36}H_{43}N_3O_9 \cdot 0.7\ H_2O$: C, 64.12; H, 6.64; N, 6.23. Found: C, 64.12; H, 6.62; N, 6.11.

EXAMPLE 123

2-{4-[(2S)-2-{[(dibenzylamino)carbonyl]amino}-3-oxo-3-(pentylamino)propyl]phenoxy}malonic acid $^1$H NMR (DMSO-$d_6$) δ7.71 (bt, J=6 Hz, 1 H), 7.25 (m, 6 H), 7.05 (m, 6 H), 6.77 (d, J=8.6 Hz, 2 H), 5.27 (s, 1 H), 4.38, 4.25 (ABq, J=17 Hz, 4 H), 4.35 (m, 1 H), 2.7–3.1 (m, 4 H), 1.1–1.4 (m, 6 H), 0.84 (t, J=7 Hz, 3 H).

MS (FAB) m/z (rel. intensity) 576 (MH$^+$, 51), 577 (17), 576 (51), 575 (8), 489 (9), 241 (9), 177 (8), 92 (10), 91 (99), 63 (9), 43 (8).

HRMS (FAB) calcd for $C_{32}H_{37}N_3O_7+H_1$ 576.2709, found 576.2706.

Anal. Calcd for $C_{32}H_{37}N_3O_7 \cdot 0.85\ H_2O$: C, 65.04; H, 6.00; N, 7.11. Found: C, 65.03; H, 6.51; N, 7.29.

EXAMPLE 124

2-{4-[(2S)-2-({[4-(tert-butoxycarbonyl)-1-piperazinyl]carbonyl}amino)-3-oxo-3-(pentylamino)propyl]phenoxy}malonic acid $^1$H NMR (DMSO-$d_6$) δ7.85 (bt, J=6 Hz, 1 H), 7.15 (d, J=8.6 Hz, 2 H), 6.79 (d, J=8.6 Hz, 2 H), 5.28 (s, 1 H), 4.16 (m, 1 H), 3.20 (bs, 8 H), 2.55–3.1 (m, 4 H), 1.38 (s, 9 H), 1.1–1.4 (m, 6 H), 0.83 (t, J=7Hz, 3 H);

MS (FAB) m/z (rel. intensity) 565 (MH$^+$, 60), 566 (18), 565 (60), 157 (41), 131 (23), 129 (16), 113 (45), 87 (61), 57 (99), 43 (19), 41 (16).

HRMS (FAB) calcd for $C_{27}H_{40}N_4O_9+H_1$ 565.2873, found 565.2896.

Anal. Calcd for $C_{27}H_{40}N_4O_9 \cdot 0.58\ H_2O$: C, 56.38; H, 7.21; N, 9.74. Found: C, 56.39; H, 6.93; N, 9.43.

EXAMPLE 125

2-{4-[(2S)-2-{[(3-carboxyanilino)carbonyl]amino}-3-oxo-3-(pentylamino)propyl]phenoxy}malonic acid Prepared by a procedure analogous to that described for Example 4 (Chart C).

$^1$H NMR (DMSO-$d_6$) δ8.86 (s, 1 H), 8.03 (bt, J=6 Hz, 1 H), 8.00 (s, 1 H), 7.45 (m, 2H), 7.30(t, J=8 Hz, 1 H), 7.08 (d, J=9Hz, 2H), 6.82 (d, J=9Hz, 2H), 6.30 (2, J=8 Hz, 1 H), 5.27 (s, 1 H), 4.36 (m, 1 H), 2.7–3.1 (m, 4 H), 1.1–1.4 (m, 6 H), 0.83 (t, J=7 Hz, 3 H);

MS (FAB) m/z (rel. intensity) 516 (MH$^+$, 99), 517 (29), 516 (99), 515 (15), 414 (20), 353 (19), 194 (14), 136 (12), 107 (13), 88 (22), 43 (13).

HRMS (FAB) calcd for $C_{25}H_{29}N_3O_9+H_1$ 516.1982, found 516.1965.

EXAMPLE 126

2-(carboxymethoxy)-5-[(2S)-2-{[(dibenzylamino) carbonyl]amino}-3-oxo-3-(pentylamino)propyl] benzoic acid Prepared by a procedure analogous to that described for Example 10 (Chart D), using Q-4 as a starting material instead of B-4 as follows. Q-4 (54 mg, 0.11 mmole) was dissolved in 4 M HCl/dioxane (1 mL) and stirred at room temp. for 1 h. The solution was concentrated in vacuo, and the resulting residue was taken up in dry THF (2 mL). To the mixture was added triethylamine (47 μL, 0.34 mmol), and the reaction was cooled to 0° C. before the addition of diphosgene (7 μL, 0.06 mmol). The reaction was stirred at 0° C. for 15 minutes before the addition of dibenzylamine (29 μL, 0.15 mmol). Stirring was continued at room temperature for 3 h, followed by the addition of 2.5 M aq LiOH (0.6 mL). The mixture was stirred vigorously for 2 h, at which point MS analysis indicated saponification was complete. The reaction was acidified with 1 M HCl (3 mL), saturated with solid NaCl, and extracted with ethyl acetate. Drying of the extracts over MgSO$_4$ and concentration in vacuo left a glass (67 mg). The crude material was sonicated with CH$_2$Cl$_2$ (20 mL) for 30 min, diluted with hexane (approx. 5 mL), and allowed to stand at room temperature for 1 h, affording a white powder (43 mg, 68% overall). $^1$H NMR (DMSO-$d_6$) δ7.82 (t, J=7 Hz, 1 H), 7.62 (bs, 1 H), 7.15–7.3 (m, 7 H), 7.06 (d, J=7 Hz, 4 H), 6.83 (d, J=9 Hz, 1 H), 6.54 (d, J=7 Hz, 1 H), 4.71 (s, 2 H), 4.35 (m, 1 H), 4.35, 4.25 (ABq, J=16 Hz, 4 H), 2.7–3.1 (m, 4 H), 1.1–1.4 (m, 6 H), 0.84 (t, J=7 Hz, 3 H); IR (mull) 3289 (b), 3088, 3064, 3030, 1735 (s), 1614 (s), 1585 (s), 1536 (s), 1496 (s), 1438 (s), 1340, 1301, 1247 (s), 1153, 700, cm$^{-1}$.

MS (FAB) m/z (rel. intensity) 576 (MH$^+$,40), 577 (14), 576 (40), 490 (4), 489 (14), 198 (7), 196 (6), 106 (6), 92 (8), 91 (99), 43 (5).

HRMS (FAB) calcd for $C_{32}H_{37}N_3O_7+H_1$ 576.2709, found 576.2704.

Anal. Calcd for $C_{32}H_{37}N_3O_7 \cdot 0.84\ H_2O$: C, 65.06; H, 6.60; N, 7.11. Found: C, 65.06; H, 6.47; N, 7.24.

EXAMPLE 127

2-{4-[(2S )-2-{[(2S )-2-[(tert-butoxycarbonyl) amino]-3-(1H-indol-3-yl)propanoyl]amino}-3-oxo-3-(pentylamino)propyl]phenoxy}malonic acid Prepared according to the general procedure described for BB-3 (Chart BB).

$^1$H NMR (DMSO-$d_6$) δ10.75 (s, 1 H), 7.84 (d, J=8 Hz, 1 H), 7.80 (bt, J=7 Hz, 1 H), 7.51 (d, J=7 Hz, 1 H), 7.29 (d, J=8 Hz, 1 H), 6.95–7.15 (m, 4 H), 6.94 (t, J=7 Hz, 1 H), 6.79 (d overlapping m, J=8 Hz, 3 H), 5.22 (s, 1 H), 4.4 (m, 1 H), 4.12 (m, 1 H), 2.6–3.1 (m, 6 H), 1.1–1.4 (m, 6 H), 1.28 (s, 9 H), 0.82 (t, J=7 Hz, 3 H);

MS (FAB) m/z (rel. intensity) 639 (MH$^+$, 7), 194 (13), 186 (17), 170 (25), 159 (42), 131 (13), 130 (99), 88 (27), 57 (48), 43 (12), 41 (14).

HRMS (FAB) calcd for $C_{33}H_{42}N_4O_9+H_1$ 639.3030, found 639.3026.

Anal. Calcd for $C_{33}H_{42}N_4O_9 \cdot 0.72\ H_2O$: C, 60.82; H, 6.72; N, 8.60. Found: C, 60.81; H, 6.70; N, 8.35.

EXAMPLE 128

(Chart R, R-3) 2-(carboxymethoxy)-5-{(2S)-3-oxo-3-(pentylamino)-2-[((2S)-3-phenyl-2-{[2-(4H-1,2,4-triazol-3-ylsulfanyl)acetyl]amino}propanoyl)amino] propyl}benzoic acid A solution of R-1 (R=(S)—CH$_2$Ph) 0.5 g, 0.8 mmol) and 4N HCl/dioxane (20 mL) was stirred at room temp for 1.5 h. The reaction was concentrated to dryness in vacuo, and the resulting residue was taken up in DMF (50 mL). To the solution was added sequentially diisopropylethylamine (1.03 g, 0.8 mmol), 1,2,4-triazole-5-ylthioacetic acid (Drysdale et al, *J. Med. Chem.* 1992, 35, 2573)(159 mg, 1 mmol), HOBT monohydrate (135 mg, 1 mmol) and EDC hydrochloride (153 mg, 0.8 mmol). The mixture was stirred overnight at room temp. Solvent was removed in vacuo, and the residue was partitioned taken up in water and extracted with ethyl acetate. The organic extracts were dried over $MgSO_4$ and concentrated in vacuo. The residue was triturated with ether and dried again in vacuo, leaving the crude diester (190 mg) as a white solid. The diester was saponified by dissolving in DMF (10 mL) and adding 5.0 mL of 1.0 N aq NaOH. After stirring for 2 h, the reaction was neutralized by the addition of 1.0 N aq HCl (5.0 mL). The solvent was removed in vacuo, and the residue was taken up in water. The insoluble solid was filtered, air-dried and washed with ether, affording the title compound (136 mg) as an off-white solid after drying in vacuo. $^1$H NMR (DMSO-$d_6$) δ8.37 (bs, 1 H), 8.23 (d, J=8 Hz, 1 H), 8.14 (d, J=8 Hz, 1 H), 7.81 (bt, 1 H), 7.43 (bs, 1 H), 7.25 (bd, J=7 Hz, 1 H), 7.1 (m, 5 H), 7.01 (d, J=7 Hz, 1 H), 4.56 (bs, 2 H), 4.45 (m, 1 H), 4.37 (m, 1 H), 3.81, 3.72 (ABq, J=15 Hz, 2 H), 2.8–3.1 (m, 4 H), 2.6–2.8 (m, 2 H), 1.1–1.4 (m, 6 H), 0.82 (t, J=7 Hz, 3 H); MS (ESI−) for $C_{30}H_{36}N_6O_8S$ m/z 639.2 (M−H)⁻.

HRMS (FAB) calcd for $C_{30}H_{36}N_6O_8S+H_1$ 641.2393, found 641.2388.

EXAMPLE 129

(Chart R, R-3) 2-(carboxymethoxy)-5-{(2S)-3-oxo-3-(pentylamino)-2-[((2S)-3-phenyl-2-{[2-(5-sulfanyl-1H-1,2,3,4-tetraazol-1-yl)acetyl]amino}propanoyl)amino]propyl}benzoic acid Prepared by a procedure analogous to that described for Example 128. $^1$H NMR (DMSO-$d_6$) δ8.55 (d, J=7 Hz, 1 H), 8.22 (d, J=8 Hz, 1 H), 7.77 (bt, J=6 Hz, 1 H), 7.55 (d, J=1 Hz, 1 H), 7.29 (dd, J=7, 1 Hz, 1 H), 7.17 (m, 5 H), 6.90 (d, J=7 Hz, 1 H), 4.94, 4.84 (ABq, J=15Hz, 2 H), 4.70 (bs, 2 H), 4.5 (m, 1 H), 4.37 (m, 1 H), 2.8–3.1 (m, 4 H), 2.65–2.8 (m, 2 H), 1.1–1.4 (m, 6 H), 0.82 (t, J=7 Hz, 3 H); MS (ESI−) for $C_{29}H_{35}N_7O_8S$ m/z 640.2 (M−H)⁻.

HRMS (FAB) calcd for $C_{29}H_{35}N_7O_8S+H_1$ 642.2346, found 642.2322.

EXAMPLE 130

(Chart R, R-3) 2-(carboxymethoxy)-5-{(2S)-3-oxo-3-(pentylamino)-2-[((2S)-3-phenyl-2-{[2-(1H-1,2,3-triazol-5-ylsulfanyl)acetyl]amino}propanoyl)amino]propyl}benzoic acid Prepared by a procedure analogous to that described for Example 128. $^1$H NMR (DMSO-$d_6$) δ8.25 (d, J=8 Hz, 1 H), 8.21 (d, J=8 Hz, 1 H), 7.83 (bt, 1 H), 7.73 (bs, 1 H), 7.43 (bs, 1 H), 7.26 (dm, J=7 Hz, 1 H), 7.15 (m, 5 H), 7.04 (d, J=7 Hz, 1 H), 4.56 (bs, 2 H), 4.48 (m, 1 H), 4.38 (m, 1 H), 3.56 (bs, 2 H), 2.6–3.1 (m, 6 H), 1.1–1.4 (m, 6 H), 0.84 (t, J=7 Hz, 3 H);

MS (FAB) m/z (rel. intensity) 641 (MH⁺, 18), 685 (17), 665 (11), 664 (20), 663 (47), 641 (18), 195 (19), 120 (99), 114 (17), 88 (25), 30 (17).

HRMS (FAB) calcd for $C_{30}H_{36}N_6O_8S+H_1$ 641.2393, found 641.2388.

EXAMPLE 131

2-{4-[(2S)-2-{[({2-[(carboxymethyl)amino]-2-oxoethyl}amino) carbonyl]amino}-3-oxo-3-(pentylamino)propyl]phenoxy}malonic acid Prepared by a procedure analogous to that described for Example 10 (Chart D). $^1$H NMR (DMSO-$d_6$) δ8.08 (bt, J=7 Hz, 1 H), 7.82 (bt, J=7 Hz, 1 H), 7.07 (d, J=8.5 Hz, 2 H), 6.80 (d, J=8.5 Hz, 2 H), 5.27 (s, 1 H), 4.22 (m, 1 H), 3.73 (s, 2 H), 3.65 and 3.55 (ABq, J=15Hz, 2 H), 2.6–3.1 (m, 4 H), 1.1–1.4 (m, 6 H), 0.82 (t, J=7Hz, 3 H);

MS (FAB) m/z (rel. intensity) 511 (MH⁺, 99), 512 (25), 511 (99), 409 (17), 371 (30), 133 (25), 129 (16), 107 (22), 88 (30), 59 (27), 43 (22).

HRMS (FAB) calcd for $C_{22}H_{30}N_4O_{10}+H_1$ 511.2040, found 511.2057.

EXAMPLE 132

(Chart T, Formula T-5) 2-[4-[(2S)-2-({(2S)-2-[(tert-butoxycarbonyl)amino]-3-phenylpropanoyl}amino)-3-oxo-3-(pentylamino)propyl]-2-(2H-1,2,3,4-tetraazol-5-yl)phenoxy]acetic acid PREPARATION OF T-1: To a solution of Q-2 (5.94 g, 12.47 mmol) in DMF (anhydrous, 30 mL) in a Heck vial was added Pd(PPh$_3$)$_4$ (0.58 g, 0.50 mmol) and zink cyanide (1.61 g, 13.72 mmol). The vial was flushed with nitrogen, tightly sealed and stirred at 80° C. for 16 h. After cooling to room temperature, the mixture was partitioned between EtOAc (50 mL) and 2 M aqueous ammonium hydroxide (50 mL). The organic layer was dried (Na$_2$SO$_4$), and concentrated. The residue was purified by column chromatography (SiO$_2$, EtOAc/n-hexane 1:1) to afford 1.76 g (38%) of T-1 as a white solid. $^1$H NMR 400 MHz (MeOH) δ0.91 (t, 3H, J=7.3, 14.4), 1.18–1.48 (m, 6H), 1.39 (s, 9H), 2.77 (dd, 1H, J=8.6, 13.7), 2.98 (dd, 1H, J=6.45, 13.7), 3.08–3.21 (m, 2H), 4.20 (m, 1H), 6.88 (d, 1H, J=8.5), 7.34 (dd, 1H, J=2.2, 8.5), 7.38 (d, 1H, 2.2).

PREPARATION OF T-2: Prepared from T-1 (0.61 g, 1.63 mmol) by the general method described for U-2 and U-3, which afforded 0.69 g (94%) of the title compound as a white solid. $^1$H NMR 400 MHz (CDCl$_3$) δ0.90 (t, 3H, J=7.1, 14.4), 1.22–1.45 (m, 6H), 1.38 (s, 9H), 2.79 (dd, 1H, J=8.8, 13.7), 3.01 (m, 1H), 3.11–3.18 (m, 2H), 3.77 (s, 3H), 4.87 (s, 2H), 7.00 (d, 1 H, J=8.7), 7.46 (dd, 1H, J=2.2, 8.7), 7.51 (d, 1H, J=2.2).

PREPARATION OF T-3: Prepared from T-2 (0.55 mg, 1.23 mmol) by the general method described for U-4 and U-5, which afforded 0.61 g (84%) of the title compound as a white solid. Mp=121.4–123.0° C. $^1$H NMR 400 MHz (MeOH) δ0.90 (t, 3H, J=7.2, 14.5), 1.21 (m, 2H), 1.29 (m, 2H), 1.37 (s, 9H), 1.40 (m, 2H), 2.75 (dd, 1H, J=9.2, 13.5), 2.91 (dd, 1H, J=7.7, 13.5), 2.97–3.06 (m, 3H), 3.12 (m, 1H), 3.75 (s, 3H), 4.24 (dd, 1H, J=5.3, 9.2), 4.51 (app t, 1H, J=7.1, 14.1), 4.87 (s, 2H), 6.98 (d, 1H, J=8.6), 7.14–7.27 (m, 5H), 7.44 (dd, 1H, J=1.9, 8.6), 7.49 (d, 1H, J=1.9).

PREPARATION OF T-4: To a suspension of T-3 (0.45 g, 0.75 mmol) in toluen in a Heck vial was added trimethylsilyl azide (0.30 mL, 2.25 mmol) and dibutyltin oxide (19 mg, 0.075 mmol). The mixture was flushed with nitrogen, tightly sealed and stirred at 110° C. for 16 h. The reaction mixture was cooled to room temperature and the volatiles were evaporated in vacuo. The residue was purified by column chromatography (SiO$_2$, EtOAc) which afforded 90 mg (19%) of T-4 as a white solid. Mp=189.5–192.8° C. $^1$H NMR 400 MHz (MeOH) δ0.85 (t, 3H, J=6.9, 14.1), 1.16–1.41 (m, 6H), 1.33 (s, 9H), 2.69 (dd, 1H, J=9.4, 13.7), 2.95–3.17 (m, 5H ), 3.79 (s, 3H), 4.22 (dd, 1H, J=4.9, 9.4), 4.58 (m, 1H), 4.99 (s, 2H), 7.09–7.24 (m, 6H), 7.42 (d, 1H, J=1.7, 6.9), 8.09 (d, 1H, J=1.7).

PREPARATION OF T-5: Prepared from T-4 (19 mg, 0.029 mmol) by the general method described for U-10 and U-11, which afforded 16 mg (90%) of the title compound as a white solid. $^1$H NMR 400 MHz (MeOH) δ0.85 (t, 3H, J=7.0, 14.2), 1.18 (m, 2H), 1.24 (m, 2H), 1.33 (s, 9H), 1.38 (m, 2H), 2.70 (dd, 1H, J=9.4, 13.8), 2.96–3.08 (m, 3H), 3.14 (m, 2H), 4.22 (dd, 1H, J=5.1, 9.4), 4.58 (m, 1H), 4.95 (s, 2H), 7.12–7.29 (m, 6H), 7.44 (dd, 1H, J=1.9, 8.5), 7.86 (br m, 0.5H), 8.01 (br m, 1H), 8.10 (d, 1H, J=1.9); $^{13}$C NMR (MeOH) δ14.3, 23.4, 28.7, 30.0, 30.2, 38.2, 39.0, 40.6, 55.8, 67.0, 80.9, 114.0, 114.9, 127.8, 129.5, 130.3, 131.5, 132.8, 135.4, 138.5, 155.9, 157.9, 172.5, 173.1, 174.1. MS (ESI) 622 (M–H). HRMS (EI) calcd for $C_{31}H_{41}N_7O_7$ 623.3068, found 623.3071. Anal. Calcd for $C_{31}H_{41}N_7O_7$: C, 59.70; H, 6.63; N, 15.72. Found: C, 59.5; H, 6.7; N, 14.0.

EXAMPLES 133–135

Chart U

PREPARATION OF U-1: Triethylamine (1.71 mL, 12.5 mmol) and benzyl alcohol (6.45 mL, 62 mmol) is added to a stirring suspension of Q-2 (2.97 g, 6.23 mmol) palladium (II)acetate (42 mg, 0.19 mmol) and 1,1'-bis (diphenylphosphino)ferrocene (DPPF, 207 mg, 0.37 mmol) in DMF (15 mL). The mixture is saturated with CO (1 atm) and stirred at 70° C. for 16 h. The mixture is allowed to reach room temperature and extracted with EtOAc (40 mL), the organic layer is washed with 10% aqueous HCl (20 mL) and brine (20 mL), dried ($Na_2SO_4$) and concentrated. The residue is purified by column chromatography ($SiO_2$, EtOAc/n-hexane 1:2), which furnished 5.7 g of a yellow oil. This crude material still contains some benzyl alcohol. Crystallization in EtOAc/n-hexane gives 0.82 g (27%) of pure U-1 as a white solid. $^1$H NMR 400 MHz CDCl$_3$) δ0.84 (t, 3H, J=7.1, 14.4), 1.13 (m, 2H), 1.23 (m, 2H,), 1.35 (m, 2H), 1.39 (s, 9H), 2.95 (d, 2H, J=6.7), 3.11 (m, 2H), 4.18 (m, 1H), 5.07 (br m, 1H), 5.37 (d, 2H, J=1,7), 5.77 (br m, 1H), 6.91 (d, 1H, J=8.5), 7.30 (dd, 1H, J=2.2, 8.5), 7.35–7.47 (m, 5H), 7.69 (d, 1H, J=2.2), 10.69.

PREPARATION OF U-2: Methyl bromoacetate (0.35 mL, 3.75 mmol) and freshly grounded $K_2CO_3$ (0.52 g, 3.75 mmol) is added to a stirring solution of U-1 (0.61 g, 1.25 mmol) in acetone (15 mL). The mixture is stirred at 50° C. over night. After cooling to ambient temperature, $H_2O$ (10 mL) is added and the mixture is extracted with EtOAc (10 mL). The organic layer is dried ($Na_2SO_4$), and concentrated. The residue is purified by column chromatography ($SiO_2$, EtOAc/n-hexane 1:1) which furnished 0.46 g (66%) of U-2 as a white solid. $^1$H NMR 400 MHz (MeOH) δ0.87 (t, 3H, J=7.1, 14.3), 1.17–1.40 (m, 6H), 1.35 (s, 9H), 2.79 (dd, 1H, J=8.4, 13.6), 2.98–3.14 (m, 3H), 3.74 (s, 3H), 4.19 (m, 1H), 4.75 (s, 2H), 5.33 (s, 2H), 6.95 (d, 1H, J=8.5), 7.32–7.39 (m, 5H), 7.46 (dd, 1H, J=1.9, 8.5), 7.67 (d, 1H, J=1.9).

PREPARATION OF U-3: From Q-3 as described for the preparation of U-2. $^1$H NMR 400 MHz (MeOH) δ0.89 (t, 3H, J=6.8, 13.9), 1.22 (m, 2H), 1.29 (m, 2H), 1.37 (s, 9H), 1.39 (m, 2H), 2.81 (dd, 1H, J=8.5, 13.3), 3.00 (dd, 1H, J=7.4, 13.3), 3.07–3.15 (m, 2H), 3.82 (s, 3H), 4.20 (m, 1H), 4.79 (s, 2H), 5.21 (s, 2H), 6.91 (d, 1H, J=8.5), 7.31–7.35 (m, 6H), 7.66 (s, 1H).

PREPARATION OF U-4: Trifluoroacetic acid (0.90 mL) is carefully added to a stirring solution of U-2 (0.44 mg, 0.78 mmol) in $CH_2Cl_2$ at 0° C. The mixture is stirred for 4 h allowing the solution to warm to ambient temperature. The volatiles are removed by vacuo and the residue is partitioned between EtOAc (15 mL) and saturated aqueous NaHCO$_3$ (2×10 mL). The organic layer is dried ($Na_2SO_4$) and concentrated to give 0.35 g (98%) of the crude amine as a yellowish oil. The amine is dissolved in $CH_2Cl_2$ (7 mL) and cooled with ice. Boc-(L)-phenylalanine (0.20 g, 0.77 mmol), 1-hydroxybenzotriazole (0.10 g, 0.77 mmol) and 1-(3-dimethylaminopropyl)-3-ethylcarbodiimide hydrochloride (EDC, 0.15 g, 0.77 mmol) is added to the solution, which is then stirred at room temperature over night. The reaction mixture is diluted with $CH_2Cl_2$ (5 mL) and washed with saturated aqueous NaHCO$_3$ (5 mL), brine (5 mL) and 10% aqueous HCl. The organic layer is dried ($Na_2SO_4$) and concentrated. The residue is purified by column chromatography ($SiQ_2$, EtOAc) which gave 0.46 g (86%) of U-4 as a white solid. $^1$H NMR 400 MHz (MeOH) δ0.86 (t, 3H, J=7.2, 14.5), 1.18 (m, 2H), 1.24 (m, 2H), 1.34 (s, 9H), 1.38 (m, 2H), 2.72 (dd, 1H, J=9.4, 13.8), 2.89–3.11 (m, 3H), 3.71 (s, 3H), 4.22 (m, 1H), 4.49 (m, 1H), 4.74 (s, 2H), 5.31 (s, 2H), 6.94 (d, 1H, J=8.6), 7.14–7.46 (m, 6H), 7.65 (d, 1H, J=1.7).

PREPARATION OF U-5: From U-3 as described for U-4. $^1$H NMR 400 MHz (MeOH) δ0.88 (t, 3H, J=7.1, 14.4), 1.18 (m, 2H), 1.28 (m, 2H), 1.34 (s, 9H), 1.37 (m, 2H), 2.74 (dd, 1H, J=9.4, 13.8), 2.93 (dd, 1H, J=7.5, 13.8), 2.97–3.05 (m, 3H), 3.12 (m, 1H), 3.82 (s, 3H), 4.23 (m, 1H), 4.50 (m, 1H), 4.79 (s, 2H), 5.18 (s, 2H), 6.69 (br d, 0.6H), 6.91 (d, 1H, J=8.6).

EXAMPLE 133

(Chart U, Formula U-6) 5-[(2S)-2-({(2S)-2-[(tert-butoxycarbonyl)amino]-3-phenylpropanoyl}amino)-3-oxo-3-(pentylamino)propyl]-2-(2-methoxy-2-oxoethoxy)benzoic acid A mixture of U-4 (0.41 g, 0.58 mmol) and 10% Pd/C (80 mg) in methanol (25 mL) is hydrogenated at atmospheric pressure for 2h. The mixture is filtered through Celite and solvent removed in vacuo to afford 0.34 g (96%) of U-6 as a white solid. $^1$H NMR 400 MHz (MeOH) δ0.89 (t, 3H, J=7.1, 14.4), 1.19–1.42 (m, 6H), 1.36 (s, 9H), 2.73 (dd, 1H, J=9.5, 13.8), 2.93–3.07 (m, 3H), 3.14 (m, 1H), 3.75 (s, 2H), 4.23 (m, 1H), 4.51 (br m, 1H), 4.81 (s, 2H), 6.96 (d, 1H, J=8.5), 7.17–7.27 (m, 5H), 7.35 (dd, 1H, J=1.8, 8.5), 7.72 (d, 1H, J=1.8), 7.84 (br m, 0.5H), 7.98 (br m, 0.2H); $^{13}$C NMR (MeOH) δ14.6, 23.7, 28.9, 30.2, 30.2, 30.4, 38.3, 39.3, 40.8, 53.0, 56.1, 58.0, 67.4, 81.1, 115.6, 122.7, 128.0, 129.7, 130.6, 132.0, 134.2, 135.9, 138.8, 157.9, 158.2, 169.7, 171.2, 172.7, 172.8, 174.3. MS (ESI) 612 (M–H).

Anal. Calcd for $C_{32}H_{43}N_3O_9$: C, 62.63; H, 7.06; N, 6.85. Found: C, 62.0; H, 7.0; N, 6.8.

PREPARATION OF U-7: From U-S as described for U-6. $^1$H NMR 400 MHz (MeOH) δ0.89 (t, 3H, J=7.1, 14.4), 1.21 (m, 2H), 1.29 (m, 2H), 1.35 (s, 9H), 1.37 (m, 2H), 2.75 (dd, 1H, J=9.3, 13.8), 2.94 (dd, 1H, J=7.4, 13.8), 2.98–3.05 (m, 3H), 3.13 (m, 1H), 3.86 (s, 3H), 4.24 (m, 1H), 4.50 (m, 1H), 4.69 (s, 2H), 6.95 (d, 1H, J=8.6), 7.17–7.27 (m, 5H), 7.35 (dd, 1H, J=1.5, 8.6), 7.64 (d, 1H, J=1.5), 7.83 (br m, 1H), 7.98 (br d, 0.6H).

PREPARATION OF U-8: To a solution of U-6 (116 mg, 0.19 mmol) in a mixture of THF (2.5 mL) and DMF (0.2 mL) was added 1.1'-carbonyldiimidazole (CDI, 61 mg, 0.38 mmol), and the mixture was refluxed at 80° C. for 1 h. The mixture was cooled to ambient temperature and hydroxylamine hydrochloride (39 mg, 0.57 mmol) was added. The reaction mixture was refluxed at 80° C. for 4 h. After cooling to room temperature the mixture was partitioned between EtOAc (3 mL) and 3 M aqueous HCl (3 mL), the organic layer was dried ($Na_2SO_4$) and concentrated. The residue was purified by column chromatography ($SiO_2$, 5% MeOH in $CH_2Cl_2$) to afford 76 mg of a red/brownish solid. This material could be further purified by chrystalization in EtOAc to give 34 mg (28%) of U-8 as a white solid. $^1$H NMR 400 MHz (MeOH) δ0.89 (t, 3H, J=7.1, 14.4), 1.20 (m, 2H), 1.29 (m, 2H), 1.35 (s, 9H), 1.38 (m, 2H), 2.70 (dd, 1H, J=9.4, 13.3), 2.91–3.17 (m, 5H), 3.81 (s, 3H), 4.21 (m, 1H), 4.54 (m, 1H), 4.86 (s, 2H, obscured by solvent peak), 6.98 (d, 1H, J=8.1), 7.16–7.27 (m, 5H), 7.34 (br d, 1H, J=8.1), 7.84 (br s, 1H).

PREPARATION OF U-9: From U-7 as described for U-8. $^1$H NMR 400 MHz (MeOH) δ0.88 (t, 3H, J=7.1, 14.5), 1.19 (m, 2H), 1.28 (m, 2H), 1.35 (s, 9H), 1.37 (m, 2H) 2.77 (dd, 1H, J=9.2, 13.7), 2.93 (dd, 1H, J=7.5), 2.98–3.06 (m, 3H), 3.13 (m, 1H), 3.90 (s, 3H), 4.22 (dd, 1H, J=5.3, 9.1), 4.50 (app t, 1H), 4.66 (s, 2H), 7.06 (d, 1H, J=8.5), 7.17–7.27 (m, 5H), 7.43 (dd, 1H, J=1.8, 8.5), 7.75 (d, 1H, 1.8).

EXAMPLE 134

(Chart U, Formula U-10) 2-{4-[(2S)-2-({(2S)-2-[(tert-butoxycarbonyl)amino]-3-phenylpropanoyl}amino)-3-oxo-3-(pentylamino)propyl]-2-[(hydroxyamino)carbonyl]phenoxy}acetic acid To a solution of U-8 (10 mg, 0.0165 mmol) in THF (200 μL) was added a 2.5 M aqueous solution of LiOH (9.9 μL, 0.0248 mmol). The mixture was stirred at ambient temperature for 2 h. The reaction mixture was acidified with 3 M HCl and extracted with EtOAc (2 mL). The organic layer was dried (Na$_2$SO$_4$), and concentrated to afford 8.0 mg (79%) of U-10 as a white solid. $^1$H NMR 400 MHz (MeOH) δ0.88 (t, 3H, J=7.1, 14.5), 1.19 (m, 2H), 1.29 (m, 2H), 1.35 (s, 9H), 1.38 (m, 2H), 2.71 (dd, 1H, J=9.5, 13.5), 2.94 (m, 1H), 2.98–3.07 (m, 3H), 3.12 (m, 2H), 4.22 (dd, 1H, J=5.1, 9.5), 4.54 (m, 1H), 4.81 (s, 2H), 6.99 (d, 1H, J=8.5), 7.17–7.27 (m, 5H), 7.35 (dd, 1H, J=1.8, 8.5), 7.85 (d, 1H, J=1.8); $^{13}$C NMR (MeOH) δ14.6, 23.7, 28.9, 30.2, 30.4, 38.4, 39.2, 40.7, 56.1, 58.0, 67.3, 81.1, 114.8, 121.9, 128.0, 129.7, 130.6, 132.4, 133.4, 135.4, 138.8, 156.3, 158.1, 165.7, 172.4, 172.8, 174.3. MS (ESI) 613 (M–H). Anal. Calcd for C$_{31}$H$_{42}$N$_4$O$_9$·½H$_2$O: C, 59.70; H, 6.95; N, 8.98. Found: C, 59.5; H, 7.0; N, 8.8.

EXAMPLE 135

(Chart U, Formula U-11) 5-[(2S)-2-({(2S)-2-[(tert-butoxycarbonyl)amino]-3-phenylpropanoyl}amino)-3-oxo-3-(pentylamino)propyl]-2-[2-(hydroxyamino)-2-oxoethoxy]benzoic acid Prepared from U-9 (10 mg, 0.016 mmol) by the above method which afforded 8.1 mg (83%) of the title compound as a white solid. $^1$H NMR 400 MHz (MeOH) δ0.88 (t, 3H, J=7.1, 14.5), 1.19 (m, 2H), 1.29 (m, 2H), 1.35 (s, 9H), 1.38 (m, 2H), 2.78 (dd, 1H), 2.95 (dd, 1H), 3.14 (m, 1H), 4.23 (dd, 1H, 5.2, 9.2), 4.51 (m, 1H), 4.68 (s, 2H), 7.04 (d, 1H, J=8.5), 7.17–7.27 (m, 5H), 7.42 (dd, 1H, J=2.1, 8.5), 7.78 (d, 1H, 2.1); $^{13}$CNMR (MeOH) δ14.3, 23.4, 286, 29.9, 30.1, 38.1, 39.0, 40.5, 55.8, 57.7, 68.9, 80.9, 115.8, 121.2, 127.7, 129.4, 130.3, 131.9, 134.2, 136.4, 138.4, 158.2, 167.6, 169.0, 172.4, 172.5, 174.0. MS (ESI) 613 (M–H). Anal. Calcd for C$_{31}$H$_{42}$N$_4$O$_9$·½H$_2$O: C, 59.70; H, 6.95; N, 8.98. Found: C, 59.6; H, 7.2; N, 8.8.

EXAMPLE 136

(Chart V, Formula V-6) 2-(4-{(2S,3E, Z)-2-[(3-carboxypropanoyl)amino]-3-nonenyl}phenoxy) malonic acid PREPARATION OF V-2: Diisobutylaluminium hydride (DIBAL-H, 20 wt. % in toluene, 72.2 mL, 101.6 mmol) was added dropwise, during 10 min, to a stirred solution of N-Boc-L-tyrosine methyl ester (V-1, 6.0 g, 20.3 mmol) in diethylether (dried over molecular sieves, 120 mL) kept at −78° C., under nitrogen atmosphere. After being stirred at −78° C. for 1 h, the reaction was quenched with MeOH (20 mL) and the mixture was poured into a saturated aqueous solution of potassium sodium tartrate (Rochelle salt, 500 mL). The mixture was allowed to warm to ambient temperature and diethylether (100 mL) was added. The ethereal layer was separated, dried (MgSO$_4$) and concentrated. The crude product was passed through a short pad of silica gel, eluting with EtOAc/n-hexane 1:1, which furnished 4.9 g (91%) of V-2 as a slightly yellow oil. $^1$H NMR 400 MHz (CDCl$_3$) δ1.44 (s, 9H), 3.02 (d, 2H, J=6.5), 4.41 (dd, 1H, J=6.5, 13.3), 5.14 (m, 1H), 6.75 (d, 2H, J=8.1), 7.00 (d, 2H, J=8.1), 9.61 (s, 1H).

PREPARATION OF V-3: Potassium-tert-butoxide (12.5 g, 111.2 mmol) was added to solution of N-hexyl-triphenylphosphonium bromide (5.9 g, 22.2 mmol) in THF (dried over molecular sieves, 60 mL) at −5° C. (ice/acetone bath), under nitrogen atmosphere. After 10 min stirring, the aldehyde V-2 (5.9 g, 22.2 mmol) dissolved in THF (30 mL) was added dropwise. The mixture was stirred at 0° C. for 10 min, and then at ambient temperature for an additional 25 min. The reaction was quenched with crushed ice and the pH was adjusted to 3–4 with 10% aqueous HCl. The mixture was extracted with EtOAc (50 mL), washed with brine (2×50 mL), dried (MgSO$_4$), and concentrated. The residue was purified by flash chromatography (SiO$_2$, EtOAc/n-hexane 1:1.5), which furnished 4.31 g (58%) of V-3 as a yellow oil. $^1$H NMR 400 MHz (CDCl$_3$) δ0.85 (t, 3H, J=6.8, 14.0), 1.19–1.28 (m, 6H), 1.43 (s, 9H), 1.85–1.97 (m, 2H), 2.64 (m, 1H), 2.82 (br m, 2H), 4.45 (br s, 1H), 5.18 (dd, 1H, J=8.9, 10.7), 5.42 (ddd, 1H, J=7.4, 10.7. 14.8), 6.73 (d, 2H, J=8.5), 7.00 (d, 2H, J=8.5).

PREPARATION OF V-4: Dibenzyl bromomalonate (4.6 g, 13.7 mmol) and potassium carbonate (2.71 g, 19.6 mmol) were added to a solution of V-3 (3.27 g, 9.81 mmol) in acetone (40 mL). The mixture was stirred at ambient temperature for 16 h. The reaction was quenched with H$_2$O (100 mL) and the mixture was extracted with EtOAc (2×50 mL). The organic layer was dried (MgSO$_4$) and concentrated. The residue was purified by flash chromatography (SiO$_2$, EtOAc/n-hexane 1:5) which furnished 5.86 g (97%) of V-4 as a yellow oil. $^1$H NMR 400 MHz CDCl$_3$) δ0.88 (t, 3H), 1.15–1.29 (m, 6H), 1.42 (s, 9H), 1.80–2.00 (m, 2H), 1.63 (m, 1H), 1.72 (m, 1H), 3.59 (s, 1H), 4.52 (br s, 1H), 5.02–5.42 (m, 7H), 6.7–7.3 (m, 14H).

PREPARATION OF V-5: Trifluoroacetic acid (2.4 mL, 31.1 mmol) was carefully added to a stirring solution of V-4 (1.74 g, 2.83 mmol) in CH$_2$Cl$_2$ (20 mL) at 0° C. Th mixture was stirred for 2 h allowing the solution to warm to ambient temperature. The volatiles were removed in vacuo and the residue was partitioned between diethylether (20 mL) and saturated aqueous NaHCO$_3$ (2×10 mL). The organic layer was dried (MgSO$_4$), and concentrated to dryness to afford 1.49 g (>100%) of the crude amine as a brown/yellow oil. The amine was dissolved in CH$_2$Cl$_2$ (20 mL) and cooled with ice to 0° C. Benzylhydrogen succinate (0.59 g, 2.83 mmol) and N'-(3-dimethylaminopropyl)-N-ethylcarbodiimide hydrochloride (EDC, 0.54 g, 2.83 mmol) was added and the mixture was stirred for 16 h allowing the solution to warm to ambient temperature. The mixture was diluted with CH$_2$Cl$_2$ (10 mL) and the organic phase was washed with 10% aqueous HCl (2×20 ml), dried (MgSO$_4$), and concentrated. TLC indicated that the product was a mixture of 4 compounds. By repeated flash chromatography, (SiO$_2$, EtOAc/n-hexane 1:3), 0.57 g (28%) of V-5 as a colorless oil could be isolated. $^1$H NMR 400 MHz (CDCl$_3$) δ0.83 (t, 3H, J=6.8, 14.0), 1.14–1.26 (m, 8H), 1.77 (m 1H), 1.94 (m, 1H), 2.41 (t, 2H), 2.69 (m, 2H), 2.83 (dd, 1H, J=5.1, 13.4), 4.86 (br m, 1H), 5.11 (s, 2H), 5.21 (s, 4H), 5.24 (s, 1H), 5.43 (m, 1H), 5.58 (br d, 1H), 6.82 (d, 2H, J=8.5), 7.05 (d, 2H, J=8.5), 7.25–7.34 (m, 15H).

PREPARATION OF V-6: A solution of V-5 (172 mg, 0.25 mmol) and 2.5 M aqueous LiOH (609 μL, 1.52 mmol) in THF (4 mL) was stirred at ambient temperature for 16 h. The reaction mixture was partitioned between EtOAc (5 mL) and saturated aqueous NaHCO$_3$ (5 mL). The water layer was acidified with 10% aqueous HCl and extracted with EtOAc (4×2 mL). The organic layer was dried (MgSO$_4$) and concentrated to dryness which furnished 96 mg (87%) of V-6 as a white solid. $^1$H NMR 400 MHz (CDCl$_3$) δ0.85 (t, 3H, J=6.8, 14.0), 1.19–1.28 (m, 6H), 1.43 (s, 9H), 1.85–1.97 (m, 2H), 2.64 (m, 1H), 2.82 (br m, 2H), 4.54 (br s, 1H), 5.18 (dd, 1H, J=8.9, 10.7), 5.42 (ddd, 1H, J=7.4, 10.7, 14.8), 6.73 (d, 2H, J=8.5), 7.00 (d, 2H, J=8.5); $^{13}$C NMR (CDCl$_3$) δ14.0, 22.5, 27.7, 28.4, 29.0 31.4, 41.4, 60.5, 80.3, 115.2, 128.9, 129.1, 130.6, 133.0, 154.7, 173.2. MS (ESI) 434 (M–H). Anal. Calcd. for C$_{22}$H$_{29}$O$_8$N.¼H$_2$O: C, 60.06; H, 6.76; N, 3.18; O 30.0. Found: C, 60.1; H, 6.7; N, 3.0; O 29.8.

EXAMPLE 137

(Chart W, W-6) 2-[4-[(2S)-2-({(2S)-2-[(tert-butoxycarbonyl)amino]-3-phenylpropanoyl}amino)-3-oxo-3-(pentylamino)propyl](carboxymethyl) anilino]acetic acid PREPARATION OF W-2: To a stirring solution of Boc-Phe (4-NO$_2$)–OH (1.0 g, 3.22 mmol) and amyl amine (0.0.280 g, 3.22 mmol) in CH$_2$Cl$_2$ at 0° C. was added EDC (0.617 g, 3.22 mmol) and the resulting solution stirred overnight allowing the solution to warm to ambient temperature. CH$_2$Cl$_2$ (100 ml) was added and the solution washed with 10% HCl/H$_2$O (3×100 ml). The organic layer was further washed with saturated aqueous NaHCO$_3$ (3×100 ml) dried over MgSO$_4$ and solvent removed under reduced pressure to afford 0.856 g title compound as a white solid. m.p. 151–152° C. $^1$H NMR δ0.86 (t, 3H), 1.22 (m, 6H), 1.40 (s, 9H), 3.16 (m, 4H), 4.31 (q, 1H), 5.02 (brs, 1H), 5.87 (brs, 1H), 7.38 (d, 2H), 8.14 (d, 2H).

PREPARATION OF W-3: A mixture of W-2 (3.43 g, 9.04 mmol) and 10% Pd/C (0.9 g) in abs. EtOH (125 mL) was hydrogenated at atmospheric pressure and room temperature for 4 h. The reaction mixture was filtered over diatomaceous earth and evaporated in vacuo leaving a off-white solid, that was purified on a silica gel flash-column eluting with ethyl acetate/n-hexane (2:1 v/v). A pinkish solid (3.01 g, 95% was isolated after pooling and evaporating pure fractions. $^1$H NMR δ0.86 (t, 3H), 1.17–1.41 (m, 15H), 2.84–2.97 (m, 2H), 3.06–3.19 (m, 2H), 3.69 (s, 2H), 4.22 (m, 1H), 5.28 (br s, NH), 6.08 (t, NH), 6.59 (d, 2H), 6.96 (d, 2H).

PREPARATION OF W-4: A magnetically stirred mixture of W-3 (410 mg, 1.17 mmol), methyl bromoacetate (300 μL, 2.2 eq.), K$_2$CO$_3$ (500 mg) and KI (100 mg) in acetonitrile (4 mL) was heated at 60° C. for 15 h and then for 6 h at ambient temperature under N$_2$-atmosphere. The reaction mixture was treated with H$_2$O (20 mL), extracted with ethyl acetate (3×15 mL) and washed with brine (30 mL). The combined organic layers were dried over Na$_2$SO$_4$, filtered and reduced to dryness giving 0.83 g of a yellow oil. Purification with flash-chromatography on silica gel eluting with ethyl acetate/n-hexane (1:1 v/v) gave 429 mg (74%) of a yellow waxy solid. $^1$H NMR δ0.87 (t, 3H), 1.16–1.42 (m, 15H), 2.85–3.04 (m, 2H), 3.08–3.22 (m, 2H), 3.75 (s, 6H), 4.13 (s, 4H), 4.25 (m, 1H), 5.05 (br s, NH), 5.76 (br s, NH), 7.04 (d, 2H), 7.53 (d, 2H).

PREPARATION OF W-5: At 0° C., TFA (0.5 mL) was added dropwise to a solution of W-4 (200 mg, 0.41 mmol) in DCM (4 mL). The resulting solution was stirred for 4 h at room temperature. Evaporation in vacuo gave a red oil that was taken up in methanol and heated shortly with activated carbon. Filtration over diatomaceous earth and removal of the solvent gave 246 mg (97%) the title compound di-TFA salt as a yellow oil. This oil was dissolved in DCM (3 mL) in stirred at 0° C. Then, HOBT (54 mg, 1 eq), Boc-L-Phe (106 mg, 1 eq), EDC (77 mg, 1 eq) and TEA (166 μL, 3 eq) were added, and this mixture was stirred for 16 h at room temperature. Ethyl acetate (30 mL) was added and washed with 2% aqueous HCl (20 mL) and saturated aqueous NaHCO$_3$ (20 mL). The organic layer was dried (Na$_2$SO$_4$) and reduced to dryness giving 210 mg of a yellow oil. Purification with flash-chromatography on silica gel eluting with ethyl acetate/n-hexane (1:1 v/v) gave 132 mg (50%) after two steps of a colorless oil. A small fraction was recrystallized from toluene giving a white solid. $^1$H NMR δ0.87 (t, 3H), 1.16–1.42 (m, 15H), 2.74–2.79 (m, 1H), 2.97–3.14 (m, 5H), 3.74 (s, 6H), 4.11 (s, 4H), 4.28 (m, 1H), 4.51 (m, 1H), 4.91 (br s, NH), 5.99 (br s, NH), 6.41 (m, NH), 6.48 (d, 2H), 6.94 (d, 2H), 7.16 (d, 2H), 7.23–7.32 (m, 3H).

PREPARATION OF W-6: To a stirred solution of W-5 (88 mg, 137 μmol) in THF (2 mL), aqueous LiOH (2.5 M, 400 μL, 7.3 eq) was added. After 3 h the reaction mixture was acidified with 10% aqueous HCl until pH 5. The milky suspension was extracted with warm ethyl acetate (3×15 mL). The combined organic layers were dried (Na$_2$SO$_4$) and evaporated in vacuo leaving a white solid (64 mg, 76%). A small portion was recrystallized from acetonitrile giving white flakes. $^1$H NMR (CD$_3$OD) δ0.91 (t, 3H), 1.20–1.42 (m, 15H), 2.01 (m, 1H), 2.79 (dd, 2H), 2.90–3.14 (m, 3H), 4.17 (s, 4H), 4.26 (dd, 1H), 4.46 (m, 1H), 6.53 (d, 2H), 7.05 (d, 2H), 7.20–7.30 (m, 5H); MS (Ionspray, [M–H]$^-$m/z 611.0; Anal. Calcd. (found) for C$_{32}$H$_{46}$N$_4$O$_9$.H$_2$O: C 60.9 (60.8) % H 7.4 (7.1) % N 8.9 (9.0) %

EXAMPLE 138

(Chart X, Formula X-7) 5-[(2S)-2-({(2S)-2-[(tert-butoxycarbonyl) amino]-3-phenylpropanoyl}amino)-3-hydroxypropyl]-2-(carboxymethoxy)benzoic acid PREPARATION OF X-1: 3-Iodo-L-tyrosine (5.0 g, 16.3 mmol) was suspended in benzyl alcohol (100 mL) and at 0° C., thionyl chloride (20 mL) was added dropwise over a 20-min period. The temperature was raised to 80° C. and HCl (g) started to evolve. The reaction mixture became yellow turbid and turned to clear colorless after 30 min. After 8 h of heating, the mixture was stirred overnight at ambient temperature. Dry diethyl ether (150 mL) was added and the flask was stored overnight at –10° C. The white product was collected on a glass-sintered funnel and dried (1.91 g). An additional amount of 2.65 g (product/start. mat. 3:1) was obtained after the addition of i-hexane and storage at –10° C. The combined material was taken up in 5% NaHCO$_3$ (200 mL) and extracted with ethyl acetate (3×150 mL). The combined organic layers were dried (Na$_2$SO$_4$) and evaporated in vacuo leaving a crude yellow oil (4.00 g; 64%). $^1$H NMR (HCl salt, CD$_3$OD) δ3.02 (d, J=6.83, 2H), 4.22 (t, J=6.83, 1H), 5.15 (?,J=3.93, 2H), 6.68 (d, J=8.28, 1H), 6.91 (dd, J$_1$=8.28, J$_2$=2.18, 1H), 7.23–7.31 (m, 5H), 7.51 (d, J=2.18, 1H).

PREPARATION OF X-2: The free base of X-1 (3.97 g, 10.0 mmol) was dissolved in dichloromethane (75 mL) and stirred at 0° C. under $N_2$-atmosphere. Then, EDC (1.92 g, 10.0 mmol), HOBT (1.35 g, 10.0 mmol)) and BOC-L-Phe (2.65 g, 10.0 mmol) were added simultaneously and triethylamine 1.39 mL, 10.0 mmol) was added dropwise. This reaction mixture was stirred for 15 h allowing to warm to ambient temperature. Ethyl acetate (200 mL) was added and the organic layer was washed with 5% HCl (2×200 mL). The combined aqueous phases were extracted with ethyl acetate (100 mL) after which the combined organic layers were washed with 10% $NaHCO_3$ (100 mL). Drying ($Na_2SO_4$), filtration and evaporation in vacuo gave an off-white foam (6.01 g, 93%). The product was purified by flash column chromatography on silica gel eluting with chloroform: white foam C.Y. 78%). $^{13}$C NMR ($CDCl_3$) δ28.24, 36.52, 38.26, 53.34, 55.85, 67.36, 85.47, 115.02, 127.06, 128.59, 128.66, 128.71, 128.75, 129.30, 129.58, 131.04, 134.86, 136.39, 138.79, 151.04, 170.58, 170.91. (Rf 0.30/i-hexane/ethyl acetate 3:1).

PREPARATION OF X-3: A mixture of X-2 (4.43 g, 6.87 mmol), $Pd(OAc)_2$ (50 mg, 3.3 mol %) and DPPF (230 mg, 6.2 mol %) in acetonitrile (20 mL) was treated with trietylamine (1.9 mL, 13.74 mmol) and methanol (4.4 mL). A carbon monoxide atmosphere was established and the reaction mixture was heated at 70° C. (Essential! Solvent vapour displaces CO if temperature is too high) for 16 h. The darkbrown reaction mixture was directly coated on silica gel and subjected to column chromatography (3×20 cm) eluting with chloroform. Pure fractions were pooled giving 2.45 g (62%) off-white solid after evaporation of the eluent. Pure material can be obtained by recrystallization from abs. ethanol. (Rf 0.15 /chloroform).

PREPARATION OF X-4: A mixture of X-3 (1.68 g, 2.91 mmol), methyl bromoacetate (0.83 uL, 3 eq.) and $K_2CO_3$ (activated, 1.20 g, 3 eq.) in acetone (20 mL) was heated at 50° C. overnight. TLC showed complete conversion and water (20 mL) was added. Extraction with dichloromethane (3×25 mL), drying ($Na_2SO_4$) and removal of the solvent at the rotavapor afforded 2.27 g of a yellow oil. Flash column chromatography on silica gel (2×20 cm) eluting with chloroform gave 1.17 g (62%) of a pure colorless oil, that solidified on standing. An additional amount (0.45 g) impure colorless oil was isolated. (Rf 0.12/chloroform).

PREPARATION OF X-5: X-4 (0.97 g, 1.50 mmol) was hydrogenated (atmospheric pressure) in abs ethanol (30 mL) using 10% Pd/C (100 mg) for 3 h. Filtration over diatomaceous earth and evaporation in vacuo of the filtrate yielded 0.76 g (91%) of a light-grey foam.

PREPARATION OF X-6: To a solution of X-5 (1.24 g, 2.24 mmol) in dry THF (10 mL) is added 1,1'-carbonyldiimidazole (CDI, 0.54 g, 3.35 mmol). The solution is stirred at room temperature over night under nitrogen atmosphere. The reaction mixture is cooled with ice and a solution of $NaBH_4$ (0.21 g, 5.59 mmol) in $H_2O$ (5 mL) is slowly added. After addition is complete, the mixture is stirred at room temperature for 10 min. The mixture is quenched with 10% aqueous HCl, and extracted with EtOAc. The organic layer is dried ($Na_2SO_4$) and concentrated. The residue is purified by flash chromatography ($SiO_2$, EtOAc) with furnished 160 mg (13%) of X-6 as a sticky foam. $^1$H NMR 400 MHz $CDCl_3$) δ1.38, 2.49, 2.68, 2.73, 3.00, 3.42, 3.57, 3.78, 3.87, 4.05, 4.27, 4.68, 6.80, 7.13–7.30, 7.61.

PREPARATION OF X-7: To a solution of X-6 (36 mg, 0.066 mmol) in THF (1.5 mL) was added a 2.5 M aqueous solution of LiOH (106 μL, 0.26 mmol). The mixture was stirred at room temperature for 4 h, and then acidified with 10% aqueous HCl and extracted with EtOAc. The organic layer was dried ($Na_2SO_4$) and concentrated to afford 33 mg (96%) of X-7 as a white solid. Mp=168.8–172.3° C. $^1$H NMR 400 MHz (MeOH) δ1.35, 2.31, 2.64–2.97, 3.52, 4.06, 4.22, 4.78, 7.00, 7.11–7.27, 7.43, 7.77; $^{13}$C NMR (MeOH) δ20.7, 28.6, 30.9, 36.8, 39.5, 57.3, 67.5, 80.6, 111.0, 115.6, 121.3, 127.6, 129.3, 130.3, 133.6, 134.0, 136.1, 138.6, 157.5, 169.1, 172.2, 174.1. MS (ESI) 516 (M−H). Anal. Calcd for $C_{26}H_{32}N_2O_9 \cdot H_2O$: C, 59,42; H, 6.33; N, 5.33. Found; C, 59.4; H, 6.3; N, 5.35.4

EXAMPLE 139

(Chart Y, Formula Y-6) 2-{4-[2-[(3-carboxypropanoyl)amino]-2-methyl-3-oxo-3-(pentylamino)propyl]phenoxy}malonic acid PREPARATION OF Y-2: To a solution of DL-α-methyl tyrosine (2.72 g; 13.9 mmol) and tetramethylammonium hydroxide pentahydrate (5.62 g; 31.0 mmol) in acetonitrile (270 mL) was added di-tert-butyldicarbonate (3.79 g; 17.4 mmol) and the resulting solution was allowed to stir 18 h at rt and concentrated [Khalil, E. M.; Subasinghe, N. L.; Johnson, R. L. *Tet. Lett.* 1996, 37, 3441]. The residue was partitioned between $Et_2O/H_2O$; the phases were separated and the aqueous phase extracted twice more with $Et_2O$. The aqueous phase was brought to pH 4 with solid citric acid and extracted with $CHCl_3$ (3×100 mL). The organic extracts were combined, dried ($Na_2SO_4$) and concentrated to afford 2.58 g (63%) 9 as a white foam. $^1$H NMR $CDCl_3$) δ6.95 (d, J=8 Hz, 2 H), 6.70 (d, J=8 Hz, 2 H), 5.17 (br s, 1 H), 3.29 (br m, 1 H), 3.11 (br m, 1 H), 1.56 (s, 3 H), 1.47 (s, 9 H).

PREPARATION OF Y-3: To a solution of Y-2 (3.23 g; 10.9 mmol), diisopropylethylamine (2.09 mL; 12.0 mmol), and amylamine (1.39 mL; 12.0 mmol) in $CH_2Cl_2$ (250 mL) was added N-[(dimethylamino)-1H-1,2,3-triazolo[4,5-b]pyridin-1-ylmethylene]-N-methylmethanammonium hexafluorophosphonate N-oxide (4.63 g; 12.2 mmol), and the reaction was allowed to stir 18 h at rt. The reaction was washed with 1 M HCl (3×100 mL), saturated aq. $NaHCO_3$ (3×100 mL), and dried ($Na_2SO_4$). Upon concentration in vacuo, the residue was dissolved in a minimum of hot EtOAc and cooled to 4° C. The resulting precipitate was collected to afford 1.92 g (5.26 mmol; 48%) Y-3 as a white solid. Mp 170–2° C.; UV $\lambda_{max}$ 225 (9820, 95% EtOH); $^1$H NMR (300 MHz, DMSO) δ0.84 (t, J=7 Hz, 3 H), 1.17–1.24 (m, 7 H), 1.38 (s, 9 H), 2.90–3.10 (m, 4 H), 3.35 (s, 2 H), 6.32 (br s, 1 H), 6.60 (d, J=8 Hz, 2 H), 6.82 (d, J=8 Hz, 2H), 7.67 (br t, 1 H), 9.10 (s, 1 H).

PREPARATION OF Y-4: To a solution of Y-3 (1.94 g; 5.33 mmol) in acetone (100 mL) was added finely ground $K_2CO_3$ (2.28 g; 16.5 mmol) and dibenzyl bromomalonate (3.07 g; 8.46 mmol). After 18 h at rt, the reaction was diluted with $H_2O$ (250 mL), extracted with EtOAc (3×100 mL), and dried ($Na_2SO_4$). Chromatography (mplc, E. Merck silica 60, 230–400) with 30% EtOAc/hexane afforded 1.11 g (32%) y-4 as a colorless oil. UV $\lambda_{max}$ 222 (13000, 95% EtOH); $^1$H NMR (300 MHz, $CDCl_3$) δ7.34–7.25 (m, 10 H), 7.01 (d, J=9 Hz, 2 H), 6.83 (d, J=9 Hz, 2 H), 6.33 (br s, 1 H), 5.26 (s, 1 H), 5.22 (s, 4 H), 3.31 (d, J=14 Hz, 1 H), 3.24–3.20 (m, 2 H), 3.00 (d, J=14 Hz, 1 H), 1.45 (s, 9 H), 1.36 (s, 3 H), 1.38–1.29 (m, 6 H), 0.88 (t, J=7 Hz, 3 H).

PREPARATION OF Y-5: HCl gas was bubbled into a solution of Y-4 (1.044 g; 1.61 mmol) for 15 min. After 4 h, the reaction was concentrated in vacuo and the residue dissolved in $CH_2Cl_2$ and triethylamine (0.49 mL; 3.54 mmol). Succinic anhydride (0.186 g; 1.86 mmol) was added and the reaction was allowed to stir 20 h at rt. An additional 0.186 g of succinic anhydride and 0.49 mL of triethylamine were added and the reaction allowed to stir an additional 20 h. The reaction was washed with 1 M HCl (2×20 mL), dried ($MgSO_4$), and chromatographed (mplc, E. Merck silica gel 60, 230–400 mesh) with 2% MeOH/$CH_2Cl_2$/0.5% AcOH to afford 0.567 g (54%) Y-5 as a colorless oil. $^1$H NMR (300 Hz, $CDCl_3$) δ7.33–7.25 (m, 10 H), 6.98 (d, J=9 Hz, 2 H), 6.81 (d, J=9 Hz, 2 H), 6.32 (br s, 1 H), 6.26 (br t, 1 H), 5.26 (s, 1 H), 5.22 (s, 4 H), 3.31–3.14 (m, 4 H), 2.70–2.67 (m, 2 H), 2.42–2.39 (m, 2 H), 1.50 (s, 3 H), 1.50–1.43 (m, 2 H), 1.30–1.24 (m, 4 H), 0.88 (t, J=7 Hz, 3 H).

PREPARATION OF Y-6: A solution of Y-5 (0.225 g; 0.348 mmol) and 10% Pd/C (0.031 g) in MeOH (10 mL) was hydrogenated at atmospheric pressure for 18 h. The reaction was filtered through Celite, concentrated, and purified by preparative RP HPLC using the conditions outlined below to afford 0.088g (54%) Y-6 as a hygroscopic white solid after lyophilization. UV $\lambda_{max}$ 223 (11400, 95% EtOH); $^1$H NMR (300 MHz, DMSO-$d_6$) δ7.59 (br s, 1 H), 7.45 (br t, 1 H), 6.96 (d, J=8 Hz, 2 H), 6.79 (d, J=8 Hz, 2 H), 5.24 (s, 1 H), 3.26 (d, J=13 Hz, 1 H), 3.05–2.93 (m, 3 H), 2.45–2.42 (m, 2 H), 2.35–2.29 (m, 2 H), 1.38–1.29 (m, 2 H), 1.24–1.14 (m, 4 H), 1.13 (s, 3 H), 0.84 (t, J=7Hz, 3 H); $^{13}$C NMR (75 MHz, DMSO-$d_6$) δ174.8, 173.8, 171.3, 167.9, 155.9, 131.9, 130.8, 114.6, 76.1, 59.7, 30.9, 29.4, 29.1, 29.0, 24.1, 22.3, 14.1; IR (mull) 3362, 2729, 2669, 2592, 1732, 1631, 1612, 1544, 1511, 1299, 1226, 1184, 1120, 855, 839$cm^{-1}$; MS(FAB) m/z 467($MH^+$), 468, 467, 252, 208, 177, 157, 88, 43, 42, 23; HRMS (FAB) calcd for $C_{22}H_{30}N_2O_9+H_1$ 467.2029, found 467.2040.

EXAMPLE 140

(Chart Z, Formula Z-6) 2-{4-[2-[(3-carboxypropanoyl)amino]-3-oxo-3-(pentylamino)propyl]-2-fluorophenoxy}malonic acid PREPARATION OF Z-2: To a suspension of commercially available 3-fluoro-DL-tyrosine (1.58 g; 7.93 mmol) in 0.5 M NaOH (19 mL) was added di-tert-butyl dicarbonate (2.12 g; 9.72 mmol) in THF (19 mL). After 26 h at rt, and additional 1.5 g of di-tert-butyl dicarbonate was added and the reaction stirred for an additional 2 h. The reaction was concentrated in vacuo to remove THF, and the residue was washed with $Et_2O$. The aqueous phase was acidified with 1 M citric acid, extracted with $CHCl_3$, and dried ($Na_2SO_4$) to afford 2.05 g (86%) Z-2 as a white foam. UV 4,, 223 (8000, 95% EtOH); $^1$H NMR (300 MHz, DMSO-$d_6$) δ7.04 (d, J=8 Hz, 1 H), 6.98 (d, J=13 Hz, 1 H), 6.82–6.78 (m, 2 H), 3.99 (ddd, J=5, 10, 14 Hz, 1 H), 2.88 (dd, J=5, 14 Hz, 1 H), 2.68 (dd, J=10, 14 Hz, 1 H), 1.30 (s, 9 H).

PREPARATION OF Z-3: N-Ethyl-N'-3-dimethylaminopropylcarbodiimide hydrochloride (1.38 g; 7.20 mmol) was added to a solution of Z-2 (1.78 g; 5.96 mmol) in $CH_2Cl_2$ (50 mL). After 10 min, amyl amine (0.83 mL; 7.2 mmol) was added and the reaction was allowed to stir 18 h at rt. The reaction was washed with 1 M citric acid (3×25 mL), dried ($Na_2SO_4$), and concentrated in vacuo to afford 1.50 g (68%) Z-3 as a white solid. Mp. 63–4° C.; UV $\lambda_{max}$ 272 (1600, 95% EtOH); $^1$H NMR (300 MHz, $CDCl_3$) δ6.94–6.79 (m, 3 H), 6.07 (t, J=6 Hz, 1 H), 5.19 (br s, 1 H), 4.23 (q, J=8 Hz, 1 H), 3.35–3.04 (m, 2 H), 2.93 (d, J=7 Hz, 2 H), 1.40 (s, 9 H), 1.32–1.18 (m, 6 H), 0.84 (t, J=7 Hz, 3 H).

PREPARATION OF Z-4: To a solution of Z-3 (1.49 g; 4.04 mmol) in acetone (60 mL) was added finely ground $K_2CO_3$ (1.72 g; 12.5 mmol) and dibenzyl bromomalonate (1.75 g; 4.83 mmol). After 18 h at rt, the reaction was diluted with $H_2O$ (250 mL), extracted with EtOAc (3×100 mL), and dried ($Na_2SO_4$). Chromatography (mplc, E. Merck silica 60, 230–400) with 30% EtOAc/hexane afforded 0.799 g (30%) Z-4 as a colorless oil which solidified upon standing. Mp. 77–78.5° C.; UV $\lambda_{max}$ 223 (12200, 95% EtOH); $^1$H NMR (300 MHz, $CDCl_3$) δ7.34–7.29 (m, 10 H), 6.97–6.81 (m, 3 H), 5.74 (br t, 1 H), 5.24 (s, 1 H), 5.23 (s, 4 H), 4.96 (br s, 1 H), 4.22–4.15 (m, 1 H), 3.15 (q, J=7 Hz, 2 H), 2.97 (d, J=7 Hz, 2 H), 1.41 (s, 9 H), 1.43–1.34 (m, 2 H), 1.29–1.16 (m, 4 H), 0.86 (t, J=7 Hz, 3 H).

PREPARATION OF Z-5: HCl gas was bubbled into a solution of Z-4 (0.490 g; 0.753 mmol) for 10 min. After 18 h, the reaction was concentrated in vacuo and the residue dissolved in $CH_2Cl_2$ (15 mL) and triethylamine (0.25 mL; 1.8 mmol). Succinic anhydride (0.088 g; 0.879 mmol) was added and the reaction was allowed to stir 18 h at rt. The reaction was diluted with $CH_2Cl_2$ (50 mL), washed with 1 M HCl (2×30 mL), dried ($MgSO_4$), and chromatographed (mplc, E. Merck silica gel 60, 230–400 mesh) with 2% MeOH/$CH_2Cl_2$/1% AcOH to afford 0.0.167 g (34%) Z-5 as a colorless oil. UV $\lambda_{max}$ 223 (11500, 95% EtOH); $^1$H NMR (300 MHz, $CDCl_3$) δ7.56 (d, J=8 Hz, 1 H), 7.32–7.23 (m, 10 H), 6.95–6.78 (m, 3 H), 5.25 (s, 1 H), 5.19 (dd, J=12, 14 Hz, 4 H), 4.69–4.61 (m, 1 H), 3.21–3.09 (m, 1 H), 3.05–2.86 (m, 3 H), 2.59–2.54 (m, 2 H), 2.47–2.40 (m, 2 H), 1.35–1.07 (m, 6 H), 0.82 (t, J=7Hz, 3 H).

PREPARATION OF Z-6: A solution of Z-5 (0.145 g; 0.223 mmol) and 10% Pd/C (0.026 g) in MeOH (10 mL) was hydrogenate at atmospheric pressure for 18 h. The reaction was filtered through Celite, concentrated, and purified by preparative RP HPLC using the conditions outlined below to afford 0.068 g (65%) Z-6 as a hygroscopic white solid after lyophilization. UV $\lambda_{max}$ 222 (10200, 95% EtOH); $^1$H NMR (300 MHz, DMSO-$d_6$) δ8.08 (d, J=8 Hz, 1 H), 7.82 (br t, 1 H), 7.07 (d, J=12 Hz, 1 H), 6.96–6.89 (m, 2 H), 5.33 (s, 1 H), 4.39–4.32 (m, 1 H), 3.06–2.94 (m, 2 H), 2.90–2.84 (m, 1 H), 2.99–2.63 (m, 1 H), 2.35–2.21 (m, 4 H), 1.46–1.11 (m, 6 H), 0.82 (t, J=7 Hz, 3 H); IR (mull) 3333, 2727, 2670, 2600, 1733, 1626, 1549, 1516, 1341, 1278, 1216, 1174, 1134, 1091, 722 $cm^{-1}$; MS (FAB) m/z 471 ($MH^+$), 471, 193, 171, 167, 153, 135, 133, 121, 103, 89; HRMS (FAB) calcd for $C_{21}H_{27}FN_2O_9+H_1$ 471.1779, found 471.1797.

EXAMPLE 141

(Chart AA, Formula AA-#) 2-(4-{3-[(2-carboxyethyl)amino]-3-oxo-2-[(pentylamino)carbonyl]propyl}phenoxy)malonic acid PREPARATION OF AA-2: To a solution of 4-hydroxybenzaldehyde (5.04 g, 41.3 mmol) was added finely ground $K_2CO_3$ (17.3 g; 125 mmol) and diethyl chloromalonate (7.34 mL; 45.4 mmol). After 18 h at rt, the reaction was concentrated in vacuo, and the residue taken up in water (200 mL). This was extracted with EtOAc (3×100 mL), dried ($Na_2SO_4$) and chromatographed (mplc, E. Merck silica gel 60, 230–400 mesh) to afford 7.97 g (69%) AA-2 as a pale yellow oil UV $\lambda_{max}$ 267 (15300, 95% EtOH); $^1$H NMR (300 MHz, $CDCl_3$) δ9.76 (s, 1 H), 7.73 (d, J=9 Hz, 2 H), 6.96 (d, J=9 Hz, 2 H), 5.24 (s, 1 H), 4.28–4.15 (m, 4 H), 1.18 (t, J=7 Hz, 6 H).

PREPARATION OF AA-4: To a solution of commercially available ethyl hydrogen malonate (12.1 g; 91.7 mmol) and amyl amine (10.6 mL; 91.7 mmol) in $CH_2Cl_2$ (100 mL) was added diethyl cyanophosphonate (13.9 mL; 91.7 mmol) over 15 min. After 1.5 h at rt, the reaction was washed with 1 M citric acid (2×50 mL), H$_2$O (50 mL), saturated aqueous NaHCO$_3$ (2×50 mL), and dried (Na$_2$SO$_4$). Chromatography (mplc, E. Merck silica gel 60, 230–400 mesh) with 30% EtOAc/heptane afforded 8.9 g (48%) AA-4 as a pale yellow oil. $^1$H NMR (300 MHz, CDCl$_3$) δ7.28 (br s, 1 H), 4.00 (q, J=7 Hz, 2 H), 3.12 (s, 2 H), 3.06 (q, J=7 Hz, 2 H), 1.35 (quintet, J=7Hz, 2H), 1.16–1.11 (m, 4 H), 1.10(t, J=7 Hz, 3 H), 0.71 (t, J=6 Hz, 3 H).

PREPARATION OF AA-5: A solution of AA-4 (7.2 g; 36 mmol), 1.0 M NaOH (35.8 mL) and THF (100mL) was allowed to stir at rt for 1 h. The reaction was concentrated in vacuo to remove THF, diluted with H$_2$O (200 mL), and washed with Et$_2$O (3×100 mL). The aqueous phase was brought to pH 1 with 3 M HCl and extracted with CH$_2$Cl$_2$ (3×100 mL). Upon drying (Na$_2$SO$_4$) and concentrating, 5.02 g (81%) AA-5 was obtained as a white solid. Mp. 66–7° C.; $^1$H NMR (300 MHz, CDCl$_3$) δ12.23 (br s, 1 H), 7.53 (br t, 1 H), 3.34 (s, 2 H), 3.25 (q, J=7 Hz, 2 H), 1.51 (quintet, J=7 Hz, 2 H), 1.33–1.27 (m, 4 H), 0.86 (t, J=7 Hz, 3 H).

PREPARATION OF AA-6: To a solution of β-alanine ethyl ester hydrochloride (1.76 g; 11.5 mmol) and triethylamine (1.60 mL; 11.5 mmol) was added AA-5 (1.99 g; 11.5 mmol) and diethyl cyanophosphonate (1.74 mL; 11.5 mmol). After 18 h at rt, the reaction was washed with 1 M citric acid (3×50 mL) and dried (MgSO$_4$). Chromatography (mplc, E. Merck silica gel 60, 230–400 mesh) with 5% MeOH/CH$_2$Cl$_2$ afforded 1.65 g (53%) AA-6 as a white solid. Mp. 102–3° C.; UV λ$_{max}$ 331 (8.99, 95% EtOH); $^1$H NMR (300 MHz, CDCl$_3$) δ7.52 (br s, 1 H), 7.26 (br s, 1 H), 4.12 (q, J=7 Hz, 2 H), 3.50 (q, J=6 Hz, 2 H), 3.20 (q, J=7 Hz, 2 H), 3.13 (s, 2 H), 2.51 (s, 2 H), 1.48 (quintet, J=7 Hz, 2 H), 1.29–1.26 (m, 4 H), 1.23 (t, J=7 Hz, 3 H), 0.86 (t, J=7 Hz, 3 H).

PREPARATION OF AA-7: A solution of AA-67 (0.981 g; 3.60 mmol), AA-2 (1.02 g; 3.62 mmol) and piperidine (1 mL) in toluene (100 mL) was brought to reflux under a Dean-Stark trap. After 21 h, the reaction was cooled, concentrated, and chromatographed (mplc, E. Merck silica gel 60, 230–400 mesh) with 1:1 EtOAc/heptane to afford 0.593 g (31%) AA-7 as an orange oil which solidified upon standing. A second chromatography using 20%–50% EtOAc/heptane separated the two isomers. Earlier eluting isomer: $^1$H NMR (300 MHz, CDCl$_3$) δ7.72 (s, 1 H), 7.40 (br t, 1 H), 7.33 (d, J=9 Hz, 2 H), 6.91 (d, J=9 Hz, 2 H), 6.33 (br t, 1 H), 5.18 (s, 1 H), 4.34–4.27 (m, 4 H), 4.00 (q, J=7 Hz, 2 H), 3.49 (q, J=6 Hz, 2 H), 3.29 (q, J=7 Hz, 2 H), 2.43 (t, J=6 Hz, 2 H), 1.54 (quintet, J=7 Hz, 2 H), 1.33–1.27 (m, 4 H), 1.30 (t, J=7 Hz, 6 H), 1.17 (t, J=7 Hz, 3 H), 0.89 (t, J=7 Hz, 3 H). Later eluting isomer: $^1$H NMR (300 MHz, CDCl$_3$) δ7.79 (br t, 1 H), 7.69 (s, 1 H), 7.37 (d, J=9 Hz, 2 H), 6.91 (d, J=9 Hz, 2 H), 5.78 (br t, 1 H), 5.19 (s, 1 H), 4.35–4.27 (m, 4 H), 4.16 (q, J=7 Hz, 2 H), 3.59 (q, J=6 Hz, 2 H), 3.21 (q, J=7 Hz, 2 H), 2.57 (t, J=6 Hz, 2 H), 1.38 (quintet, J=7 Hz, 2 H), 1.35–1.24 (m, 11 H), 1.24–1.14 (m, 2 H), 0.84 (t, J=7 Hz, 3 H).

PREPARATION OF AA-8: A mixture of E and Z AA-7 (0.580 g; 1.08 mmol) in MeOH (25 mL) was hydrogenated at atmospheric pressure with 10% Pd/C (0.059 g) for 18 h. The reaction was filtered through a pad of Celite, concentrated, and chromatographed (flash, silica gel) with 60% EtOAc/heptane to afford 0.408 g (70%) AA-8 as a white solid. Mp. 88–90° C.; UV λ$_{max}$ 222 (11900, 95% EtOH); $^1$H NMR (300 MHz, CDCl$_3$) δ7.07 (d, J=9 Hz, 2 H), 7.00 (br t, 1 H), 6.82 (d, J=9 Hz, 2 H), 6.71 (br t, 1 H), 5.12 (s, 1 H), 4.32–4.25 (m, 4 H), 4.10 (q, J=7 Hz, 2 H), 3.39 (q, J=6 Hz, 2 H), 3.14–3.02 (m, 5 H), 2.45–2.30 (m, 2 H), 1.38 (quintet, J=7 Hz, 2 H), 1.34–1.18 (m, 13 H), 0.85 (t, J=7 Hz, 3 H).

PREPARATION OF AA-9: A solution of AA-8 (0.313 g; 0.583 mmol), 1.0 M NaOH (2.92 mL), H$_2$O (7 mL) and THF (10 mL) was stirred at rt. After 3 hr, the reaction was concentrated in vacuo to remove THF, diluted with H$_2$O (10 mL) and washed with CH$_2$Cl$_2$ (5 mL). The aqueous phase was brought to pH 2 with 1 M HCl, and allowed to stir until a white precipitate appeared (approx. 1 h). This was collected, washed with H$_2$O and dried to afford 0.216 g (82%) AA-9. UV λ$_{max}$ 225 (10700, 95% EtOH); $^1$H NMR (300 MHz, DMSO-d$_6$) δ7.86 (br t, 1 H), 7.75 (br t, 1 H), 6.99 (d, J=9 Hz, 2 H), 6.78 (d, J=9 Hz, 2 H), 5.12 (s, 1 H), 3.23–3.17 (m, 3 H), 2.99–2.95 (m, 2 H), 2.87–2.85 (m, 2 H), 2.27 (t, J=7 Hz, 2 H), 1.31–1.11 (m, 6 H), 0.81 (t, J=7 Hz, 3 H); $^{13}$C NMR (75 MHz, DMSO-d$_6$) δ173.3, 169.4, 169.0, 168.7, 156.2, 131.9, 129.8, 115.0, 75.6, 55.4, 32.2, 34.8, 34.1, 29.0, 28.9, 22.2, 14.4; IR (drift) 3283, 3053, 2953, 2928, 2871, 2859, 1768, 1725, 1663, 1639, 1551, 1512, 1275, 1245, 1205 cm$^{-1}$; MS (FAB) m/z 453 (MH$^+$), 475, 454, 453, 431, 139, 107, 105, 103, 91, 23; HRMS (FAB) calcd for C$_{21}$H$_{28}$N$_2$O$_9$+H$_1$ 453.1873, found 453.1859.

EXAMPLE 142

(Chart CC, Formula CC-7) 2-[4-[2-({(2R)-2-[(tert-butoxycarbonyl)amino]-3-phenylpropanoyl}amino)-3-oxo-3-(pentylamino)propyl]-2-(2-hydroxy-2-oxoethoxy)phenoxy]acetic acid PREPARATION OF CC-2: K$_2$CO$_3$ (0.776 g; 5.61 mmol) and ethyl bromoacetate (0.63 mL; 5.6 mmol) were added to a solution of benzyl 2-[(tert-butoxycarbonyl)amino]-3-(3,4-dihydroxyphenyl)propanoate (CC-1) [Kaiser, Ado; Koch, Wolfgang; Scheer, Marcel; Woelcke, Uwe. N-Acyl-3,4-dihydroxy-L-phenylalanines Ger. Offen., 32 pp. DE 2153811 720504](0.997 g; 2.57 mmol) in acetone (100 mL). After 18 h at rt, the reaction was concentrated in vacuo, and the residue partitioned between H$_2$O (100 mL)/EtOAc (50 mL). The phases were separated, the aqueous phase was extracted with EtOAc (50 mL) and the organic phases were combined and dried (Na$_2$SO$_4$). Chromatography (mplc, E. Merck silica gel 60, 230–400 mesh) with 30% EtOAc/hexane afforded 0.691 g (48%) benzyl 3-[3,4-bis(2-ethoxy-2-oxoethoxy)phenyl]-2-[(tert-butoxycarbonyl)amino]propanoate (CC-2) as a colorless oil. UV λ$_{max}$ 224 (8550, 95% EtOH); $^1$H NMR (300 MHz, CDCl$_3$) δ7.36–7.28 (m, 5 H), 6.73 (d, J=8 Hz, 1 H), 6.62 (m, 2 H), 5.16–5.10 (m, 2 H), 4.94 (br d, 1 H), 4.67–4.51 (m, 5 H), 4.28–4.21 (m, 4 H), 2.92–2.88 (m, 2 H), 1.41 (s, 9 H), 1.32–1.26 (m, 6 H).

PREPARATION OF CC-3: 10% Pd/C (554 mg) was added to CC-2 (2.94 g, 5.25 mmol) followed by the addition of 100 mL of MeOH. The reaction mixture was stirred at rt under a H$_2$ atmosphere for 14 h, filtered through celite, concentrated and purified by column chromatography (1% AcOH, 5% MeOH/CH$_2$Cl$_2$) to afford CC-3 as a clear oil (1.86 g, 3.75 mmol, 71% yield). UV λ$_{max}$ 221 (7890, 95% Ethanol); (400 MHz, CDCl$_3$) δ6.74–6.85 (m, 3 H), 4.97 (s, 1 H), 4.70 (s, 2 H), 4.69 (s, 2 H), 4.53 (s, 1 H), 4.27 (m, 4 H), 3.06 (s, 2 H), 1.44 (s, 9 H), 1.29 (m, 6 H).

PREPARATION OF CC-4: CC-3 (1.64 g, 3.50 mmol) was dissolved in 75 mL of CH$_2$Cl$_2$, to the solution was added amylamine (450 μL, 3.88 mmol), triethylamine (610 μL, 4.02 mmol), and diethyl cyanophosphonate (610 μL, 4.38 mmol). The reaction mixture was stirred for 18 h, quenched with 10% aq citric acid, extracted with CH$_2$Cl$_2$ and washed with water. The organic layer was dried over NaSO$_4$, filtered and condensed. The residue was purified by flash chromatography (30% EtOAc-50% EtOAc/heptane) to afford CC-4 as a white solid (964 mg, 1.79 mmol, 51% yield). UV λ$_{max}$ 221 (8920, 95% ETHANOL; $^1$H NMR (400 MHz, CDCl$_3$) δ7.28 (s, 1 H), 6.76–6.84 (m, 3 H), 5.75 (s, 1 H), 5.05 (s, 1H), 4.70 (s, 2 H), 4.68 (s, 2 H), 4.21–4.30 (m, 4 H), 4.19 (m, 1 H), 3.14 (m, 2 H), 3.02 (dd, J=14, 6 Hz, 1 H), 2.90 (dd, J=14, 8 Hz, 1 H), 1.43 (s, 9 H), 1.15–1.41 (m, 12 H), 0.87 (t, J=7 Hz, 3 H).

PREPARATION OF CC-5: CC-4 (765 mg, 1.42 mmol) was dissolved in 25 mL of 20% TFA/CH$_2$Cl$_2$ solution, the reaction mixture was stirred for 1 h at rt then condensed to afford a yellow oil. The oil was redissolved in CH$_2$Cl$_2$ washed with NaHCO$_3$ and water. The organic layer was dried over NaSO$_4$, filtered and condensed. The residue was purified by flash chromatography (5% MeOH sat. NH$_3$/CH$_2$Cl$_2$) to afford CC-5 as a clear oil. $^1$H NMR (400 MHz, CDCl$_3$) δ6.76–6.84 (m, 3 H), 4.69 (s, 4 H), 4.25 (q, J=10 Hz, 4 H), 3.54 (m, 1 H), 3.13–3.25 (m, 3 H), 2.60 (dd, J=18, 13 Hz, 1 H), 1.50 (m, 2 H), 1.26–1.3 (m, 10 H), 0.89 (t, J=9 Hz, 3 H).

PREPARATION OF CC-6: CC-5 (362 mg, 0.826 mmol) was dissolved in 50 mL of CH$_2$Cl$_2$ to the solution was added triethylamine (160 μL, 1.18 mmol), diethylcyanophosphonate (160 μL, 1.06) and Boc-L-Phe (262 mg, 0.99 mmol). The reaction mixture was stirred at rt for 16 h, quenched with 10% aq citric acid, extracted with CH$_2$Cl$_2$ and washed with water. The organic layer was dried over NaSO$_4$, filtered, and condensed. The residue was purified by column chromatography (5% MeOH/CH, Cl$_2$) to afford CC-6 (1:1 mixture of diastereomers) as a white solid (418 mg, 0.610 mmol, 74% yield). UV λ$_{max}$ 224 (10300, MeOH); $^1$H NMR (400 MHz, CDCl$_3$) δ7.18–7.32 (m, 5 H), 6.63–6.46 (m, 3 H), 6.34 (m, 1 H), 5.98–6.07 (m, 1 H), 5.00–5.07 (m, 1 H), 4.67–4.71 (m, 4 H), 4.55 (m, 1 H), 4.09–4.28 (m, 5 H), 2.90–3.18 (m, 5 H), 2.52–2.82 (m, 1H), 1.15–1.43 (m, 21 H), 0.86 (m, 3 H).

PREPARATION OF CC-7: CC-6 (160 mg, 0.243 mmol) was dissolved in 15 mL of THF, to the solution was added 1.0 N NaOH (800 , L, 0.800 mmol), the reaction mixture was stirred for 16 h at rt. The reaction was quenched with 10% citric acid, extracted with CH$_2$Cl$_2$, the organic layer was dried over NaSO$_4$, filtered and condensed to afford CC-7 as a white solid (122 mg, 0.201 mmol, 83% yield). UV λ$_{max}$ 226 (9460, MeOH; $^1$H NMR (400 MHz, DMSO-d6) δ12.90 (s, 2 H), 7.76–8.24 (m, 2 H), 7.10–7.24 (m, 5 H), 6.65–6.90 (m, 4 H), 4.61 (m, 4 H), 4.40 (m, 1 H), 4.11 (m, 1 H), 2.63–2.87 (m, 6 H), 1.15–1.35 (m, 15 H), 0.84 (m, 3 H); $^{13}$C NMR (100 MHz, DMSO-d6) δ180.9, 180.8, 180.7, 179.9, 179.8, 179.7, 179.7, 179.6, 164.9, 164.6, 156.5, 155.5, 155.4, 147.5, 147.5, 147.4, 140.7, 140.3, 138.6, 138.5, 137.5, 137.4, 135.6, 131.6, 131.4, 124.8, 123.6, 123.6, 87.7, 87.6, 81.9, 74.9, 74.7, 74.6, 65.4, 65.2, 63.6, 63.3, 52.2, 48.0, 47.9, 46.9, 46.7, 39.9, 38.1, 38.0, 38.0, 37.9, 37.6, 37.2, 31.3, 23.3; IR (drift) 3316, 2958, 2931, 1756, 1710, 1688, 1646, 1614, 1551, 1517, 1271, 1250, 1192, 1168, 1145 cm$^{-1}$. HRMS (FAB) calcd for C$_{32}$H$_{43}$N$_3$O$_{10}$+H$_1$ 630.3026, found 630.3038.

EXAMPLE 143

(Chart DD, Formula DD-3) 2-(carboxymethoxy)-5-[(2S)-3-oxo-2-{[(2R)-2-(2-oxo-1-pyrrolidinyl)-3-phenylpropanoyl]amino}-3-(pentylamino)propyl] benzoic acid PREPARATION OF DD-1: Q-4 (2.30 g, 4.53 mmol) was dissolved in 20 mL of 20% TFA/CH$_2$Cl$_2$ solution, the reaction mixture was stirred at rt for 5 h. The solution was condensed, dissolved in CH$_2$Cl$_2$, washed with saturated aq NaHCO$_3$, organics dried over NaSO$_4$. Purified by column chromatography (5%MeOH (sat. NH$_3$)/CH$_2$Cl$_2$) to afford DD-1 as a clear oil (1.48 g, 3.62 mmol, 80% yield). [α]$_D$=18° (c 0.64, methanol); UV λ$_{max}$ 226 (9750, MeOH); $^1$H NMR (300 MHz, CDCl$_3$) δ7.65 (d, J=2 Hz, 1 H), 7.32 (d, J=2 Hz, 1 H), 7.29 (d, J=2 Hz, 1 H), 6.85 (d, J=9 Hz, 1 H), 4.68 (s, 2 H), 4.35 (q, J=7 Hz, 2 H), 4.25 (q, J=7 Hz, 2 H), 3.56 (dd, J=9,4 Hz, 1 H), 3.21 (m, 3 H), 2.71 (dd, J=14, 9 Hz, 1 H), 1.25–1.50 (m, 12 H), 0.89 (t, J=7 Hz, 3 H).

PREPARATION OF DD-3: (2S)-2-(2-Oxo-1-pyrrolidinyl)-3-phenylpropanoic acid [Ocain, T.D.; Deininger, D.D., U.S. Pat. No. 5,023,338](124 mg, 0.532 mmol) was added to 15 ml of CH$_2$Cl$_2$, to the reaction mixture was added triethyl amine (75 μL, 0.54 mmol), DD-1 (225 mg, 0.551 mmol) and diethyl cyanophosphonate (90 μL, 0.59 mmol). The reaction mixture was stirred at rt for 12 h, diluted with CH$_2$Cl$_2$, quenched with 10% aq citric acid, washed with water, organics dried over NaSO$_4$, filtered and condensed. The resulting product DD-2 was dissolved in 10 mL THF/water (1:1), to the reaction mixture was added 1 N NaOH solution (600 μL, 0.600 mmol), the reaction mixture was stirred at rt for 2 h then quenched with 10% aq citric acid, extracted with EtOAc, washed with water, dried organics over NaSO$_4$, filtered, and condensed. Purified by column chromatography (10% MeOH/CH$_2$Cl$_2$, 1% AcOH, to give a white solid as a diastereomer mixture 7:1, (175 mg, 0.31 mmol, 56% yield). Separated major diastereomers by HPLC to give DD-3 as a white solid. Mp. 96–97° C.; $^1$H NMR (400 MHz, DMSO) δ7.98 (d, J=8 Hz, 1 H), 7.87 (t, J=4 Hz, 1 H), 7.56 (d, J=2 Hz, 1 H), 7.32 (dd, J=10,2 Hz, 1 H), 7.20 (m, 2 H), 7.12 (m, 3 H), 6.91 (d, J=9 Hz, 1 H), 4.80 (dd, J=10, 5 Hz, 1 H), 4.71 (s, 3 H), 4.45 (m, 1 H), 2.90–3.12 (m, 5 H), 2.72–2.83 (m, 3 H), 2.07 (m, 1 H), 1.89 (m, 1 H), 1.75 (m, 1 H), 1.62 (m, 1 H), 1.36 (m, 2 H), 1.14–1.23 (m, 5 H), 0.85 (t, J=7 Hz, 3 H); $^{13}$C NMR (100 MHz, DMSO) δ174.2, 170.5, 170.1, 169.2, 167.0, 155.3, 137.7, 133.6, 131.6, 130.4, 128.7, 128.0, 126.2, 121.0, 113.4, 65.5, 54.6, 54.2, 43.0, 38.5, 36.3, 33.8, 30.2, 28.6, 28.5, 21.8, 17.6, 13.9; MS (ESI+) for C$_{30}$H$_{37}$N$_3$O$_8$ m/z 568.2 (M+H)$^+$.

EXAMPLE 144

(Chart EE, Formula EE-4) 5-[(2S)-2-({(2S)-2-[(tert-butoxycarbonyl)amino]-3-phenylpropanoyl}amino)-3-oxo-3-(pentylamino)propyl]-2-[carboxy(fluoro) methoxy]benzoic acid PREPARATION OF EE-1: Triethylamine (3.37 mL; 24.2 mmol) was added to a solution of Q-2 (5.76 g; 12.1 mmol), 1,1'-bis(diphenylphosphino)ferrocene (0.400 g; 0.721 mmol) and palladium (II) acetate (0.0814 g; 0.362 mmol) in 25 mL DMF/10 mL benzyl alcohol. The reaction was placed under a CO atmosphere and heated to 60° C. for 12 h. The reaction was diluted with EtOAc (75 mL), washed with 1 M HCl (3×25 mL), and dried (Na$_2$SO$_4$). The organic phase was filtered, absorbed onto silica gel, and chromatographed (flash, silica gel) with 20% EtOAc/heptane. The white precipitate which formed in the resulting fractions was collected and washed with 20% EtOAc/heptane to afford 1.47 g EE-1. The filtrate was combined with the remaining product-containing fractions and rechromatographed with 10%–20% EtOAc/heptane to afford an additional 0.902 g EE-1 as a solid. The mixed cuts (containing residual benzyl alcohol) were evaporated to dryness at 70° C./1 Torr to afford an additional 0.527 g EE-1 as a solid. Total yield: 2.90 g (49%). $^1$H NMR (300 MHz, CDCl$_3$) δ10.70 (s, 1 H), 7.68 (d, J=2 Hz, 1 H), 7.46–7.35 (m, 5 H), 7.30 (dd, J=2, 9 Hz, 1 H), 6.89 (d, J=9 Hz, 1 H), 6.12 (br t, 1 H), 5.36 (s, 2 H), 5.25 (br d, 1 H), 4.25–4.22 (m, 1 H), 3.15–3.07 (m, 2 H), 2.97–2.92 (m, 2 H), 1.37 (s, 9 H), 1.41–1.14 (m, 6 H), 0.85 (t, J=7 Hz, 3 H).

PREPARATION OF EE-2: Ethyl bromofluoroacetate (0.26 mL; 2.2 mmol) was added to EE-1 (0.902 g; 1.86 mmol) and finely ground $K_2CO_3$ (1.28 g; 9.24 mmol) in acetone (100 mL) and the reaction was stirred 18 h at rt. The reaction was filtered throught Whatman 42 paper, concentrated, and chromatographed (flash, silica) with 30%–50% EtOAc/heptane to afford 0.809 g (74%) EE-2 as a white solid. Mp. 88–90° C.; $[\alpha]^{25}_D$=1° (c 0.91, chloroform); UV $\lambda_{max}$ 229 (10300, 95% EtOH); $^1$H NMR (300 MHz, CDCl$_3$) δ7.73 (t, J=3 Hz, 1 H), 7.42–7.28 (m, 6 H), 7.16 (d, J=8 Hz, 1 H), 6.27 (br s, 1 H), 5.88 (dd, J=1, 60 Hz, 1 H), 5.35–5.30 (m, 3 H), 4.28–4.21 (m, 3 H), 3.12–3.08 (m, 3 H), 2.99–2.94 (m, 1 H), 1.39–1.17 (m, 6 H), 1.36 (s, 9 H), 1.29 (t, J=7 Hz, 3 H), 0.85 (t, J=7 Hz, 3 H).

PREPARATION OF EE-3: Trifluoroacetic acid (12 mL) was added to a solution of EE-2 (0.659 g; 1.12 mmol) in $CH_2Cl_2$ (36 mL) and allowed to stir at rt for 20 min. The reaction was concentrated, and the residue was dissolved in $CH_2Cl_2$ (70 mL), washed with 5% $NaHCO_3$ (12 mL), water (2×12 mL), and dried (MgSO$_4$). Removal of the solvent in vacuo afforded (0.543 g) of a yellow oil, which was used without further purification. A 0.438 g portion of this oil in $CH_2Cl_2$ (40 mL) was treated with triethylamine (0.187 g; 1.34 mmol), N-tert-butyl-L-phenylalanine (0.286 g; 1.08 mmol), and diethylcyanophosphonate (0.203 g; 1.34 mmol). After 18 h at rt, the reaction was diluted with $CH_2Cl_2$ (40 mL), washed with 1 M citric acid (2×20 mL), and dried (MgSO$_4$). Chromatography (flash, silica) with 50% EtOAc/heptane) afforded 0.504 g (76%) EE-3 as a white solid. $[\alpha]^{25}_D$=−24° (c 1.02, chloroform); UV $\lambda_{max}$ 230 (10500, 95% EtOH); $^1$H NMR (300 MHz, CDCl$_3$) δ7.42–7.14 (m, 13 H), 6.74 (br s, 1 H), 6.36 (br s, 1 H), 5.88 (dd, J=5, 60 Hz, 1 H), 5.31 (s, 2 H), 5.14 (br t, 1 H), 4.65–4.61 (m, 1 H), 4.35–4.32 (m, 1 H), 4.26–4.22 (m, 2 H), 3.20–2.89 (m, 6 H), 1.33–1.16 (m, 18 H), 0.85 (t, J=7 Hz, 3 H).

PREPARATION OF EE-4: A solution of EE-3 (0.389 g; 0.529 mmol) in MeOH (25 mL) was hydrogenated at atmospheric pressure with 10% Pd/C (80.3 mg), After 23 h the catalyst was removed by filtration through Whatman 42 paper, and the filtrate concentrated to a white solid. Mass spectroscopy showed a mixture of methyl and ethyl esters: MS (ESI–) for $C_{39}H_{48}FN_3O_9$ m/z 630.1 (M–H)$^-$. MS (ESI–) for $C_{40}H_{50}FN_3O_9$ m/z 644.1 (M–H)$^-$. A 99.3 mg portion of this mixture was treated with 0.0509 M LiOH (6.35 mL) in THF (6 mL). After 15 min, rxn concentrated in vacuo to remove THF, acidified with 1 M citric acid. The resulting solid was purified by preparative RP HPLC to afford 21 mg EE-4 as a white solid after lyophilization. UV $\lambda_{max}$ 229 (8470, 95% EtOH); $^1$H NMR (300 MHz, DMSO-d$_6$) δ7.96–7.94 (m, 2 H), 7.62 (s, 1 H), 7.6–7.4 (m, 1 H), 7.24–7.17 (M, 6 H), 9.91 (br d, 1 H), 6.17 (d, J=59 Hz, 1 H), 4.50–4.40 (m, 1 H), 4.14–4.04 (m, 1 H), 3.08–2.91 (m, 3 H), 2.86–2.79 (m, 2 H), 2.71–2.61 (m, 1 H), 1.37–1.12 (m, 15 H), 0.84 (t, J=7 Hz, 3 H); IR (drift) 3311, 2959, 2931, 2871, 2860, 1689, 1646, 1525, 1498, 1450, 1441, 1368, 1291, 242, 1166 cm$^{-1}$; MS (FAB) m/z 618 (MH$^+$), 518, 120, 88, 86, 57, 43, 41, 39, 29, 23; HRMS (FAB) calcd for $C_{31}H_{40}FN_3O_9$+ $H_1$ 618.2827, found 618.2851.

EXAMPLE 145

(Chart FF, Formula FF-2) 5-{(2S)-2-({(2S)-2-[(tert-butoxycarbonyl)amino]-3-phenylpropanoyl}amino)-3-oxo-3-[(4-phenylbutyl)amino]propyl}-2-(carboxymethoxy)benzoic acid To a solution of X-5 (100 mg, 0.18 mmol) in dichloromethane (500 uL) was added 1-hydroxybenzotriazole (31 mg, 0.23 mmol) in N,N-dimethylformamide (100 uL) and 4-phenylbutylamine (46 uL, 0.29 mmol). The mixture was cooled in an ice bath and 1-(3-dimethylaminopropyl)-3-ethylcarbodiimide hydrochloride (44 mg, 0.23 mmol) in dichloromethane (2 mL) was added. The mixture was stirred in room temperature for 3 h. The reaction mixture was applied on a small silica gel column (5 mL) packed in dichloromethane and the amide FF-1 was eluted using a stepwise gradient of dichloromethane-acetonitrile. The amide was then dissolved in tetrahydrofuran-methanol (3 mL, 2:1) and aqueous sodium hydroxide (1.5 mL, 2%) was added. The mixture was stirred at room temperature for 6 h. Acetic acid (40 uL) was added and the mixture was concentrated. The material was purified by reversed phase HPLC (Vydac C-18 column) using a water-acetonitrile gradient and lyophilized to give FF-2 (34 mg) as a white solid. $^1$H-NMR (400 MHz, CD$_3$OD) δ7.76 (s, 1H), 7.38 (d, J=8.5 Hz, 1H), 7.26–7.11 (m, 10H), 6.98 (d, J=8.5 Hz, 1H), 4.76 (s, 2H), 4.50 (t, J=6.9 Hz, 1H), 4.23 (dd, J=5.2 Hz, J=9.3 Hz, 1H), 3.21–2.72 (m, 6H), 2.58 (t, J=7.5 Hz, 2H), 1.54 (m, 2H), 1.42 (m 2H), 1.34 (s, 9H); IR (KBr) 3296, 2925, 1738, 1687, 1643 cm$^{-1}$; HRMS m/z 661.2987 (calc. of monoisotopic mass for $C_{36}H_{43}N_3O_9$ gives 661.2999).

CHART A

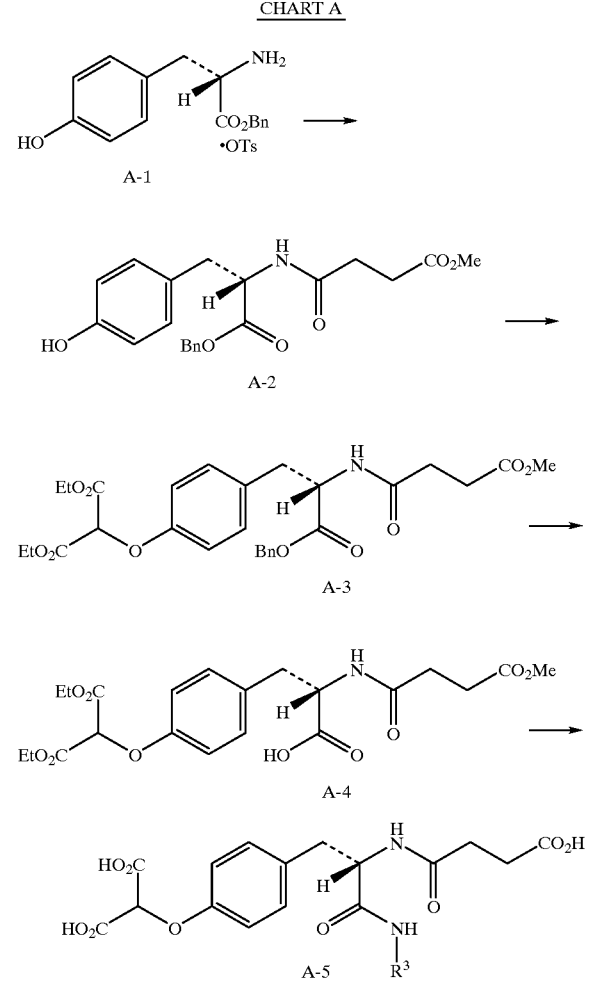

CHART B
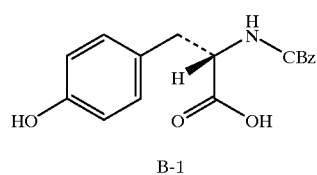
B-1
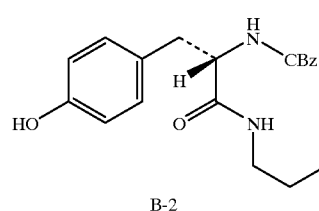
B-2
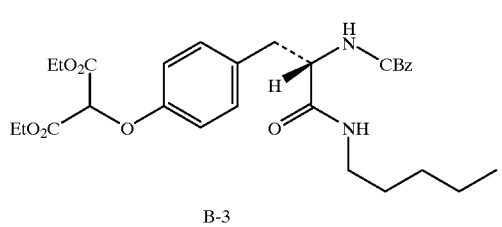
B-3
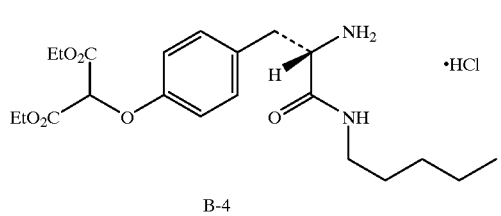
B-4
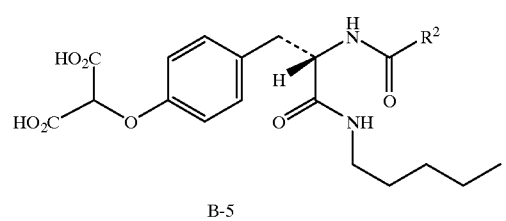
B-5
CHART C
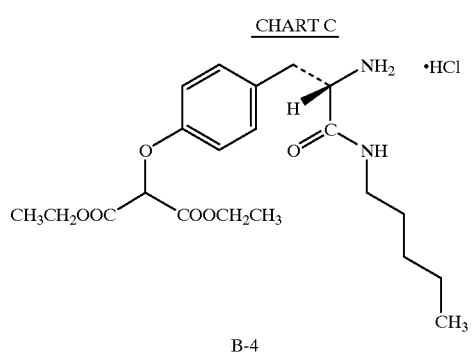
B-4
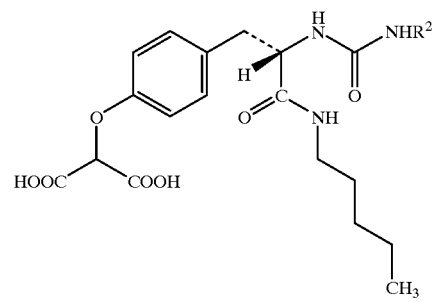
C-1
CHART D
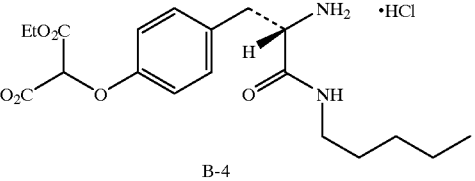
B-4
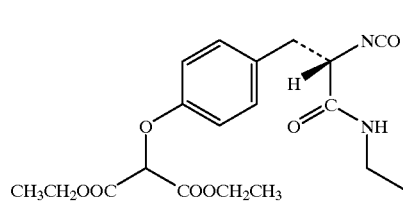
D-1
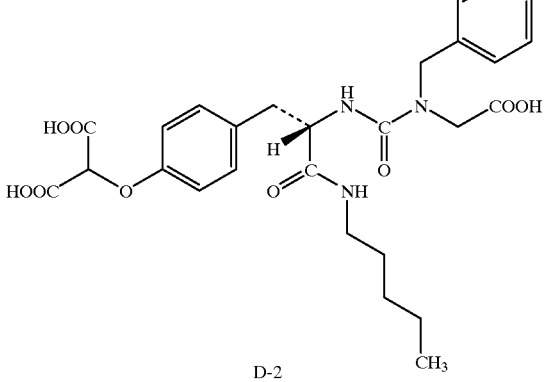
D-2

CHART E
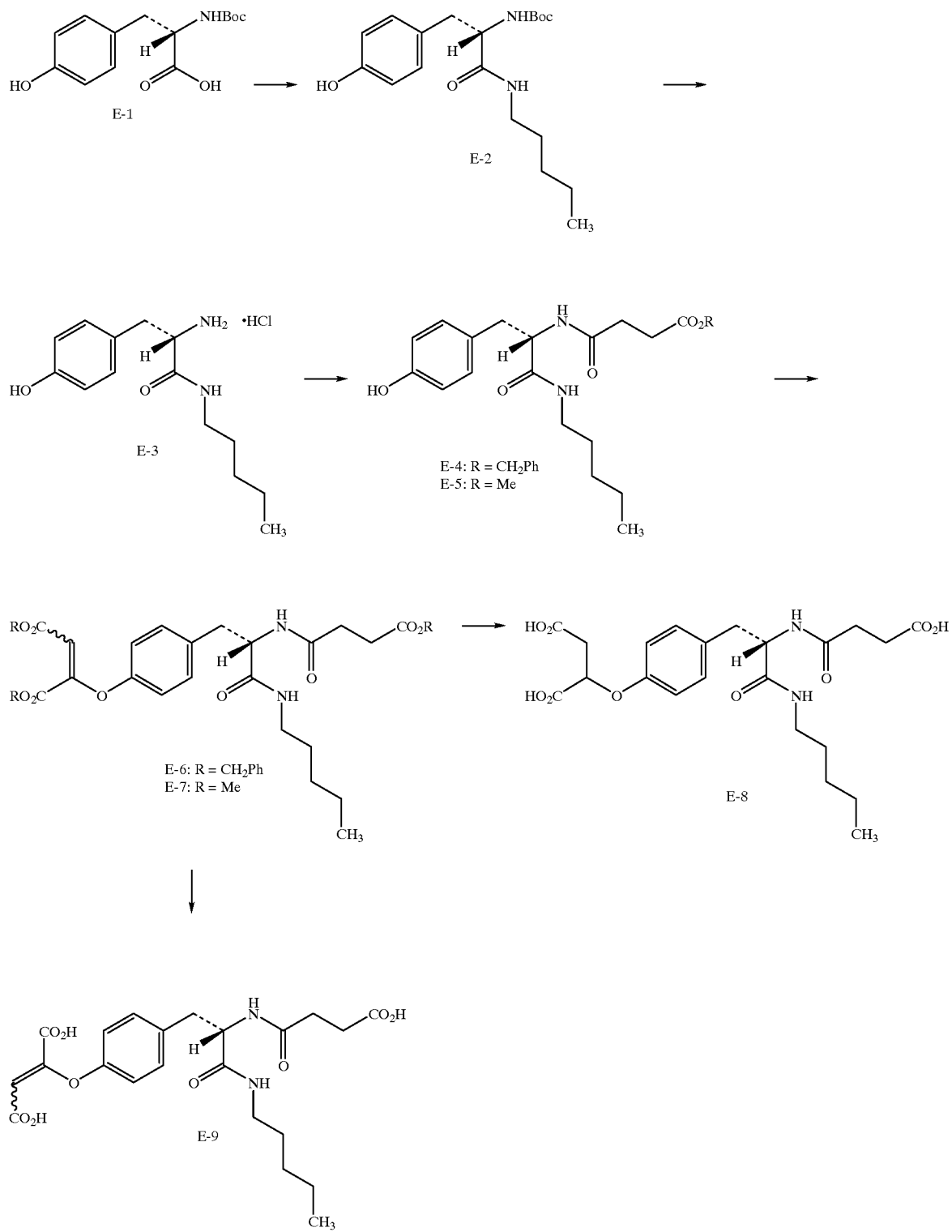

CHART F
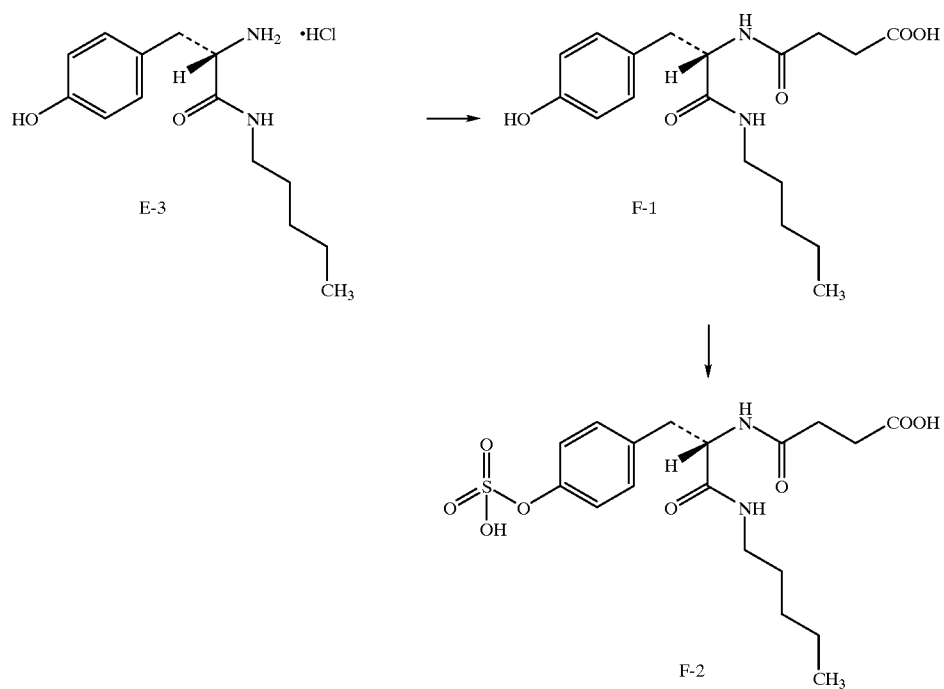
CHART G
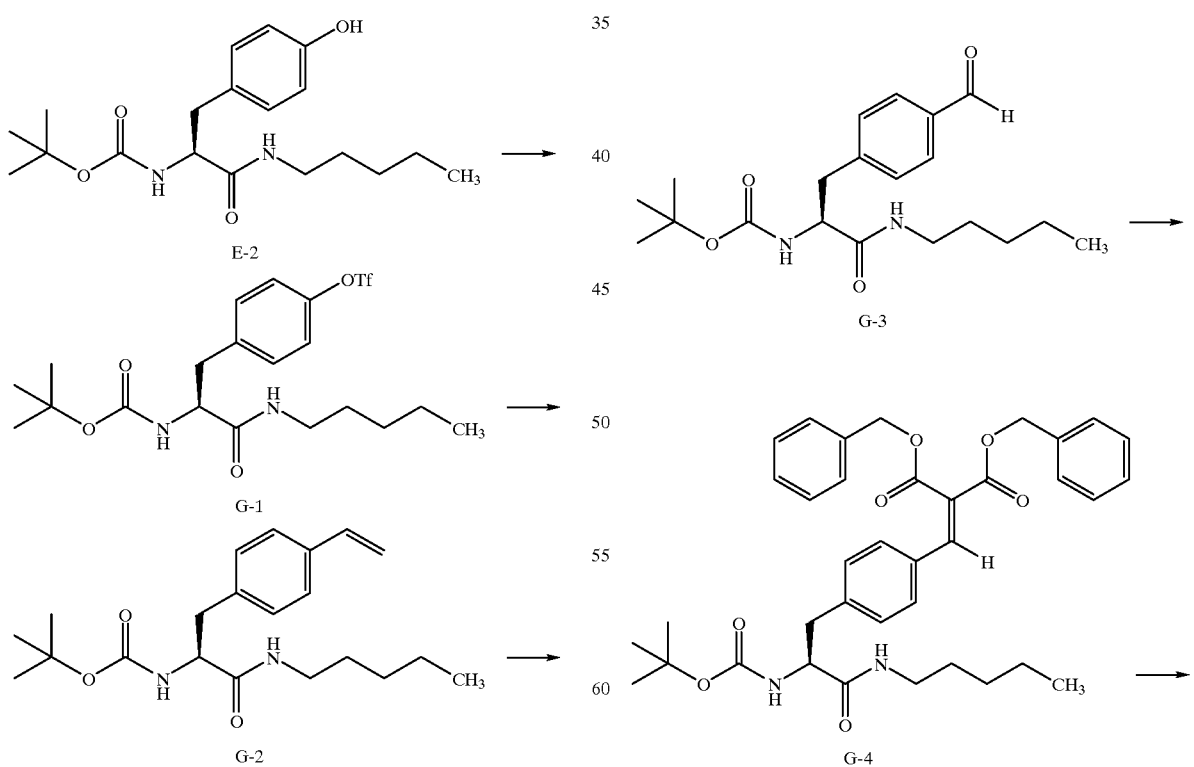

79
-continued
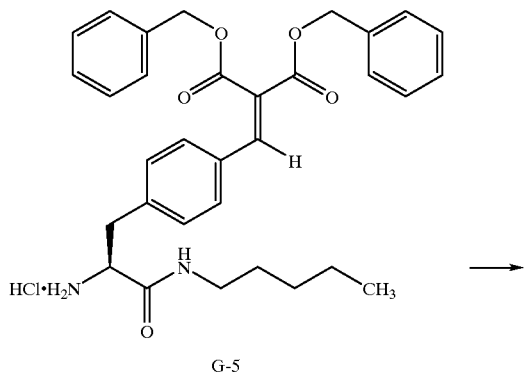
G-5
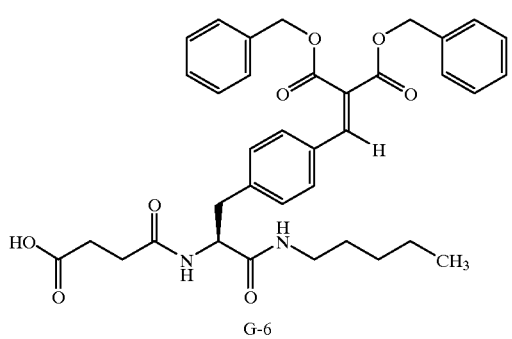
G-6
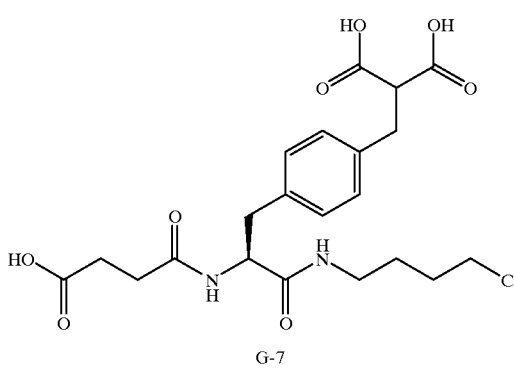
G-7
CHART H
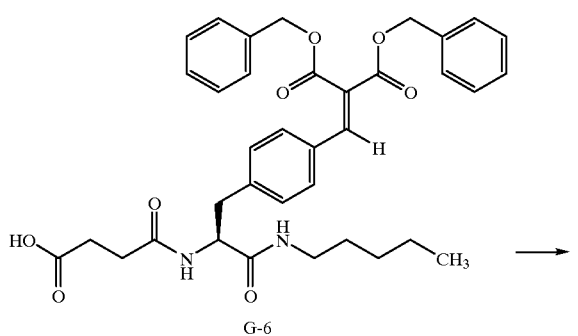
G-6
80
-continued
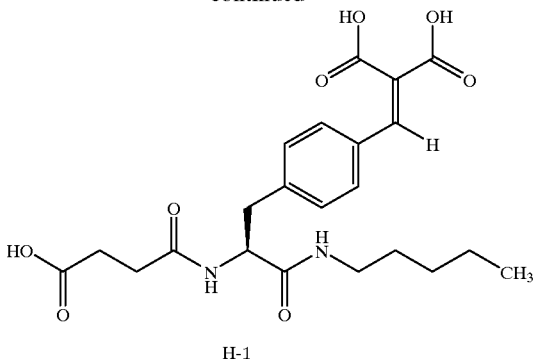
H-1
CHART I
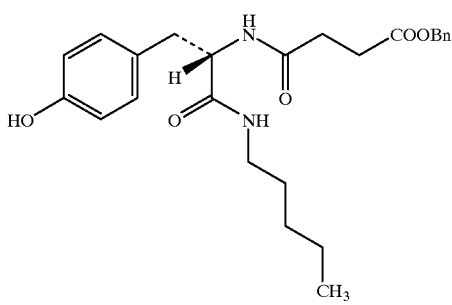
E-4
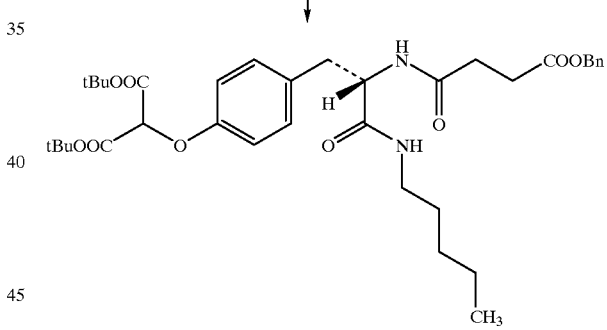
I-1
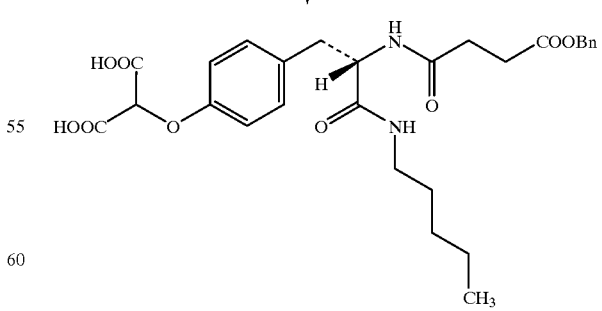
I-2

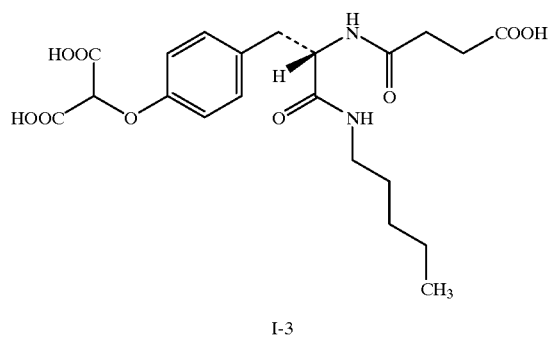
I-3
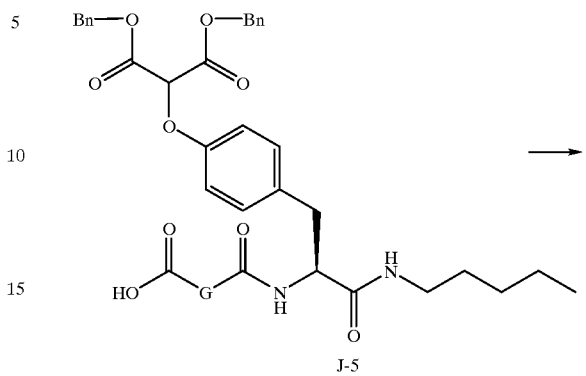
J-5
CHART J
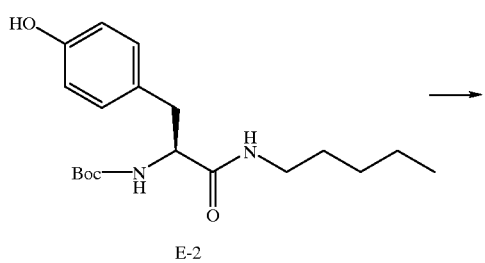
E-2
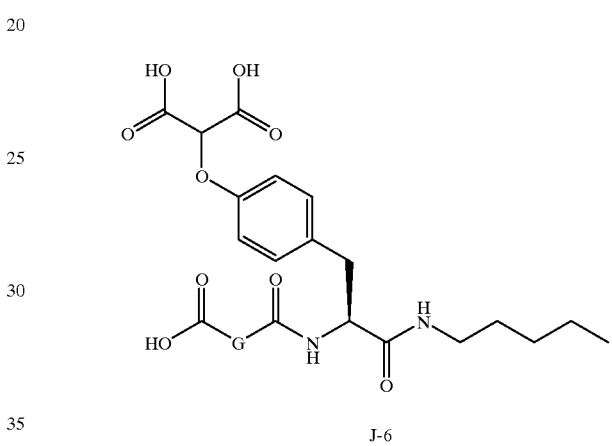
J-6
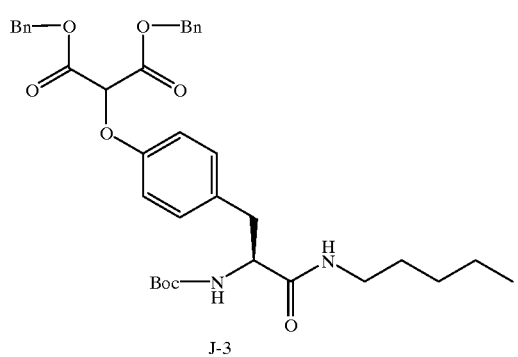
J-3
CHART K
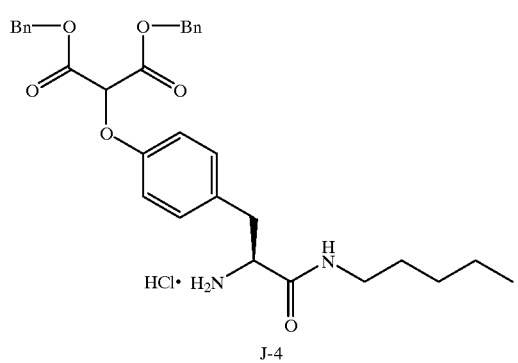
J-4
K-1
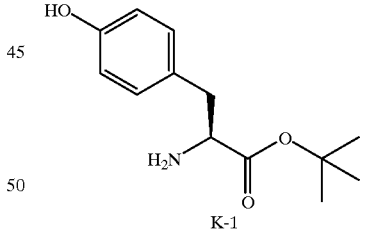
K-2

-continued
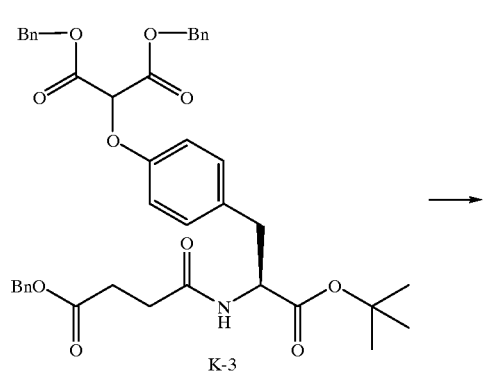
K-3
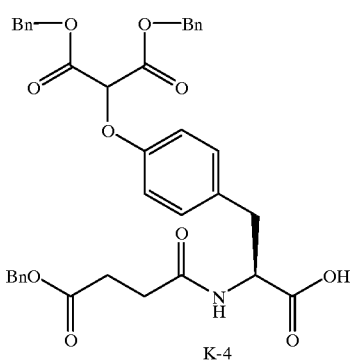
K-4
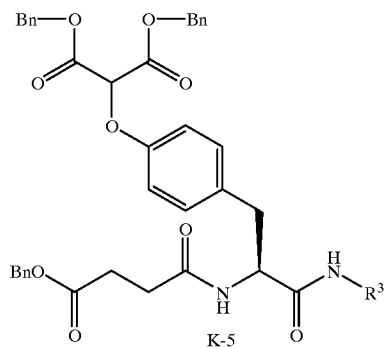
K-5
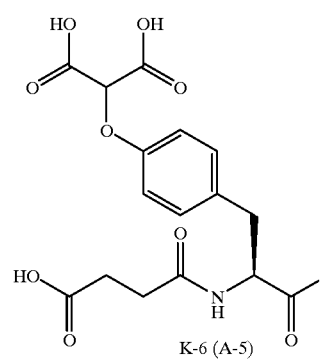
K-6 (A-5)
CHART L
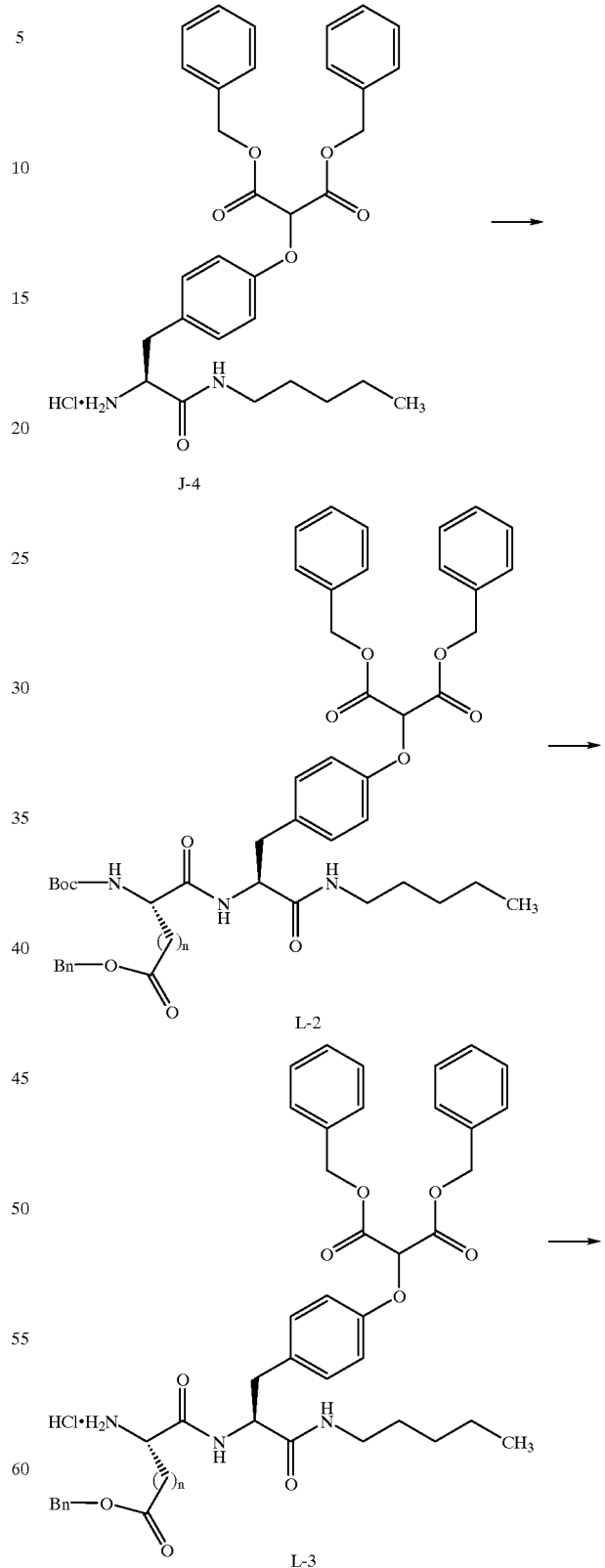
J-4
L-2
L-3

85
-continued
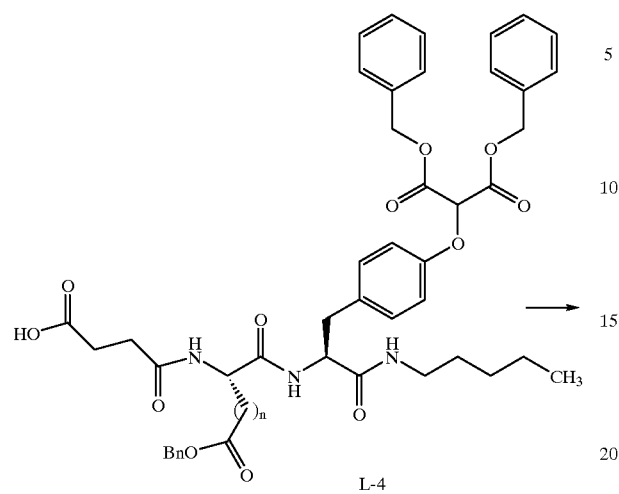
L-4
L-5
CHART M
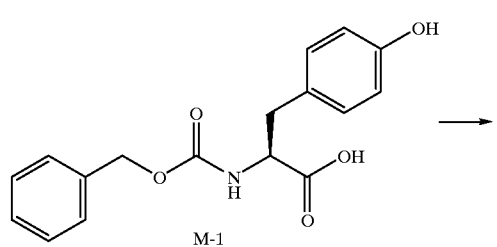
M-1
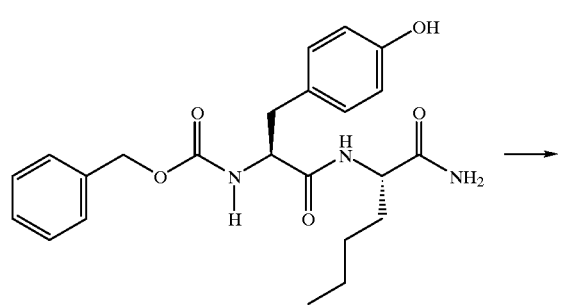
M-2
86
-continued
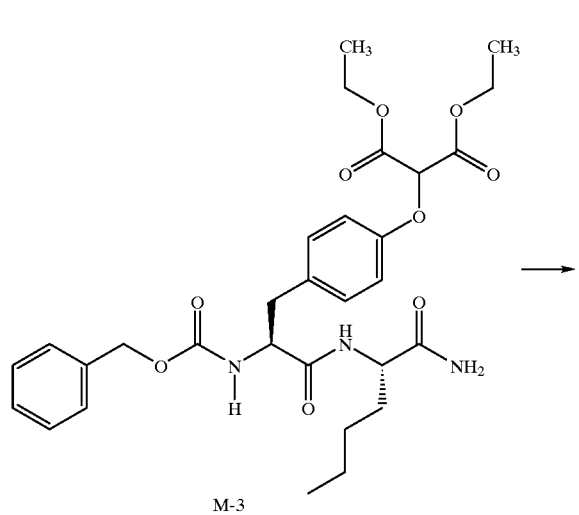
M-3
M-4
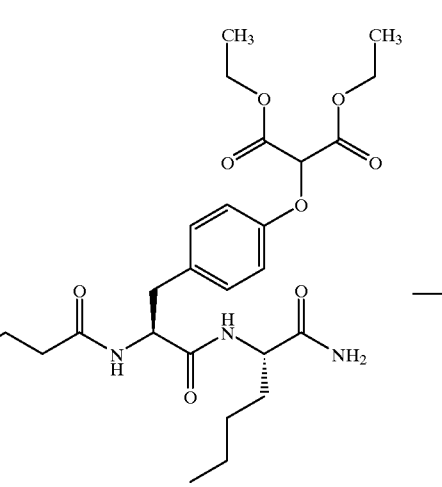
M-5

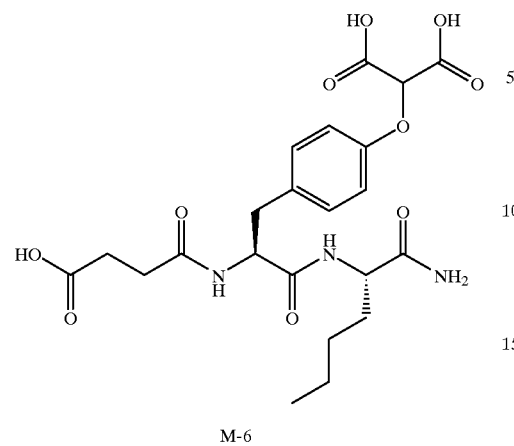
M-6
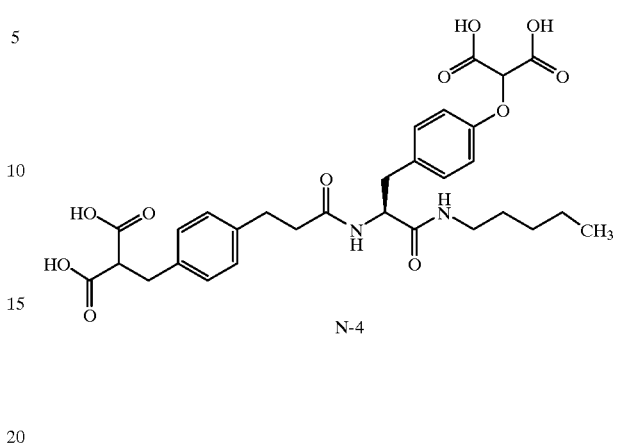
N-4
CHART N
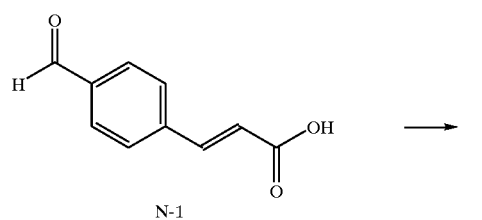
N-1
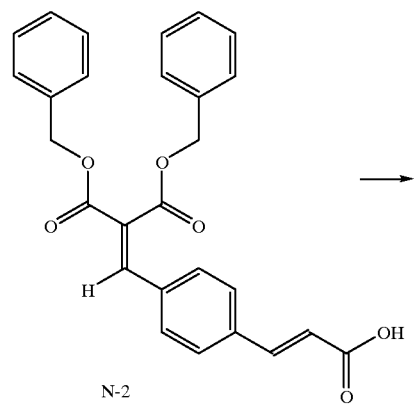
N-2
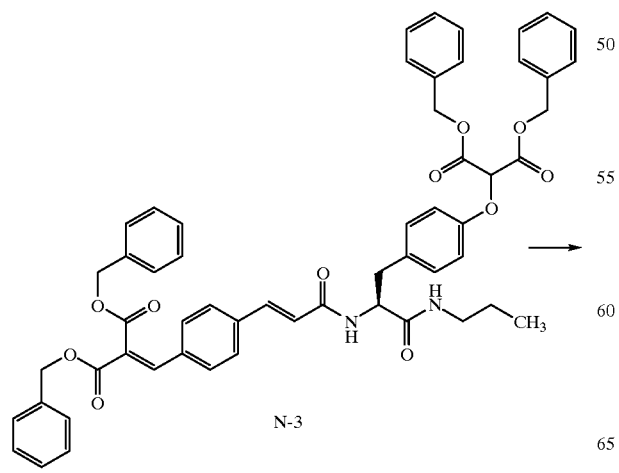
N-3
CHART O
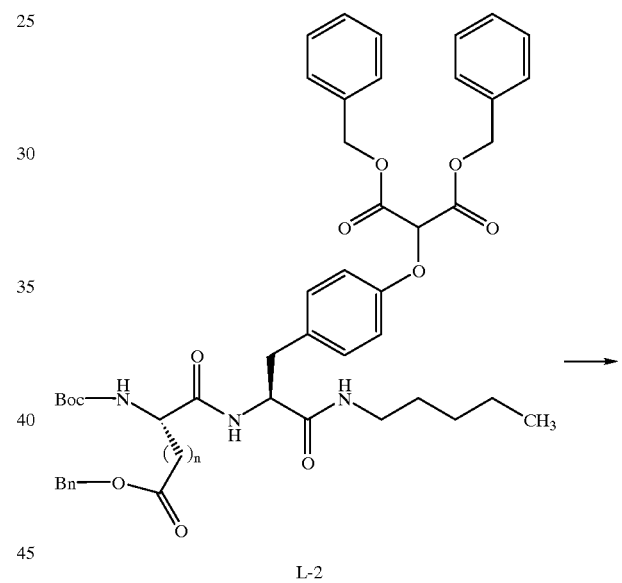
L-2
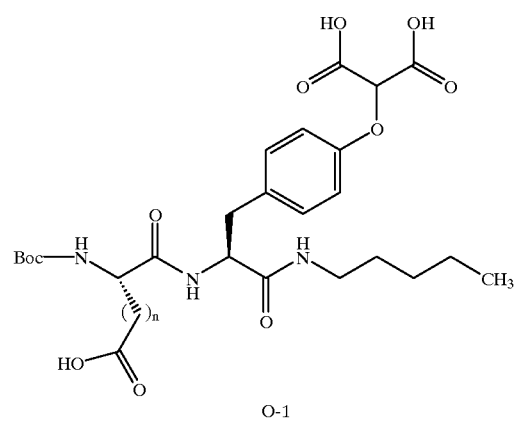
O-1

CHART P
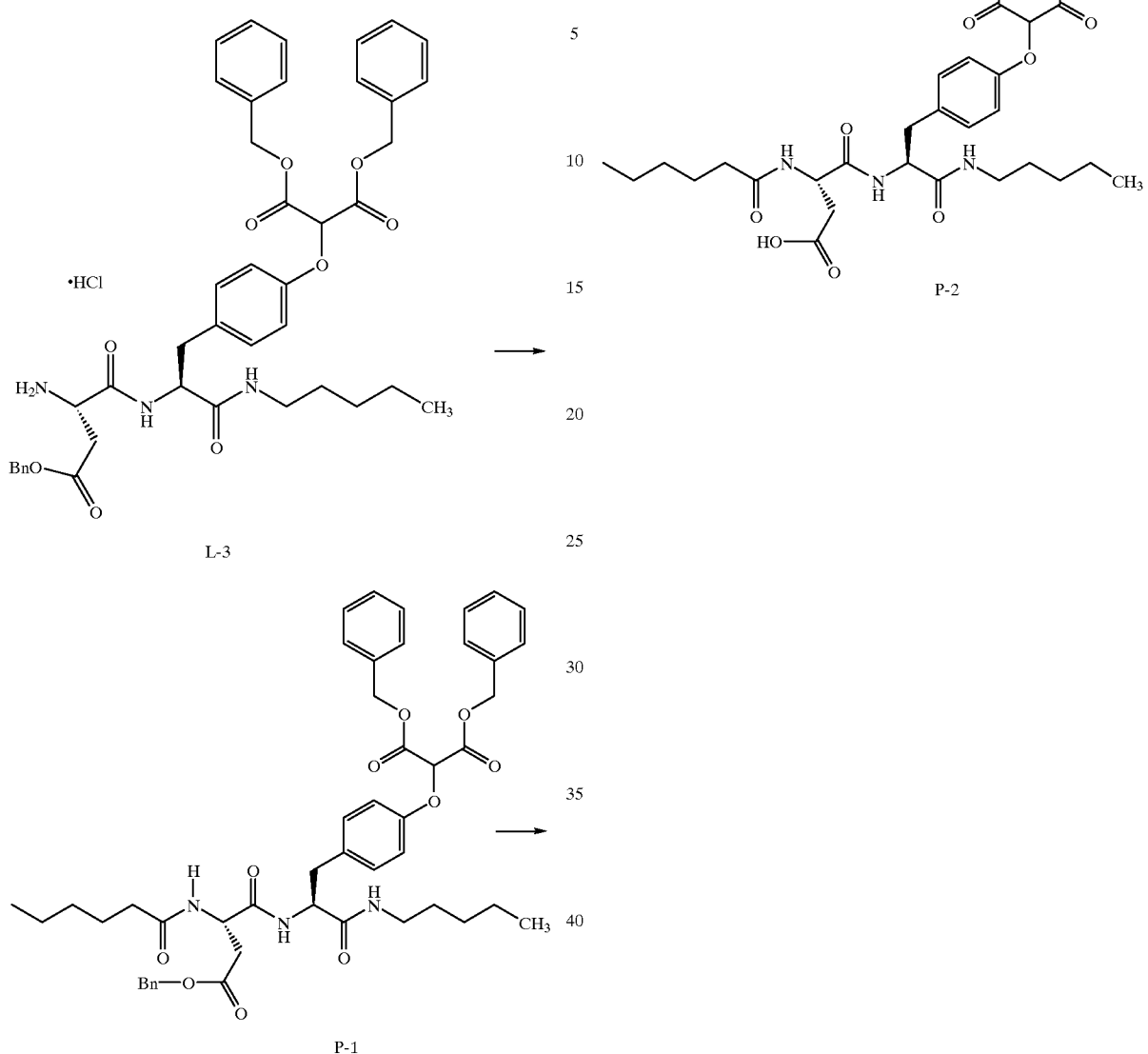
CHART Q
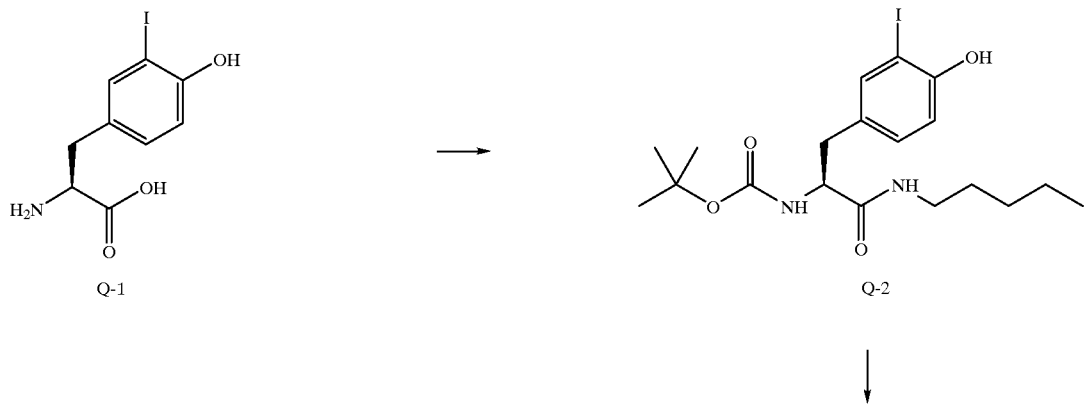

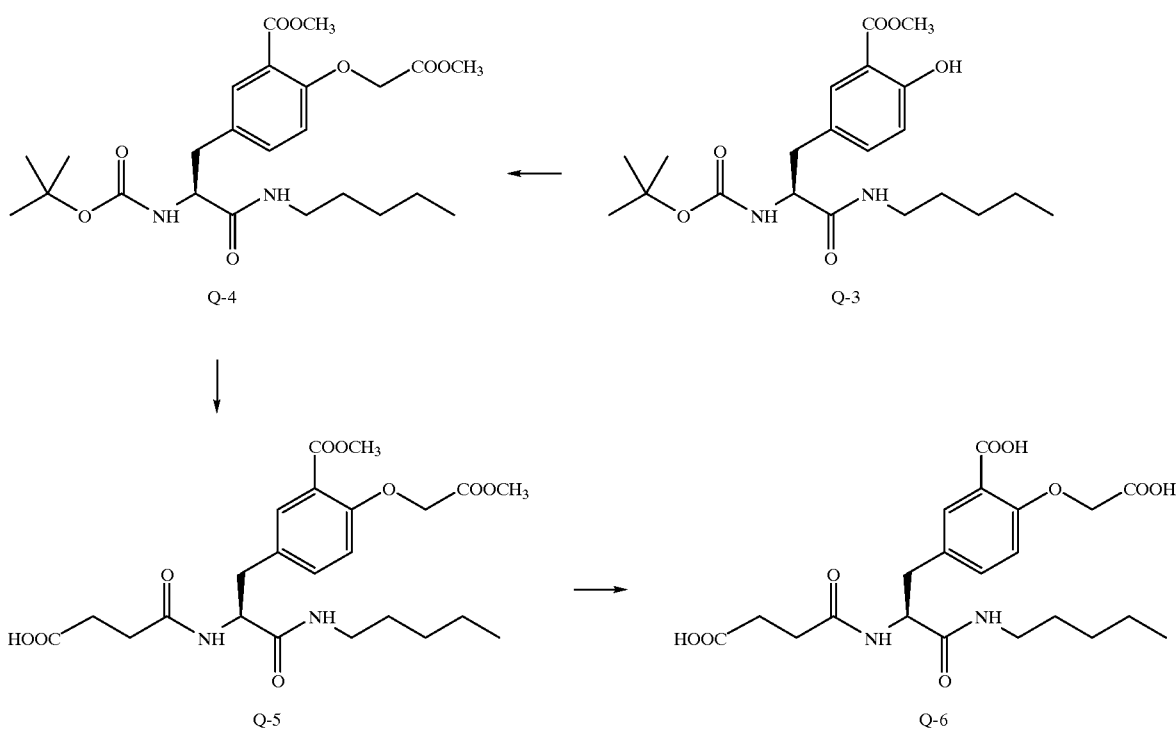
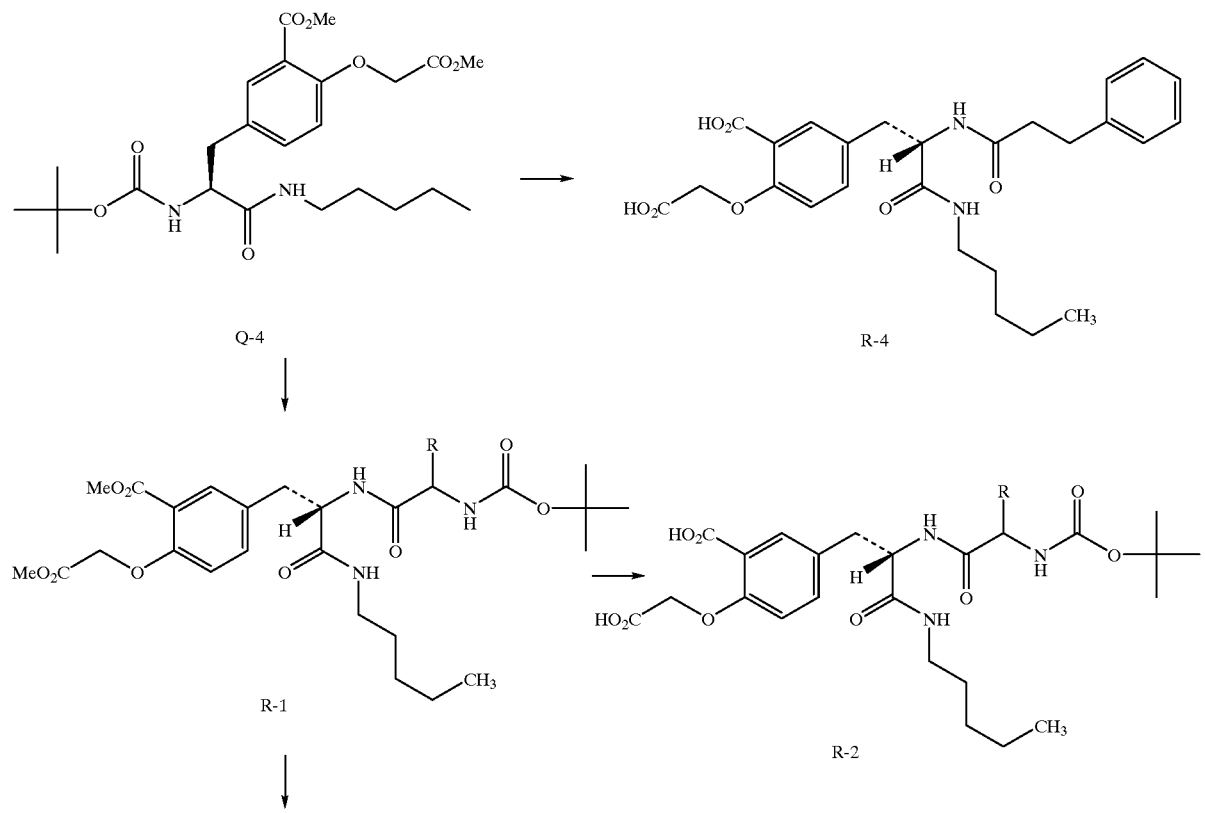
CHART R

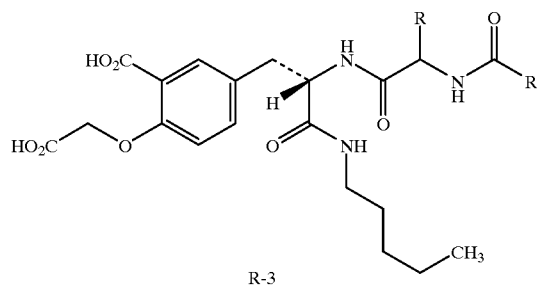
R-3
CHART S
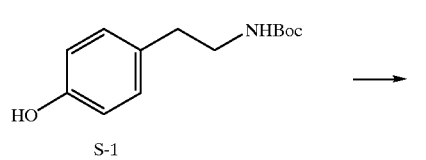
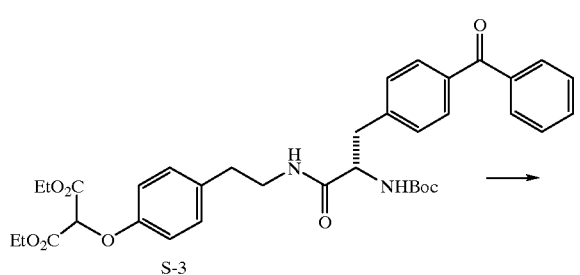
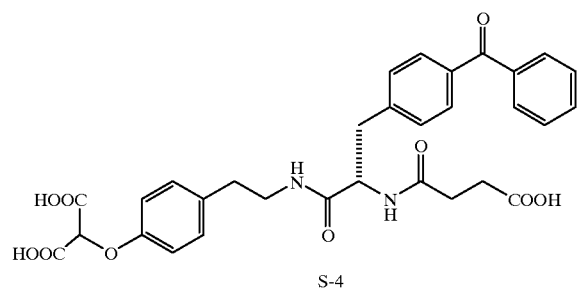
S-4
CHART T
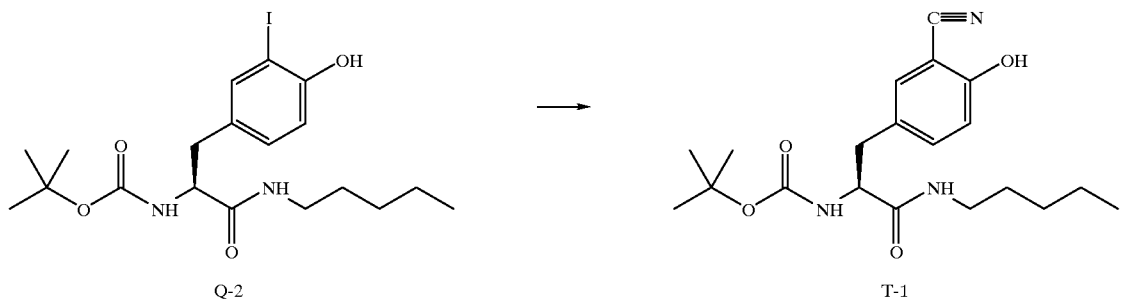

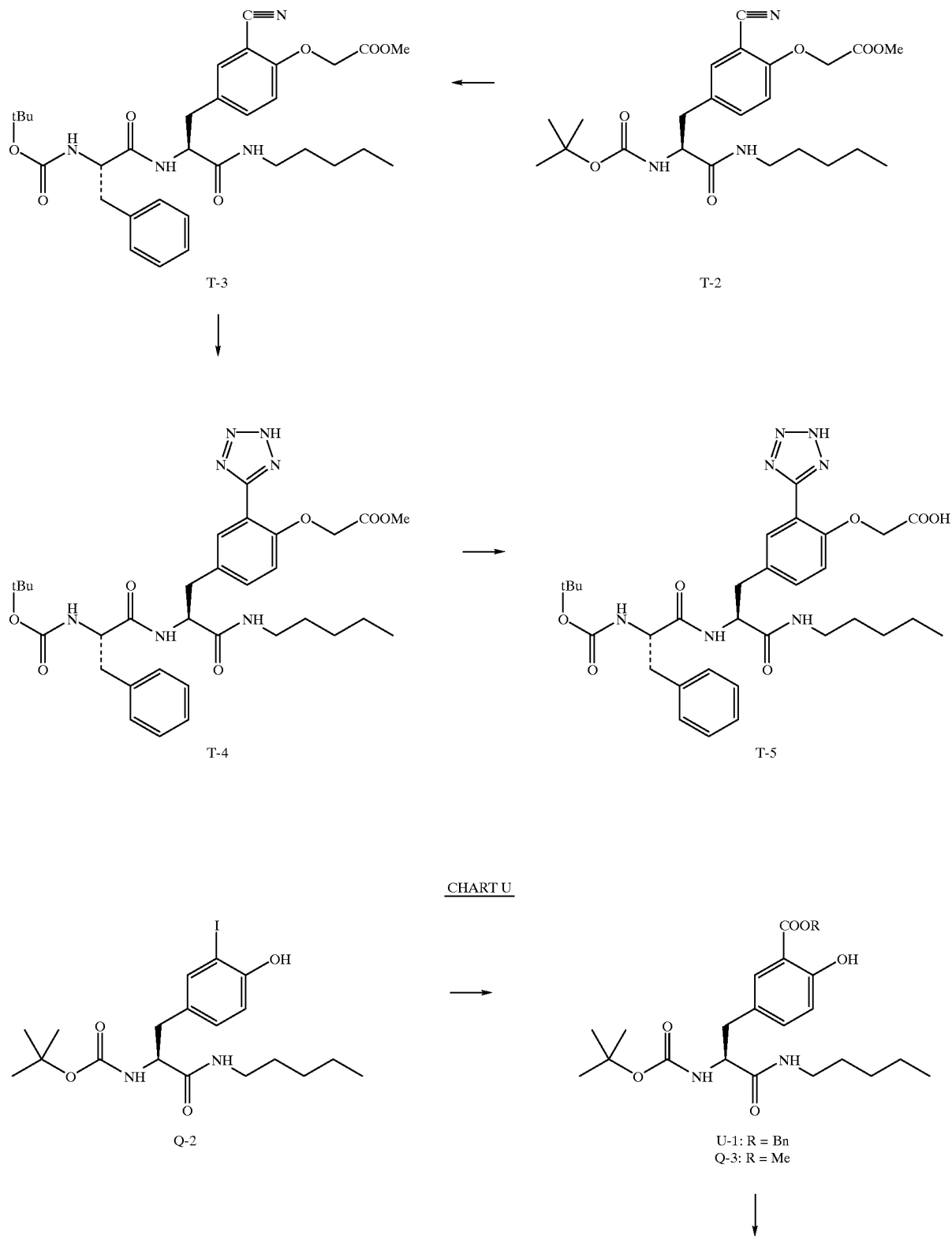

-continued
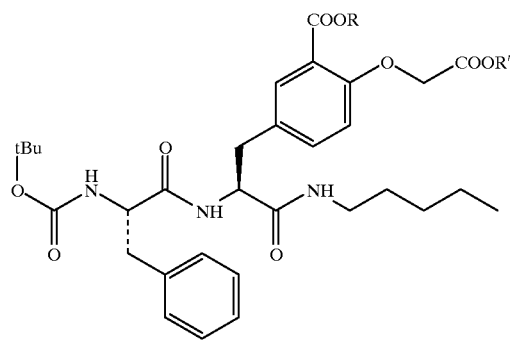
U-4: R = Bn, R' = Me
U-5: R = Me, R' = Bn
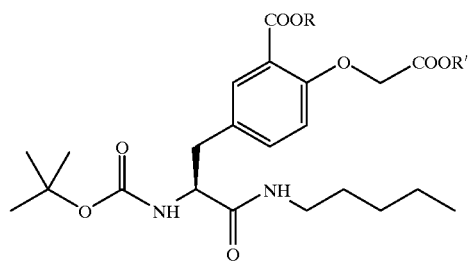
U-2: R = Bn, R' = Me
U-3: R = Me, R' = Bn
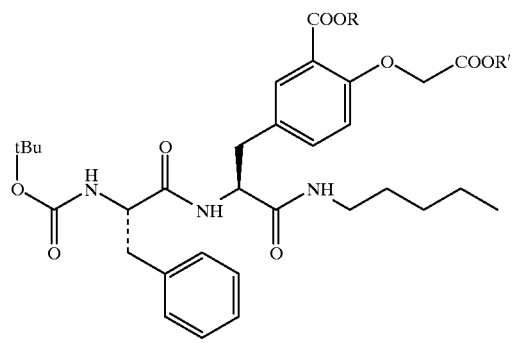
U-6: R = H, R' = Me
U-7: R = Me, R' = H
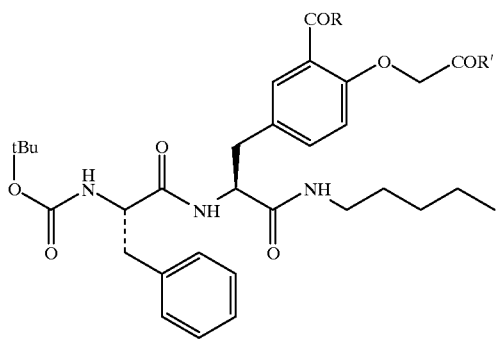
U-8: R = NHOH, R' = OMe
U-9: R = OMe, R' = NHOH
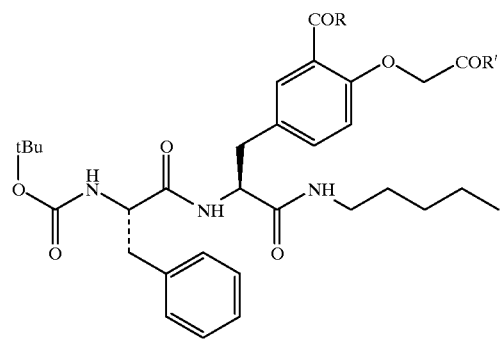
U-10: R = NHOH, R' = OH
U-11: R = OH, R' = NHOH CHART V
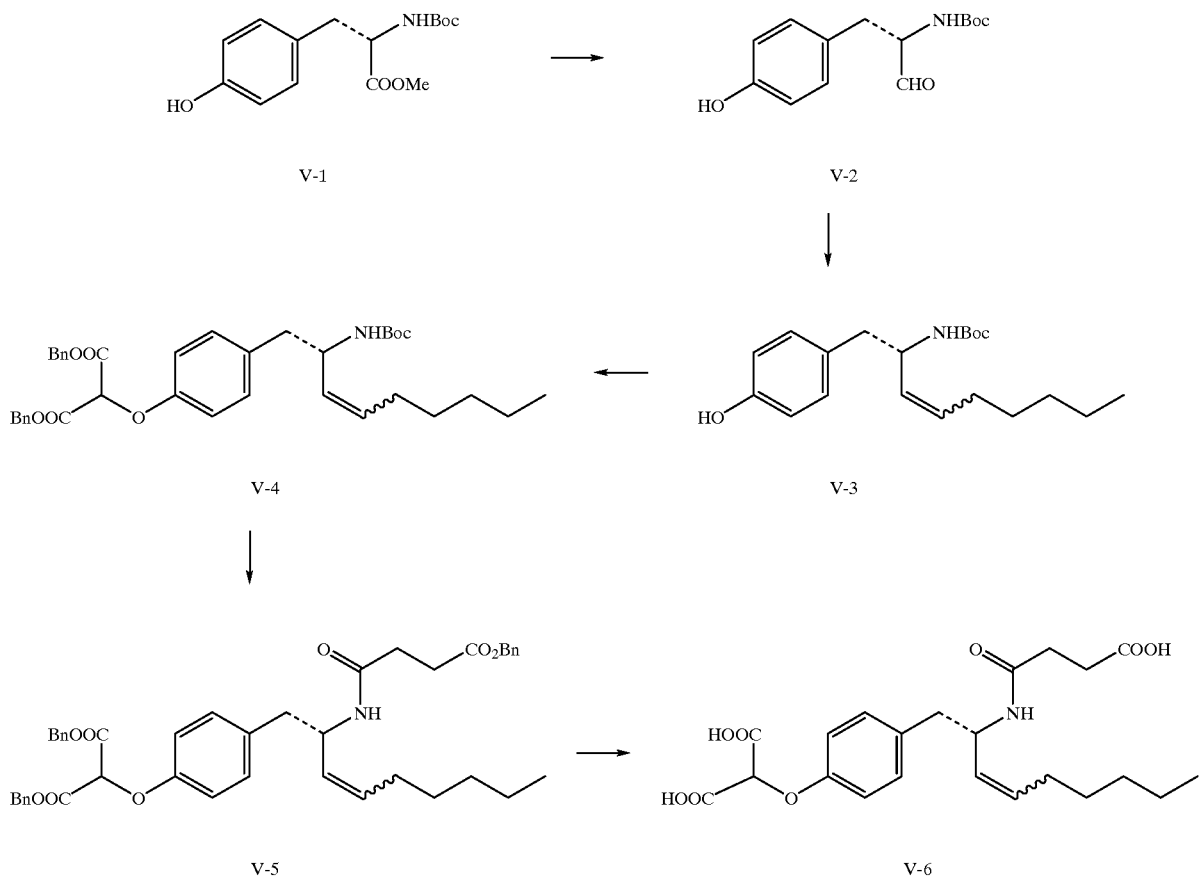
CHART W
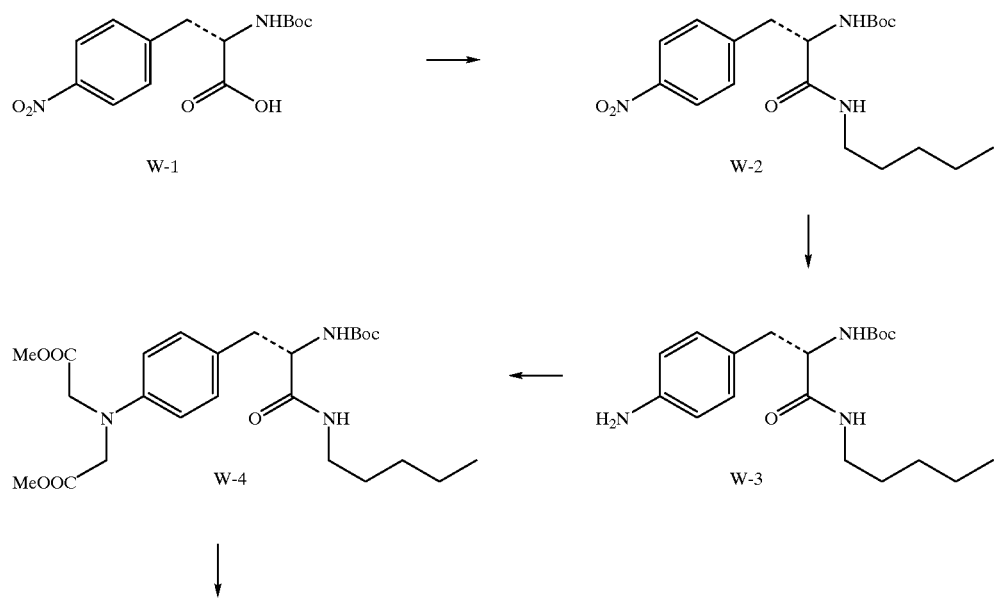

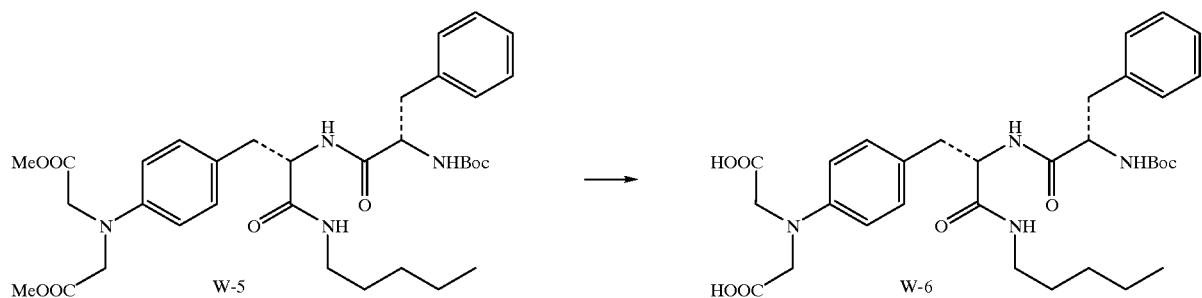
CHART X
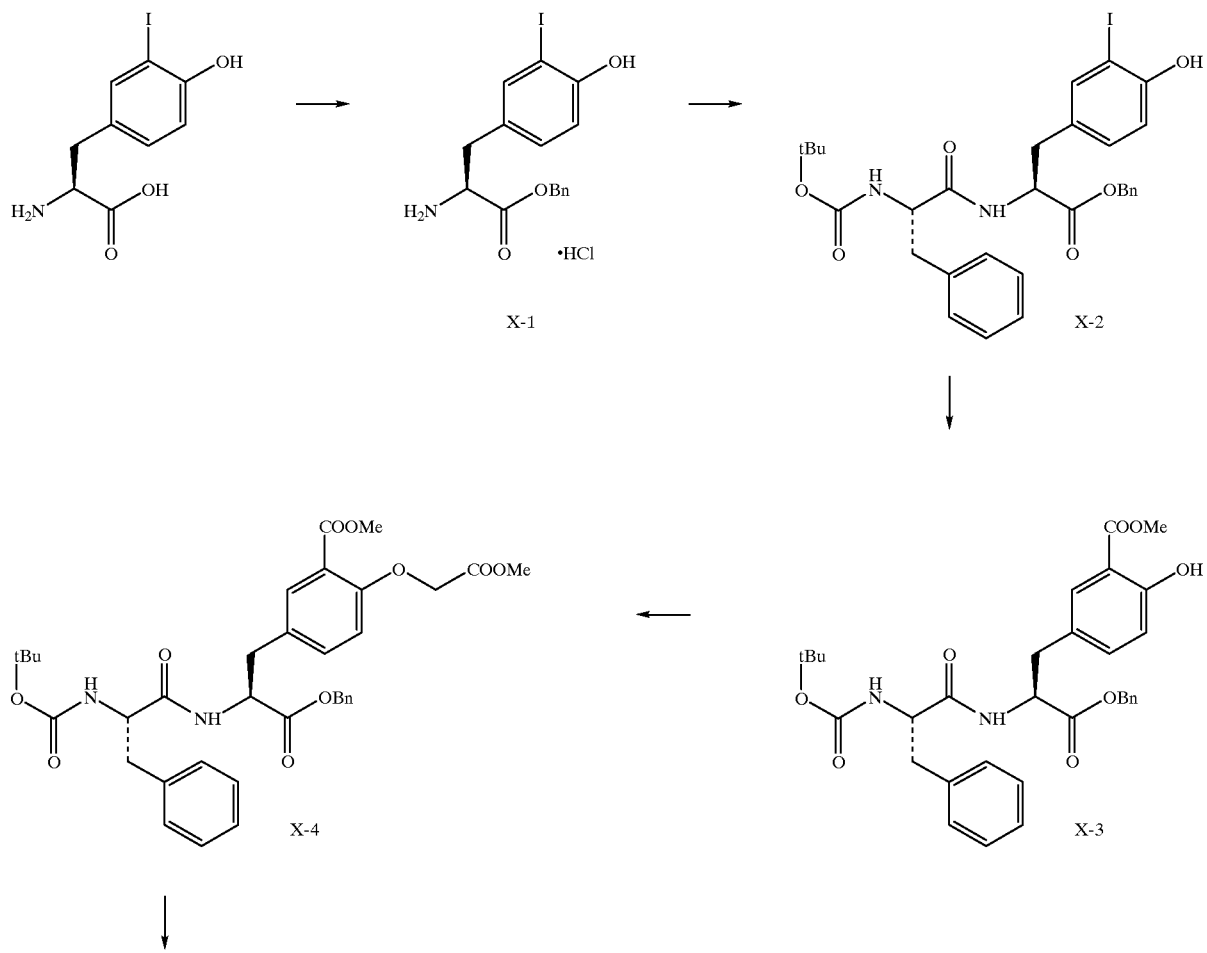

103
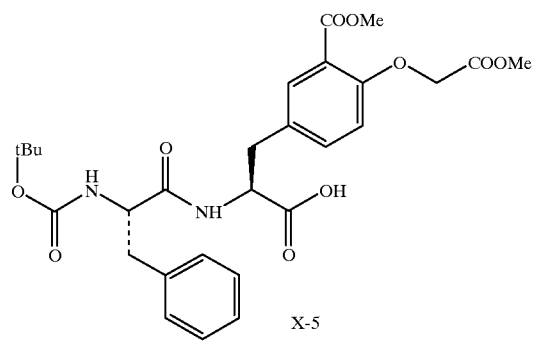
X-5
104
-continued
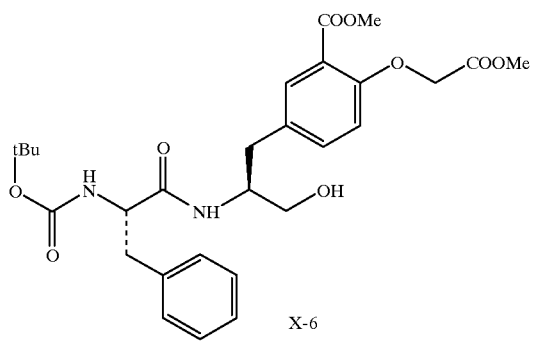
X-6
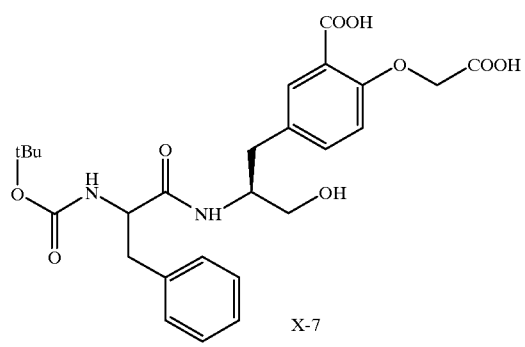
X-7
CHART Y
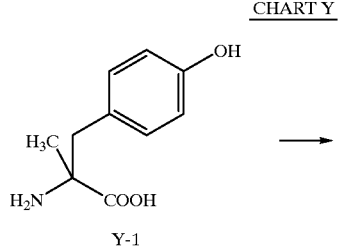
Y-1
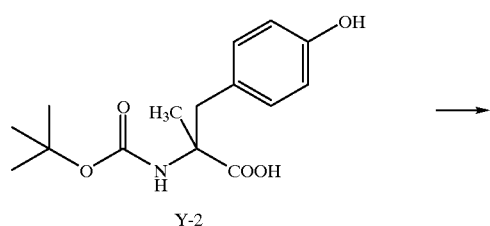
Y-2
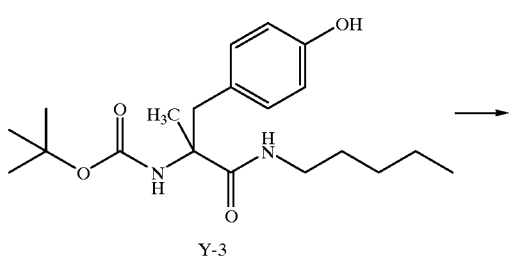
Y-3
-continued
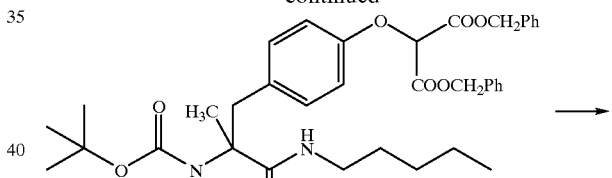
Y-4
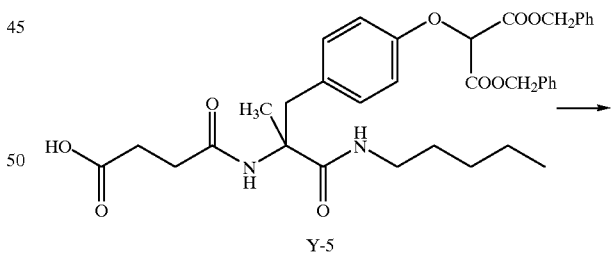
Y-5
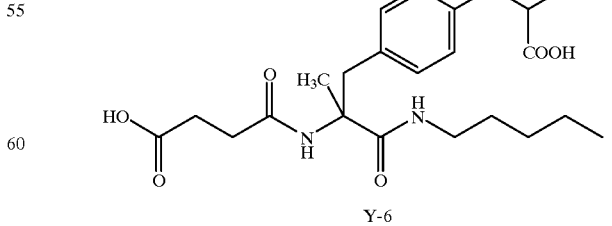
Y-6

CHART Z
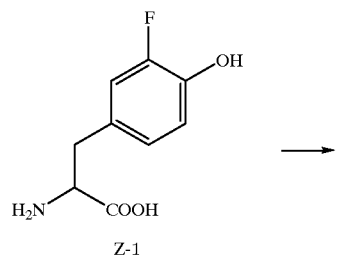
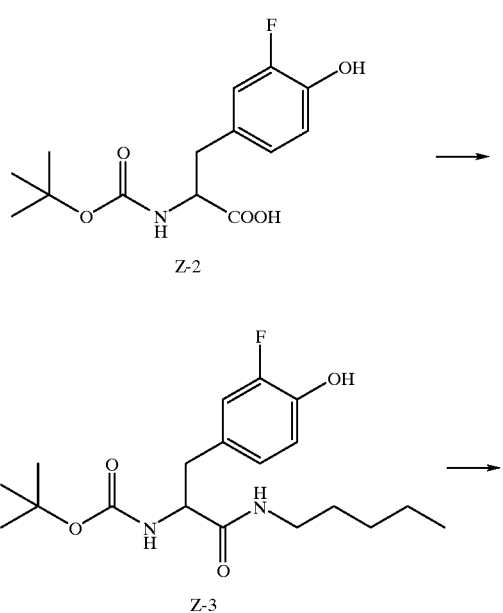
-continued
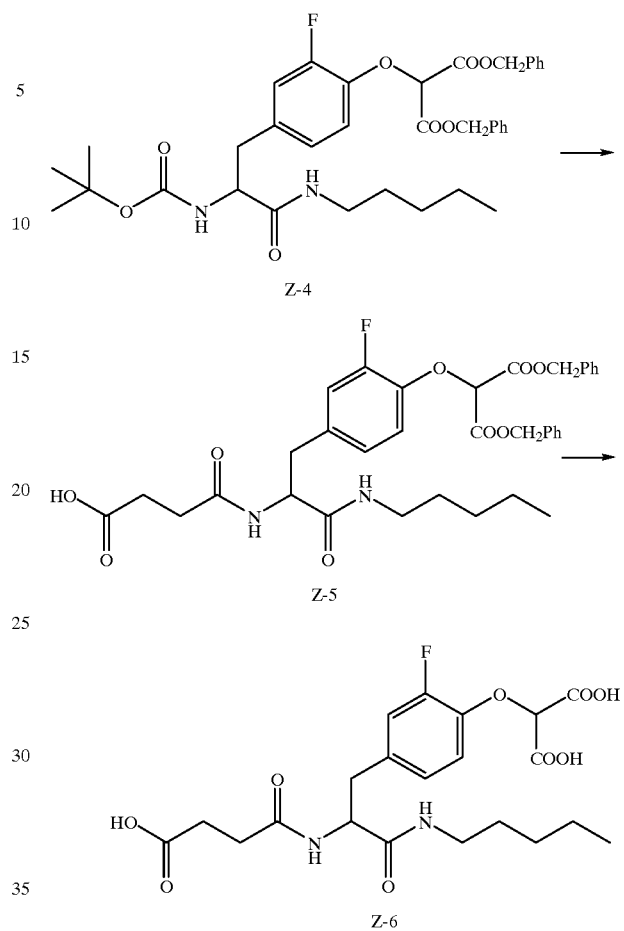
CHART AA
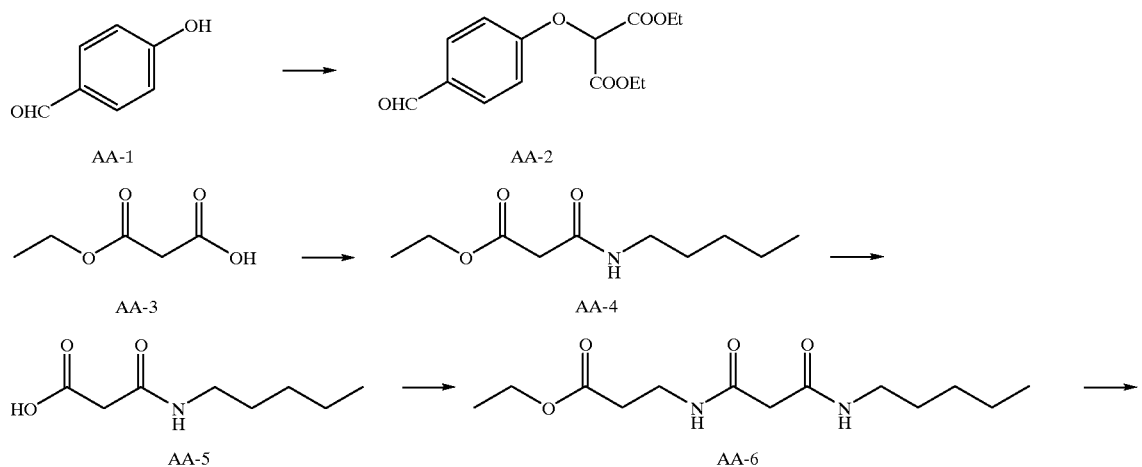

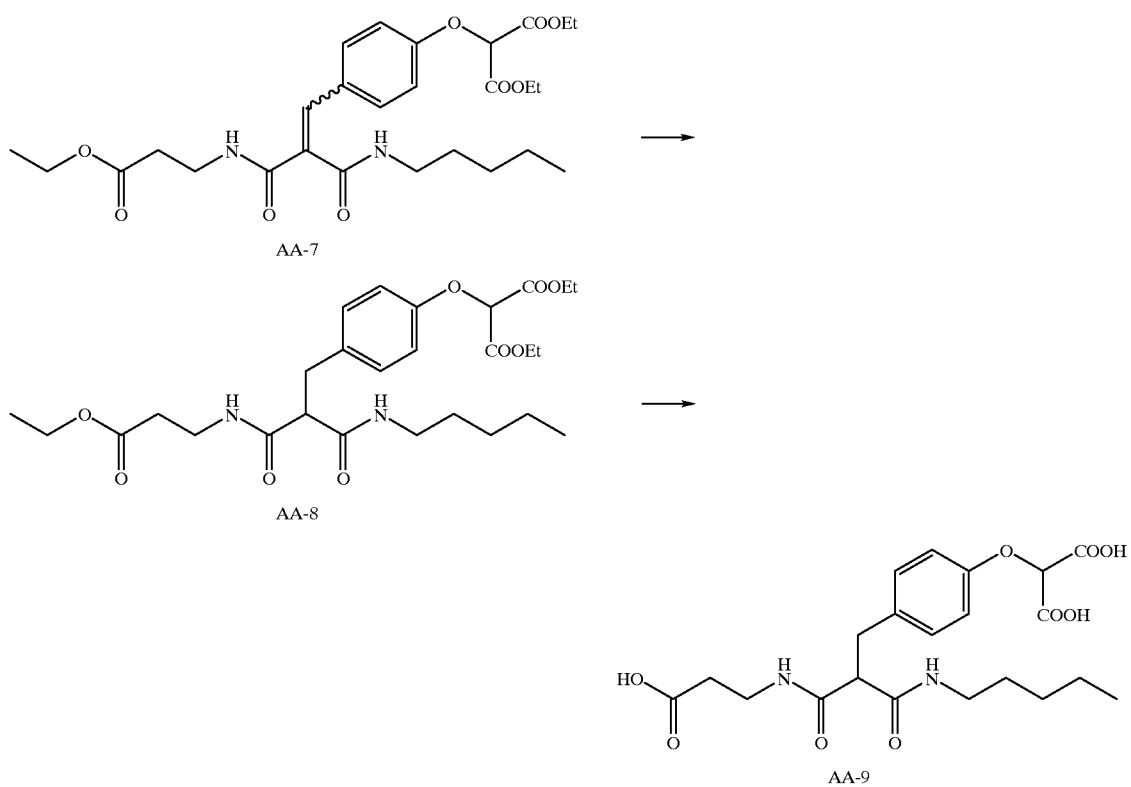
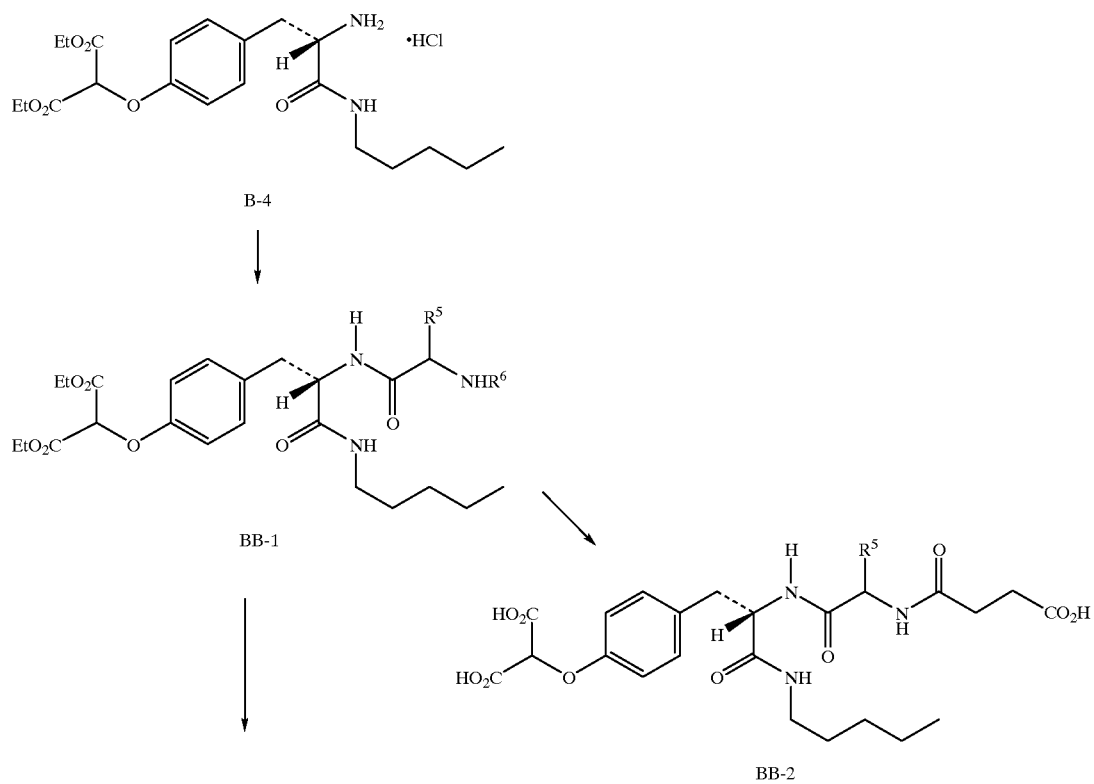
CHART BB

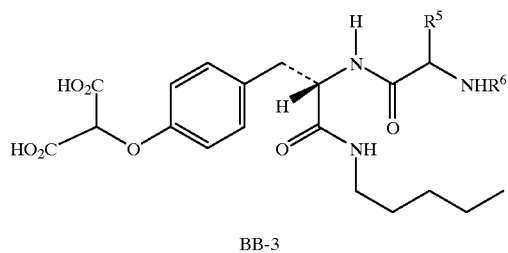
BB-3
CHART CC
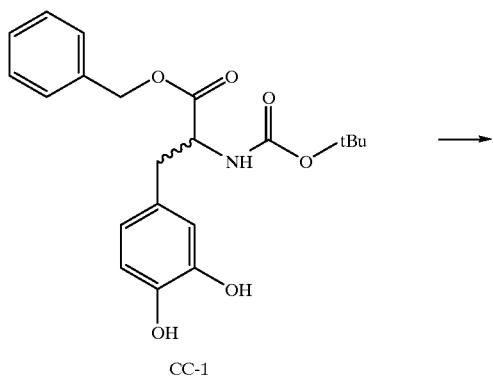
CC-1
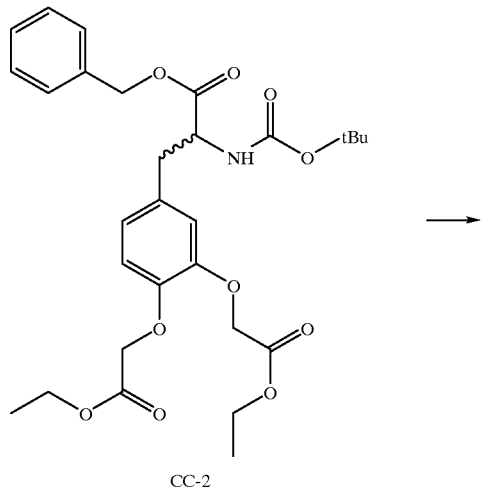
CC-2
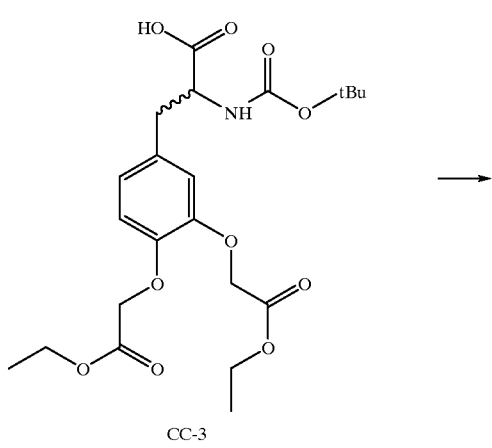
CC-3
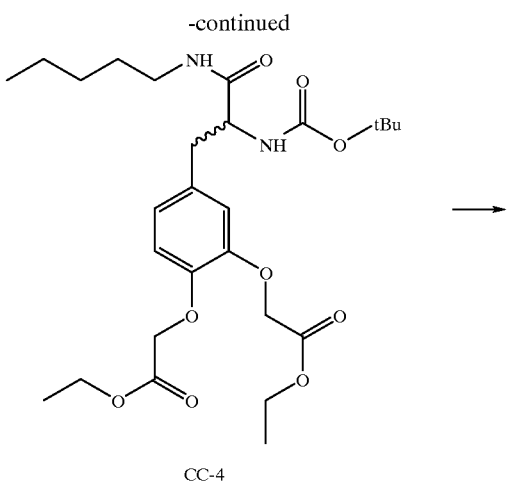
CC-4
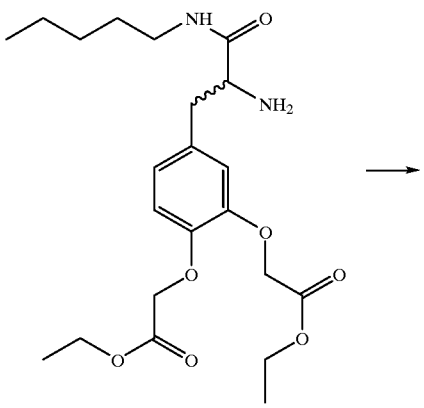
CC-5
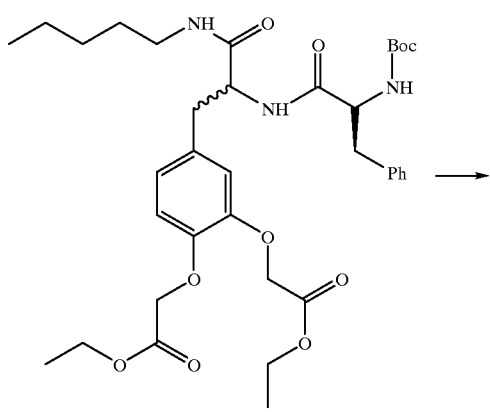
CC-6

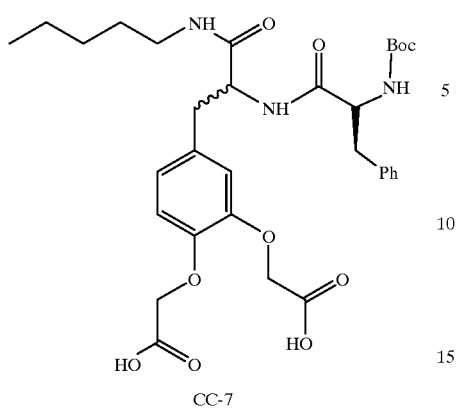
CC-7
CHART DD
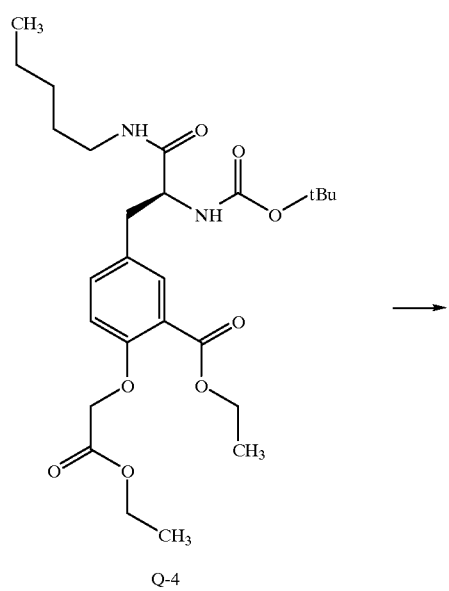
Q-4
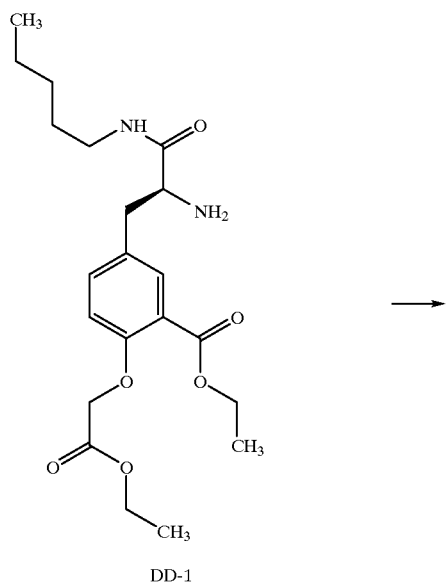
DD-1
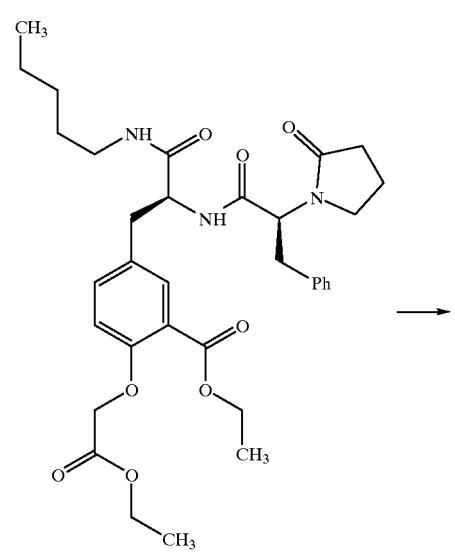
DD-2
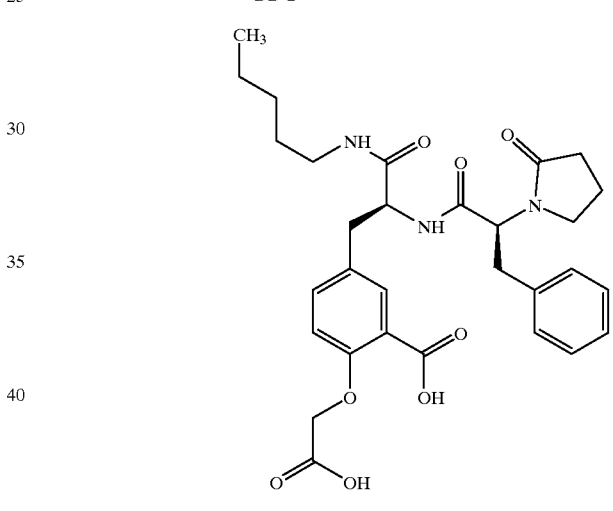
DD-3
CHART EE
Q-2 →
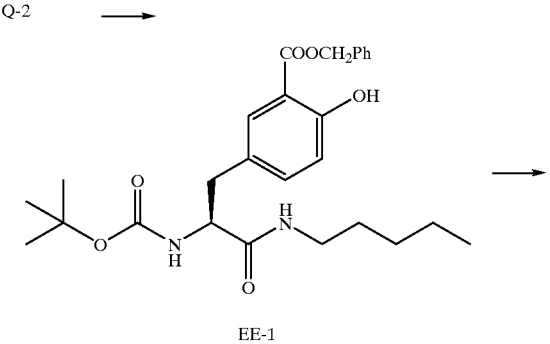
EE-1

113
-continued
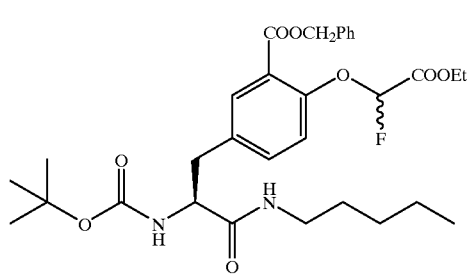
EE-2
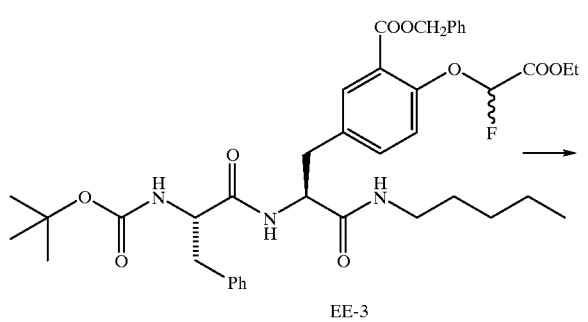
EE-3
114
-continued
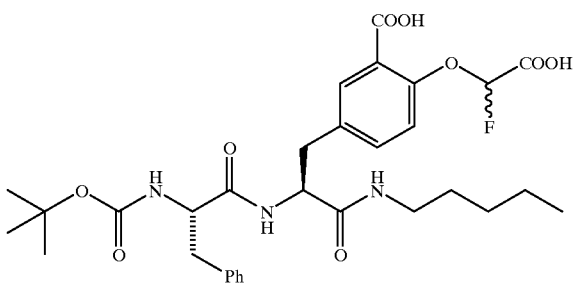
EE-4
CHART FF
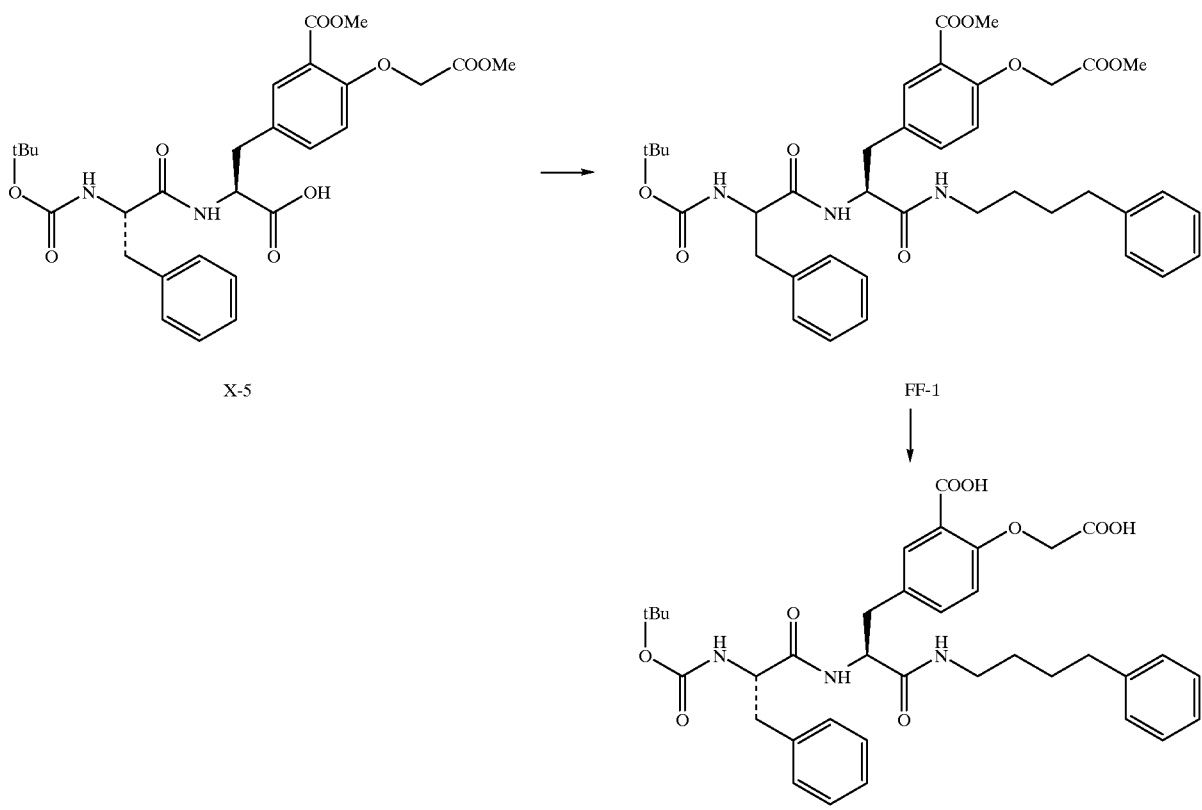

TABLE 1

| Example Number, Structure | PTP1 Inhib Conc (μM) | % Inhib |
|---|---|---|
| Example 1 | 100 | 80 |
|  | 10 | 8 |
|  | 1 | 3 |
| Example 3 | 100 | 81 |
|  | 100 | 76 |
|  | 10 | 25 |
|  | 1 | 1 |
| Example 2 | 10 | 9 |
|  | 1 | 4 |
|  | 100 | 39 |
| Example 12 | 10 | 17 |
|  | 1 | 2 |
|  | 100 | 67 |

TABLE 1-continued
| Example Number, Structure | PTP1 Inhib | |
|---|---|---|
| | Conc (μM) | % Inhib |
| Example 13 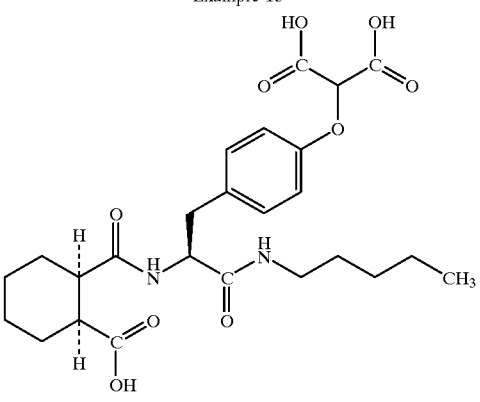 | 10<br>1<br>100 | 13<br>3<br>62 |
| Example 14 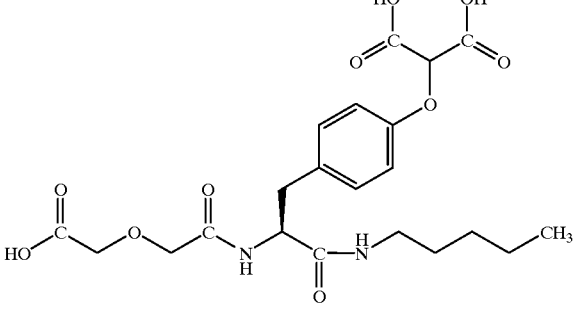 | 10<br>1<br>100 | 12<br>3<br>53 |
| Example 15 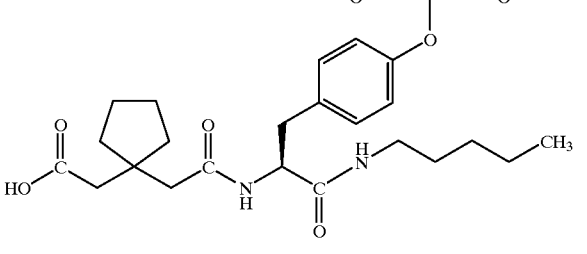 | 10<br>1<br>100 | 20<br>2<br>72 |
| Example 16 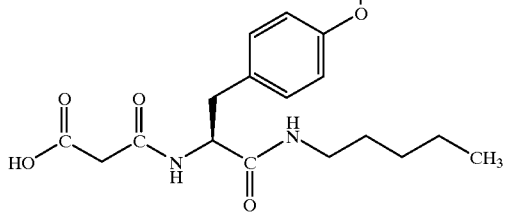 | 10<br>100<br>1 | 20<br>74<br>4 |

TABLE 1-continued

| Example Number, Structure | PTP1 Inhib | |
|---|---|---|
| | Conc (μM) | % Inhib |
| Example 56 | 100 | 34 |
| | 10 | 1 |
| | 1 | 0 |
| Example 17 | 100 | 67 |
| | 10 | 18 |
| | 1 | 0 |
| Example 18 | 100 | 63 |
| | 10 | 14 |
| | 1 | 2 |
| Example 19 | 100 | 41 |
| | 10 | 5 |
| | 1 | 4 |

TABLE 1-continued

| Example Number, Structure | PTP1 Inhib | |
|---|---|---|
| | Conc (μM) | % Inhib |
| Example 29 | 100 | 74 |
| | 10 | 17 |
| | 1 | 3 |
| Example 30 | 100 | 73 |
| | 10 | 21 |
| | 1 | 0 |
| Example 21 | 100 | 83 |
| | 10 | 33 |
| | 1 | 1 |
| Example 22 | 100 | 57 |
| | 10 | 11 |
| | 1 | 0 |

TABLE 1-continued

| Example Number, Structure | PTP1 Inhib Conc (μM) | % Inhib |
|---|---|---|
| Example 31 | 100 | 46 |
| | 10 | 7 |
| | 1 | 0 |
| Example 32 | 100 | 48 |
| | 10 | 6 |
| | 1 | 0 |
| Example 33 | 100 | 23 |
| | 10 | 2 |
| | 1 | 0 |
| Example 55 | 10 | 9 |
| | 100 | 50 |
| | 1 | 0 |

TABLE 1-continued

| Example Number, Structure | PTP1 Inhib Conc (μM) | % Inhib |
|---|---|---|
| Example 34 | 100 | 35 |
| | 10 | 6 |
| | 1 | 0 |
| Example 57 | 100 | 39 |
| | 10 | 4 |
| | 1 | 3 |
| Example 41 | 100 | 45 |
| | 10 | 3 |
| | 1 | 0 |
| Example 35 | 100 | 26 |
| | 10 | 3 |
| | 1 | 2 |

TABLE 1-continued

| Example Number, Structure | PTP1 Inhib | |
|---|---|---|
| | Conc (μM) | % Inhib |
| Example 23 | 100 | 37 |
| | 10 | 4 |
| | 1 | 0 |
| Example 24 | 100 | 72 |
| | 10 | 20 |
| | 1 | 1 |
| Example 4 | 10 | 23 |
| | 100 | 75 |
| | 1 | 4 |
| Example 5 | 10 | 18 |
| | 100 | 63 |
| | 1 | 6 |

TABLE 1-continued

| Example Number, Structure | PTP1 Inhib Conc (μM) | % Inhib |
|---|---|---|
| Example 26 | 100 | 96 |
| | 10 | 75 |
| | 1 | 27 |
| Example 25 | 100 | 90 |
| | 10 | 53 |
| | 1 | 13 |
| Example 42 | 100 | 63 |
| | 10 | 24 |
| | 1 | 12 |
| Example 43 | 100 | 72 |
| | 10 | 23 |
| | 1 | 8 |

TABLE 1-continued

| Example Number, Structure | PTP1 Inhib | |
|---|---|---|
| | Conc ($\mu$M) | % Inhib |
| Example 44 | 100 | 61 |
| | 10 | 18 |
| | 1 | 7 |
| Example 45 | 100 | 51 |
| | 10 | 3 |
| | 1 | 4 |
| Example 46 | 100 | 63 |
| | 10 | 19 |
| | 1 | 4 |
| Example 6 | 100 | 81 |
| | 10 | 34 |
| | 1 | 8 |

TABLE 1-continued

| Example Number, Structure | PTP1 Inhib Conc (μM) | % Inhib |
|---|---|---|
| Example 39 | 10 | 3 |
| | 100 | 34 |
| | 1 | 0 |
| Example 7 | 100 | 72 |
| | 10 | 21 |
| | 1 | 2 |
| | 100 | 74 |
| | 10 | 21 |
| | 1 | 3 |
| Example 8 | 10 | 64 |
| | 100 | 94 |
| | 1 | 16 |
| Example 47 | 10 | 15 |
| | 100 | 66 |
| | 1 | 4 |

TABLE 1-continued

| Example Number, Structure | PTP1 Inhib Conc (μM) | % Inhib |
|---|---|---|
| Example 27 | 100 | 83 |
|  | 10 | 34 |
|  | 1 | 5 |
| Example 28 | 100 | 96 |
|  | 10 | 76 |
|  | 1 | 25 |
| Example 9 | 100 | 94 |
|  | 10 | 64 |
|  | 1 | 17 |

TABLE 1-continued
| Example Number, Structure | PTP1 Inhib Conc (μM) | % Inhib |
|---|---|---|
| Example 38 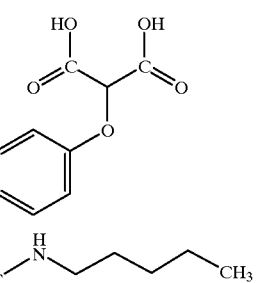 | 100<br>10<br>1 | 79<br>29<br>5 |
| Example 10 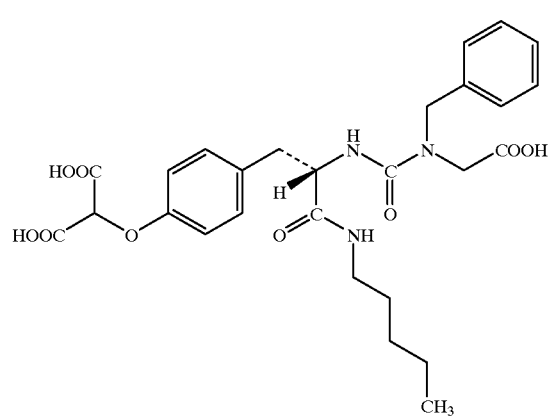 | 10<br>100<br>1 | 25<br>75<br>3 |
| Example 36 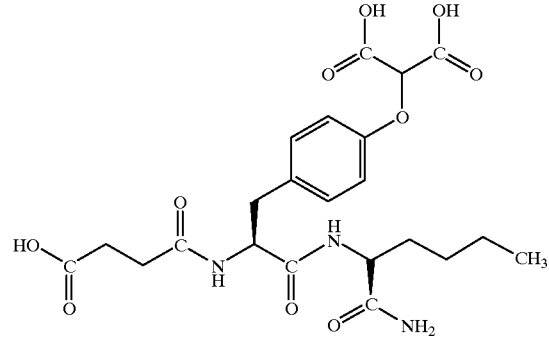 | 100<br>10<br>1 | 93<br>63<br>16 |

TABLE 1-continued

| Example Number, Structure | PTP1 Inhib Conc (μM) | % Inhib |
|---|---|---|
| Example 48 | 100 | 57 |
| | 10 | 13 |
| | 1 | 1 |
| Example 52 | 100 | 90 |
| | 10 | 51 |
| | 1 | 10 |
| Example 37 | 10 | 57 |
| | 100 | 91 |
| | 1 | 14 |
| Example 40 | 100 | 33 |
| | 10 | 6 |
| | 1 | 3 |

TABLE 1-continued

| Example Number, Structure | PTP1 Inhib Conc (μM) | % Inhib |
|---|---|---|
| Example 49 | 100 | 43 |
| | 10 | 7 |
| | 1 | 1 |
| Example 51 | 100 | 51 |
| | 10 | 11 |
| | 1 | 0 |
| Example 53 | 100 | 94 |
| | 10 | 62 |
| | 1 | 16 |
| Example 54 | 100 | 98 |
| | 10 | 87 |
| | 1 | 42 |

TABLE 1-continued
| Example Number, Structure | PTP1 Inhib Conc (μM) | % Inhib |
|---|---|---|
| Example 50 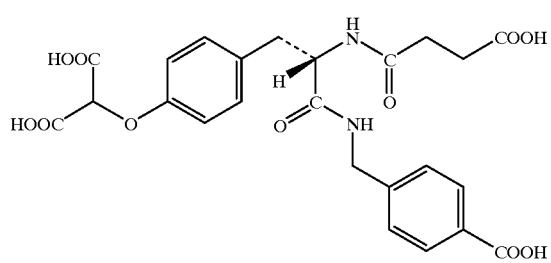 | 100<br>10<br>1 | 56<br>14<br>3 |
| Example 11 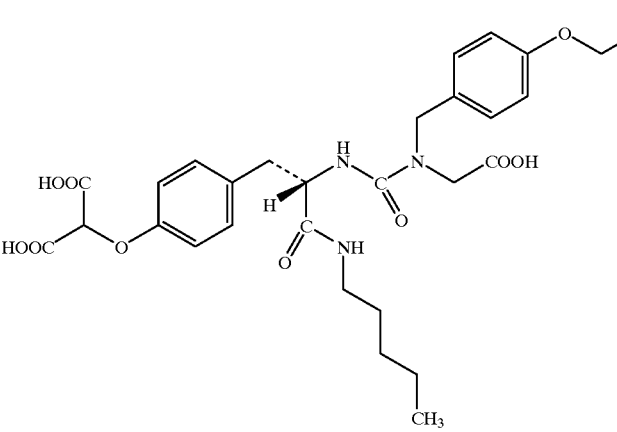 | 100<br>10<br>1 | 90<br>35<br>5 |
| Example 58 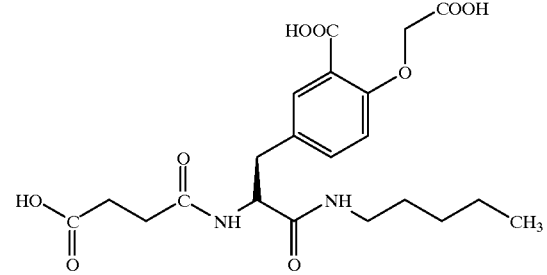 | 100<br>10<br>1 | 93<br>63<br>17 |

TABLE 2

| PNU-number, Structure | PTP1B Inhib | | PTP1 Inhib | |
| --- | --- | --- | --- | --- |
| | PTP1B. Conc (μM) | PTP1B. % Inhib | PTP1N. Conc (μM) | PTP1N. % Inhib |

EXAMPLE 59

| | | | 100 | 98 |
| --- | --- | --- | --- | --- |
| | | | 10 | 80 |
| | | | 1 | 30 |

EXAMPLE 65

| 100 | 90 | 100 | 91 |
| --- | --- | --- | --- |
| 10 | 42 | 10 | 44 |
| 1 | 9 | 1 | 10 |

EXAMPLE 60

| | | | 100 | 54 |
| --- | --- | --- | --- | --- |
| | | | 10 | 13 |
| | | | 1 | 4 |

TABLE 2-continued

| PNU-number, Structure | PTP1B Inhib | | PTP1 Inhib | |
|---|---|---|---|---|
| | PTP1B. Conc ($\mu$M) | PTP1B. % Inhib | PTP1N. Conc ($\mu$M) | PTP1N. % Inhib |
| EXAMPLE 98 | | | 100<br>10<br>1 | 60<br>13<br>1 |
| EXAMPLE 72 | | | 100<br>10<br>1 | 89<br>47<br>9 |
| EXAMPLE 61 | | | 100<br>10<br>1 | 98<br>70<br>11 |

TABLE 2-continued

| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 66 | | | 100 | 85 |
| | | | 10 | 12 |
| | | | 1 | 3 |
| EXAMPLE 62 | | | 10 | 83 |
| | | | 1 | 37 |
| | | | 100 | 97 |
| EXAMPLE 67 | | | 100 | 89 |
| | | | 10 | 36 |
| | | | 1 | 5 |

TABLE 2-continued

| PNU-number, Structure | PTP1B Inhib | | PTP1 Inhib | |
|---|---|---|---|---|
| | PTP1B. Conc ($\mu$M) | PTP1B. % Inhib | PTP1N. Conc ($\mu$M) | PTP1N. % Inhib |
| EXAMPLE 63 | 100 | 99 | 100 | 97 |
| | 10 | 87 | 10 | 84 |
| | 1 | 45 | 1 | 37 |
| EXAMPLE 68 | | | 100 | 90 |
| | | | 10 | 36 |
| | | | 1 | 8 |
| EXAMPLE 69 | 100 | 91 | 100 | 88 |
| | 10 | 48 | 10 | 42 |
| | 1 | 7 | 1 | 9 |

TABLE 2-continued

| | PTP1B Inhib | | PTP1 Inhib | |
|---|---|---|---|---|
| | PTP1B. Conc ($\mu$M) | PTP1B. % Inhib | PTP1N. Conc ($\mu$M) | PTP1N. % Inhib |
| PNU-number, Structure | | | | |
| EXAMPLE 64 | | | 100 | 98 |
| | | | 10 | 83 |
| | | | 1 | 32 |
| EXAMPLE 70 | 100 | 83 | 100 | 76 |
| | 10 | 36 | 10 | 22 |
| | 1 | 7 | 1 | 0 |
| EXAMPLE 116 | | | 100 | 93 |
| | | | 10 | 57 |
| | | | 1 | 8 | see comment

TABLE 2-continued

| PNU-number, Structure | PTP1B Inhib | | PTP1 Inhib | |
|---|---|---|---|---|
| | PTP1B. Conc (µM) | PTP1B. % Inhib | PTP1N. Conc (µM) | PTP1N. % Inhib |
| EXAMPLE 71 | | | 100 | 32 |
| | | | 10 | 0 |
| | | | 1 | 0 |
| EXAMPLE 117 | 100 | 97 | 100 | 93 |
| | 10 | 74 | 10 | 55 |
| | 1 | 21 | 1 | 8 |
| EXAMPLE 118 | | | 100 | 92 |
| | | | 10 | 51 |
| | | | 1 | 4 |

TABLE 2-continued

| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 131 | | | 100 | 93 |
| | | | 10 | 56 |
| | | | 1 | 12 |
| EXAMPLE 119 | 100 | 97 | 100 | 96 |
| | 10 | 63 | 10 | 55 |
| | 1 | 14 | 1 | 8 |
| EXAMPLE 139 | | | 100 | 34 |
| | | | 10 | 6 |
| | | | 1 | 3 |
| EXAMPLE 140 | | | 100 | 78 |
| | | | 10 | 29 |
| | | | 1 | 4 |
| EXAMPLE 99 | | | 100 | 57 |
| | | | 10 | 15 |
| | | | 1 | 3 |

TABLE 2-continued

| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 73 | | | 100<br>10<br>1 | 87<br>42<br>9 |
| EXAMPLE 120 | 100<br>10<br>1 | 90<br>45<br>6 | | |
| EXAMPLE 81 | 100<br>10<br>1<br>100<br>10<br>1<br>100<br>10<br>1 | 97<br>78<br>30<br>89<br>54<br>15<br>87<br>43<br>8 | 100<br>10<br>1 | 97<br>84<br>40 |

TABLE 2-continued

| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 121 | 100 | 58 | | |
| | 10 | 9 | | |
| | 1 | 3 | | |
| EXAMPLE 122 | 100 | 42 | | |
| | 10 | 8 | | |
| | 1 | 5 | | |
| EXAMPLE 123 | 100 | 95 | | |
| | 10 | 65 | | |
| | 1 | 18 | | |
| | 100 | 93 | | |
| | 10 | 59 | | |
| | 1 | 14 | | |

TABLE 2-continued
| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 124 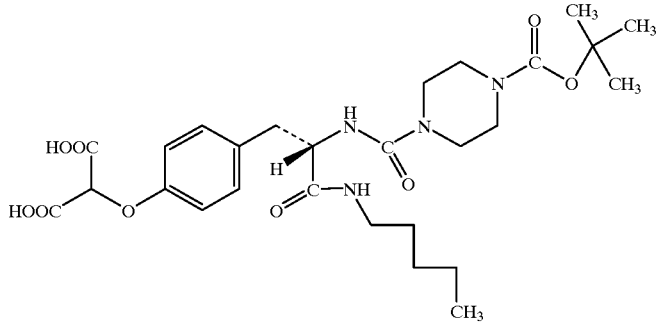 | 100<br>10<br>1<br>100<br>10<br>1 | 95<br>68<br>19<br>92<br>63<br>19 | | |
| EXAMPLE 125 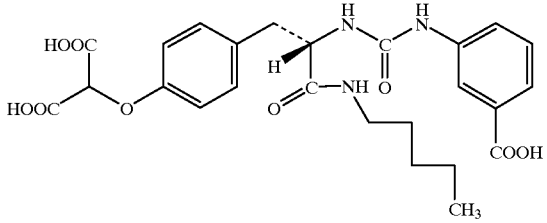 | 100<br>10<br>1 | 94<br>63<br>17 | | |
| EXAMPLE 100 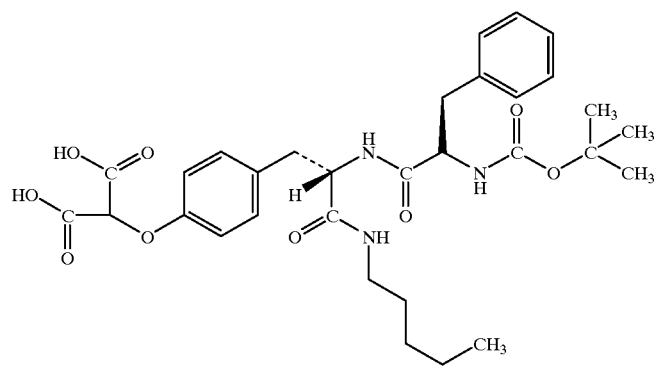 | 100<br>10<br>1 | 44<br>8<br>2 | | |
| EXAMPLE 101 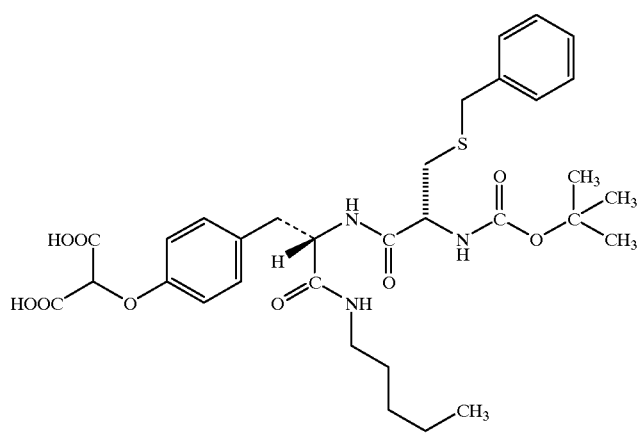 | 100<br>10<br>1<br>10<br>100<br>1 | 75<br>14<br>2<br>16<br>83<br>3 | | |

TABLE 2-continued
| PNU-number, Structure | PTP1B Inhib | | PTP1 Inhib | |
| --- | --- | --- | --- | --- |
| | PTP1B. Conc ($\mu$M) | PTP1B. % Inhib | PTP1N. Conc ($\mu$M) | PTP1N. % Inhib |
EXAMPLE 74
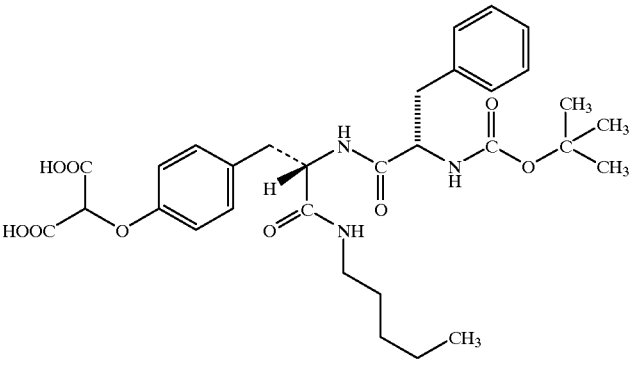
| | | |
| --- | --- | --- |
| 100 | 86 | |
| 10 | 40 | |
| 1 | 9 | |
EXAMPLE 102
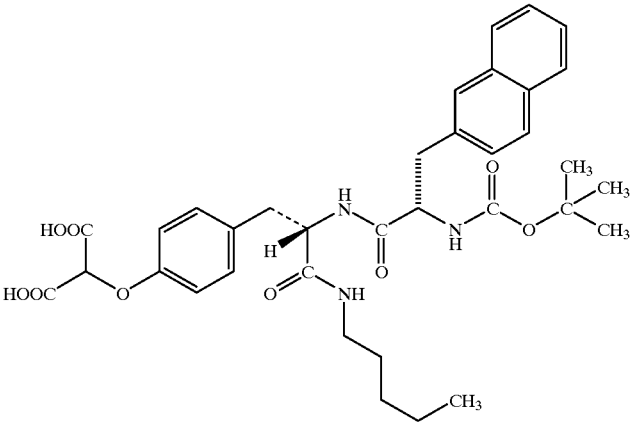
| | | |
| --- | --- | --- |
| 100 | 93 | |
| 10 | 29 | |
| 1 | 1 | |
| 100 | 90 | |
| 10 | 29 | |
| 1 | 3 | |
EXAMPLE 103
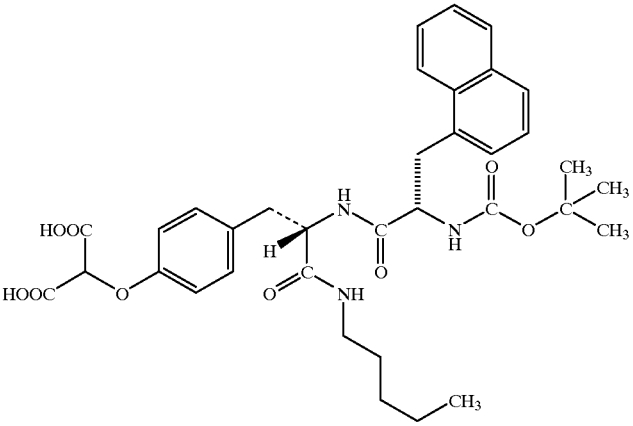
| | | |
| --- | --- | --- |
| 100 | 86 | |
| 10 | 33 | |
| 1 | 3 | |

TABLE 2-continued
| | PTP1B Inhib | | PTP1 Inhib | |
| --- | --- | --- | --- | --- |
| PNU-number, Structure | PTP1B. Conc (μM) | PTP1B. % Inhib | PTP1N. Conc (μM) | PTP1N. % Inhib |
EXAMPLE 104
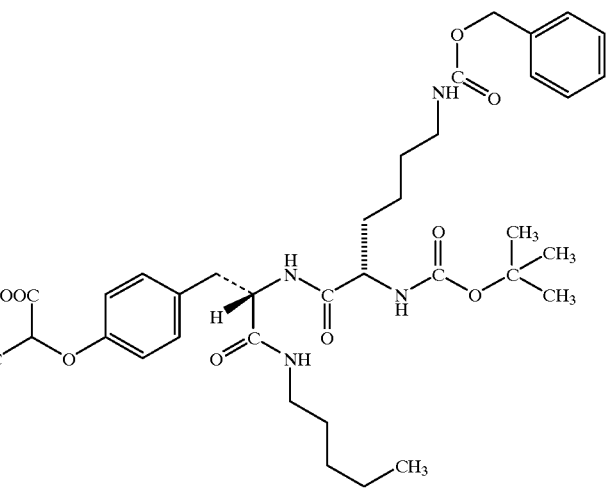
| | 100 | 79 | | |
EXAMPLE 104
| | 10 | 28 | | |
| | 1 | 6 | | |
EXAMPLE 126
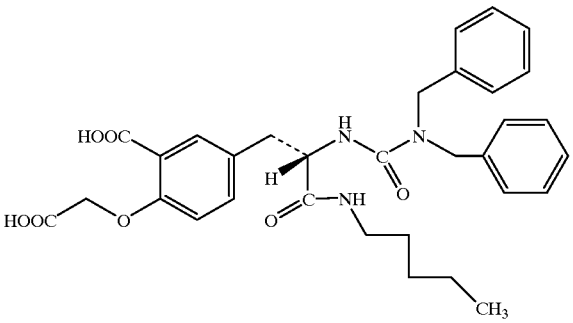
| | 100 | 87 | | |
| | 10 | 45 | | |
| | 1 | 11 | | |
EXAMPLE 105
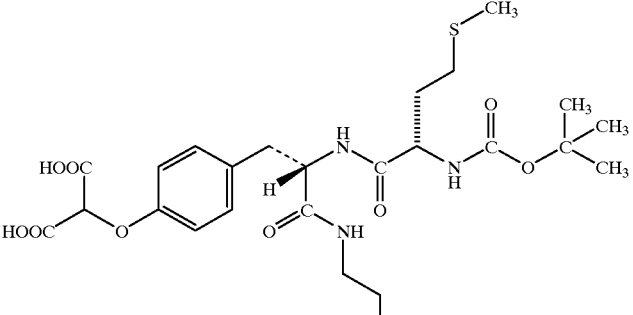
| | 100 | 74 | | |
| | 10 | 25 | | |
| | 1 | 5 | | |
| | 100 | 82 | | |
| | 10 | 30 | | |
| | 1 | 5 | | |

TABLE 2-continued
| PNU-number, Structure | PTP1B Inhib | | PTP1 Inhib | |
|---|---|---|---|---|
| | PTP1B. Conc ($\mu$M) | PTP1B. % Inhib | PTP1N. Conc ($\mu$M) | PTP1N. % Inhib |
| EXAMPLE 106 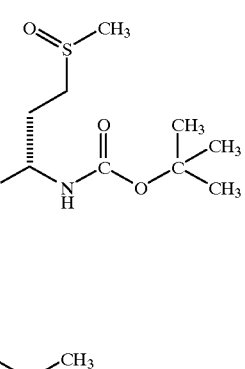 | 100<br>10<br>1 | 67<br>21<br>7 | | |
| EXAMPLE 107 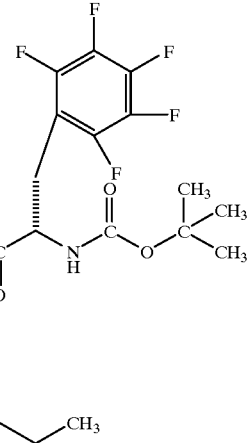 | 100 | 80 | | |
| EXAMPLE 107 | 10<br>1 | 25<br>5 | | |
| EXAMPLE 97 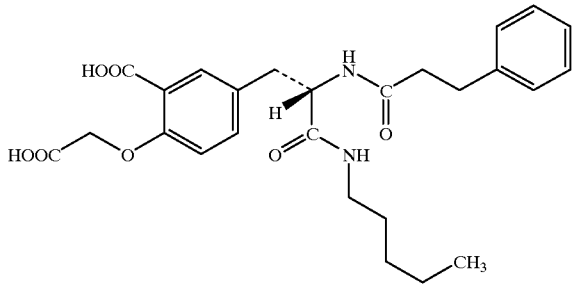 | 100<br>10<br>1 | 60<br>15<br>4 | | |

TABLE 2-continued

| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 108 | 100<br>10<br>1 | 76<br>24<br>4 | | |
| EXAMPLE 109 | 100<br>10<br>1 | 71<br>19<br>3 | | |
| EXAMPLE 110 | 100<br>10<br>1 | 85<br>40<br>9 | | |

TABLE 2-continued

| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 111 | 100 | 66 | | |
| | 10 | 19 | | |
| | 1 | 6 | | |
| EXAMPLE 112 | 100 | 90 | | |
| | 10 | 50 | | |
| | 1 | 10 | | |
| EXAMPLE 113 | 100 | 58 | | |
| | 10 | 7 | | |
| | 1 | 2 | | |
| | 100 | 77 | | |
| | 10 | 17 | | |
| | 1 | 2 | | |

TABLE 2-continued

| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 82 | 100<br>10<br>1<br>100<br>10<br>1 | 98<br>93<br>64<br>98<br>92<br>66 | | |
| EXAMPLE 75 | 100<br>10<br>1 | 86<br>40<br>9 | | |
| EXAMPLE 76 | 100<br>10<br>1 | 92<br>54<br>12 | | |

TABLE 2-continued

| PNU-number, Structure | PTP1B Inhib | | PTP1 Inhib | |
|---|---|---|---|---|
| | PTP1B. Conc ($\mu$M) | PTP1B. % Inhib | PTP1N. Conc ($\mu$M) | PTP1N. % Inhib |
| EXAMPLE 77 | 100<br>10<br>1 | 93<br>62<br>14 | | |
| EXAMPLE 114 | 100<br>10<br>1 | 69<br>19<br>2 | | |
| EXAMPLE 115 | 100<br>10<br>1<br>100<br>10<br>1 | 97<br>81<br>32<br>96<br>78<br>28 | | |

TABLE 2-continued
| PNU-number, Structure | PTP1B Inhib | | PTP1 Inhib | |
| --- | --- | --- | --- | --- |
| | PTP1B. Conc ($\mu$M) | PTP1B. % Inhib | PTP1N. Conc ($\mu$M) | PTP1N. % Inhib |
EXAMPLE 128
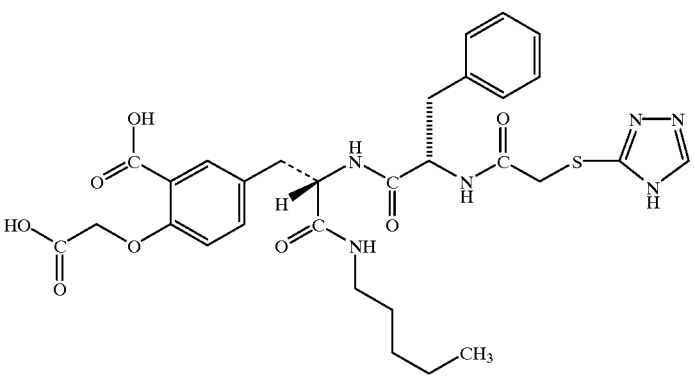
| | 100 | 96 | | |
| --- | --- | --- | --- | --- |
| | 10 | 82 | | |
| | 1 | 36 | | |
EXAMPLE 129
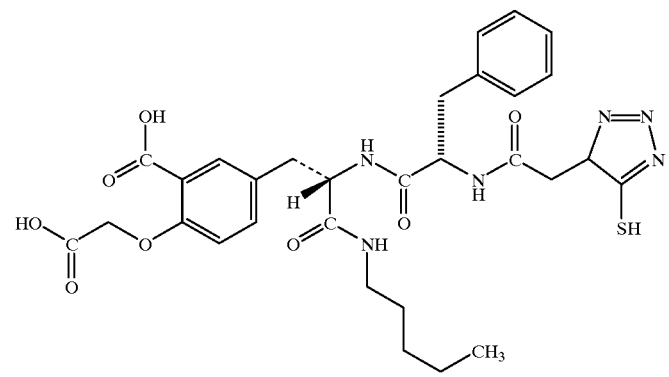
| | 100 | 98 | | |
| --- | --- | --- | --- | --- |
| | 10 | 91 | | |
| | 1 | 57 | | |
EXAMPLE 130
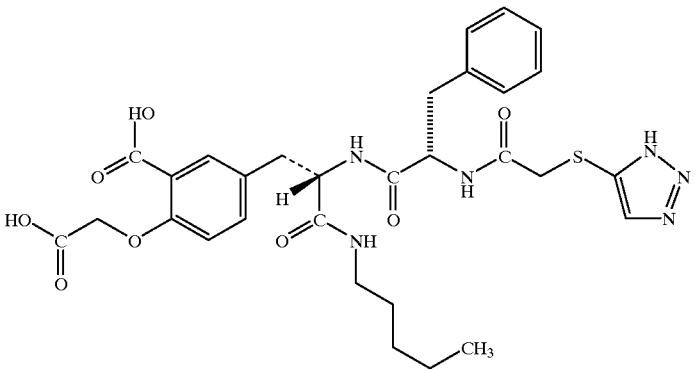
| | 100 | 98 | | |
| --- | --- | --- | --- | --- |
| | 10 | 88 | | |
| | 1 | 49 | | |

TABLE 2-continued

| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 132 | 100<br>10<br>1<br>100<br>10<br>1<br>100<br>10<br>1 | 87<br>39<br>8<br>87<br>33<br>0<br>97<br>77<br>27 | | |
| EXAMPLE 133 | 100<br>10<br>1 | 25<br>5<br>3 | | |
| EXAMPLE 141 | 100<br>10<br>1 | 48<br>15<br>9 | | |

TABLE 2-continued

| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 78 | 100<br>10<br>1 | 62<br>16<br>4 | | |
| EXAMPLE 83 | 100<br>10<br>1 | 87<br>88<br>47 | | |
| EXAMPLE 84 | 100<br>10<br>1 | 98<br>87<br>45 | | |

TABLE 2-continued

| PNU-number, Structure | PTP1B Inhib | | PTP1 Inhib | |
|---|---|---|---|---|
| | PTP1B. Conc ($\mu$M) | PTP1B. % Inhib | PTP1N. Conc ($\mu$M) | PTP1N. % Inhib |
| EXAMPLE 85 | 100<br>10<br>1 | 96<br>70<br>19 | | |
| EXAMPLE 86 | 100<br>10<br>1 | 96<br>77<br>28 | | |
| EXAMPLE 87 | 100<br>10<br>1 | 97<br>83<br>37 | | |

TABLE 2-continued

| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 137 | 100 | 29 | | |
| | 10 | 6 | | |
| | 1 | 3 | | |
| EXAMPLE 79 | 100 | 94 | | |
| | 10 | 65 | | |
| | 1 | 19 | | |
| EXAMPLE 134 | 100 | 54 | | |
| | 10 | 13 | | |
| | 1 | 5 | | |

TABLE 2-continued

| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 88 | 100<br>10<br>1 | 96<br>78<br>23 | | |
| EXAMPLE 89 | 100<br>10<br>1 | 96<br>75<br>19 | | |
| EXAMPLE 90 | 100<br>10<br>1 | 95<br>73<br>15 | | |

TABLE 2-continued

| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 127 | 100 | 89 | | |
| | 10 | 44 | | |
| | 1 | 10 | | |
| EXAMPLE 135 | 100 | 30 | | |
| | 10 | 8 | | |
| | 1 | 6 | | |
| EXAMPLE 91 | 100 | 98 | | |
| | 10 | 86 | | |
| | 1 | 43 | | |

TABLE 2-continued

| PNU-number, Structure | PTP1B Inhib | | PTP1 Inhib | |
|---|---|---|---|---|
| | PTP1B. Conc ($\mu$M) | PTP1B. % Inhib | PTP1N. Conc ($\mu$M) | PTP1N. % Inhib |
| EXAMPLE 92 | 100<br>10<br>1 | 98<br>88<br>46 | | |
| EXAMPLE 93 | 100<br>10<br>1 | 98<br>85<br>39 | | |
| EXAMPLE 94 | 100<br>10<br>1 | 98<br>85<br>39 | | |

TABLE 2-continued

| PNU-number, Structure | PTP1B Inhib | | PTP1 Inhib | |
|---|---|---|---|---|
| | PTP1B. Conc (μM) | PTP1B. % Inhib | PTP1N. Conc (μM) | PTP1N. % Inhib |
| EXAMPLE 95 | 100<br>10<br>1 | 97<br>87<br>46 | | |
| EXAMPLE 142 | 100<br>10<br>1 | 25<br>5<br>1 | | |
| EXAMPLE 80 | 100<br>10<br>1 | 86<br>43<br>8 | | |

TABLE 2-continued

| PNU-number, Structure | PTP1B Inhib | | PTP1 Inhib | |
|---|---|---|---|---|
| | PTP1B. Conc ($\mu$M) | PTP1B. % Inhib | PTP1N. Conc ($\mu$M) | PTP1N. % Inhib |
| EXAMPLE 96 | 100<br>10<br>1 | 95<br>74<br>22 | | |
| EXAMPLE 143 | 100<br>10<br>1 | 94<br>71<br>24 | | |
| EXAMPLE 144 | 100<br>10<br>1 | 95<br>76<br>34 | | |

TABLE 2-continued

| | PTP1B Inhib | | PTP1 Inhib | |
|---|---|---|---|---|
| PNU-number, Structure | PTP1B. Conc ($\mu$M) | PTP1B. % Inhib | PTP1N. Conc ($\mu$M) | PTP1N. % Inhib |
| EXAMPLE 145 | 100 | 98 | | |
| | 10 | 93 | | |
| | 1 | 64 | | |
| EXAMPLE 138 | 100 | 80 | | |
| | 10 | 31 | | |
| | 1 | 5 | | |
| EXAMPLE 136 | | | 100 | 70 |
| | | | 10 | 14 |
| | | | 1 | 1 |

What is claimed is:

1. A compound of formula I

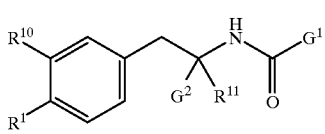

wherein $R^1$ is selected from the group consisting of:
 (a) —$OSO_3H$,
 (b) —$OCH(COOR^5)_2$,
 (c) —$OCH_2(COOR^5)$,
 (d) —$OCH(COOR^5)CH_2COOR^5$,
 (e) —$OC(COOR^5)=CHCOOR^5$,
 (f) —$CH_2CH(COOR^5)_2$,
 (g) —$CH=C(COOR^5)_2$,
 (h) —$OCH_2CONHOH$,
 (i) —$N(CH_2COOR^5)_2$, and
 (j) —$OCHF(COOR^5)$;

$G^1$ is selected from the group consisting of:
 (a) —$C_1$–$C_{10}$ alkyl, optionally substituted by 1 or 2 —$COOR^5$ bonded to the same or different carbon atoms; or with —$CONH_2$, (b) —$C_3$-$C_8$ cycloalkyl, optionally substituted by one —$COOR^5$,
(c) —$C_0$-$C_6$ alkyl-phenyl, optionally substituted by 1 or 2 —$COOR^5$ bonded to the same or different carbon atom, or by —$CH_2CH(COOR^5)_2$,
(d) —$CH(R^7)$—NH—X—$R^6$, and

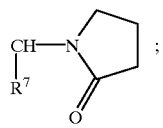 (e)

$G^2$ is $CONHR^3$;
$R^3$ is selected from the group consisting of:
(a) —$C_1$-$C_{12}$ alkyl, optionally substituted by 1–3 O, S, N, —O—$C_1$-$C_4$ alkyl, —S—$C_1$-$C_4$ alkyl, —O—$G^3$, —S—$G^3$, or OH,
(b) —$C_1$-$C_4$ alkyl-$C_3$-$C_6$ cycloalkyl,
(c) —$C_2$-$C_{12}$ alkenyl,
(d) —$C_3$-$C_{12}$ alkynyl,
(e) —$C_0$-$C_{10}$ alkyl $(G^3)_n$, wherein alkyl is optionally substituted by 1–3 of O, S, or N, and
(f) —$CH(CONH_2)C_1$-$C_{12}$ alkyl;

$R^5$ is selected from the group consisting of:
(a) hydrogen,
(b) —$C_1$-$C_{10}$ alkyl, and
(c) —$C_1$-$C_5$ alkyl-phenyl;

$R^6$ is selected from the group consisting of:
(a) —$C_1$-$C_{10}$ alkyl,
(b) —$C_0$-$C_6$ alkyl-$G^3$,
(c) —$C_1$-$C_6$ alkyl-$CONH_2$,
(d) —$C_1$-$C_6$ alkyl-NH—$COOR^5$,
(e) —$C_1$-$C_6$ alkyl-$OR^5$,
(f) —$C_1$-$C_6$ alkyl-$NHSO_2Me$,
(g) —$C_1$-$C_6$ alkyl-O—$G^3$,
(h) —$C_1$-$C_6$ alkyl-S—$G^3$, and
(i) —$C_1$-$C_6$ alkyl-$COOR^5$;

$R^7$ is selected from the group consisting of:
(a) hydrogen,
(b) —$C_1$-$C_6$ alkyl-$G^3$,
(c) —$C_1$-$C_6$ alkyl-$COOR^5$,
(d) —$C_1$-$C_6$ alkyl-$CONH_2$,
(e) —$C_1$-$C_6$ alkyl-NH—$COOR^5$,
(f) —$C_1$-$C_{10}$ alkyl,
(g) —$C_1$-$C_{10}$ cycloalkyl,
(h) —$C_1$-$C_6$ alkyl-S—$R^5$, and
(i) —$C_1$-$C_6$ alkyl-S(=O)$R^5$;

$G^3$ is selected from the group consisting of:
(a) phenyl substituted by 0–3 $R^9$,
(b) naphthyl substituted by 0–3 $R^9$, and
(c) het substituted by 0–3 $R^9$;

het is a 5- or 6-membered saturated or unsaturated ring containing from 1–4 heteroatoms selected from the group consisting of N, O and S, and including any bicyclic group in which any of the above heterocyclic rings is fused to a benzene ring, $C_3$-$C_8$ cycloalkyl, or another hetercycle, and if chemically feasible, the nitrogen and sulfur atoms may be in the oxidized forms;

$R^9$ is selected from the group consisting of:
(a) $C_1$-$C_8$ alkyl substituted by 0–3 halo,
(b) $C_2$-$C_8$ alkenyl,
(c) OH,
(d) —O—$C_1$-$C_5$ alkyl,
(e) —O—$C_0$-$C_5$ alkyl-phenyl,
(f) —$(CH_2)_n$—O—$C_1$-$C_5$ alkyl substituted by 0–3 hydroxy,
(g) halo,
(h) $NH_2$,
(i) amino-$C_1$-$C_5$ alkyl,
(j) mono- or di-$C_1$-$C_5$ alkylamino,
(k) —C(O)—$C_1$-$C_5$ alkyl,
(l) —CHO,
(m) —C(O)—$C_0$-$C_5$ alkyl-phenyl,
(n) —$COOR^5$,
(o) —CON $(R^5)_2$,
(p) —$C_3$-$C_7$ cycloalkyl,
(q) —$NO_2$,
(r) —CN,
(S) —$SO_3H$,
(t) —$SO_2N(R^5)_2$,
(u) —$O((CH_2)_2$—O$)_n$—$CH_3$,
(v) —$(CH_2$—O$)_n$—$C_1$-$C_3$ alkyl,
(w) —$NR^5(CO)$—$NR^5$,
(x) —$CF_3$,
(y) —$NR^5(CO)C_1$-$C_5$ alkyl,
(z) —$N(R^5)$—$SO_2$—$R^5$,
(a1) —O—C(O)—$R^5$,
(b1) —S(O)—$R^5$,
(c1) —$SR^5$, and
(d1) —$SO_2$—$R^5$;

$R^{10}$ is selected from the group consisting of:
(a) hydrogen,
(b) $CO_2R^5{}_7$,
(c) CONHOH,
(d) 5-tetrazolyl,
(e) F, and
(f) —$OCH_2CO_2R^5$;

$R^{11}$ is selected from the group consisting of:
(a) hydrogen, and
(b) methyl;

X is CO, $SO_2$, or $CO_2$; and n is 0, 1, 2, or 3, or a pharmaceutically acceptable salt thereof, provided that when $R^{10}$ is H, $R^1$ is other than —$OCH_2(CO_2R^5)$.

2. The compound of claim 1, of formula III or IV

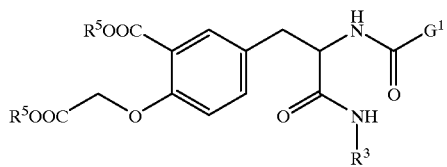 III

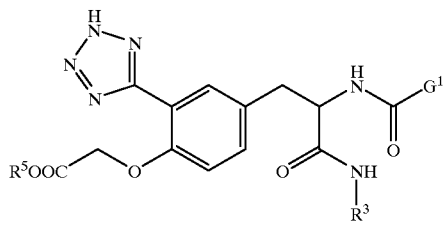 IV wherein $G^1$, $R^3$ and $R^5$ are as defined in claim 1 and the chiral center depicted in III is in the (S) configuration.

3. The compound of claim 2 wherein $G^1$ is
a) —$CH(CH_2phenyl)NHCO_2t$-Bu,
b) —$CH(CH_2phenyl)NHCOC_1$-$C_3$ alkyl-$G^3$, c) —CH(CH$_2$phenyl)NHCOC$_1$–C$_3$ alkyl-CO$_2$R$^5$
d)

[Structure: CH-N in pyrrolidinone ring with CH$_2$-Ph substituent]

wherein R$^3$ is
a) —C$_5$–C$_6$ alkyl, or
b) —C$_3$–C$_6$ alkyl-phenyl;
wherein R$^5$ is —H;
wherein the configuration of the chiral center(s) is (S).

4. The compound of claim 1 selected from the group consisting of:

(S)-4-Oxo-4-[[2-oxo-2-(pentylamino)-1-[[4-(sulfooxy)phenyl]methyl]ethyl]amino]-butanoic acid;
(S)-[4-[2-[[1,4-Dioxo-4-(phenylmethoxy)butyl]amino]-3-oxo-3-(pentylamino)-propyl]phenoxy]propanedioic acid;
(S)-[4-[2-[(3-Carboxy-1-oxopropyl)amino]-3-oxo-3-(pentylamino)propyl]phenoxy]propanedioic acid;
(S)-N-[[[1-[[4-(Dicarboxymethoxy)phenyl]methyl]-2-oxo-2-(pentylamnino)ethyl]amino]carbonyl]-L-glutamic acid;
(S)-[4-[2-[[[(Carboxymethyl)(phenylmethyl)amino]carbonyl]amino]-3-oxo-3-(pentylamino)propyl]phenoxy]propanedioic acid;
(S)-[4-[2-[[[(Carboxymethyl)[[4-(phenylmethoxy)phenyl]methyl]amino]carbonyl]-amino]-3-oxo-3-(pentylamino)propyl]phenoxy]propanedioic acid;
(S)-[4-[2-[(4-Carboxy-1-oxobutyl)amino]-3-oxo-3-(pentylamino)propyl]phenoxy]propanedioic acid;
[1R-[1(S*),2]]-[4-[2-[[(2-Carboxycyclohexyl)carbonyl]amino]-3-oxo-3-(pentyl-amino)propyl]phenoxy]propanedioic acid;
(S)-[4-[2-[[(Carboxymethoxy)acetyl]amino]-3-oxo-3-(pentylamino)propyl]-phenoxy]propanedioic acid;
(S)-[4-[2-[[[1-(Carboxymethyl)cyclopentyl]acetyl]amino]-3-oxo-3(pentylamino)-propyl]phenoxy]propanedioic acid;
(S)-[4-[2-[(Carboxyacetyl)amino]-3-oxo-3-(pentylamino)propyl]phenoxy]propanedioic acid;
(S)-[4-[2-[(4-Carboxy-3,3-dimethyl-1-oxobutyl)amino]-3-oxo-3(pentylamino)-propyl]phenoxy]propanedioic acid;
(S)-[4-[2-[(2-Carboxybenzoyl)amino]-3-oxo-3-(pentylamino)propyl]phenoxy]-propanedioic acid;
[2(S)]-[4-[2-[[(3-Carboxybicyclo[2.2.2]oct-2-yl)carbonyl]amino]-3-oxo-3-(pentylamino)propyl]phenoxy]propanedioic acid;
(S)-3-[[[1-[[4-(Dicarboxymethoxy)phenyl]methyl]-2-oxo-2-(pentylamino)ethyl]amino]carbonyl]pentanedioic acid;
[1(S)]-[4-[2-[[(2-Carboxycyclopropyl)carbonyl]amino]-3-oxo-3-(pentylamino)-propyl]-phenoxy]propanedioic acid;
[2(S)]-[4-[2-[[(3-Carboxybicyclo[2.2.1]hept-2-yl)carbonyl]amino]-3-oxo-3-(pentylamino)propyl]phenoxy]propanedioic acid;
[1R-[1(S*), 2]]-[4-[2-[[(2-Carboxycyclohexyl)carbonyl]amino]-3-oxo-3-(pentylamino)propyl]phenoxy]propanedioic acid;
N-[(1,1-Dimethylethoxy)carbonyl]-L-α-aspartyl-O-(dicarboxymethyl)-N-pentyl-L-tyrosinamide;
N-(3-Carboxy-1-oxopropyl)-L-α-aspartyl-O-(dicarboxymethyl)-N-pentyl-L-tyrosinamide;
N-[(1,1-Dimethylethoxy)carbonyl]-L-α-glutamyl-O-(dicarboxymethyl)-N-pentyl-L-tyrosinamide;
N-(3-Carboxy-1-oxopropyl)-L-α-glutamyl-O-(dicarboxymethyl)-N-pentyl-L-tyrosinamide;
(S)-[4-[2-[(3-Carboxy-1-oxopropyl)amino]-3-(hexylamino)-3-oxopropyl]phenoxy]propanedioic acid;
(S)-[4-[2-[(3-Carboxy-1-oxopropyl)amino]-3-[(cyclohexylmethyl)amino-3-oxopropyl]phenoxy]propanedioic acid;
(S)-[4-[2-[(3-Carboxy-1-oxopropyl)amino]-3-oxo-3-[(2-phenoxyethyl)amino]-propyl]phenoxy]propanedioic acid;
(S)-[4-[2-[(3-Carboxy-1-oxopropyl)amino]-3-[[2-(4-hydroxyphenyl)ethyl]amino]-3-oxopropyl]phenoxy]propanedioic acid;
(S)-[4-[2-[(3-Carboxy-1-oxopropyl)amino]-3-[[(4-carboxyphenyl)methyl]amino]-3-oxopropyl]phenoxy]propanedioic acid;
(S)-[4-[2-[(4-Amino-1,4-dioxobutyl)amino]-3-oxo-3-(pentylamino)propyl]phenoxy]propanedioic acid;
N-[(Phenylmethoxy)carbonyl]-L-α-aspartyl-O-(dicarboxymethyl)-N-pentyl-L-tyrosinamide;
N-[(1,1-Dimethylethoxy)carbonyl]-D-α-aspartyl-O-(dicarboxymethyl)-N-pentyl-L-tyrosinamide;
4-Benzoyl-N-(3-carboxy-1-oxopropy)-L-phenylalanyl-O-(dicarboxymethyl)-N-pentyl-L-tyrosinamide;
(S)-2-[4-[2-[(3-Carboxy-1-oxopropyl)amino]-3-oxo-3-(pentylamino)propyl]phenoxy]-2-butenedioic acid;
[2(S)]-[4-[2-[(3-Carboxy-1-oxopropyl)amino]-3-oxo-3-(pentylamino)propyl]phenoxy]butanedioic acid;
(R)-[4-[2-[(3-Carboxy-1-oxopropyl)amino]-3-oxo-3(pentylamino)-propyl]phenoxy]propanedioic acid;
(S)-2-(Carboxymethoxy)-5-[2-[(3-carboxy-1-oxopropyl)amino]-3-oxo-3-(pentylamino)propyl]benzoic acid;
2-{(4-[(2S)-2-({2S)-3-[4-(benzyloxy)phenyl]-2-[(3-carboxypropanoyl)amino]-propanoyl}amino)-3-oxo-3-(pentylamino)propyl]phenoxy}malonic acid;
2-{4-[(2S)-2-({(2S)-3-(4-benzoylphenyl)-2-[(tert-butoxycarbonyl)amino]propanoyl}amino)-3-oxo-3-(pentylamino)propyl]phenoxy}malonic acid;
2-{4-[(2S)-2-({(2R)-3-(4-benzoylphenyl)-2-[(3-carboxypropanoyl)amino]propanoyl}amino)-3-oxo-3-(pentylamino)propyl]phenoxy}malonic acid;
2-{4-[2-({(2S)-3-(4-benzoylphenyl)-2-[(3-carboxypropanoyl)amino]propanoyl}amino)ethyl]phenoxy}malonic acid;
2-{4-[(2S)-2-[((2S)-3-(4-benzoylphenyl)-2-{[3-(4-hydroxyphenyl)propanoyl]-amino}propanoyl)amino]-3-oxo-3-(pentylamnino)propyl]phenoxy}malonic acid;
2-{(4-[(2S)-2-[((2S )-2-[(3-carboxypropanoyl)amino]-3-{4-[(2,6-dichlorobenzyl)oxy]phenyl}propanoyl)amino]-3-oxo-3-(pentylamino)propyl]phenoxy}malonic acid;
2-{(4-[(2S)-2-[((2S)-2-[(tert-butoxycarbonyl)amino]-3-{4-[(2,6-dichlorobenzyl)oxy]phenyl}propanoyl)amino]-3-oxo-3-(pentylamino)propyl]phenoxy}malonic acid;
2-{(4-[(2S)-2-({(2S)-3-[4-(tert-butoxy)phenyl]-2-[(3-carboxypropanoyl)-amino]propanoyl}amino)-3-oxo-3-(pentylamino)propyl]phenoxy}malonic acid;
2-{(4-[(2S)-2-({(2S )-2-[(tert-butoxycarbonyl)amino]-3-[4-(tert-butoxy)phenyl]propanoyl}amino)-3-oxo-3-(pentylamino)propyl]phenoxy}malonic acid;
2-{4-[(2S)-2-({(2S )-2-[(3-carboxypropanoyl)amino]-3-phenylpropanoyl}amino)-3-oxo-3-(pentylamino)propyl]phenoxy}malonic acid;
2-{4-{[(2S)-2-{[(2S )-2-[(tert-butoxycarbonyl)amino]-3-(4-methoxyphenyl)propanoyl]amino}-3-oxo-3-(pentylamino)propyl]phenoxy}malonic acid;
2-{4-[(2S)-2-({(2S)-2-{[(tert-butoxycarbonyl)amino]-3-phenylpropanoyl}amino)-3-oxo-3-(pentylamino)propyl]phenoxy}malonic acid;

2-{4-[(2S)-2-{[(2S)-2-[(3-carboxypropanoyl)amino]-3-(4-methoxyphenyl)-propanoyl]amino}-3-oxo-3-(pentylamino)propyl]phenoxy}malonic acid;

2-{4-[(2S)-2-({(2S)-2-[(tert-butoxycarbonyl)amino]propanoyl}amino)-3-oxo-3-(pentylamino)propyl]phenoxy}malonic acid;

2-{4-[(2S)-2-({(2S)-3-[4-(benzyloxy)phenyl]-2-[(tert-butoxycarbonyl)(methyl)amino]propanoyl}amino)-3-oxo-3-(pentylamino)propyl]phenoxy}malonic acid;

2-{4-[(2S)-2-({[benzyl(4-carboxybenzyl)amino]carbonyl}amino)-3-oxo-3-(pentylamino)propyl]phenoxy}malonic acid;

2-{4-[(2S)-2-[({[4-(carboxymethyl)benzyl][3-(trifluoromethyl)benzyl]amino}carbonyl)amino]-3-oxo-3-(pentylamino)propyl]phenoxy}malonic acid;

2-{4-[(2S)-2-{[({2-[(carboxymethyl)amino]-2-oxoethyl}amino)carbonyl]amino}-3-oxo-3-(pentylamino)propyl]phenoxy}malonic acid;

2-{4-[(2S)-2-{[({1-[4-(benzyloxy)benzyl]-2-hydroxy-2-oxoethyl}amino)carbonyl]amino}-3-oxo-3-(pentylamino)propyl]phenoxy}malonic acid;

2-{4-[2-[(3-carboxypropanoyl)amino]-2-methyl-3-oxo-3-(pentylamino)propyl]phenoxy}malonic acid;

2-{4-[2-[(3-carboxypropanoyl)amino]-3-oxo-3-(pentylamino)propyl]-2-fluorophenoxy}malonic acid;

2-[4-((2S)-2-[(3-carboxypropanoyl)amino]-3-{[(1S)-1-(hydroxymethyl)-3-methylbutyl]amino}-3-oxopropyl)phenoxy]malonic acid;

2-{4-[(2S)-2-{[(2S)-2-(acetylamino)-3-(4-benzoylphenyl)propanoyl]amino}-3-oxo-3-(pentylamino)propyl]phenoxy}malonic acid;

2-{4-[(2S)-2-[({[4-(aminosulfonyl)benzyl][3-(trifluoromethyl)benzyl]amino}carbonyl)amino]-3-oxo-3-(pentylamino)propyl]phenoxy}malonic acid;

5-[(2S)-2-({(2S)-2-[(tert-butoxycarbonyl)amino]-3-phenylpropanoyl}amino)-3-oxo-3-(pentylamino)propyl]-2-(carboxymethoxy)benzoic acid;

2-{4-[(2S)-2-[({(3-carboxybenzyl)[3-(trifluoromethyl)benzyl]amino}carbonyl)amino]-3-oxo-3-(pentylamino)propyl]phenoxy}malonic acid;

2-{4-[(2S)-2-[({benzyl[1-(carboxymethyl)-3-phenylpropyl]amino}carbonyl)amino]-3-oxo-3-(pentylamino)propyl]phenoxy}malonic acid;

2-{(4-[(2S)-2-{[(dibenzylamino)carbonyl]amino}-3-oxo-3-(pentylamino)propyl]phenoxy}malonic acid;

2-{4-[(2S)-2-({[4-(tert-butoxycarbonyl)-1-piperazinyl]carbonyl}amino)-3-oxo-3-(pentylamino)propyl]phenoxy}malonic acid;

2-{4-[(2S)-2-{[(3-carboxyanilino)carbonyl]amino}-3-oxo-3-(pentylamino)propyl]phenoxy}malonic acid;

2-{(4-[(2S)-2-({(2S)-2-[(tert-butoxycarbonyl)amino]-3-phenylpropanoyl}amino)-3-oxo-3-(pentylamino)propyl]phenoxy}malonic acid:

2-{4-[(2S)-2-({(2R)-3-(benzylsulfanyl)-2-[(tert-butoxycarbonyl)amino]propanoyl}-amino)-3-oxo-3-(pentylamino)propyl]phenoxy}malonic acid;

2-{4-[(2S)-2-[((2S)-2-{[(tert-butylamino)carbonyl]amino}-3-phenylpropanoyl)amino]-3-oxo-3-(pentylamino)propyl]phenoxy}malonic acid;

2-{4-[(2S)-2-{[(2S)-2-[(tert-butoxycarbonyl)amino]-3-(2-naphthyl)propanoyl]amino}-3-oxo-3-(pentylamino)propyl]phenoxy}malonic acid;

2-{4-[(2S)-2-{[(2S)-2-[(tert-butoxycarbonyl)amino]-3-(1-naphthyl)propanoyl]amino}-3-oxo-3-(pentylamino)propyl]phenoxy}malonic acid;

2-{4-[(2S)-2-({(2S)-6-{[(benzyloxy)carbonyl]amino}-2-[(tert-butoxycarbonyl)-amino]hexanoyl}amino)-3-oxo-3-(pentylamino)propyl]phenoxy}malonic acid;

2-(carboxymethoxy)-5-[(2S)-2-{[(dibenzylamino)carbonyl]amino}-3-oxo-3-(pentylamino)propyl]benzoic acid;

2-{(4-[(2S )-2-{[(2S)-2-[(tert-butoxycarbonyl)amino]-4-(methylsulfanyl)butanoyl]amino}-3-oxo-3-(pentylamino)propyl]phenoxy}malonic acid;

2-{(4-[(2S)-2-{[(2S)-2-[(tert-butoxycarbonyl)amino]-4-(methylsulfinyl)butanoyl]amino}-3-oxo-3-(pentylamnino)propyl]phenoxy}malonic acid;

2-{4-[(2S)-2-{[(2S)-2-[(tert-butoxycarbonyl)amino]-3-(2,3,4,5,6-pentafluorophenyl)propanoyl]amino}-3-oxo-3-(pentylamino)propyl]phenoxy}malonic acid;

2-(carboxymethoxy)-5-(2S)-3-oxo-3-(pentylamino)-2-[(3-phenylpropanoyl)amino]propyl}benzoic acid;

2-{4-[(2S)-2-({(2S)-2-[(tert-butoxycarbonyl)amino]-4-methylpentanoyl}amino)-3-oxo-3-(pentylamino)propyl]phenoxy}malonic acid;

2-{4-[(2S)-2-({(2S)-3-(benzyloxy)-2-[(tert-butoxycarbonyl)amino]propanoyl-amino)-3-oxo-3-(pentylamino)propyl]phenoxy}malonic acid;

2-{4-[(2S)-2-({(2S)-4-amino-2-[(tert-butoxycarbonyl)amino]-4-oxobutanoyl}amino)-3-oxo-3-(pentylamino)propyl]phenoxy}malonic acid;

2-{(4-[(2S)-2-[(2-{[(benzyloxy)carbonyl]amino}acetyl)amino]-3-oxo-3-(pentylamino)propyl]phenoxy}malonic acid;

2-{4-[(2S)-2-{[(2S)-2-[(tert-butoxycarbonyl)amino]-3-(4-hydroxyphenyl)propanoyl]amino}-3-oxo-3-(pentylamino)propyl]phenoxy}malonic acid;

2-(4-[(2S)-2-({(2S)-2[(tert-butoxycarbonyl)amino]-4-phenylbutanoyl}amino)-3-oxo-3-(pentylamino)propyl]phenoxy}malonic acid;

2-(carboxymethoxy)-5-[(2S)-2-({(2S)-2-[(3-carboxypropanoyl)amino]-3-phenylpropanoyl}amino)-3-oxo-3-(pentylamino)propyl]benzoic acid;

2-{4-[(2S)-2-({(2S)-2-[(methylsulfonyl)amino]-3-phenylpropanoyl}amino)-3-oxo-3-(pentylamino)propyl]phenoxy}malonic acid;

2-{4-[(2S)-2-[((2S)-2-{[3-(diethylamino)propanoyl]amino}-3-phenylpropanoyl)-amino]-3-oxo-3-(pentylamino)propyl]phenoxy}malonic acid hydrochloride;

2-(4-{(2S,5S)-5-benzyl-13,13-dimethyl-4,7,11-trioxo-2-[(pentylamino)carbonyl]-12-oxa-3,6,10-triazatetradec-1-yl}phenoxy)malonic acid;

5-[(2S)-2-([(2S)-2-[(tert-butoxycarbonyl)amino]-3-phenylpropanoyl}amino)-3-oxo-3-(pentylamino)propyl]-2-(carboxymethoxy)benzoic acid;

5-[(2S)-2-{[(2S )-2-[(tert-butoxycarbonyl)amino]-3-(4-hydroxyphenyl)propanoyl]amino}-3-oxo-3-(pentylamino)propyl]-2-(carboxymethoxy)benzoic acid;

2-(carboxymethoxy)-5-{(2S)-3-oxo-3-(pentylamino)-2-[((2S)-3-phenyl-2-{[2-(4H-1,2,4-triazol-3-ylsulfanyl)acetyl]amino}propanoyl)amino]propyl}benzoic acid;

2-(carboxymethoxy)-5-{(2S)-3-oxo-3-(pentylamino)-2-[((2S )-3-phenyl-2-{[2-(5-sulfanyl-1H-1,2,3,4-tetraazol-1-yl)acetyl]amino}propanoyl)amino]propyl}benzoic acid;

2-(carboxymethoxy)-5-{(2S)-3-oxo-3-(pentylamino)-2-[((2S)-3-phenyl-2-{[2-(1H-1,2,3-triazol-5-ylsulfanyl)acetyl]amino}propanoyl)amino]propyl}benzoic acid;

2-[4-[(2S)-2-({(2S)-2-[(tert-butoxycarbonyl)amino]-3-phenylpropanoyl}amino)-3-oxo-3-(pentylamino)propyl]-2-(2H-1,2,3,4-tetraazol-5-yl)phenoxy]acetic acid;

5-[(2S)-2-({(2S)-2-[(tert-butoxycarbonyl)amino]-3-phenylpropanoyl}amino)-3-oxo-3-(pentylamino)propyl]-2-(2-methoxy-2-oxoethoxy)benzoic acid;

2-(4-{3-[(2-carboxyethyl)amino]-3-oxo-2-[(pentylamino)carbonyl]propyl}phenoxy)malonic acid;

2-{4-[(2S)-2-({(2S)-2-[(benzylsulfonyl)amino]-3-phenylpropanoyl}amino)-3-oxo-3-(pentylamino)propyl]phenoxy}malonic acid;
2-(carboxymethoxy)-5-[(2S)-2-[((2S)-2-{[2-(1H-indol-3-yl)acetyl]amino}-3-phenylpropanoyl)amino]-3-oxo-3-(pentylamino)propyl]benzoic acid;
2-(carboxymethoxy)-5-[(2S)-3-oxo-3-(pentylamino)-2-({(2S)-3-phenyl-2-[(2-phenylacetyl)amino]propanoyl}amino)propyl]benzoic acid;
2-(carboxymethoxy)-5-[(2S)-3-oxo-3-(pentylamino)-2-({(2S)-3-phenyl-2-[(4-phenylbutanoyl)amino]propanoyl}amino)propyl]benzoic acid;
5-[(2S)-2-{[(2S)-2-(acetylamino)-3-phenylpropanoyl]amino}-3-oxo-3-(pentylamino)propyl]-2-(carboxymethoxy)benzoic acid;
2-(carboxymethoxy)-5-[(2S)-2-({(2S)-2-[(3-methoxypropanoyl)amino]-3-phenylpropanoyl}amino)-3-oxo-3-(pentylamino)propyl]benzoic acid;
2-[4-[(2S)-2-({(2S)-2-[(tert-butoxycarbonyl)amino]-3-phenylpropanoyl}amino)-3-oxo-3-(pentylamino)propyl](carboxymethyl)anilino]acetic acid;
2-{4-[(2S )-2-({(2S )-2-[(3-methoxypropanoyl)amino]-3-phenylpropanoyl}amino)-3-oxo-3-(pentylamino)propyl]phenoxy}malonic acid;
2-{4-[(2S )-2-({(2S)-2-[(tert-butoxycarbonyl)amino]-3-phenylpropanoyl}amino)-3-oxo-3-(pentylamino)propyl]-2-[(hydroxyamino)carbonyl]phenoxy}acetic acid;
2-(carboxymethoxy)-5-[(2S)-2-({(2S)-2-[(4-hydroxybutanoyl)amino]-3-phenylpropanoyl}amino)-3-oxo-3-(pentylamino)propyl]benzoic acid;
5-{(2S,5S)-5-benzyl-13,13-dimethyl-4,7,11-trioxo-2-[(pentylamino)carbonyl]-12-oxa-3,6,10-triazatetradec-1-yl}-2-(carboxymethoxy)benzoic acid;
5-{(2S,5S)-5-benzyl-4,7,11,-tetraoxo-2-[(pentylamino)carbonyl]-11lambda$^6$-thia-3,6,10-triazadodec-1-yl}-2-(carboxymethoxy)benzoic acid;
2-{(4-[(2S)-2-{[(2S)-2-[(tert-butoxycarbonyl)amino]-3-(1H-indol-3-yl)propanoyl]amino}-3-oxo-3-(pentylamino)propyl]phenoxy}malonic acid;
5-[(2S)-2-({(2S)-2-[(tert-butoxycarbonyl)amino]-3-phenylpropanoyl}amino)-3-oxo-3-(pentylamino)propyl]-2-[2-(hydroxyamino)-2-oxoethoxy]benzoic acid;
2-(carboxymethoxy)-5-[(2S)-2-[((2S)-2-{[2-(3-hydroxyphenyl)acetyl]amino}-3-phenylpropanoyl)amino]-3-oxo-3-(pentylamino)propyl]benzoic acid;
2-(carboxymethoxy)-5-[(2S)-2-[((2S)-2-{[2-(4-hydroxyphenyl)acetyl]amino}-3-phenylpropanoyl)amino]-3-oxo-3-(pentylamino)propyl]benzoic acid;
2-(carboxymethoxy)-5-[(2S)-2-[((2S)-2-{[2-(4-methylphenyl)acetyl]amino}-3-phenylpropanoyl)amino]-3-oxo-3-(pentylamino)propyl]benzoic acid;
2-(carboxymethoxy)-5-((2S)-3-oxo-3-(pentylamino)-2-{[(2S)-3-phenyl-2-({2-[4-(trifluoromethyl)phenyl]acetyl}amino)propanoyl]amino}propyl)benzoic acid;
2-(carboxymethoxy)-5-[(2S)-2-[((2S)-2-{[2-(4-methoxyphenyl)acetyl]amino}-3-phenylpropanoyl)amino]-3-oxo-3-(pentylamino)propyl]benzoic acid;
2-[4-[2-({(2R)-2-[(tert-butoxycarbonyl)amino]-3-phenylpropanoyl}amino)-3-oxo-3-(pentylamino)propyl]-2-(2-hydroxy-2-oxoethoxy)phenoxy]acetic acid;
5-[(2S)-2-({(2S)-2-[(tert-butoxycarbonyl)amino]propanoyl}amino)-3-oxo-3-(pentylamino)propyl]-2-(carboxymethoxy)benzoic acid;
2-(carboxymethoxy)-5-[(2S)-3-oxo-3-(pentylamino)-2-({(2S)-3-phenyl-2-[(3-phenylpropanoyl)amino]propanoyl}amino)propyl]benzoic acid;
2-(carboxymethoxy)-5-[(2S)-3-oxo-2-{[(2R)-2-(2-oxo-1-pyrrolidinyl)-3-phenylpropanoyl]amino}-3-(pentylamino)propyl]benzoic acid;
5-[(2S)-2-({(2S)-2-[(tert-butoxycarbonyl)amino]-3-phenylpropanoyl}amino)-3-oxo-3-(pentylamino)propyl]-2-[carboxy(fluoro)methoxy]benzoic acid; and
5-{(2S)-2-({(2S)-2-[(tert-butoxycarbonyl)amino]-3-phenylpropanoyl}amino)-3-oxo-3-[(4-phenylbutyl)amino]propyl}-2-(carboxymethoxy)benzoic acid.

5. A method for treating noninsulin-dependent diabetes mellitus in a patient in need of such treatment, comprising:

administering said compound according to claim 2 or a pharmaceutically acceptable salt thereof to said patient.

6. The method according to claim 1, wherein said compound or a pharmaceutically acceptable salt thereof is administered orally, intranasally, transdermally, subcutaneously or parenterally.

7. The compound according to claim 1, wherein $R^1$ is —OCH(COOR$^5$)$_2$, and wherein $R^5$ is the same as defined above.

8. The compound according to claim 1, said compound having the formula III or IV:

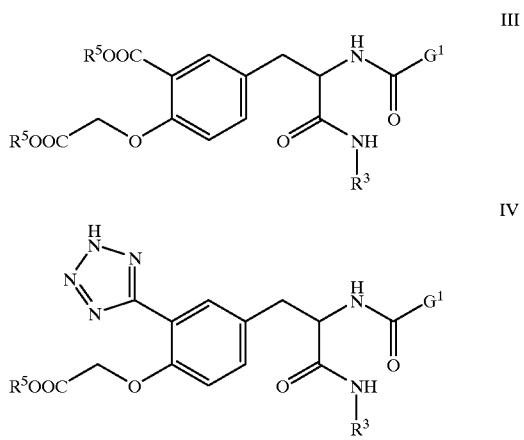

wherein $G^1$, $R^3$ and $R^5$ are the same as defined above.

9. The compound according to claim 7, wherein $R^1$ is —OCH(COOH)$_2$.

10. The compound according to claim 9, having the formula

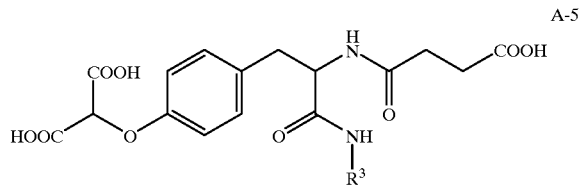

A-5 wherein $R^3$ is the same as defined above.

11. The compound according to claim 9, having the formula B-5:

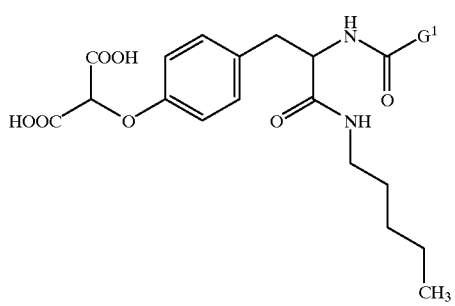

B-5 wherein G¹ is the same as defined above.

12. The compound according to claim 1, wherein said compound exists in (S)-configuration.

13. The compound according to claim 1, wherein the pharmaceutically acceptable salt of formula I is selected from the group consisting of lithium, sodium and potassium.

14. A pharmaceutical composition comprising:
   a compound according to claim 1 as an active ingredient; and
   a pharmaceutically and pharmacologically acceptable excipient.

15. A method for treating noninsulin-dependent diabetes mellitus in a patient in need of such treatment, comprising:
   administering a compound according to claim 1 to said patient.

16. The method according to claim 15, wherein said compound or pharmaceutically acceptable salt thereof is administered orally, intranasally, transdermally, subcutaneously or parenterally.

17. The method according to claim 15, wherein said compound or pharmaceutically acceptable salt thereof is administered in a dose of 0.1 to 1000 mg/kg body weight per day.

18. The method according to claim 17, wherein said compound or pharmaceutically acceptable salt thereof is administered in a dose of 0.1 to 100 mg/kg body weight per day.

19. The method according to claim 16, wherein said compound or pharmaceutically acceptable salt thereof is administered orally.

20. The method according to claim 16, wherein said compound or pharmaceutically acceptable salt thereof is administered parenterally.

21. A method for treating noninsulin-dependent diabetes mellitus in a patient in need of such treatment, comprising:
   administering a compound according to claim 8 or a pharmaceutically acceptable salt thereof to said patient.

22. The method according to claim 21, wherein said compound or a pharmaceutically acceptable salt thereof is administered orally, intranasally, transdermally, subcutaneously or parenterally.

23. The method according to claim 21, wherein said compound or pharmaceutically acceptable salt thereof is administered in a dose of 0.1 to 1000 mg/kg body weight per day.

24. The method according to claim 23, wherein said compound or pharmaceutically acceptable salt thereof is administered in a dose of 0.1 to 100 mg/kg body weight per day.

25. The method according to claim 22, wherein said compound or pharmaceutically acceptable salt thereof is administered orally.

26. The method according to claim 22, wherein said compound or pharmaceutically acceptable salt thereof is administered parenterally.

* * * * *